(12) United States Patent
Huletsky et al.

(10) Patent No.: US 7,449,289 B2
(45) Date of Patent: *Nov. 11, 2008

(54) **METHODS FOR DETECTION AND IDENTIFICATION OF METHICILLIN-RESISTANT *STAPHYLOCOCCUS AUREUS***

(75) Inventors: Ann Huletsky, Sillery (CA); Valery Rossbach, Gatineau (CA)

(73) Assignee: Geneohm Sciences Canada, Inc., Quebec (CA)

(*) Notice: Subject to any disclaimer, the term of this patent is extended or adjusted under 35 U.S.C. 154(b) by 210 days.

This patent is subject to a terminal disclaimer.

(21) Appl. No.: 10/479,674

(22) PCT Filed: Jun. 4, 2002

(86) PCT No.: PCT/CA02/00824

§ 371 (c)(1),
(2), (4) Date: Sep. 7, 2004

(87) PCT Pub. No.: WO02/099034

PCT Pub. Date: Dec. 12, 2002

(65) Prior Publication Data

US 2005/0019893 A1 Jan. 27, 2005

(30) Foreign Application Priority Data

Jun. 4, 2001 (CA) .................................. 2348042

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/23.7; 536/24.32; 536/24.33

(58) Field of Classification Search ................ None
See application file for complete search history.

(56) References Cited

U.S. PATENT DOCUMENTS

| 4,683,195 A | 7/1987 | Mullis et al. |
| 4,683,202 A | 7/1987 | Mullis |
| 5,437,978 A | 8/1995 | Ubukata et al. |
| 5,496,706 A | 3/1996 | Kuusela et al. |

(Continued)

FOREIGN PATENT DOCUMENTS

EP        0 527 628        2/1993

(Continued)

OTHER PUBLICATIONS

Ito T et al: "Structural comparison of three types of staphylococcal cassette chromosome med integrated in the chromosome in methicillini-resistant *Staphylococcus aureaus*." Antimicrobial Agents and Chemotherapy, U.S. May 2001, 'Online! vol. 45, No. 5, May 2001, pp. 1323-1336; XP002238384; ISSN: 0066-4804.

(Continued)

*Primary Examiner*—Diana B Johannsen
(74) *Attorney, Agent, or Firm*—Knobbe Martens Olson & Bear LLP

(57) ABSTRACT

The present invention describes novel SCCmec right extremity junction sequences for the detection of methicillin-resistant *Staphyloccocus aureus* (MRSA). It relates to the use of these DNA sequences for diagnostic purposes.

5 Claims, 10 Drawing Sheets

U.S. PATENT DOCUMENTS

| | | | |
|---|---|---|---|
| 5,702,895 | A | 12/1997 | Matsunaga et al. |
| 5,776,712 | A | 7/1998 | Kuusela et al. |
| 5,780,610 | A | 7/1998 | Collins et al. |
| 5,866,366 | A | 2/1999 | Kallender |
| 6,090,592 | A | 7/2000 | Adams et al. |
| 6,117,635 | A | 9/2000 | Nazarenko et al. |
| 6,117,986 | A | 9/2000 | Nardone et al. |
| 6,156,507 | A | 12/2000 | Hiramatsu et al. |
| 2006/0252078 | A1* | 11/2006 | Huletsky et al. ............... 435/6 |

FOREIGN PATENT DOCUMENTS

| | | |
|---|---|---|
| EP | 0 887 424 | 12/1998 |
| JP | 11056371 | 3/1999 |
| WO | WO 92/02638 | 8/1991 |
| WO | WO 92/05281 | 4/1992 |
| WO | WO 01/23604 A2 | 4/2001 |

OTHER PUBLICATIONS

& Database EMBL 'Online! May 14, 2001; retrieved from EBI, Database accession No. AB037671, XP002238391.

Database EMBL 'Online! Jan. 7, 2000; retrieved from EBI Database accession No. AB014433; XP002238392.

Hiramatsu K et al: "Genetic Basis for Molecular Epidemiology of MRSA" J Infect Chemother, vol. 2, 1996, pp. 117-129; XP001122060.

Oliveiera D C et al: "Genetic organization of the downstream region of the mecA element in methicillin-resistant *Staphylococcus aureus* isolates carrying different polymorphisms of this region." Antimicrobial Agents and Chemotherapy. US, Jul. 2000, vol. 44, No. 7, Jul. 2000; pp. 1906-1910; XP002238385; ISSN: 0066-4804.

Ito T et al: "Cloning and nucleotide sequence determination of the entire mvc DNA of pre-methicillin-resistant *Staphylococcus aureus* N315." Antimicrobial Agents and Chemotherapy. US, Jul. 1999; vol. 43, No. 6, Jun. 1999; pp. 1449-1468; XP002238386; ISSN: 0066-4804.

Katayama Y et al: "A new class of genetic element, *Staphylococcus* cassette chromosome mec, encodes methicillin resistance in *Staphylococcus aureus*." Antimicrobial Agents and Chemotherapy, U.S. Jun. 2000; vol. 44, No. 6, Jun. 2000; pp. 1549-1555; XP002238387; ISSN: 0066-4804.

Kuroda M et al: "Whole geno me sequencing of meticillin-resistant *Staphylococcus aureus*" Lancet The, Lancet Limited. London, G.B., vol. 357, No. 9264; Apr. 21, 2001; pp. 1225-1240; XP004246103; ISSN: 0140-6736.

Ma Xiao Zue et al: "Novel type of staphylococcal cassette chromosome mec identified in community-acquired methicillin-resistant *Staphylococcus aureus* strains." Antimicrobial Agents and Chemotherapy, vol. 46, No. 4, Apr. 2002; pp. 1147-1152; XP002238388; ISSN: 0066-4804.

Oliveiera D C et al: "The evolution of pandemic clones of methicillin-resistant *Staphylococcus aureus*: identification of two ancestral genetic backgrounds and the associated mec elements." Microbial Drug Resistance (Larchmont, N.Y) U.S. 2001 Winter, vol. 7, No. 4, Jan. 2001; pp. 349-361; XP009004903; ISSN: 1076-6294.

Baba Tadashi et al: Genome and virulence determinants of high virulence community-acquired MRSA. Lancet, England May 25, 2002; vol. 359, No. 9320; May 25, 2002; pp. 1819-1827; XP002238389; ISSN: 0140-6737.

Al-Soud, et al. "Capacity of nine thermostable DNA Polymerases to mediate DNA amplification in the presence of PCR-Inhibiting samples." *Appl. Environ. Microbial.* 64(10): 3748-3753 (1998).

Al-Soud, et. al. "Effects of amplification facilitators on diagnostic PCR in the presence of blood, feces, and meat." *J. Clin. Microbiol.* 38(12): 4463-4470 (2002).

Chakrabarti, et al. "Novel Sulfoxides Facilitate GC-Rich Template Amplification." *Biotechniques.* 32: 866-874 (2002).

De Lencastre, et al. Methicillin-Resistant *Staphylococcus aureus* disease in a Portuguese Hospital: Characterization of clonal Types by a Combination of DNA Typing Methods. Eur. *J. Clin. Microbiol. Infect. Dis.* 13: 64-73 (1994).

Deplano, et al. "In Vivo deletion of the methicillin resistance mec region from the chromosome of I *Staphylococcus aureus* strains." *J. Antimicrob. Chemotherapy*, 46-617-619 (2000).

Egholm, et al. "PNA hybridizes to complementary oligoncleotides obeying the Watson-Crick hydrogen-bonding rules." *Nature.* 365: 566-568 (1993).

Flores, et. al. "A rapid, inexpensive method for eluting DNA from Agarose or Acrylamide gel slices without toxic or chaotropic materials." *Biotechniques.* 13: 205-206 (1992).

GenBank accession No. AF422691, version AF422691.1, Apr. 29, 2002, Oliveira et al.

GenBank accession No. AF411934, version AF411934.1, Mar. 5, 2002, Oliveira et al.

Hiramatsu, et al. "Analysis of Borderline-Resistant Strains of Methicillin-Resistant *Staphylococcus aureus* Using Polymerase Chain Reaction." *Microbiol. Immunol.* 36: 445-453 (1992).

Hiramatsu, et al. "The emergence and evolution of methicillin-resistant *Staphylococcus aureus.*" *Trends in Microbiology.* 9(10): 486-493 (2001).

Inglis, et al. "Induced deletions within a cluster of resistance genes in the mec region of the chromosome of *Staphylococcus aureus.*" *Gen Microbiol.* 136:2231-2239 (1990).

Inglis, et al. "Methicillin-Sensitive and Resistant Homologues of *Staphylococcus aureus* Occur together among Clinical Isolates." *J. Infect. Dis.* N167:323-328 (1993).

Katayama, et al. "A New Class of Genetic Element, *Staphylococcus* Cassette Chromosome mec, Encodes Methicillin resistance in *Staphylococcus aureus.*" *Antimicrob. Agents Chemother.* 44(6):1549-1555 (2000).

Kellogg, et al. "TaqStart Antibody™: "Hot Start" PCR facilitated by a neutralizing monoclonal antibody directed against *Taq* DNA Polymerase." *Biotechniques.* 16:1134-1137 (1994).

Koshkin, et al. "LNA (locked nucleic acids): Synthesis of the Adenine, Cytosine, Guanine, 5-Methylcytosine, Thymine and Uracil Bicyclonucleoside Monomers, Oligomerisation, and unprecedented nucleic acid recognition." *Tetrahedron.* 54:3607-3630 (1998).

Kuroda, et al. "Whole genome sequencing of methicillin-resistant *Staphylococcus aureus.*" *The Lancet.* 357: 1225-1240 (2001).

Lawrence et al. "Consecutive isolation of homologous strains of methicillin-resistant and methicillin-susceptible *Staphylococcus aureus* from a hospitalized child." *J. Hosp. Infect.* 33:49-53 (1996).

Martineau, et. al. "Correlation between the Resistance Genotype Determined by Multiplex PCR Assays and the Antibiotic Susceptibility Patterns of *Staphylococcus aureaus* and *Staphylococcus epidermis.*" *Antimicrob. Chemotherapy.* 44(2): 231-238 (2000).

Murakami, et al. "Identification of Methicillin-Resistant Strains of Staphylococci by Polymerase Chain Reaction." *J. Clin Microbiol.* 29(10):2240-2244 (1991).

Nichols, et al. "A universal nucleoside for use at ambiguous sites in DNA primers." *Nature.* 369:492-493 (1994).

Partial International Search Report for International Application No. PCT/CA 02/00824 dated May 12, 2003.

Saito, et. al. "Immunological Detection of Penicillin-Binding Protein 2' of Methicillin-Resistant Staphylococci by Using Monoclonal Antibodies Prepared from Synthetic Peptides." *J. Clin. Microbiol.* 33(9): 2498-2500 (1995).

Simor, et al. "Characterization and Proposed Nomenclature of Epidemic Strains of Methicillin-Resistant *Staphylococcus aureus* in Canada." *CCDR* 25-12: 105-112 (Jun. 15, 1999).

Suzuki, et al. "Survey of Methicillin-Resistant Clinical Strains of Coagulase-Negative Staphylococci for *mecA* Gene Distribution." *Antimicrob. Agents Chemother.* 36(2): 429-434 (1992).

Ubukata, et. al. "Homology of *mecA* Gene in Methicillin-Resistant *Staphylococcus aureus* to that of *staphylococcus aureus.*" *Antimicrob, Agents Chemother.* 34(1):170-172 (1990).

Ubukata, et. al. "Rapid Detection of the *mecA* Gene in Methicillin-Resistant Staphylococci by Enzymatic Detection of Polymerase Chain Reaction Products." *J. Clin. Microbiol.* 30(70):1728-1733 (1992).

Wada, et al. "Southern Hybridization Analysis of the mecA Deletion from Methicillin-Resistant *Staphylococcus aureus.*" Biochem. *Biophys. Res. Comm.*, 176: 1319-1326 (1991).

Westin, et al. "Anchored multiplex amplification on a microelectronic chip array." Nat. Biotechnol. 18:199-204 (2000).
Wilson, et al. "Inhibition and Facilitation of Nucleic Acid Amplification." Appl. Environ. Microbiol. 63:3741-3751 (1997).
Archer and Niemeyer. "Origin and Evolution of DNA Associated with Resistance to Methicillin in Staphylococci." Trends in Microbiology. 2(10):343-347 (1994).
Archer, et al. "Dissemination among Staphylococci of DNA Sequences Associated with Methicillin Resistance." Antimicrobial Agents and Chemotherapy. 38(3):447-54 (1994).
Barberis-Maino. IS431, a staphylococcai insertion sequence-like element related to IS26 from *Proteus vulgaris*. Gene. 59:107-13 (1983).
Berger-Bachi, et al. Insertional Inactivation of Staphylococcal Methicillin Resistance by Tn551. Journal of Bacteriology. 154(1):479-87 (1983).
Derbise, et al. "Mapping the Regions Carrying the Three Contiguous Antibiotic Resistance Genes *aadE, sat4, and aphA-3* in the Genome of Staphylococci." Antimicrobial Agents and Chemotherapy. 41(5): 1024-32 (1997).
Dubin, et al. "Physical Mapping of the *mec* Region of an American Methicillin-Resistant *Staphylococcus aureus* Strain." Antimicrobial Agents and Chemotherapy. 35(8):1661-65 (1991).
Gerberding, et al. Comparison of conventional susceptibility Tests with Direct Detection of Penicillin-Binding Protein 2a in borderline Oxacillin-Resistant Strains of *Staphylococcus aureus*. Antimicrobial Agents and Chemotherapy. 35(12):2574-79 (1991).
Hiramatsu, et al. "Molecular Cloning and Nucleotide Sequence Determination of the Regulator Region of *mecA* gene in methicillin-resistant *Staphylococcus aureus*." FEBS. 298(2.3):133-36 (1992).
Huletsky, et al. "New Real-Time PCR Assay for Rapid Detection of Methicillin-Resistant *Staphylococcus aureus* Directly from Specimens Containing a Mixture of Staphylococci." Journal of Clinical Microbiology. 42(5): 1875-84 (2004).
Ito and Hiramatsu. "Acquisition of Methicillin Resistance and Progression of Multiantibiotic Resistance in Methicillin- Resistant *Staphylococcus aureus*." Yonsei Medical Journal. 39(6):526-33 (1998).
Kitagawa, et al. "Rapid Diagnosis of Methicillin-Resistant *Staphylococcus aureus* Bacteremia by Nested Polymerase Chain Reaction." Annals of Surgery. 224(5):665-71 (1996).
Kluytmans. Food-Initiated Outbreak of Methicillin-Resistant *Staphylococcus aureus* Analyzed by Pheno and Genotyping. Journal of clinical Microbiology. 33(5):1121-28 (1995).
Lawrence, et al. "Use of the Coagulase Gene Typing Method for Detection of Carriers of Methicillin-Resistant *Staphylococcus aureus*." Journal of Antimicrobial Chemotherapy. 37:687-96 (1996).
Lin, et al. "Sequence Analysis and Molecular Characterization of Genes Required for the Biosynthesis of Type 1 Capsular Polysaccharide in *Staphylococcus aureus*." Journal of Bacteriology. 176(22):7005-16 (1994).
Lychansky and Pattee. "Isolation of Transposon Tn551 Insertions Near Chromosomal Markers of Interest in *Staphylococcus aureus*." Journal of Baacteriology. 159(3):894-99 (1984).
Luijendijk, et al. "Comparison of Five Tests for Identification of *Staphylococcus aureus* Clinical Samples." Joural of Clinical Microbiology. 34(9):2267-69 (1996).
Luong, et al. "Type I Capsule Genes of *Staphylococcus aureus* Are Carried in a Staphyloccal Cassette Chromosome genetic Element." Antimicrobial Agents and Chemotherapy. 46(4):1147-52 (2002).
Mulligan, et al. "Methicillin-Resistant *Staphylococcus aureus*: a Consensus Review of the Microbiology, Pathogenesis, and Epidemiology with Implications for Prevention and Management." Am J Med. 94(3):313-28 (1993). Abstract only.
Muraki. Detection of Methicillin-Resistant *Staphylococcus aureus* using PCR and non-radioactive DNA probes (II). Rinsho Byori. 41(1): 1159-66 (1993). Abstract only.
Pattee, et al. "Genetic and Physical Mapping of the Chromosome of *Staphylococcus aureus*." Molecular Biology of the Staphylococci. VCH Publishers. 41-58 (1990).
Stewart, et al. "IS257 and Small Plasmid Insertions in the *mec* Region of the Chromosome of *Staphylococcus aureus*." Plasmid. 31:12-20 (1994).

Suzuki, et al. "Distribution of *mec* Regulator Genes in Methicillin-Resistant *Staphylococcus* Clinical Strains." Antimicrobial Agents and Chemotherapy. 37(6):1219-26 (1993).
Tokue, et al. "Comparison of a Polymerase Chain Reaction Assay and a Convetional Microbiologic Method for Detection of Methicillin-Resistant *Staphylococcus aureus*." Antimicrobial Agents and Chemotherapy. 36(1):6-9 (1992).
Ubukata, et al. "Restriction Maps of the Regions Coding for Methicillin and Tobramycin Resistances on Chromosomal DNA in Methicillin-Resistant Staphylococci." Antimicrobial Agents and Chemotherapy. 33(9):1624-26 (1989).
Unal, et al. "Detection of Methicillin-Resistant Staphylococci by Using the Polymerase Chain Reaction." Journal of Clinical Microbiology. 30(7):1685-91 (1992).
Unal, et al. "Comparison of Tests for Detection of Methicillin-Resistant *Staphylococci aureus* in a Clinical Microbiology Laboratory." Antimicrobial Agents and Chemotherapy. 38(2):345-47 (1994).
Van Belkum, et al. "Comparison of Phage Typing and DNA Fingerprinting by Polymerase Chain Reaction of Discrimination of Methicillin-Resistant *Staphylococcus aureus* Strains." Journal of Clinical Microbiology. 31(4):798-803 (1993).
Vannuffel, et al. "Specific Detection of Methicillin-Resistant *Staphylococcus* Species by Multiplex PCR." Journal of Clinical Microbiology. 33(11):2864-67 (1995).
Wallet, et al. "Choice of a Routine Method for Detecting Methicillin-Resistance in Staphylococci." Journal of Antimicrobial Chemotherapy. 37:901-909 (1996).
Wu, et al. "Genetic Organization of the *mecA* Region in Methicillin-Susceptible and Methicillin-Resistant Strains of *Staphylococcus sciuri*." Journal of Bacteriology. 180(2):236-42 (1998).
Arnheim, et al. "Polymerase Chain Reaction." C&EN. 36-47 (1990).
Barringer, et al. "Blunt-end and single strand ligations by *Escherichia coli* ligase: influence on an in vitro amplification scheme." Gene. 89:117-122 (1990).
Elghanian et al. "Selective Colorimetric Detection of Polynucleotides Based on the Distance-Dependent Optical Properties of Gold Nanoparticles." (1997) Science 277:1078-1081.
GenBank accession No. AB014440, version AB014440.1, Jul. 6, 1999, Ito et al.
GenBank accession No. AB063172, version AB063172.2, Jun. 12, 2001, Ito et al.
GenBank accession No. AB121219, version AB121219.1, Sep. 26, 2003, Ito et al.
GenBank accession No. AF270046, version AF270046.1, May 22, 2000, Taylor et al.
GenBank accession No. BK001539, version BK001539.1, Aug. 15, 2003, Mongkolrattanothai et al.
GenBank accession No. BX571856, version BX57156.1, Jun. 23, 2004, Holden et al.
GenBank accession No. U10927, version U10927.2, Nov. 1, 2001, Lin et al.
Guatelli, et al. "Isotherma, in vitro amplification of nucleic acids by a multienzyme reaction modeled after retroviral replication." Proc. Natl. Acad. Sci. USA, 87:1874-1878 (1990).
Ito et al. Novel Type V Staphylococcal Cassette Chromosome *mec* Driven by a Novel Cassette Chromosome Recombinase, *ccrC*. Antimicrob. Agents Chemother. 48:2637-2651 (2004).
Kimmel, et al. "Preparations of cDNA and the Generation of cDNA Libraries: Overview." Methods in Enzymology. 152:307-316 (1987).
Kwoh, et al. "Transcription-based amplification system and detection of amplified human immunodeficiency virus type 1 with a bead-based sandwich hybridization format." Proc. Natl. Acad. Sci. USA 86:1173-1177 (1989).
Landegren, et al. "A Ligase-Mediated Gene Detection Technique." (1988) Science 241:1077-1080.
Leach et al. "Theoretical Investigations of Novel Nucleic Acid Bases." (1992) J. Am. Chem. Soc. 114:3675-3683.
Lomell, et al. "Quantitative Assays Based on the Use of Replicatable Hybridization Probes." Clinical Chemistry. 35(9):1826-1831 (1989).
Mantsch et al. "Structural Enzymatic Properties of Adenine 1-Oxide Nucleotides." (1975) Biochem. 14(26):5593-5601.
Newton et al. "Instrumentation, Reagents and Consumables." PCR, 2nd Ed., Springer-Verlag (New York: 1997), Chapter 2, p. 8-28.

Oliveira, et al. "Multiplex PCR Strategy for Rapid Identification of Structural Types and Variants of the *mec* Element in Methicillin-Resistant *Staphylococcus aureus*." Antimicrob. Agents Chemother. 46:2155-2161 (2002).

Oliveira et al. "Secrets of success of a human pathogen: molecular evolution of pandemic clones of meticillin-resistant *Staphylococcus aureus*." Lancet Infect Dis. 2:180-9 (2002).

Piccirilli et al. "Enzymatic incorporation of a new base pair into DNA and RNA extends the genetic alphabet." (1990) Nature. 343:33-37.

Sooknanan, R. NASBA. A detection and amplification system uniquely suited for RNA. (1995) Biotechnology 13:563-564.

Switzer et al. "Enzymatic Recognition of the Base Pair between Isocytidine and Isoguanosine." (1993) Biochemistry 32:10489-10496.

Thewell, et al. "Mode of action and application of Scorpion primers to mutation detection." (2000), Nucl. Acids Res. 28(19):3752-3761.

Tor et al. "Site-Specific Enzymatic Incorporation of an Unnatural Base, $N^6$-(6-Aminohexyl)isoguanosine, into RNA." (1993) J. Am. Chem. Soc. 115:4461-4467.

Tyagi et al. "Molecular Beacons: Probes that Fluoresce upon Hybridization." (1996) Nat. Biotech. 14:303-308.

Van Brunt, J. "Amplifying Genes: PCR and its Alternatives." Biotechnology, 8:291-294 (1990).

Wu, et a. "The Ligation Amplification Reaction (LAR)-Amplification of Specific DNA Sequences Using Sequential Rounds of Template-Dependent Ligation." (1989) Genomics 4:560-569.

\* cited by examiner

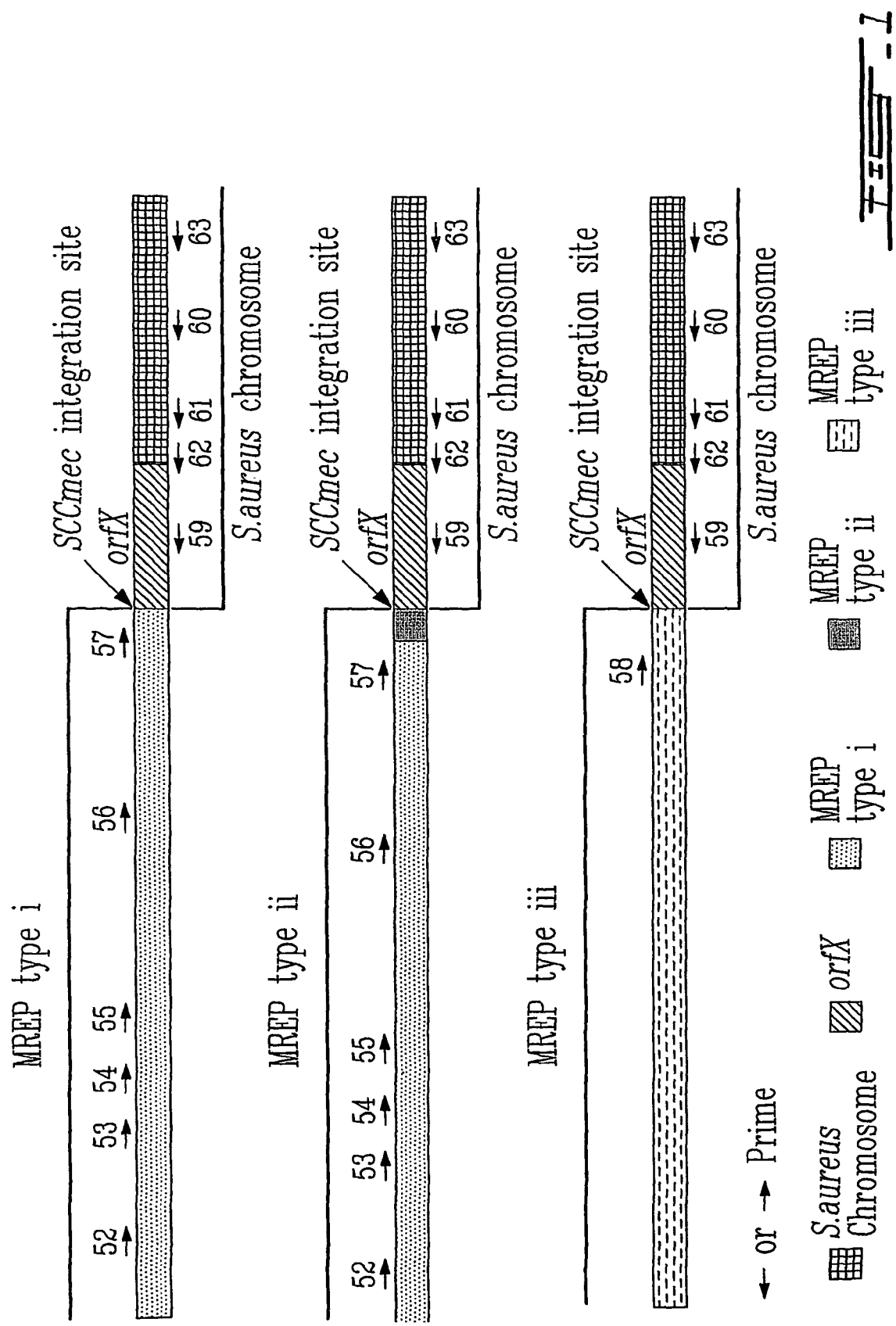

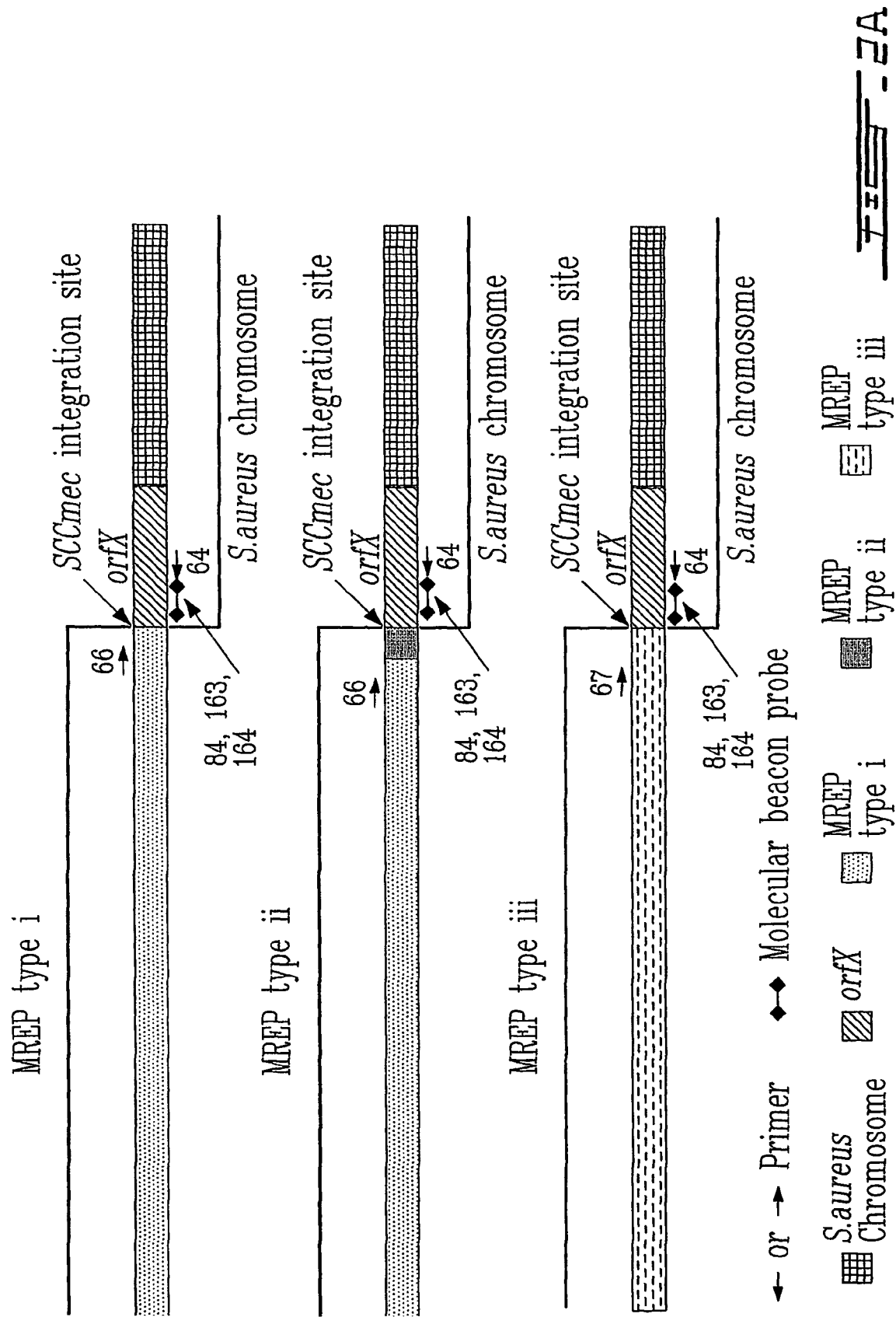

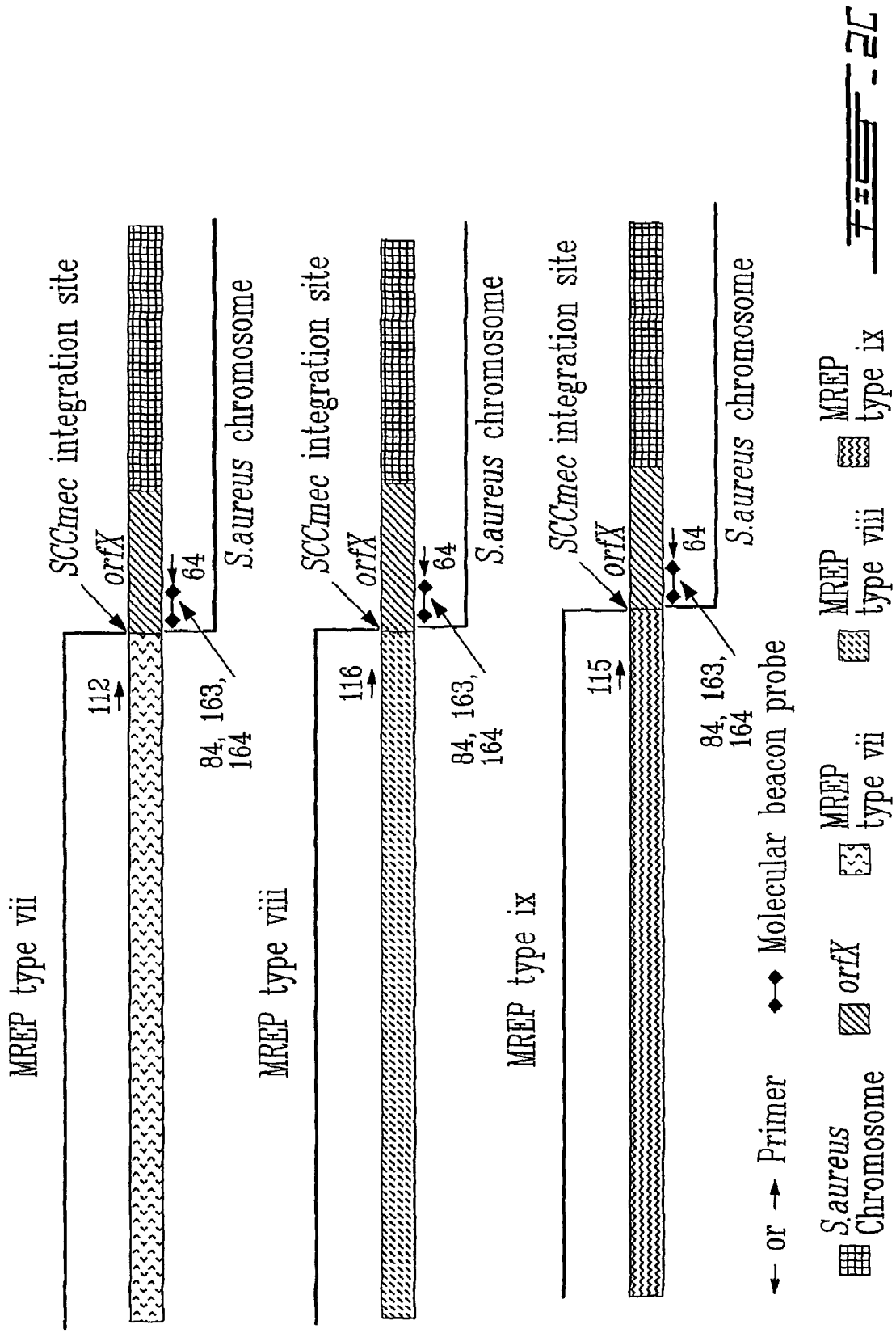

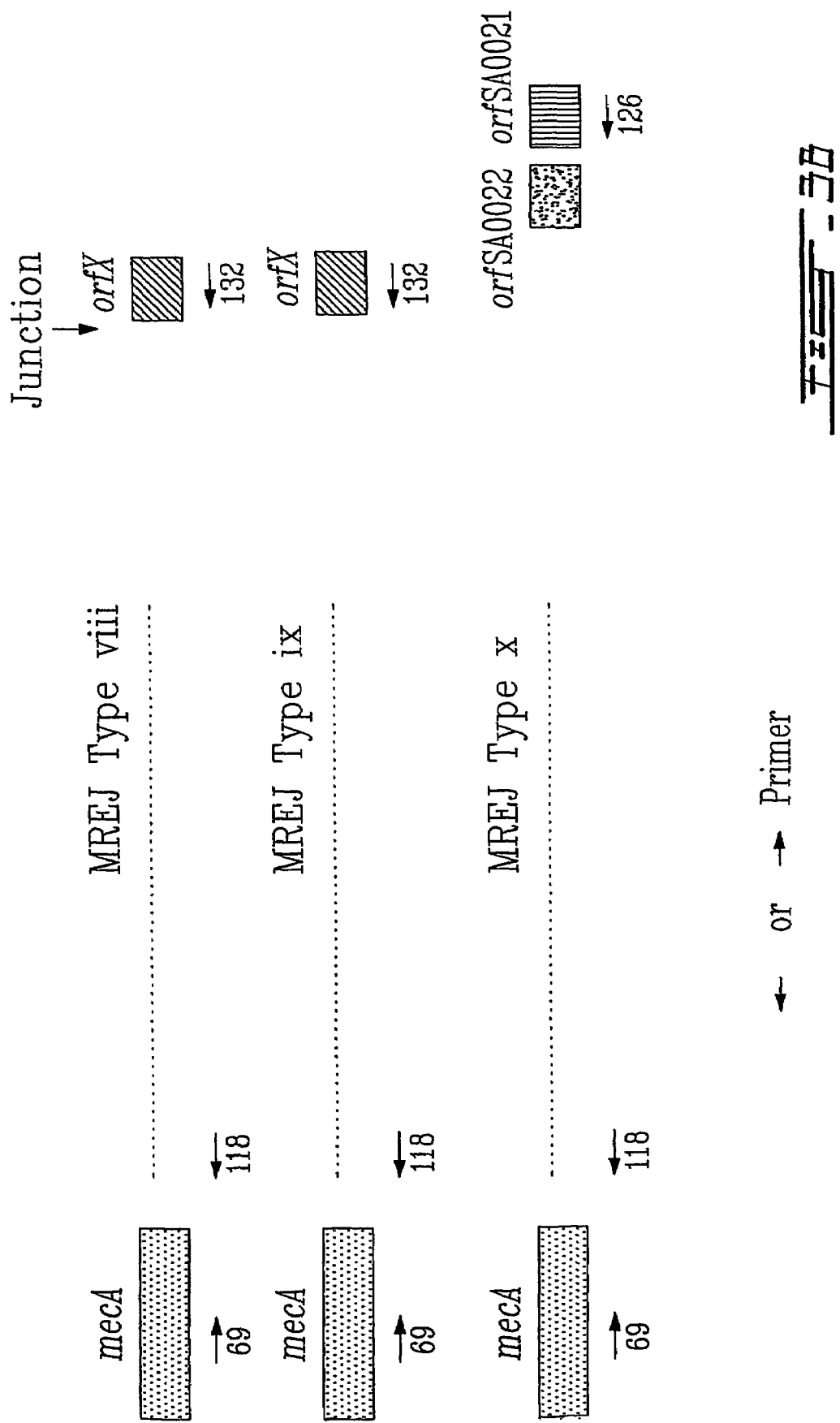

METHODS FOR DETECTION AND IDENTIFICATION OF METHICILLIN-RESISTANT *STAPHYLOCOCCUS AUREUS*

CROSS-REFERENCE TO RELATED APPLICATIONS

This application is the National Stage under 35 U.S.C. §371 of International Patent Application PCT/CA02/00824, filed on Jun. 4, 2002, which claims priority to Canadian patent application 2,348,042, filed on Jun. 4, 2001.

REFERENCE TO SEQUENCE LISTING, TABLE, OR COMPUTER PROGRAM LISTING

The duplicate copes of a CD ROM marked "Copy 1" and "Copy 2" containing a Sequence Listing filed in electronic format on May 23, 2006, entitled GENOM.051NP.txt, were created May 23, 2006, and are 191,488 bytes in size. The information on these duplicate CD-ROMs is herein incorporated by reference in its entirety.

BACKGROUND OF THE INVENTION

Clinical Significance of *Staphylococcus aureus*

The coagulase-positive species *Staphylococcus aureus* is well documented as a human opportunistic pathogen. Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abcesses. Food poisoning mediated by staphylococcal enterotoxins is another important syndrome associated with *S. aureus*. Toxic shock syndrome, a community-acquired disease, has also been attributed to infection or colonization with toxigenic *S. aureus* (Murray et al. Eds, 1999, Manual of Clinical Microbiology, 7th Ed., ASM Press, Washington, D.C.).

Methicillin-resistant *S. aureus* (MRSA) emerged in the 1980s as a major clinical and epidemiologic problem in hospitals. MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defence. Since MRSA can spread easily from patient to patient via personnel, hospitals over the world are confronted with the problem to control MRSA. Consequently, there is a need to develop rapid and simple screening or diagnostic tests for detection and/or identification of MRSA to reduce its dissemination and improve the diagnosis and treatment of infected patients.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the choromosomal mecA gene and functions as a β-lactam-resistant transpeptidase. The mecA gene is absent from methicillin-sensitive *S. aureus* but is widely distributed among other species of staphylococci and is highly conserved (Ubukata et al., 1990, Antimicrob. Agents Chemother. 34:170-172).

By nucleotide sequence determination of the DNA region surrounding the mecA gene from *S. aureus* strain N315 (isolated in Japan in 1982), Hiramatsu et al. have found that the mecA gene is carried by a novel genetic element, designated staphylococcal cassette chromosome mec (SCCmec), inserted into the chromosome. SCCmec is a mobile genetic element characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). The element is precisely excised from the chromosome of *S. aureus* strain N315 and integrates into a specific *S. aureus* chromosomal site in the same orientation through the function of a unique set of recombinase genes comprising ccrA and ccrB. Two novel genetic elements that shared similar structural features of SCCmec were found by cloning and sequencing the DNA region surrounding the mecA gene from MRSA strains NCTC 10442 (the first MRSA strain isolated in England in 1961) and 85/2082 (a strain from New Zealand isolated in 1985). The three SCCmec have been designated type I (NCTC 10442), type II (N315) and type III (85/2082) based on the year of isolation of the strains (Ito et al., 2001, Antimicrob. Agents. Chemother. 45:1323-1336) (FIG. 1). Hiramatsu et al. have found that the SCCmec DNAs are integrated at a specific site in the methicillin-sensitive *S. aureus* (MSSA) chromosome. They characterized the nucleotide sequences of the regions around the left and right boundaries of SCCmec DNA (i.e. attL and attR, respectively) as well as those of the regions around the SCCmec DNA integration site (i.e. attBscc which is the bacterial chromosome attachment site for SCCmec DNA). The attBscc site was located at the 3' end of a novel open reading frame (ORF), orfX. The orfX potentially encodes a 159-amino acid polypeptide sharing identity with some previously identified polypeptides, but of unknown function (Ito et al., 1999, Antimicrob. Agents Chemother. 43:1449-1458). Recently, a new type of SCCmec (type IV) has been described by both Hiramatsu et al. (Ma et al, 2002, Antimicrob. Agents Chemother. 46:1147-1152) and Oliveira et al. (Oliveira et al, 2001, Microb. Drug Resist. 7:349-360). The sequences of the right extremity of the new type IV SCCmec from *S. aureus* strains CA05 and 8/6-3P published by Hiramatsu et al. (Ma et al., 2002, Antimicrob. Agents Chemother. 46:1147-1152) were nearly identical over 2000 nucleotides to that of type II SCCmec of *S. aureus* strain N315 (Ito et al., 2001, Antimicrob. Agents Chemother. 45:1323-1336). No sequence at the right extremity of the SCCmec type IV is available from the *S. aureus* strains HDE288 and PL72 described by Oliveira et al. (Oliveira et al., 2001, Microb. Drug Resist. 7:349-360).

Previous methods used to detect and identify MRSA (Saito et al., 1995, J. Clin. Microbiol. 33:2498-2500; Ubukata et al., 1992, J. Clin. Microbiol. 30:1728-1733; Murakami et al., 1991, J. Clin. Microbiol. 29:2240-2244; Hiramatsu et al., 1992, Microbiol. Immunol. 36:445-453), which are based on the detection of the mecA gene and *S. aureus*-specific chromosomal sequences, encountered difficulty in discriminating MRSA from methicillin-resistant coagulase-negative staphylococci (CNS) because the mecA gene is widely distributed in both *S. aureus* and CNS species (Suzuki et al., 1992, Antimicrob. Agents. Chemother. 36:429-434). Hiramatsu et al. (U.S. Pat. No. 6,156,507) have described a PCR assay specific for MRSA by using primers that can specifically hybridize to the right extremities of the 3 types of SCCmec DNAs in combination with a primer specific to the *S. aureus* chromosome, which corresponds to the nucleotide sequence on the right side of the SCCmec integration site. Since nucleotide sequences surrounding the SCCmec integration site in other staphylococcal species (such as *S. epidermidis* and *S. haemolyticus*) are different from those found in *S. aureus*, this PCR assay was specific for the detection of MRSA. This PCR assay also supplied information for MREP typing (standing for <<mec right extremity polymorphism>>) of SCCmec DNA (Ito et al., 2001, Antimicrob. Agents Chemother. 45:1323-1336; Hiramatsu et al., 1996, J. Infect. Chemother. 2:117-129). This typing method takes advantage of the polymorphism at the right extremity of SCCmec DNAs adjacent to the integration site among the three types of SCCmec. Type III has a unique nucleotide sequence while type II has an insertion of 102 nucleotides to the right terminus of SCCmec type II. The MREP typing method described by Hiramatsu et al. (Ito et al., 2001, Antimicrob. Agents Chemother. 45:1323-1336; Hiramatsu et al., 1996, J. Infect. Chemother. 2:117-129) defines the SCCmec type I as MREP type i, SCCmec type II as MREP type ii and SCCmec type III as MREP type iii. It should be noted that the MREP typing method cannot differentiate the new SCCmec type IV described by Hiramatsu et al. (Ma et al., 2002, Antimicrob. Agents Chemother. 46:1147-1152) from SCCmec type II because these two SCCmec types exhibit the same nucleotide sequence to the right extremity.

The set of primers described by Hiramatsu et al. as being the optimal primer combination (SEQ ID NOs.: 22, 24, 28 in U.S. Pat. No. 6,156,507 corresponding to SEQ ID NOs.: 56, 58 and 60, respectively, in the present invention) have been used in the present invention to test by PCR a variety of MRSA and MSSA strains (FIG. 1 and Table 1). Twenty of the 39 MRSA strains tested were not amplified by the Hiramatsu et al. multiplex PCR assay (Tables 2 and 3). Hiramitsu's method indeed was successful in detecting less than 50% of the tested 39 MRSA strains. This finding demonstrates that some MRSA strains have sequences at the right extremity of SCCmec-chromosome right extremity junction different from those identified by Hiramatsu et al. Consequently, the system developed by Hiramatsu et al. does not allow the detection of all MRSA. The present invention relates to the generation of SCCmec-chromosome right extremity junction sequence data required to detect more MRSA strains in order to improve the Hiramatsu et al. assay. There is a need for developing more ubiquitous primers and probes for the detection of most MRSA strains around the world.

SUMMARY OF THE INVENTION

It is an object of the present invention to provide a specific, ubiquitous and sensitive method using probes and/or amplification primers for determining the presence and/or amount of nucleic acids from all MRSA strains.

Ubiquity of at least 50% amongst the strains representing MRSA strains types IV to X is an objective of this invention.

Therefore, in accordance with the present invention is provided a method to detect the presence of a methicillin-resistant *Staphylococcus aureus* (MRSA) strain in a sample, the MRSA strain being resistant because of the presence of an SCCmec insert containing a mecA gene, said SCCmec being inserted in bacterial nucleic acids thereby generating a polymorphic right extremity junction (MREJ), the method comprising the step of annealing the nucleic acids of the sample with a plurality of probes and/or primers, characterized by:

(i) the primers and/or probes are specific for MRSA strains and capable of annealing with polymorphic MREJ nucleic acids, the polymorphic MREJ comprising MREJ types i to x; and (ii) the primers and/or probes altogether can anneal with at least four MREJ types selected from MREJ types i to x.

In a specific embodiment, the primers and/or probes are all chosen to anneal under common annealing conditions, and even more specifically, they are placed altogether in the same physical enclosure.

A specific method has been developed using primers and/or probes having at least 10 nucleotides in length and capable of annealing with MREJ types i to iii, defined in any one of SEQ ID NOs: 1, 20, 21, 22,23, 24, 25, 41, 199; 2, 17, 18, 19, 26, 40, 173, 174, 175, 176, 177, 178, 179, 180, 181, 182, 183, 185, 186, 197; 4, 5, 6, 7, 8, 9, 10, 11, 12, 13, 14, 15, 16, 104, 184, 198 and with one or more of MREJ types iv to ix, having SEQ ID NOs: 42, 43, 44, 45, 46, 51; 47, 48, 49, 50; 171; 165, 166; 167; 168. To be perfectly ubiquitous with the all the sequenced MREJs, the primers and/or probes altogether can anneal with said. SEQ ID NOs of MREJ types i to ix.

The following specific primers and/or probes having the following sequences have been designed:

| | |
|---|---|
| 66, 100, 101, 105, 52, 53, 54, 55, 56, 57, 64, 71, 72, 73, 74, 75, 76, 70, 103, 130, 132, 158, 159, 59, 62, 126, 127, 128, 129, 131, 200, 201, 60, 61, 63 32, 83, 84, 160, 161, 162, 163, 164 85, 86, 87, 88, 89 | for the detection of MREJ type i |
| 66, 97, 99, 100, 101, 106, 117, 118, 124, 125, 52, 53, 54, 55, 56, 57 64, 71, 72, 73, 74, 75, 76, 70, 103, 130, 132, 158, 159 59, 62 126, 127 128, 129, 131, 200, 201 60, 61, 63 32, 83, 84, 160, 161, 162, 163, 164 85, 86, 87, 88, 89 | for the detection of MREJ type ii |
| 67, 98, 102, 107, 108 64, 71, 72, 73, 74, 75, 76, 70, 103, 130, 132, 158, 159 58, 59, 62 126, 127 128, 129, 131, 200, 201 60, 61, 63 32, 83, 84, 160, 161, 162, 163, 164 85, 86, 87, 88, 89 | for the detection of MREJ type iii |
| 79, 77, 145, 147 64, 71, 72, 73, 74, 75, 76, 70, 103, 130, 132, 158, 159 59, 62 126, 127 128, 129, 131, 200, 201 60, 61, 63 68 32, 83, 84, 160, 161, 162, 163, 164 85, 86, 87, 88, 89 | for the detection of MREJ type iv |
| 65, 80, 146, 154, 155 64, 71, 72, 73, 74, 75, 76, 70, 103, 130, 132, 158, 159 59, 62 126, 127 128, 129, 131, 200, 201 60, 61, 63 32, 83, 84, 160, 161, 162, 163, 164 85, 86, 87, 88, 89 | for the detection of MREJ type v |

-continued

| | |
|---|---|
| 202, 203, 204 | for the detection of MREJ type vi |
| 64, 71, 72, 73, 74, 75, 76, 70, | |
| 103, 130, 132, 158, 159 | |
| 59, 62 | |
| 126, 127 | |
| 128, 129, 131, 200, 201 | |
| 60, 61, 63 | |
| 32, 83, 84, 160, 161, 162, 163, 164 | |
| 85, 86, 87, 88, 89 | |
| 112, 113, 114, 119, 120, 121, 122 | for the detection of MREJ type vii, |
| 123, 150, 151, 153 | |
| 64, 71, 72, 73, 74, 75, 76, 70, 103, | |
| 130, 132, 158, 159 | |
| 59, 62 | |
| 126, 127 | |
| 128, 129, 131, 200, 201 | |
| 60, 61, 63 | |
| 32, 83, 84, 160, 161, 162, 163, 164 | |
| 85, 86, 87, 88, 89 | |
| 115, 116, 187, 188, 207, 208 | for the detection of MREJ type viii |
| 64, 71, 72, 73, 74, 75, 76, 70, | |
| 103, 130, 132, 158, 159 | |
| 59, 62 | |
| 126, 127 | |
| 128, 129, 131, 200, 201 | |
| 60, 61, 63 | |
| 32, 83, 84, 160, 161, 162, 163, 164 | |
| 85, 86, 87, 88, 89 | |
| 109, 148, 149, 205, 206 | for the detection of MREJ type ix. |
| 64, 71, 72, 73, 74, 75, 76 | |
| 70, 103, 130, 132, 158, 159 | |
| 59, 62 | |
| 126, 127 | |
| 128, 129, 131, 200, 201 | |
| 60, 61, 63 | |
| 32, 83, 84, 160, 161, 162, 163, 164 | |
| 85, 86, 87, 88, 89 | |

Amongst these, the following primer pairs having the following sequences are used:

| | |
|---|---|
| 64/66, 64/100, 64/101; 59/52, | for the detection of type i MREJ |
| 59/53, 59/54, 59/55, 59/56, 59/57, | |
| 60/52, 60/53, 60/54, 60/55, 60/56 | |
| 60/57, 61/52, 61/53, 61/54, 61/55 | |
| 61/56, 61/57, 62/52, 62/53, 62/54 | |
| 62/55, 62/56, 62/57, 63/52, 63/53 | |
| 63/54, 63/55, 63/56, 63/57 | |
| 64/66, 64/97, 64/99, 64/100, 64/101 | for the detection of type ii MREJ |
| 59/52, 59/53, 59/54, 59/55, 59/56, | |
| 59/57, 60/52, 60/53, 60/54, 60/55, | |
| 60/56, 60/57, 61/52, 61/53, 61/54, | |
| 61/55, 61/56, 61/57, 62/52, 62/53, | |
| 62/54, 62/55, 62/56, 62/57, 63/52 | |
| 63/53, 63/54, 63/55, 63/56, 63/57 | |
| 64/67, 64/98, 64/102; 59/58, | for the detection of type iii MREJ |
| 60/58, 61/58, 62/58, 63/58 | |
| 64/79 | for the detection of type iv MREJ |
| 64/80 | for the detection of type v MREJ |
| 64/204 | for the detection of type vi MREJ |
| 64/112, 64/113 | for the detection of type vii MREJ |
| 64/115, 64/116 | for the detection of type viii MREJ |
| 64/109 | for the detection of type ix MREJ |

As well, amongst these, the following probes having the following sequences are used:

SEQ ID NOs: 32, 83, 84, 160, 161, 162, 163, 164 for the detection of MREJ types i to ix.

In the most preferred embodied method, the following primers and/or probes having the following nucleotide sequences are used together. The preferred combinations make use of:
i) SEQ ID NOs: 64, 66, 84, 163, 164 for the detection of MREJ type i
ii) SEQ ID NOs: 64, 66, 84, 163, 164 for the detection of MREJ type ii
iii) SEQ ID NOs: 64, 67, 84, 163, 164 for the detection of MREJ type iii
iv) SEQ ID NOs: 64, 79, 84, 163, 164 for the detection of MREJ type iv
v) SEQ ID NOs: 64, 80, 84, 163, 164 for the detection of MREJ type v
vi) SEQ ID NOs: 64, 112, 84, 163, 164 for the detection of MREJ type vii.

All these probes and primers can even be used together in the same physical enclosure.

It is another object of this invention to provide a method for typing a MRJE of a MRSA strain, which comprises the steps of: reproducing the above method with primers and/or probes specific for a determined MREJ type, and detecting an annealed probe or primer as an indication of the presence of a determined MREJ type.

It is further another object of this invention to provide a nucleic acid selected from SEQ ID NOs:
i) SEQ ID NOs: 42, 43, 44, 45, 46, 51 for sequence of MREJ type iv;
ii) SEQ ID NOs: 47, 48, 49, 50 for sequence of MREJ type v;
iii) SEQ ID NOs: 171 for sequence of MREJ type vi;
iv) SEQ ID NOs: 165, 166 for sequence of MREJ type vii;
v) SEQ ID NOs: 167 for sequence of MREJ type viii;
vi) SEQ ID NOs: 168 for sequence of MREJ type ix.

Oligonucleotides of at least 10 nucleotides in length which hybridize with any of these nucleic acids and which hybridize with one or more MREJ of types selected from iv to ix are also objects of this invention. Amongst these, primer pairs (or probes) having the following SEQ ID NOs:

| | |
|---|---|
| 64/66, 64/100, 64/101; 59/52, | for the detection of type i MREJ |
| 59/53, 59/54, 59/55, 59/56, 59/57, | |
| 60/52, 60/53, 60/54, 60/55, 60/56 | |
| 60/57, 61/52, 61/53, 61/54, 61/55 | |
| 61/56, 61/57, 62/52, 62/53, 62/54 | |
| 62/55, 62/56, 62/57, 63/52, 63/53 | |
| 63/54, 63/55, 63/56, 63/57 | |
| 64/66, 64/97, 64/99, 64/100, 64/101 | for the detection of type ii MREJ |
| 59/52, 59/53, 59/54, 59/55, 59/56, | |
| 59/57, 60/52, 60/53, 60/54, 60/55, | |
| 60/56, 60/57, 61/52, 61/53, 61/54, | |
| 61/55, 61/56, 61/57, 62/52, 62/53, | |
| 62/54, 62/55, 62/56, 62/57, 63/52 | |
| 63/53, 63/54, 63/55, 63/56, 63/57 | |
| 64/67, 64/98, 64/102; 59/58, | for the detection of type iii MREJ |
| 60/58, 61/58, 62/58, 63/58 | |
| 64/79 | for the detection of type iv MREJ |
| 64/80 | for the detection of type v MREJ |
| 64/204 | for the detection of type vi MREJ |
| 64/112, 64/113 | for the detection of type vii MREJ |
| 64/115, 64/116 | for the detection of type viii MREJ |
| 64/109 | for the detection of type ix MREJ, | are also within the scope of this invention.

Further, internal probes having nucleotide sequences defined in any one of SEQ ID NOs: 32, 83, 84, 160, 161, 162, 163, 164, are also within the scope of this invention. Compositions of matter comprising the primers and/or probes annealing or hybridizing with one or more MREJ of types selected from iv to ix as well as with the above nucleic acids, comprising or not primers and/or probes, which hybridize with one or more MREJ of types selected from i to iii, are further objects of this invention. The preferred compositions would comprise the primers having the nucleotide sequences defined in SEQ ID NOs:

| | |
|---|---|
| 64/66, 64/100, 64/101; 59/52, 59/53, 59/54, 59/55, 59/56, 59/57, 60/52, 60/53, 60/54, 60/55, 60/56 60/57, 61/52, 61/53, 61/54, 61/55 61/56, 61/57, 62/52, 62/53, 62/54 62/55, 62/56, 62/57, 63/52, 63/53 63/54, 63/55, 63/56, 63/57 | for the detection of type i MREJ |
| 64/66, 64/97, 64/99, 64/100, 64/101 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52 63/53, 63/54, 63/55, 63/56, 63/57 | for the detection of type ii MREJ |
| 64/67, 64/98, 64/102; 59/58, 60/58, 61/58, 62/58, 63/58 | for the detection of type iii MREJ |
| 64/79 | for the detection of type iv MREJ |
| 64/80 | for the detection of type v MREJ |
| 64/204 | for the detection of type vi MREJ |
| 64/112, 64/113 | for the detection of type vii MREJ |
| 64/115, 64/116 | for the detection of type viii MREJ |
| 64/109 | for the detection of type ix MREJ, | or probes, which SEQ ID NOs are: 32, 83, 84, 160, 161, 162, 163, 164, or both.

DETAILED DESCRIPTION OF THE INVENTION

Here is particularly provided a method wherein each of MRSA nucleic acids or a variant or part thereof comprises a selected target region hybridizable with said primers or probes developed to be ubiquitous;

wherein each of said nucleic acids or a variant or part thereof comprises a selected target region hybridizable with said primers or probes;

said method comprising the steps of contacting said sample with said probes or primers and detecting the presence and/or amount of hybridized probes or amplified products as an indication of the presence and/or amount of MRSA.

In the method, sequences from DNA fragments of SCC-mec-chromosome right extremity junction, therafter named MREJ standing for <<mec right extremity junction>> including sequences from SCCmec right extremity and chromosomal DNA to the right of the SCCmec integration site are used as parental sequences from which are derived the primers and/or the probes. MREJ sequences include our proprietary sequences as well as sequences obtained from public databases and from U.S. Pat. No. 6,156,507 and were selected for their capacity to sensitively, specifically, ubiquitously and rapidly detect the targeted MRSA nucleic acids.

Our proprietary DNA fragments and oligonucleotides (primers and probes) are also another object of this invention.

Composition of matters such as diagnostic kits comprising amplification primers or probes for the detection of MRSA are also objects of the present invention.

In the above methods and kits, probes and primers are not limited to nucleic acids and may include, but are not restricted to, analogs of nucleotides. The diagnostic reagents constituted by the probes and the primers may be present in any suitable form (bound to a solid support, liquid, lyophilized, etc.).

In the above methods and kits, amplification reactions may include but are not restricted to: a) polymerase chain reaction (PCR), b) ligase chain reaction (LCR), c) nucleic acid sequence-based amplification (NASBA), d) self-sustained sequence replication (3SR), e) strand displacement amplification (SDA), f) branched DNA signal amplification (bDNA), g) transcription-mediated amplification (TMA), h) cycling probe technology (CPT), i) nested PCR, j) multiplex PCR, k) solid phase amplification (SPA), l) nuclease dependent signal amplification (NDSA), m) rolling circle amplification technology (RCA), n) Anchored strand displacement amplification, o) Solid-phase (immobilized) rolling circle amplification.

In the above methods and kits, detection of the nucleic acids of target genes may include real-time or post-amplification technologies. These detection technologies can include, but are not limited to fluorescence resonance energy transfer (FRET)-based methods such as adjacent hybridization of probes (including probe-probe and probe-primer methods), TaqMan probe, molecular beacon probe, Scorpion probe, nanoparticle probe and Amplifluor probe. Other detection methods include target gene nucleic acids detection via immunological methods, solid phase hybridization methods on filters, chips or any other solid support. In these systems, the hybridization can be monitored by fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize the nucleic acids of target genes.

In a preferred embodiment, a PCR protocol is used for nucleic acid amplification.

A method for detection of a plurality of potential MRSA strains having different MREJ types may be conducted in separate reactions and physical enclosures, one type at the time. Alternatively, it could be conducted simultaneously for different types in separate physical enclosures, or in the same physical enclosures. In the latter scenario a multiplex PCR reaction could be conducted which would require that the oligonucleotides are all capable of annealing with a target reagion under common conditions. Since many probes or primers are specific for a determined MREJ type, typing a MRSA strain is a possible embodiment. When a mixture of oligonucleotides annealing together with more than one type is used in a single physical enclosure or container, different labels would be used to distinguish one type from another.

We aim at developing a DNA-based test or kit to detect and identify MRSA. Although the sequences from orfX genes and some SCCmec DNA fragments are available from public databases and have been used to develop DNA-based tests for detection of MRSA, new sequence data allowing to improve MRSA detection and identification which are object of the present invention have either never been characterized previously or were known but not shown to be located at the right extremity of SCCmec adjacent to the integration site (Table 4). These novel sequences could not have been predicted nor detected by the MRSA-specific PCR assay developed by Hiramatsu et al. (U.S. Pat. No. 6,156,507). These sequences will allow to improve current DNA-based tests for the diagnosis of MRSA because they allow the design of ubiquitous primers and probes for the detection and identification of more MRSA strains including all the major epidemic clones from around the world.

The diagnostic kits, primers and probes mentioned above can be used to detect and/or identify MRSA, whether said diagnostic kits, primers and probes are used for in vitro or in situ applications. The said samples may include but are not limited to: any clinical sample, any environmental sample, any microbial culture, any microbial colony, any tissue, and any cell line.

It is also an object of the present invention that said diagnostic kits, primers and probes can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration cuture medium, any cellular stain, any culture on specific cell lines, and any infectivity assay on animals.

In the methods and kits described herein below, the oligonucleotide probes and amplification primers have been derived from larger sequences (i.e. DNA fragments of at least 100 base pairs). All DNA sequences have been obtained either from our proprietary sequences or from public databases (Tables 5, 6, 7, 8 and 9).

It is clear to the individual skilled in the art that oligonucleotide sequences other than those described in the present invention and which are appropriate for detection and/or identification of MRSA may also be derived from the proprietary fragment sequences or selected public database sequences. For example, the oligonucleotide primers or probes may be shorter but of a lenght of at least 10 nucleotides or longer than the ones chosen; they may also be selected anywhere else in the proprietary DNA fragments or in the sequences selected from public databases; they may also be variants of the same oligonucleotide. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from said DNA fragment sequences for use in amplification methods other than PCR. Consequently, the core of this invention is the detection and/or identification of MRSA by targeting genomic DNA sequences which are used as a source of specific and ubiquitous oligonucleotide probes and/or amplification primers. Although the selection and evaluation of oligonucleotides suitable for diagnostic purposes require much effort, it is quite possible for the individual skilled in the art to derive, from the selected DNA fragments, oligonucleotides other than the ones listed in Tables 5, 6, 7, 8 and 9 which are suitable for diagnostic purposes. When a proprietary fragment or a public database sequence is selected for its specificity and ubiquity, it increases the probability that subsets thereof will also be specific and ubiquitous.

The proprietary DNA fragments have been obtained as a repertory of sequences created by amplifying MRSA nucleic acids with new primers. These primers and the repertory of nucleic acids as well as the repertory of nucleotide sequences are further objects of this invention (Tables 4, 5, 6, 7, 8 and 9).

Claims therefore are in accordance with the present invention.

SEQUENCES FOR DETECTION AND IDENTIFICATION OF MRSA

In the description of this invention, the terms <<nucleic acids>> and <<sequences>> might be used interchangeably. However, <<nucleic acids>> are chemical entities while <<sequences>> are the pieces of information encoded by these <<nucleic acids>>. Both nucleic acids and sequences are equivalently valuable sources of information for the matter pertaining to this invention.

Oligonucleotide Primers and Probes Design and Synthesis

As part of the design rules, all oligonucleotides (probes for hybridization and primers for DNA amplification by PCR) were evaluated for their suitability for hybridization or PCR amplification by computer analysis using standard programs (i.e. the GCG Wisconsin package programs, the primer analysis software Oligo™ 6 and MFOLD 3.0). The potential suitability of the PCR primer pairs was also evaluated prior to their synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.). Oligonucleotide amplification primers were synthesized using an automated DNA synthesizer (Applied Biosystems). Molecular beacon designs were evaluated using criteria established by Kramer et al. (http://www.molecular-beacons.org).

The oligonucleotide sequence of primers or probes may be derived from either strand of the duplex DNA. The primers or probes may consist of the bases A, G, C, or T or analogs and they may be degenerated at one or more chosen nucleotide position(s) (Nichols et al., 1994, Nature 369:492-493). Primers and probes may also consist of nucleotide analogs such as Locked Nucleic Acids (LNA) (Koskin et al., 1998, Tetrahedron 54:3607-3630), and Peptide Nucleic Acids (PNA) (Egholm et al., 1993, Nature 365:566-568). The primers or probes may be of any suitable length and may be selected anywhere within the DNA sequences from proprietary fragments, or from selected database sequences which are suitable for the detection of MRSA.

Variants for a given target microbial gene are naturally occurring and are attributable to sequence variation within that gene during evolution (Watson et al., 1987, Molecular Biology of the Gene, $4^{th}$ ed., The Benjamin/Cummings Publishing Company, Menlo Park, Calif.; Lewin, 1989, Genes IV, John Wiley & Sons, New York, N.Y.). For example, different strains of the same microbial species may have a single or more nucleotide variation(s) at the oligonucleotide hybridization site. The person skilled in the art is well aware of the existence of variant nucleic acids and/or sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variations at the primer hybridization site, one has to amplify a larger DNA target with PCR primers outside that hybridization site. Sequencing of this larger fragment will allow the detection of sequence variation at this primer hybridization site. A similar strategy may be applied to show variations at the hybridization site of a probe. Insofar as the divergence of the target nucleic acids and/or sequences or a part thereof does not affect significantly the sensitivity and/or specificity and/or ubiquity of the amplification primers or probes, variant microbial DNA is under the scope of this invention. Variants of the selected primers or probes may also be used to amplify or hybridize to a variant target DNA.

DNA Amplification

For DNA amplification by the widely used PCR method, primer pairs were derived from our proprietary DNA fragments or from public database sequences.

During DNA amplification by PCR, two oligonucleotide primers binding respectively to each strand of the heat-denatured target DNA from the microbial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Briefly, the PCR protocols on a standard thermocycler (PTC-200 from MJ Research Inc., Watertown, Mass.) were as follows: Treated standardized bacterial suspensions or genomic DNA prepared from bacterial cultures or clinical specimens were amplified in a 20 µl PCR reaction mixture. Each PCR reaction contained 50 mM KCl, 10 mM Tris-HCl (pH 9.0), 2.5 mM $MgCl_2$, 0.4 µM of each primer, 200 µM of each of the four dNTPs (Pharmacia Biotech), 3.3 µg/µl bovine serum albumin (BSA) (Sigma-Aldrich Canada Ltd, Oakville, Ontario, Canada) and 0.5 unit of Taq DNA polymerase (Promega Corp., Madison, Wis.) combined with the TaqStart™ antibody (BD Biosciences, Palo Alto, Calif.). The TaqStart™ antibody, which is a neutralizing monoclonal antibody to Taq DNA polymerase, was added to all PCR reactions to enhance the specificity and the sensitivity of the amplifications (Kellogg et al., 1994, Biotechniques 16:1134-1137). The treatment of bacterial cultures or of clinical specimens consists in a rapid protocol tolyse the microbial cells and eliminate or neutralize PCR inhibitors (described in co-pending application U.S. 60/306,163). For amplification from purified genomic DNA, the samples were added directly to the PCR amplification mixture. An internal control, derived from sequences not found in the target MREJ sequences or in the human genome, was used to verify the efficiency of the PCR reaction and the absence of significant PCR inhibition.

The number of cycles performed for the PCR assays varies according to the sensitivity level required. For example, the sensitivity level required for microbial detection directly from a clinical specimen is higher than for detection from a microbial culture. Consequently, more sensitive PCR assays having more thermal cycles are probably required for direct detection from clinical specimens.

The person skilled in the art of nucleic acid amplification knows the existence of other rapid amplification procedures such as ligase chain reaction (LCR), reverse transcriptase PCR (RT-PCR), transcription-mediated amplification (TMA), self-sustained sequence replication (3SR), nucleic acid sequence-based amplification (NASBA), strand displacement amplification (SDA), branched DNA (bDNA), cycling probe technology (CPT), solid phase amplification (SPA), rolling circle amplification technology (RCA), solid phase RCA, anchored SDA and nuclease dependent signal amplification (NDSA) (Lee et al., 1997, Nucleic Acid Amplification Technologies: Application to Disease Diagnosis, Eaton Publishing, Boston, Mass.; Persing et al., 1993, Diagnostic Molecular Microbiology: Principles and Applications, American Society for Microbiology, Washington, D.C.; Westin et al., 2000, Nat. Biotechnol. 18:199-204). The scope of this invention is not limited to the use of amplification by PCR, but rather includes the use of any nucleic acid amplification method or any other procedure which may be used to increase the sensitivity and/or the rapidity of nucleic acid-based diagnostic tests. The scope of the present invention also covers the use of any nucleic acids amplification and detection technology including real-time or post-amplification detection technologies, any amplification technology combined with detection, any hybridization nucleic acid chips or array technologies, any amplification chips or combination of amplification and hybridization chip technologies. Detection and identification by any nucleotide sequencing method is also under the scope of the present invention.

Any oligonucleotide derived from the *S. aureus* MREJ DNA sequences and used with any nucleic acid amplification and/or hybridization technologies are also under the scope of this invention.

Evaluation of the MRSA Detection Method Developed by Hiramatsu et al.

According to Hiramatsu et al. (Ito et al., 1999, Antimicrob. Agents Chemother. 43:1449-1458; Katayama et al., 2000, Antimicrob. Agents Chemother. 44:1549-1555; Ito et al., 2001, Antimicrob. Agents Chemother. 45:1323-1336, Ma et al., 2002, Antimicrob. Agents Chemother. 46:1147-1152), four types of SCCmec DNA are found among MRSA strains. They have found that SCCmec DNAs are integrated at a specific site of the MSSA chromosome (named orfX). They developed a MRSA-specific multiplex PCR assay including primers that can hybridize to the right extremity of SCCmec types I, II and III (SEQ ID NOs.: 18, 19, 20, 21, 22, 23, 24 in U.S. Pat. No. 6,156,507 corresponding to SEQ ID NOs.: 52, 53, 54, 55, 56, 57, 58, respectively, in the present invention) as well as primers specific to the *S. aureus* chromosome to the right of the SCCmec integration site (SEQ ID NO.: 25, 28, 27, 26, 29 in U.S. Pat. No. 6,156,507 corresponding to SEQ ID NOs.: 59, 60, 61, 62, 63, respectively, in the present invention) (Table 1 and FIG. 1). The set of primers described by Hiramatsu et al. as being the optimal primer combination (SEQ ID NOs.: 22, 24 and 28 in U.S. Pat. No. 6,156,507 corresponding to SEQ ID NOs.: 56, 58 and 60 in the present invention) was used in the present invention to test by PCR a variety of MRSA, MSSA, methicillin-resistant CNS (MRCNS) and methicillin-sensitive CNS (MSCNS) strains (Table 2). A PCR assay performed using a standard thermocycler (PTC-200 from MJ Research Inc.) was used to test the ubiquity, the specificity and the sensitivity of these primers using the following protocol: one µl of a treated standardized bacterial suspension or of a genomic DNA preparation purified from bacteria were amplified in a 20 µl PCR reaction mixture. Each PCR reaction contained 50 mM KCl, 10 mM Tris-HCl (pH 9.0), 0.1% Triton X-100, 2.5 mM $MgCl_2$, 0.4 µM of each of the SCCmec- and *S. aureus* chromosome-specific primers (SEQ ID NOs.: 22, 24 and 28 in U.S. Pat. No. 6,156,507 corresponding to SEQ ID NOs.: 56, 58 and 60 in the present invention), 200 µM of each of the four dNTPs (Pharmacia Biotech), 3.3 µg/µl BSA (Sigma), and 0.5 U Taq polymerase (Promega) coupled with TaqStart™ Antibody (BD Biosciences).

PCR reactions were then subjected to thermal cycling 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 µg/ml ofethidium bromide. Twenty of the 39 MRSA strains tested were not amplified with the PCR assay developed by Hiramatsu et al. (Example 1, Tables 2 and 3).

With a view of establishing a rapid diagnostic test for MRSAs, the present inventors developed new sets of primers specific to the right extremity of SCCmec types I and II (SEQ ID NOs.: 66, 100 and 101) (Annex 1), SCCmec type II (SEQ ID NOs.: 97 and 99), SCCmec type III (SEQ ID NOs.: 67, 98 and 102) and in the *S. aureus* chromosome to the right of the SCCmec integration site (SEQ ID NOs.: 64, 70, 71, 72, 73, 74, 75 and 76) (Table 5). These primers, amplifying short amplicons (171 to 278 bp), are compatible for use in rapid PCR assays (Table 7). The design of these primers was based on analysis of multiple sequence alignments of orfX and SCCmec sequences described by Hiramatsu et al. (U.S. Pat. No. 6,156,507) or available from GenBank (Table 10, Annex I). These different sets of primers were used to test by PCR a variety of MRSA, MSSA, MRCNS and MSCNS strains. Several amplification primers were developed to detect all three SCCmec types (SEQ ID NOs.: 97 and 99 for SCCmec type II, SEQ ID NOs.: 66, 100 and 101 for SCCmec types I and II and SEQ ID NOs.: 67, 98 and 102 for SCCmec type III). Primers were chosen according to their specificity for MRSA strains, their analytical sensitivity in PCR and the length of the PCR product. A set of two primers was chosen for the SCCmec right extremity region (SEQ ID NO.: 66 specific to SCCmec types I and II; SEQ ID NO.: 67 specific to SCCmec type III). Of the 8 different primers designed to anneal on the S. aureus chromosome to the right of the SCCmec integration site (targeting orfX gene) (SEQ ID NOs.: 64, 70, 71, 72, 73, 74, 75 and 76), only one (SEQ ID.: 64) was found to be specific for MRSA based on testing with a variety of MRSA, MSSA, MRCNS and MSCNS strains (Table 12). Consequently, a PCR assay using the optimal set of primers (SEQ ID NOs.: 64, 66 and 67) which could amplify specifically MRSA strains containing SCCmec types I, II and III was developed (FIG. 2, Annex I). While the PCR assay developed with this novel set of primers was highly sensitive (i.e allowed the detection of 2 to 5 copies of genome for all three SCCmec types) (Table 11), it had the same shortcomings (i.e. lack of ubiquity) of the test developed by Hiramatsu et al. The 20 MRSA strains which were not amplified by the Hiramatsu et al. primers were also not detected by the set of primers comprising SEQ ID NOs.: 64, 66 and 67 (Tables 3 and 12). Clearly, diagnostic tools for achieving at least 50% ubiquity amongst the tested strains are needed.

With a view to establish a more ubiquitous (i.e. ability to detect all or most MRSA strains) detection and identification method for MRSA, we determined the sequence of the MREJ present in these 20 MRSA strains which were not amplified. This research has led to the discovery and identification of seven novel distinct MREJ target sequences which can be used for diagnostic purposes. These seven new MREJ sequences could not have been predicted nor detected with the system described in U.S. Pat. No. 6,156,507 by Hiramatsu et al. Namely, the present invention represents an improved method for the detection and identification of MRSA because it provides a more ubiquitous diagnostic method which allows for the detection of all major epidemic MRSA clones from around the world.

Sequencing of MREJ Nucleotide Sequences from MRSA Strains not Amplifiable with Primers Specific to SCCmec Types I, II and III Since DNA from twenty MRSA strains were not amplified with the set of primers developed by Hiramatsu et al. (SEQ ID NOs.: 22, 24 and 28 in U.S. Pat. No. 6,156,507 corresponding to SEQ ID NOs.: 56, 58 and 60 in the present invention) (Tables 2 and 3) nor with the set of primers developed in the present invention based on the same three SCCmec types (I, II and III) sequences (SEQ ID NOs.: 64, 66 and 67) (Table 12), the nucleotide sequence of the MREJ was determined for sixteen of these twenty MRSA strains.

Transposase of IS431 is often associated with the insertion of resistance genes within the mec locus. The gene encoding this transposase has been described frequently in one or more copies within the right segment of SCCmec (Oliveira et al., 2000, Antimicrob. Agents Chemother. 44:1906-1910; Ito et al., 2001, Antimicrob. Agents Chemother. 45:1323-36). Therefore, in a first attempt to sequence the novel MREJ for 16 of the 20 MRSA strains described in Table 3, a primer was designed in the sequence of the gene coding for the transposase of IS431 (SEQ ID NO.: 68) and combined with an orfX-specific primer to the right of the SCCmec integration site (SEQ ID NO.: 70) (Tables 5 and 8). The strategy used to select these primers is illustrated in FIG. 3.

The MREJ fragments to be sequenced were amplified using the following amplification protocol: one µL of treated cell suspension (or of a purified genomic DNA preparation) was transferred directly into 4 tubes containing 39 µL of a PCR reaction mixture. Each PCR reaction contained 50 mM KCl, 10 mM Tris-HCl (pH 9.0), 0.1% Triton X-100, 2.5 mM MgCl$_2$, 1 µM of each of the 2 primers (SEQ ID NOs.: 68 and 70), 200 µM of each of the four dNTPs, 3.3 µ/µl of BSA (Sigma-Aldrich Canada Ltd) and 0.5 unit of Taq DNA polymerase (Promega) coupled with the TaqStart™ Antibody (BD Bisociences). PCR reactions were submitted to cycling using a standard thermocycler (PTC-200 from MJ Research Inc.) as follows: 3 min at 94° C. followed by 40 cycles of 5 sec at 95° C. for the denaturation step, 30 sec at 55° C. for the annealing step and 2 min at 72° C. for the extension step.

Subsequently, the four PCR-amplified mixtures were pooled and 10 µL of the mixture were resolved by electrophoresis in a 1.2% agarose gel containing 0.25 µg/mL of ethidium bromide. The amplicons were then visualized with an Alpha-Imager (Alpha Innotech Corporation, San Leandro, Calif.) by exposing to UV light at 254 nm. Amplicon size was estimated by comparison with a 1 kb molecular weight ladder (Life Technologies, Burlington, Ontario, Canada). The remaining PCR-amplified mixture (150 µL, total) was also resolved by electrophoresis in a 1.2% agarose gel. The amplicons were then visualized by staining with methylene blue (Flores et al., 1992, Biotechniques, 13:203-205). Amplicon size was once again estimated by comparison with a 1 kb molecular weight ladder. Of the sixteen strains selected from the twenty described in Table 3, six were amplified using SEQ ID NOs.: 68 and 70 as primers (CCRI-178, CCRI-8895, CCRI-8903, CCRI-1324, CCRI-1331 and CCRI-9504). For these six MRSA strains, an amplification product of 1.2 kb was obtained. The band corresponding to this specific amplification product was excised from the agarose gel and purified using the QIAquick™ gel extraction kit (QIAGEN Inc., Chatsworth, Calif.). The gel-purified DNA fragment was then used directly in the sequencing protocol. Both strands of the MREJ amplification products were sequenced by the dideoxynucleotide chain termination sequencing method by using an Applied Biosystems automated DNA sequencer (model 377) with their Big Dye™ Terminator Cycle Sequencing Ready Reaction Kit (Applied Biosystems, Foster City, Calif.). The sequencing reactions were performed by using the same primers (SEQ ID NOs.: 68 and 70) and 10 ng/100 bp per reaction of the gel-purified amplicons. Sequencing of MREJ from the six MRSA strains (CCRI-178, CCRI-8895, CCRI-8903, CCRI-1324, CCRI-1331 and CCRI-9504) described in Table 3 yielded SEQ ID NOs.: 42, 43, 44, 45, 46 and 51, respectively (Table 4).

In order to ensure that the determined sequence did not contain errors attributable to the sequencing of PCR artefacts, we have sequenced two preparations of the gel-purified MREJ amplification products originating from two independent PCR amplifications. For most target fragments, the sequences determined for both amplicon preparations were identical. Furthermore, the sequences of both strands were 100% complementary thereby confirming the high accuracy of the determined sequence. The MREJ sequences determined using the above strategy are described in the Sequence Listing and in Table 4.

In order to sequence MREJ in strains for which no amplicon had been obtained using the strategy including primers specific to the transposase gene of IS431 and orfX, another strategy using primers targeting mecA and orfX sequences was used to amplify longer genomic fragments. A new PCR primer targeting mecA (SEQ ID NO.: 69) (Table 8) to be used in combination with the same primer in the orfX sequence (SEQ ID NO.: 70). The strategy used to select these primers is illustrated in FIG. 3.

The following amplification protocol was used: Purified genomic DNA (300 ng) was transferred to a final volume of 50 µl of a PCR reaction mixture. Each PCR reaction contained 1× Herculase buffer (Stratagene, La Jolla, Calif.), 0.8 µM of each of the 2 primers (SEQ ID NOs.: 69 and 70), 0.56 mM of each of the four dNTPs and 5 units of Herculase (Stratagene). PCR reactions were subjected to cycling using a standard thermal cycler (PTC-200 from MJ Research Inc.) as follows: 2 min at 92° C. followed by 35 or 40 cycles of 10 sec at 92° C. for the denaturation step, 30 sec at 55° C. for the annealing step and 30 min at 68° C. for the extension step.

Subsequently, 10 µL of the PCR-amplified mixture were resolved by electrophoresis in a 0.7% agarose gel containing 0.25 µg/mL of ethidium bromide. The amplicons were then visualized as described above. Amplicon size was estimated by comparison with a 1 kb molecular weight ladder (Life Technologies). A reamplification reaction was then performed in 2 to 5 tubes using the same protocol with 3 µl of the first PCR reaction used as test sample for the second amplification. The PCR-reamplified mixtures were pooled and also resolved by electrophoresis in a 0.7% agarose gel. The amplicons were then visualized by staining with methylene blue as described above. An amplification product of approximately 12 kb was obtained using this amplification strategy for all strains tested. The band corresponding to the specific amplification product was excised from the agarose gel and purified as described above. The gel-purified DNA fragment was then used directly in the sequencing protocol as described above. The sequencing reactions were performed by using the same amplification primers (SEQ ID NOs.: 69 and 70) and 425-495 ng of the gel-purified amplicons per reaction. Subsequently, internal sequencing primers (SEQ ID NOs.: 65, 77 and 96) (Table 8) were used to obtain sequence data on both strands for a larger portion of the amplicon. Five of the 20 MRSA strains (CCRI-1331, CCRI-1263, CCRI-1377, CCRI-1311 and CCRI-2025) described in Table 3 were sequenced using this strategy, yielding SEQ ID NOs.: 46, 47, 48, 49 and 50, respectively (Table 4). Sequence within mecA gene was also obtained from the generated amplicons yielding SEQ ID NOs: 27, 28, 29, 30 and 31 from strains CCRI-2025, CCRI-1263, CCRI-1311, CCRI-1331 and CCRI-1377, respectively (Table 4). Longer sequences within the mecA gene and from downstream regions were also obtained for strains CCRI-2025, CCRI-1331, and CCRI-1377 as described below.

In order to obtain longer sequences of the orfX gene, two other strategies using primers targeting mecA and orfX sequences (at the start codon) was used to amplify longer chromosome fragments. A new PCR primer was designed in orfX (SEQ ID NO.: 132) to be used in combination with the same primer in the mecA gene (SEQ ID NO.: 69). The strategy used to select these primers is illustrated in FIG. 3. Eight S. aureus strains were amplified using primers SEQ ID NOs.: 69 and 132 (CCRI-9860, CCRI-9208, CCRI-9504, CCRI-1331, CCRI-9583, CCRI-9681, CCRI-2025 and CCRI-1377). The strategy used to select these primers is illustrated in FIG. 3.

The following amplification protocol was used: Purified genomic DNA (350 to 500 ng) was transferred to a 50 µl PCR reaction mixture. Each PCR reaction contained 1× Herculase buffer (Stratagene), 0.8 µM of each of the set of 2 primers (SEQ ID NOs.: 69 and 132), 0.56 mM of each of the four dNTPs and 7.5 units of Herculase (Stratagene) with 1 mM $MgCl_2$. PCR reactions were subjected to thermocycling as described above.

Subsequently, 5 µL of the PCR-amplified mixture were resolved by electrophoresis in a 0.8% agarose gel containing 0.25 µg/mL of ethidium bromide. The amplicons were then visualized as described above. For one S. aureus strain (CCRI-9583), a reamplification was then performed by using primers SEQ ID NOs.: 96 and 158 (FIG. 3) in 4 tubes, using the same PCR protocol, with 2 µl of the first PCR reaction as test sample for the second amplification. The PCR-reamplified mixtures were pooled and also resolved by electrophoresis in a 0.8% agarose gel. The amplicons were then visualized by staining with methylene blue as described above. A band of approximately 12 to 20 kb was obtained using this amplification strategy depending on the strains tested. The band corresponding to the specific amplification product was excised from theagarose gel and purified using the QIAquick™ gel extraction kit or QIAEX II gel extraction kit (QIAGEN Inc.). Two strains, CCRI-9583 and CCRI-9589, were also amplified with primers SEQ ID NOs.: 132 and 150, generating an amplification product of 1.5 kb. Long amplicons (12-20 kb) were sequenced using 0.6 to 1 µg per reaction, while short amplicons (1.5 kb) were sequenced using 150 ng per reaction. Sequencing reactions were performed using different sets of primers for each S. aureus strain: 1) SEQ ID NOs.: 68, 70, 132, 145, 146, 147, 156, 157 and 158 for strain CCRI-9504; 2) SEQ ID NOs.: 70, 132, 154 and 155 for strain CCRI-2025; 3) SEQ ID NOs.: 70, 132, 148, 149, 158 and 159 for strain CCRI-9681; 4) SEQ ID NOs.: 70, 132, 187, and 188 for strain CCRI-9860; 5) SEQ ID NOs: 70, 132, 150 and 159 for strain CCRI-9589, 6) SEQ ID NOs.: 114, 123, 132, 150 and 158 for strain CCRI-9583; 7) SEQ ID NOs.: 70, 132, 154 and 155 for strain CCRI-1377, 8) SEQ ID NOs.: 70, 132, 158 and 159 for strain CCRI-9208; 9) SEQ ID NOs: 68, 70, 132, 145, 146, 147 and 158 for strain CCRI-1331; and 10) SEQ ID NOs.: 126 and 127 for strain CCRI-9770.

In one strain (CCRI-9770), the orfX and orfSA0022 genes were shown to be totally or partially deleted based on amplification using primers specific to these genes (SEQ ID NOs: 132 and 159 and SEQ ID NOs.: 128 and 129, respectively) (Table 8). Subsequently, a new PCR primer was designed in orfSA0021 (SEQ ID NO.: 126) to be used in combination with the same primer in the mecA gene (SEQ ID NO.: 69). An amplification product of 4.5 kb was obtained with this primer set.

Amplification, purification of amplicons and sequencing of amplicons were performed as described above.

To obtain the sequence of the SSCmec region containing mecA for ten of the 20 MRSA strains described in Table 3 (CCRI-9504, CCRI-2025, CCRI-9208, CCRI-1331, CCRI-9681, CCRI-9860, CCRI-9770, CCRI-9589, CCRI-9583 and CCRI-1377), the primer described above designed in mecA (SEQ ID NO.: 69) was used in combination with a primer designed in the downstream region of mecA (SEQ ID NO.: 118) (Table 8). An amplification product of 2 kb was obtained for all the strains tested. For one strain, CCRI-9583, a re-amplification with primers SEQ ID NOs.: 96 and 118 was performed with the amplicon generated with primers SEQ ID NOs.: 69 and 132 described above. The amplication, re-amplification, purification of amplicons and sequencing reactions were performed as described above. Sequencing reactions were performed with amplicons generated with SEQ ID NOs.: 69 and 132 described above or SEQ ID NOs.: 69 and 118. Different sets of sequencing primers were used for each *S. aureus* strain: 1) SEQ ID NOs.: 69, 96, 117, 118, 120, 151, 152 for strains CCRI-9504, CCRI-2025, CCRI-1331, CCRI-9770 and CCRI-1377; 2) SEQ ID NOs.: 69, 96, 118 and 120 for strains CCRI-9208, CCRI-9681 and CCRI-9589; 3) SEQ ID NOs.: 69, 96, 117, 118, 120 and 152 for strain CCRI-9860; and 4) SEQ ID NOs.: 96, 117, 118, 119, 120, 151 and 152 for strain CCRI-9583.

The sequences obtained for 16 of the 20 strains non-amplifiable by the Hiramatsu assay (Table 4) were then compared to the sequences available from public databases. In all cases, portions of the sequence had an identity close to 100% to publicly available sequences for orfX (SEQ ID NOs.: 42-51, 165-168 and 171) or mecA and downstream region (SEQ ID NOs.: 27-31, 189-193, 195, 197-199 and 225). However, while the orfX portion of the fragments (SEQ ID NOs.: 42-51, 165-168 and 171) shared nearly 100% identity with the orfX gene of MSSA strain NCTC 8325 described by Hiramatsu et al. (SEQ ID NO.: 3), the DNA sequence within the right extremity of SCCmec itself was shown to be very different from those of types I, II, III and IV described by Hiramatsu et al. (Table 13, FIG. 4). Six different novel sequence types were obtained.

It should be noted that Hiramatsu et al. demonstrated that SCCmec type I could be associated with MREP type i, SCCmec types II and IV are associated with MREP type ii, and SCCmec type III is associated with MREP type iii. Our MREJ sequencing data from various MRSA strains led to the discovery of 6 novel MREP types designated types iv, v vi, vii, viii, and ix. The MREJ comprising distinct MREP types were named according to the MREP numbering scheme. Hence, MREP type i is comprised within MREJ type i, MREP type ii is comprised within MREJ type ii and so on up to MREP type ix.

The sequences within the right extremity of SCCmec obtained from strains CCRI-178, CCRI-8895, CCRI-8903, CCRI-1324, CCRI-1331 and CCRI-9504 (SEQ ID NOs.: 42, 43, 44, 45, 46 and 51) were nearly identical to each other and exhibited nearly 100% identity with IS431 (GenBank accession numbers AF422691, ABO37671, AF411934). However, our sequence data revealed for the first time the location of this IS431 sequence at the right extremity of SCCmec adjacent to the integration site. Therefore, as the sequences at the right extremity of SCCmec from these 6 MRSA strains were different from those of SCCmec type I from strain NCTC 10442, SCCmec type II from strain N315, SCCmec type III from strain 85/2082 and SCCmec type IV from strains CA05 and 8/6-3P described by Hiramatsu et al. (Ito et al., 2001, Antimicrob. Agents Chemother. 45:1323-1336; Ma et al., 2002, Antimicrob. Agents Chemother. 46:1147-1152), these new sequences were designated as MREP type iv (SEQ ID NOs.: 42-46 and 51). A BLAST search with the SCCmec portion of MREP type iv sequences produced significant alignments with sequences coding for portions of a variety of known transposases. For example, when compared to Genbank accession no. AB037671, MREP type iv from SEQ ID NO. 51 shared 98% identity with the putative transposase of IS431 and its downstream region; two gaps of 7 nucleotides each were also present in the alignment.

Sequences obtained from strains CCRI-1263, CCRI-1377, CCRI-1311 and CCRI-2025 (SEQ ID NOs.: 47-50) were nearly identical to each other and different from all three SCCmec types and MREP type iv and, consequently, were designated as MREP type v. When compared with Genbank sequences using BLAST, MREP type v sequences did not share any significant homology with any published sequence, except for the first 28 nucleotides. That short stretch corresponded to the last 11 coding nucleotides of orfX, followed by the 17 nucleotides downstream, including the right inverted repeat (IR-R) of SCCmec.

Sequence obtained from strain CCRI-9208 was also different from all three SCCmec types and MREP types iv and v and, consequently, was designated as MREP type vi (SEQ ID NO.: 171). Upon a BLAST search, MREP type vi was shown to be unique, exhibiting no significant homology to any published sequence.

Sequences obtained from strains CCRI-9583 and CCRI-9589 were also different from all three SCCmec types and MREP types iv to vi and were therefore designated as MREP type vii (SEQ ID NOs.: 165 and 166). Upon a BLAST search, MREP type vii was also shown to be unique, exhibiting no significant homology to any published sequence.

Sequence obtained from strain CCRI-9860 was also different from all three SCCmec types and MREP types iv to vii and was therefore designated as MREP type viii (SEQ ID NO.: 167). Sequence obtained from strain CCRI-9681 was also different from all three SCCmec types and MREP types iv to viii and was therefore designated as MREP type ix (SEQ ID NO.: 168). BLAST searches with the SCCmec portion of MREP types viii and ix sequences yielded significant alignments, but only for the first ~150 nucleotides of each MREP type. For example, the beginning of the MREP type viii sequence had 88% identity with a portion of Genbank accession no. AB063173, but no significant homology with any published sequence was found for the rest of the sequence. In the same manner, the first ~150 nucleotides of MREP type ix had 97% identity with the same portion of AB063173, with the rest of the sequence being unique. The short homologous portion of MREP types viii and ix corresponds in AB063173 to the last 14 coding nucleotides of orfX, the IR-R of SCCmec, and a portion of orfCM009. Although sharing resemblances, MREP types viii and ix are very different from one another; as shown in Table 13, there is only 55.2% identity between both types for the first 500 nucleotides of the SCCmec portion. Finally, we did not obtain any sequence within SSCmec from strain CCRI-9770. However, as described in the section "Sequencing of MREJ nucleotide sequences from MRSA strains not amplifiable with primers specific to SCCmec types I, II and III", this strain has apparently a partial or total deletion of the or and orfSA0022 genes in the chromosomal DNA to the right of the SCCmec integration site and this would represent a new right extremity junction. We therefore designated this novel sequence as MREP type x (SEQ ID NO.: 172). Future sequencing should reveal whether this so called MREJ type x contains a novel MREP type x or if the lack of amplification is indeed caused by variation in the chromosomal part of the MREJ.

The sequences of the first 500-nucleotide portion of the right extremity of all SCCmec obtained in the present invention were compared to those of SCCmec types I, II and III using GCG programs Pileup and Gap. Table 13 depicts the identities at the nucleotide level between SCCmec right extremities of the six novel sequences with those of SCCmec types I, II and III using the GCG program Gap. While SCCmec types I and II showed nearly 79.2% identity (differing only by a 102 bp insertion present in SCCmec type II) (FIGS. 1, 2 and 4), all other MREP types showed identities varying from 40.9 to 57.1%. This explains why the right extremities of the novel MREP types iv to ix disclosed in the present invention could not have been predicted nor detected with the system described by Hiramatsu et al.

Four strains (CCRI-1312, CCRI-1325, CCRI-9773 and CCRI-9774) described in Table 3 were not sequenced but rather characterized using PCR primers. Strains CCRI-1312 and CCRI-1325 were shown to contain MREP type v using specific amplification primers described in Examples 4, 5 and 6 while strains CCRI-9773 and CCRI-9774 were shown to contain MREP type vii using specific amplification primers described in Example 7.

To obtain the complete sequence of the SCCmec present in the MRSA strains described in the present invention, primers targeting the S. aureus chromosome to the left (upstream of the mecA gene) of the SCCmec integration site were developed. Based on available public database sequences, 5 different primers were designed (SEQ ID NOs.: 85-89). (Table 9). These primers can be used in combination with S. aureus chromosome-specific primers in order to sequence the entire SCCmec or, alternatively, used in combination with a mecA-specific primer (SEQ ID NO.: 81) in order to sequence the left extremity junction of SCCmec. We have also developed several primers specific to known SCCmec sequences spread along the locus in order to obtain the complete sequence of SCCmec (Table 9). These primers will allow to assign a SCCmec type to the MRSA strains described in the present invention.

Selection of Amplification Primers from SCCmec/orfX Sequences

The MREJ sequences determined by the inventors or selected from public databases were used to select PCR primers for detection and identification of MRSA. The strategy used to select these PCR primers was based on the analysis of multiple sequence alignments of various MREJ sequences.

Upon analysis of the six new MREP types iv to ix sequence data described above, primers specific to each new MREP type sequence (SEQ ID NOs.: 79, 80, 109, 112, 113, 115, 116 and 204) were designed (FIG. 2, Table 5, Examples 3, 4, 5, 6, 7 and 8). Primers specific to MREP types iv, v and vii (SEQ ID NOs.: 79, 80 and 112) were used in multiplex with the three primers to detect SCCmec types I, II and III (SEQ ID NOs: 64, 66 and 67) and the primer specific to the S. aureus orfX (SEQ ID NO. 64) (Examples 3, 4, 5, 6 and 7). Primers specific to MREP types vi, viii and ix (SEQ ID NOs.: 204, 115, 116 and 109) were also designed and tested against their specific target (Example 8).

Detection of Amplification Products

Classically, the detection of PCR amplification products is performed by standard ethidium bromide-stained agarose gel electrophoresis as described above. It is however clear that other methods for the detection of specific amplification products, which may be faster and more practical for routine diagnosis, may be used. Examples of such methods are described in co-pending patent application WO01/23604 A2.

Amplicon detection may also be performed by solid support or liquid hybridization using species-specific internal DNA probes hybridizing to an amplification product. Such probes may be generated from any sequence from our repertory and designed to specifically hybridize to DNA amplification products which are objects of the present invention. Alternatively, amplicons can be characterized by sequencing. See co-pending patent application WO01/23604 A2 for examples of detection and sequencing methods.

In order to improve nucleic acid amplification efficiency, the composition of the reaction mixture may be modified (Chakrabarti and Schutt, 2002, Biotechniques, 32:866-874; Al-Soud and Radstrom, 2002, J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include the use of various polymerases or the addition of nucleic acid amplification facilitators such asbetaine, BSA, sulfoxides, protein gp32, detergents, cations, tetramethylamonium chloride and others.

In a preferred embodiment, real-time detection of PCR amplification was monitored using molecular beacon probes in a SmartCycler® apparatus (Cepheid, Sunnyvale, Calif.). A multiplex PCR assay containing primers specific to MREP types i to v and orfX of S. aureus (SEQ ID NOs.: 64, 66, 67, 79 and 80), a molecular beacon probe specific to the orfX sequence (SEQ ID NO. 84, see Annex II and FIG. 2) and an internal control to monitor PCR inhibition was developed. The internal control contains sequences complementary to MREP type iv- and orfX-specific primers (SEQ ID NOs. 79 and and 64). The assay also contains a molecular beacon probe labeled with tetrachloro-6-carboxyfluorescein (TET) specific to sequence within DNA fragment generated during amplification of the internal control. Each PCR reaction contained 50 mM KCl, 10 mM Tris-HCl (pH 9.0), 0.1% Triton X-100, 3.45 mM $MgCl_2$, 0.8 µM of each of the MREP-specific primers (SEQ ID NOs.: 66 and 67) and orfX-specific primer (SEQ ID NO.: 64), 0.4 µM of each of the MREP-specific primers (SEQ ID NOs.: 79 and 80),80 copies of the internal control, 0.2 µM of the TET-labeled molecular beacon probe specific to the internal control, 0.2 µM of the molecular beacon probe (SEQ ID NO.: 84) labeled with 6-carboxyfluorescein (FAM), 330 µM of each of the four dNTPs (Pharmacia Biotech), 3.45 µg/µl of BSA (Sigma), and 0.875 U Taq polymerase (Promega) coupled with TaqStart™ Antibody (BD Biosciences). The PCR amplification on the Smart Cycler® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies (Example 5). None of the 26 MRCNS or 10 MSCNS tested were positive with this multiplex assay. The eight MRSA strains (CCRI-9208, CCRI-9770, CCRI-9681, CCRI-9860, CCRI-9583, CCRI-9773, CCRI-9774, CCRI-9589) which harbor the new MREP types vi, viii, ix and x sequences described in the present invention remained undetectable (Example 5).

In a preferred embodiment, detection of MRSA using the real-time multiplex PCR assay on the Smart Cycler® apparatus (Cepheid, Sunnyvale, Calif.) directly from clinical specimens was evaluated. A total of 142 nasal swabs were collected during a MRSA hospital surveillance program at the Montreal General Hospital (Montreal, Quebec, Canada). The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in co-pending patent application number U.S. 60/306,163. Classical identification of MRSA was performed by standard culture methods.

The PCR assay detected 33 of the 34 samples positive for MRSA based on the culture method. As compared to culture, the PCR assay detected 8 additional MRSA positive specimens for a sensitivity of 97.1% and a specificity of 92.6% (Example 6). This multiplex PCR assay represents a rapid and powerful method for the specific detection of MRSA carriers directly from nasal specimens and can be used with any types of clinical specimens such as wounds, blood or blood culture, CSF, etc.

In a preferred embodiment, a multiplex PCR assay containing primers specific to MREP types i, ii, iii, iv, v and vi and orfX of *S. aureus* (SEQ ID NOs.: 66, 67, 79, 80 and 112), and three molecular beacons probes specific to orfX sequence which allowed detection of the two sequence polymorphisms identified in this region of the orfX sequence was developed. Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable (Example 7). Primers specific to MREP types vi, viii and ix (SEQ ID NOs.: 204, 115, 116 and 109) were also designed and were shown to detect their specific target strains (Example 8). While the primers and probes derived from the teaching of Hiramatsu et al., permitted the detection of only 48.7% (19 strains out of 39) of the MRSA strains of Table 2, the primers and probes derived from the present invention enable the detection of 97.4% of the strains (38 strains out of 39) (see exemples 7 and 8). Therefore it can be said that our assay has a ubiquity superior to 50% for the MRSA strains listed in Table 2.

Specificity, Ubiquity and Sensitivity Tests for Oligonucleotide Primers and Probes The specificity of oligonuoleotide primers and probes was tested by amplification of DNA or by hybridization with staphylococcal species. All of the staphylococcal species tested were likely to be pathogens associated with infections or potential contaminants which can be isolated from clinical specimens. Each target DNA could be released from microbial cells using standard chemical and/or physical treatments to lyse the cells (Sambrook et al., 1989, Molecular Cloning: A Laboratory Manual, 2$^{nd}$ ed., Cold Spring Harbor Laboratory Press, Cold Spring Harbor, N.Y.) or alternatively, genomic DNA purified with the GNOME™ DNA kit (Qbiogene, Carlsbad, Calif.) was used. Subsequently, the DNA was subjected to amplification with the set of primers. Specific primers or probes hybridized only to the target DNA.

Oligonucleotides primers found to amplify specifically DNA from the target MRSA were subsequently tested for their ubiquity by amplification (i.e. ubiquitous primers amplified efficiently most or all isolates of MRSA). Finally, the analytical sensitivity of the PCR assays was determined by using 10-fold or 2-fold dilutions of purified genomic DNA from the targeted microorganisms. For most assays, sensitivity levels in the range of 2-10 genome copies were obtained. The specificity, ubiquity and analytical sensitivity of the PCR assays were tested either directly with bacterial cultures or with purified bacterial genomic DNA.

Molecular beacon probes were tested using the Smart Cycler® platform as described above. A molecular beacon probe was considered specific only when it hybridized solely to DNA amplified from the MREJ of *S. aureus*. Molecular beacon probes found to be specific were subsequently tested for their ubiquity (i.e. ubiquitous probes detected efficiently most or all isolates of the MRSA) by hybridization to bacterial DNAs from various MRSA strains.

Bacterial Strains

The reference strains used to build proprietary SCCmec-chromosome right extremity junction sequence data subrepertories, as well as to test the amplification and hybridization assays, were obtained from (i) the American Type Culture Collection (ATCC), (ii) the Laboratoire de santé publique du Québec (LSPQ) (Ste-Anne de Bellevue, Québec, Canada), (iii) the Centers for Disease Control and Prevention (CDC) (Atlanta, GA), (iv) the Institut Pasteur (Paris, France), and V) the Harmony Collection (London, United Kingdom) (Table 14). Clinical isolates of MRSA, MSSA, MRCNS and MSCNS from various geographical areas were also used in this invention (Table 15). The identity of our MRSA strains was confirmed by phenotypic testing and reconfirmed by PCR analysis using *S. aureus*-specific primers and mecA-specific primers (SEQ ID NOs.: 69 and 81) (Martineau et al., 2000, Antimicrob. Agents Chemother. 44:231-238).

For sake of clarity, below is a list of the Examples, Tables, Figures and Annexes of this invention.

DESCRIPTION OF THE EXAMPLES

Example 1: Primers developed by Hiramatsu et al. can only detect MRSA strains belonging to MREP types i, ii, and iii while missing prevalent novel MREP types.

Example 2: Detection and identification of MRSA using primers specific to MREP types i, ii and iii sequences developed in the present invention.

Example 3: Development of a multiplex PCR assay on a standard thermocycler for detection and identification of MRSA based on MREP types i, ii, iii, iv and v sequences.

Example 4: Development of a real-time multiplex PCR assay on the Smart Cycler® for detection and identification of MRSA based on MREP types i, ii, iii, iv and v sequences.

Example 5: Development of a real-time multiplex PCR assay on the Smart Cycler® for detection and identification of MRSA based on MREP types i, ii, iii, iv and v sequences and including an internal control.

Example 6: Detection of MRSA using the real-time multiplex assay on the Smart Cycler® based on MREP types i, ii, iii, iv and v sequences for the detection of MRSA directly from clinical specimens.

Example 7: Development of a real-time multiplex PCR assay on the Smart Cycler® for detection and identification of MRSA based on MREP types i, ii, iii, iv, v, vi and vii sequences.

Example 8: Developement of real-time PCR assays on the Smart Cycler® for detection and identification of MRSA based on MREP types vi, viii and ix.

DESCRIPTION OF THE TABLES

Table 1 provides information about all PCR primers developed by Hiramatsu et al. in U.S. Pat. No. 6,156,507.

Table 2 is a compilation of results (ubiquity and specificity) for the detection of SCCmec-orfX right extremity junction using primers described by Hiramatsu et al. in U.S. Pat. No. 6,156,507 on a standard thermocycler.

Table 3 is a list of MRSA strains not amplifiable using primers targeting types I, II and III of SCCmec-orfX right extremity junction sequences.

Table 4 is a list of novel sequences revealed in the present invention.

Table 5 provides information about all primers developed in the present invention.

Table 6 is a list of molecular beacon probes developed in the present invention.

Table 7 shows amplicon sizes of the different primer pairs described by Hiramatsu et al. in U.S. Pat No. 6,156,507 or developed in the present invention.

Table 8 provides information about primers developed in the present invention to sequence the SCCmec-chromosome right extremity junction.

Table 9 provides information about primers developed in the present invention to obtain sequence of the complete SCCmec.

Table 10 is a list of the sequences available from public databases (GenBank, genome projects or U.S. Pat. No. 6,156,507) used in the present invention to design primers and probes.

Table 11 gives analytical sensitivity of the PCR assay developed in the present invention using primers targeting types I, II and III of SCCme-orfX right extremity junction sequences and performed using a standard thermocycler.

Table 12 is a compilation of results (ubiquity and specificity) for the detection of MRSA using primers developed in the present invention which target types I, II and III of SCCmec-orfX right extremity junction sequences and performed using a standard thermocycler.

Table 13 shows a comparison of sequence identities between the first 500 nucleotides of SCCmec right extremities between 9 types of MREP.

Table 14 provides information about the reference strains of MRSA, MSSA, MRCNS and MSCNS used to validate the PCR assays developed in the present invention.

Table 15 provides information about the origin of clinical strains of MRSA, MSSA, MRCNS and MSCNS used to validate the PCR assays described in the present invention.

Table 16 depicts the analytical sensitivity of the PCR assay developed in the present invention using primers targeting 5 types of MREP sequences and performed on a standard thermocycler.

Table 17 is a compilation of results (ubiquity and specificity) for the PCR assay developed in the present invention using primers targeting 5 types of MREP sequences and performed on a standard thermocycler.

Table 18 depicts the analytical sensitivity of the PCR assay developed in the present invention using the Smart Cycler® platform for the detection of 5 types of MREP.

Table 19 is a compilation of results (ubiquity and specificity) for the PCR assay developed in the present invention using primers and a molecular beacon probe targeting 5 types of MREP sequences and performed on the Smart Cycler® platform.

Table 20 depicts the analytical sensitivity of the PCR assay developed in the present invention using the Smart Cycler® platform for the detection of 6 MREP types.

Table 21 is a compilation of results (ubiquity and specificity) for the PCR assay developed in the present invention using primers and a molecular beacon probe targeting 6 types of MREP sequences and performed on the Smart Cycler® platform.

DESCRIPTION OF THE FIGURES

FIG. 1 is a diagram illustrating the position of the primers developed by Hiramatsu et al. (U.S. Pat. No. 6,156,507) in the SCCmec-chromosome right extremity junction for detection and identification of MRSA.

FIG. 4 illustrates a sequence alignment of nine MREP types.

FIGURE LEGENDS

FIG. 1. Schematic organization of types I, II and III SCC-mecorfX right extremity junctions and localization of the primers (SEQ ID NOs: 52-63) described by Hiramatsu et al. for the detection and identification of MRSA. Amplicon sizes are depicted in Table 7.

Figure 2B:
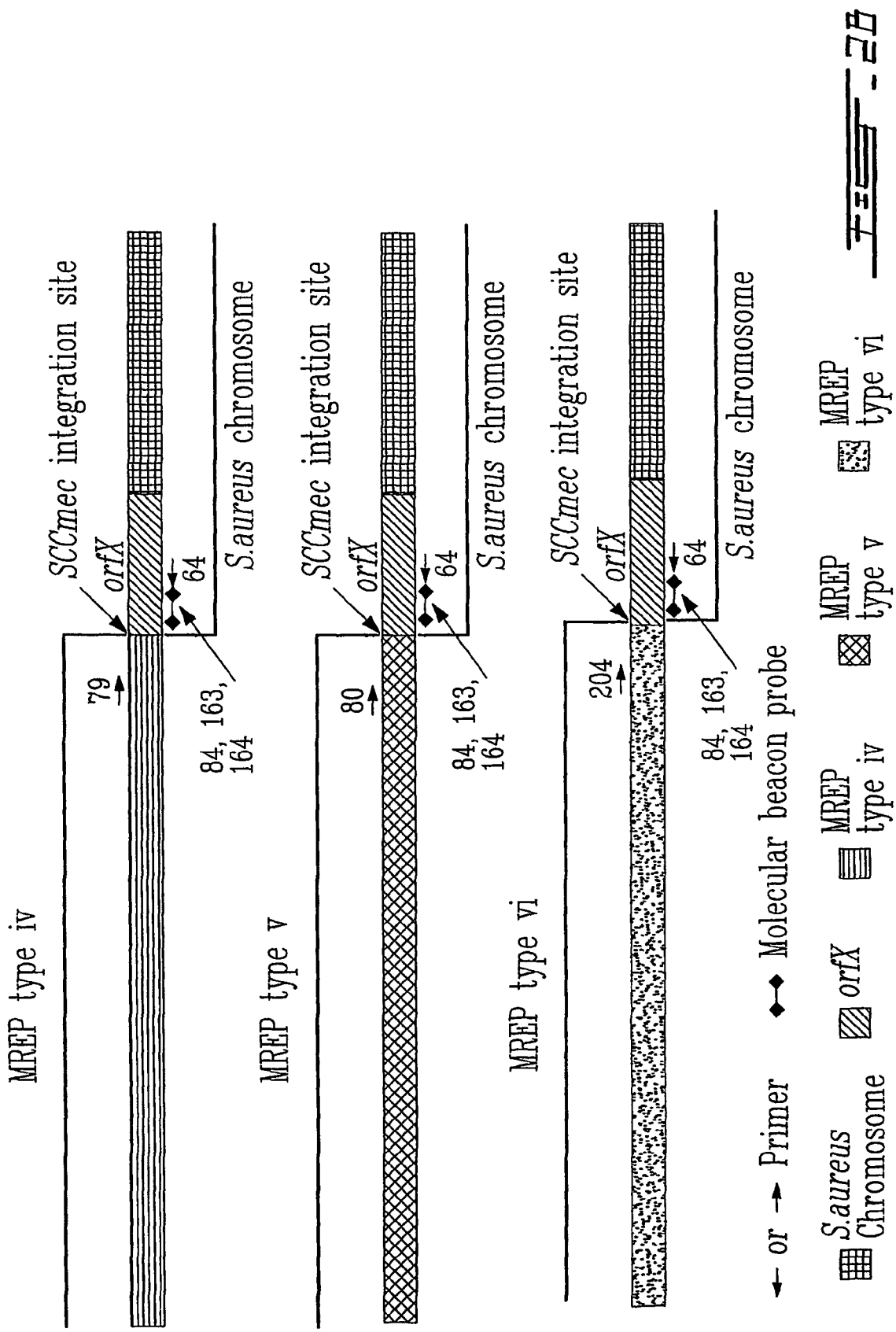
FIG. 2 is a diagram illustrating the position of the primers selected in the present invention in the SCCmec-orfX right extremity junction for detection and identification of MRSA.

FIG. 2. Schematic organization of MREP types i, ii, iii, iv, v, vi, vii, viii and ix and localization of the primers and molecular beacon targeting all MREP types (SEQ ID NOs. 20, 64, 66, 67, 79, 80, 84, 112, 115, 116, 84, 163 and 164) which were developed in the present invention. Amplicon sizes are depicted in Table 7.

Figure 3A:
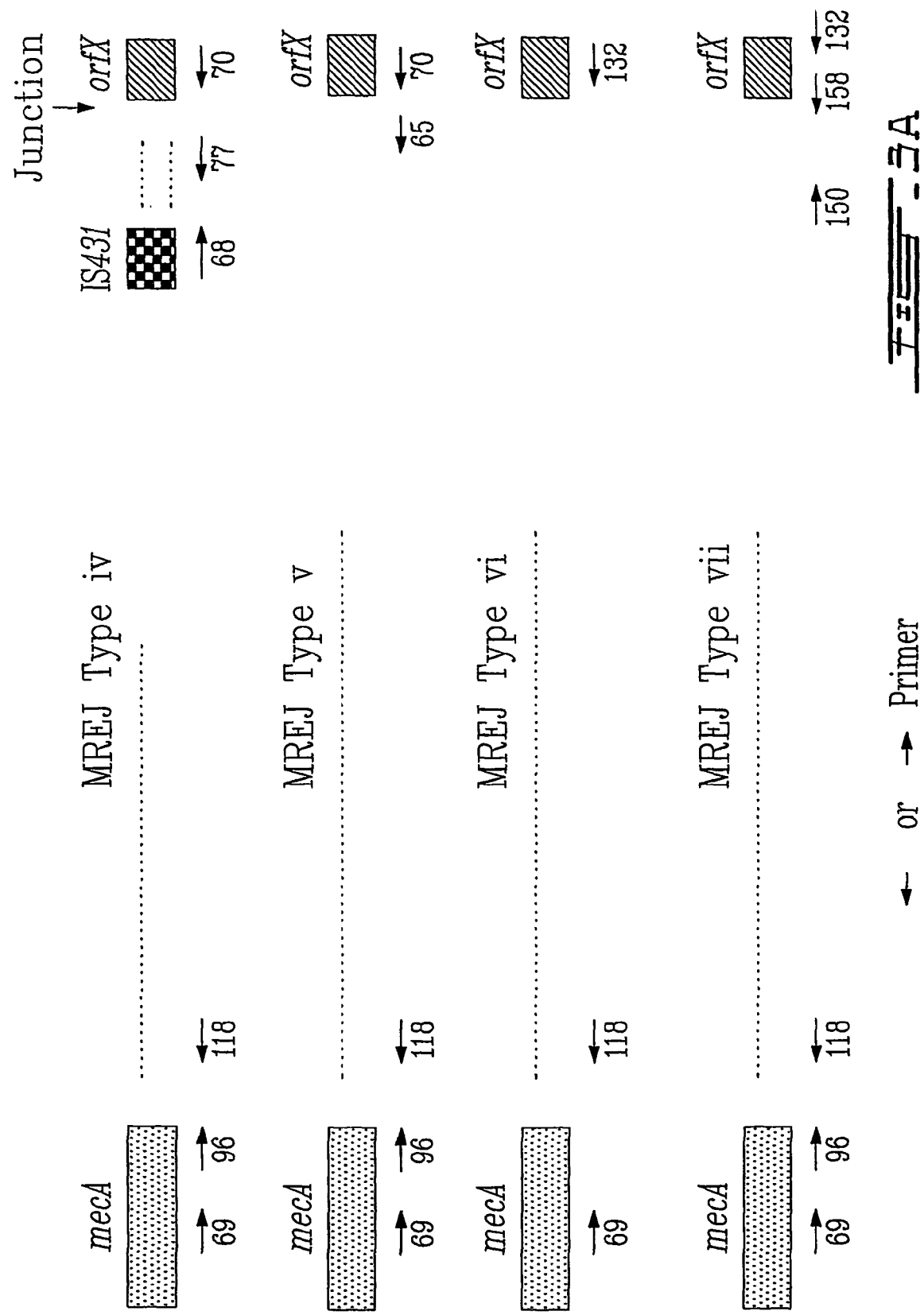
FIG. 3 is a diagram illustrating the position of the primers selected in the present invention to sequence new MREP types.

FIG. 3. Schematic organization of the SCCmec-chromosome right extremity junctions and localization of the primers (SEQ ID NOs. 65, 68, 69, 70, 77, 96, 118, 126, 132, 150 and 158) developed in the present invention for the sequencing of MREP types iv, v, vi, vii, viii, ix and x.

Figure 4B:
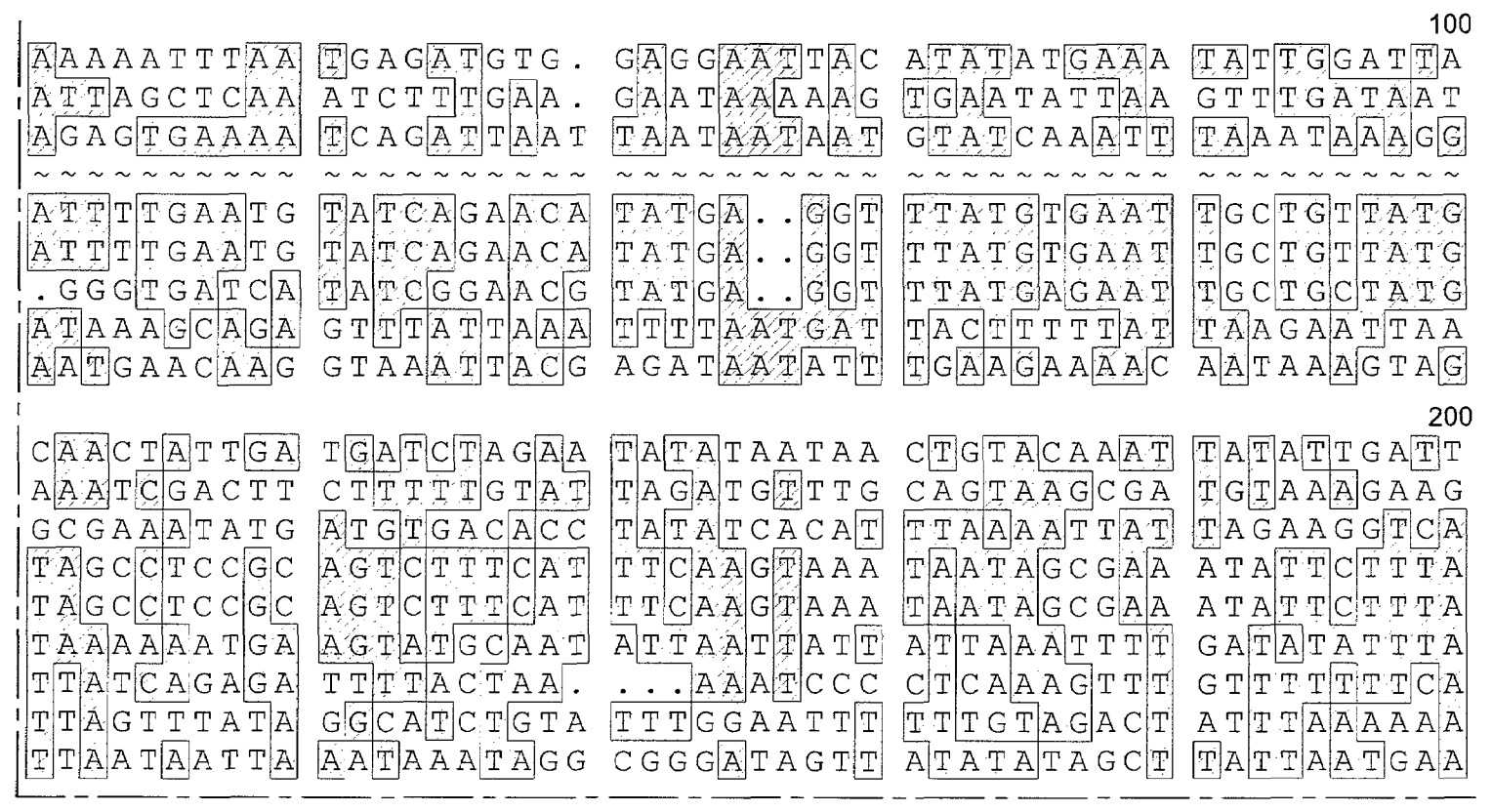
Figure 4D:
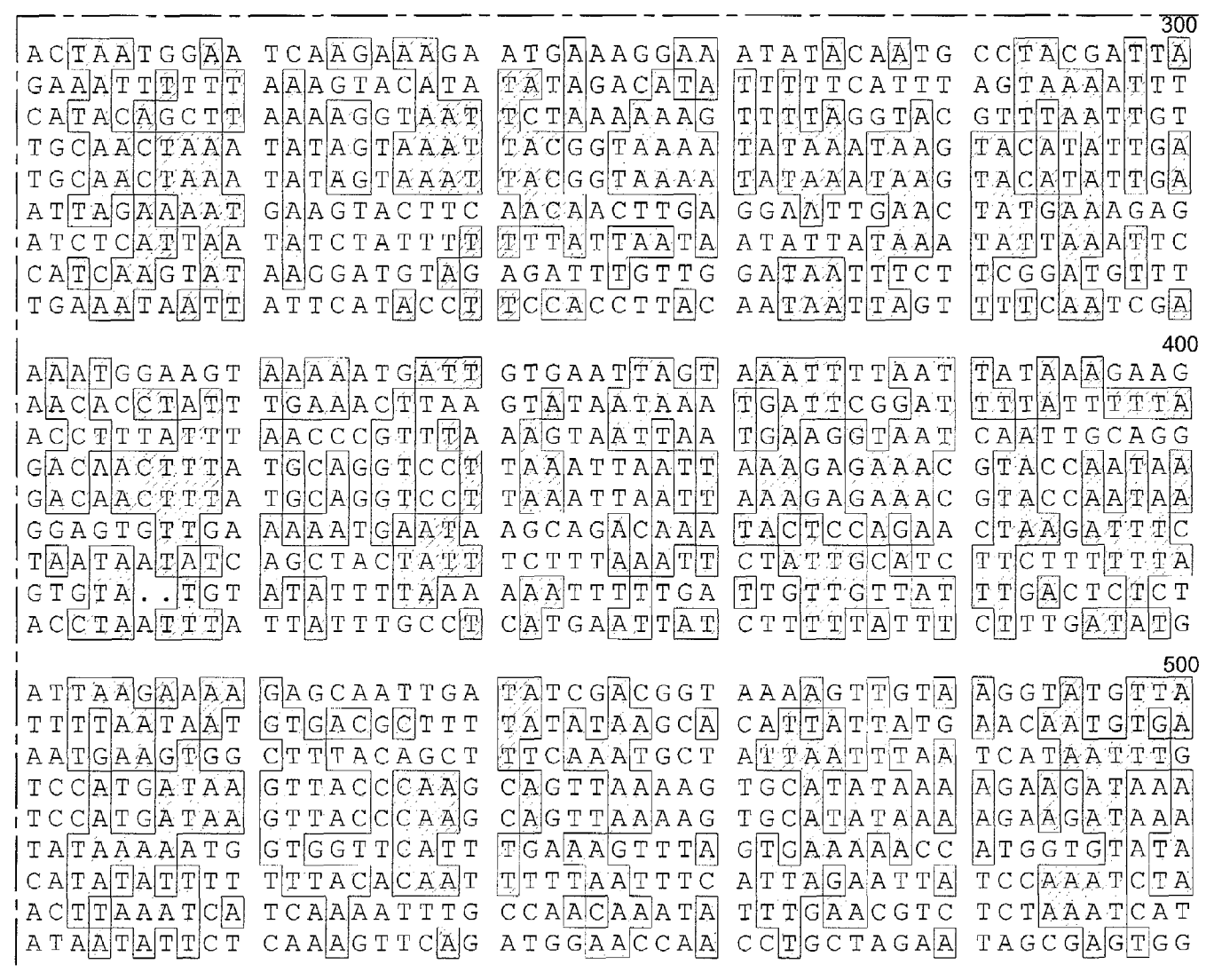

FIG. 4. Multiple sequence alignment of representatives of nine MREP types (represented by the reverse complement of nucleotides 2193-2588 of SEQ ID NO: 1 for type I, the reverse complement of nucleotides 1972-2469 of SEQ ID NO: 2 for type ii, the reverse complement of nucleotides 305-797 of SEQ ID NO: 104 for type iii, nucleotides 435-932 of SEQ ID NO: 51 for type iv, nucleotides 427-924 of SEQ ID NO: 50 for type v, nucleotides 451-948 of SEQ ID NO: 171 for type vi, nucleotides 451-947 of SEQ ID NO: 165 for type vii, nucleotides 445-935 of SEQ ID NO: 167 for type viii, and nucleotides 442-937 of SEQ ID NO: 168 for type ix).

DESCRIPTION OF THE ANNEXES

The Annexes show the strategies used for the selection of primers and internal probes:

Annex I illustrates the strategy for the selection of primers from SCCmec and orfX sequences specific for SCCmec types I and III.

Annex II illustrates the strategy for the selection of specific molecular beacon probes for the real-time detection of SCC-mec-orfX right extremity junctions.

As shown in these Annexes, the selected amplification primers may contain inosines and/or base ambiguities. Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches were used. The inclusion of inosine and/or of degeneracies in the amplification primers allows mismatch tolerance thereby permitting the amplification of a wider array of target nucleotide sequences (Dieffenbach and Dveksler, 1995, PCR Primer: A Laboratory Manual, Cold Spring Harbor Laboratory Press, Plainview, N.Y.).

EXAMPLES

Example 1

Primers Developed by Hiramatsu et al. can only detect MRSA strains belonging to MREP types i, ii, and iii while missing prevalent novel MREP types.

As shown in FIG. 1, Hiramatsu et al. have developed various primers that can specifically hybridize to the right extremities of types I, II and III SCCmec DNAs. They combined these primers with primers specific to the *S. aureus* chromosome region located to the right of the SCCmec integration site for the detection of MRSA. The primer set (SEQ ID NOs.: 22, 24 and 28 in U.S. Pat. No. 6,156,507 corresponding to SEQ ID NOs.: 56, 58 and 60 in the present invention) was shown by Hiramatsu et al. to be the most specific and ubiquitous for detection of MRSA. This set of primers gives amplification products of 1.5 kb for SCCmec type I, 1.6 kb for SCCmec type II and 1.0 kb for SCCmec type III (Table 7). The ubiquity and specificity of this multiplex PCR assay was tested on 39 MRSA strains, 41 MSSA strains, 9 MRCNS strains and 11 MSCNS strains (Table 2). One µL of a treated standardized bacterial suspension or of a bacterial genomic DNA preparation purified from bacteria were amplified in a 20 µl PCR reaction mixture. Each PCR reaction contained 50 mM KCl, 10 mM Tris-HCl (pH 9.0), 0.1% Triton X-100, 2.5 mM $MgCl_2$, 0.4 µM of each of the SCCmec- and orfX-specific primers (SEQ ID NOs.: 56, 58 and 60), 200 µM of each of the four dNTPs (Pharmacia Biotech), 3.3 µg/µl of BSA (Sigma), and 0.5 U Taq polymerase (Promega) coupled with TaqStart™ Antibody (BD Biosciences).

PCR reactions were then subjected to thermal cycling: 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 µg/ml of ethidium bromide.

None of the MRCNS or MSCNS strains tested were detected with the set of primers detecting SCCmec types I, II and III. Twenty of the 39 MRSA strains tested were not detected with this multiplex PCR assay (Tables 2 and 3). One of these undetected MRSA strains corresponds to the highly epidemic MRSA Portuguese clone (strain CCRI-9504; De Lencastre et al., 1994. Eur. J. Clin. Microbiol. Infect. Dis. 13:64-73) and another corresponds to the highly epidemic MRSA Canadian clone CMRSA1 (strain CCRI-9589; Simor et al. CCDR 1999, 25-12, June 15). These data demonstrate that the primer set developed by Hiramatsu et al. (SEQ ID NOs.: 22, 24 and 28 in U.S. Pat. No. 6,156,507 corresponding to SEQ ID NOs.: 56, 58 and 60 in the present invention) is not ubiquitous for the detection of MRSA and suggest that some MRSA strains have sequences at the SCCmec right extremity junction which are different from those identified by Hiramatsu et al. other types of SCCmec sequences or other sequences at the right extremity of SCCmec (MREP type) are found in MRSA. A limitation of this assay is the non-specific detection of 13 MSSA strains (Table 2).

Example 2

Detection and identification of MRSA using primers specific to MREP types i, ii and iii sequences developed in the present invention. Based on analysis of multiple sequence alignments of orfX and SCCmec sequences described by Hiramatsu et al. or available from GenBank, a set of primers (SEQ ID NOs: 64, 66, 67) capable of amplifying short segments of types I, II and III of SCCmec-orfX right extremity junctions from MRSA strains and discriminating from MRCNS (Annex I and FIG. 2) were designed. The chosen set of primers gives amplification products of 176 bp for SCCmec type I, 278 pb for SCCmec type II and 223 bp for SCCmec type III and allows rapid PCR amplification. These primers were used in multiplex PCR to test their ubiquity and specificity using 208 MRSA strains, 252 MSSA strains, 41 MRCNS strains and 21 MRCNS strains (Table 12). The PCR amplification and detection was performed as described in Example 1. PCR reactions were then subjected to thermal cycling (3 minutes at 94° C. followed by 30 or 40 cycles of 1 second at 95° C. for the denaturation step and 30 seconds at 60° C. for the annealing-extension step, and then followed by a terminal extension of 2 minutes at 72° C.) using a standard thermocycler (PTC-200 from MJ Research Inc.). Detection of the PCR products was made as described in Example1.

None of the MRCNS or MSCNS strains tested were detected with this set of primers (Table 12). However, the twenty MRSA strains which were not detected with the primer set developed by Hiramatsu et al. (SEQ ID NOs: 56, 58 and 60) were also not detected with the primers developed in the present invention (Tables 3 and 12). These data also demonstrate that some MRSA strains have sequences at the SCCmec-chromosome right extremity junction which are different from those identified by Hiramatsu et al. Again, as observed with the Hiramatsu primers, 13 MSSA strains were also detected non-specifically (Table 12). The clinical significance of this finding remains to be established since these apparent MSSA strains could be the result of a recent deletion in themes locus (Deplano et al., 2000, J. Antimicrob. Chemotherapy, 46:617-619; Inglis et al., 1990, J. Gen. Microbiol., 136:2231-2239; Inglis et al., 1993, J. Infect. Dis., 167:323-328; Lawrence et al. 1996, J. Hosp. Infect., 33:49-53; Wada et al., 1991, Biochem. Biophys. Res. Comm., 176:1319-1326).

Example 3

Development of a multiplex PCR assay on a standard thermocycler for detection and identification of MRSA based on MREP types i, ii, iii, iv and v sequences. Upon analysis of two of the new MREP types iv and v sequence data described in the present invention, two new primers (SEQ ID NOs.: 79 and 80) were designed and used in multiplex with the three primers SEQ ID NOs.: 64, 66 and 67 described in Example 2. PCR amplification and detection of the PCR products was performed as described in Example 2. Sensitivity tests performed by using ten-fold or two-fold dilutions of purified genomic DNA from various MRSA strains of each MREP type showed a detection limit of 5 to 10 genome copies (Table 16). Specificity tests were performed using 0,1 ng of purified genomic DNA or 1 µl of a standardized bacterial suspension. All MRCNS or MSCNS strains tested were negative with this multiplex assay (Table 17). Twelve of the 20 MRSA strains which were not detected with the multiplex PCR described in Examples 1 and 2 were now detected with this multiplex assay. Again, as observed with the Hiramatsu primers, 13 MSSA strains were also detected non-specifically (Table 12). The eight MRSA strains (CCRI-9208, CCRI-9583, CCRI-9773, CCRI-9774, CCRI-9589, CCRI-9860, CCRI-9681, CCRI-9770) and which harbor the new MREP types vi, vii, viii, ix and x sequences described in the present invention remained undetectable.

Example 4

Development of a real-time multiplex PCR assay on the Smart Cycler® for detection and identification of MRSA based on MREP types i, ii, iii, iv and v sequences. The multiplex PCR assay described in Example 3 containing primers (SEQ ID NOs.: 64, 66, 67, 79 and 80) was adapted to the SmartCycler platform (Cepheid). A molecular beacon probe specific to the orfX sequence was developed (SEQ ID NO. 84, see Annex II). Each PCR reaction contained 50 mM KCl, 10 mM Tris-HCl (pH 9.0), 0.1% Triton X-100, 3.5 mM $MgCl_2$, 0.4 µM of each of the SCCmec- and orfX-specific primers (SEQ ID NOs.: 64, 66, 67, 79 and 80), 0.2 µM of the FAM-labeled molecular beacon probe (SEQ ID NO.: 84), 200

µM of each of the four dNTPs, 3.3 µg/µl of BSA, and 0.5 U Taq polymerase coupled with TaqStart™ Antibody. The PCR amplification on the Smart Cycler® was performed as follows: 3 min. at 94° C. for initial denaturation, then forty-five cycles of three steps consisting of 5 seconds at 95° C. for the denaturation step, 15 seconds at 59° C. for the annealing step and 10 seconds at 72° C. for the extension step. Fluorescence detection was performed at the end of each annealing step. Sensitivity tests performed by using purified genomic DNA from several MRSA strains of each MREP type showed a detection limit of 2 to 10 genome copies (Table 18). None of the MRCNS or MSCNS were positive with this multiplex assay (Table 19). Again, as observed with the Hiramatsu primers, 13 MSSA strains were also detected non-specifically. Twelve of the twenty MRSA strains which were not detected with the multiplex PCR described in Examples 1 and 2 were detected by this multiplex assay. As described in Example 3, the eight MRSA strains which harbor the new MREP types vi, vii, viii, ix and x sequences described in the present invention remained undetectable.

Example 5

Development of a real-time multiplex PCR assay on the Smart Cycler® for detection and identification of MRSA based on MREP types i, ii, iii, iv and v sequences including an internal control. The multiplex PCR assay described in Example 4 containing primers specific to MREP types i to v and orfX of S. aureus (SEQ ID NOs.: 64, 66, 67, 79 and 80) and a molecular beacon probe specific to the orfX sequence (SEQ ID NO. 84, see Annex II) was optimized to include an internal control to monitor PCR inhibition. This internal control contains sequences complementary to MREP type iv- and orfX-specific primers (SEQ ID NOs. 79 and and 64). The assay also contains a TET-labeled molecular beacon probe specific to sequence within the amplicon generated by amplification of the internal control. Each PCR reaction contained 50 mM KCl, 10 mM Tris-HCl (pH 9.0), 0.1% Triton X-100, 3.45 mM $MgCl_2$, 0.8 µM of each of the MREP-specific primers (SEQ ID NOs.: 66 and 67) and orfX-specific primer (SEQ ID NO.: 64), 0.4 µM of each of the MREP-specific primers (SEQ ID NOs.: 79 and 80), 80 copies of the internal control, 0.2 µM of the TET-labeled molecular beacon probe specific to the internal control, 0.2 µM of the FAM-labeled molecular beacon probe (SEQ ID NO.: 84), 330 µM of each of the four dNTPs (Pharmacia Biotech), 3.45 µg/µl of BSA (Sigma), and 0.875 U Taq polymerase (Promega) coupled with TaqStart™ Antibody (BD Biosciences). The PCR amplification on the Smart Cycler® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies. None of the 26 MRCNS or 10 MSCNS were positive with this multiplex assay. Again, as observed with the Hiramatsu primers, 13 MSSA strains were also detected non-specifically. As described in Examples 3 and 4, the eight MRSA strains which harbor the new MREP types vi to x sequences described in the present invention remained undetectable.

Example 6

Detection of MRSA using the real-time multiplex assay on the Smart Cycler® based on MREP types i, ii, iii, iv and v sequences directly from clinical specimens. The assay described in Example 5 was adapted for detection directly from clinical specimens. A total of 142 nasal swabs collected during a MRSA hospital surveillance program at the Montreal General Hospital (Montreal, Quebec, Canada) were tested. The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in co-pending patent application number U.S. 60/306,163. Classical identification of MRSA was performed by standard culture methods.

The PCR assay described in Example 5 detected 33 of the 34 samples positive for MRSA based on the culture method. As compared to culture, the PCR assay detected 8 additional MRSA positive specimens for a sensitivity of 97.1% and a specificity of 92.6%. This multiplex PCR assay represents a rapid and powerful method for the specific detection of MRSA carriers directly from nasal specimens and can be used with any type of clinical specimens such as wounds, blood or blood culture, CSF, etc.

Example 7

Development of a real-time multiplex PCR assay on the Smart Cycler® for detection and identification of MRSA based on MREP types i, ii, iii, iv, v and vii sequences. Upon analysis of the new MREP type vii sequence data described in the present invention (SEQ ID NOs.:165 and 166), two new primers (SEQ ID NOs.: 112 and 113) were designed and tested in multiplex with the three primers SEQ ID NOs.: 64, 66 and 67 described in Example 2. Primer SEQ ID NO.: 112 was selected for use in the multiplex based on its sensitivity. Three molecular beacon probes specific to the orfX sequence which allowed detection of two sequence polymorphisms identified in this region of the orfX sequence, based on analysis of SEQ ID NOs.: 173-186, were also used in the multiplex (SEQ ID NOs.: 84, 163 and 164). Each PCR reaction contained 50 mM KCl, 10 mM Tris-HCl (pH 9.0), 0.1% Triton X-100, 3.45 mM $MgCl_2$, 0.8 µM of each of the SCCmec-specific primers (SEQ ID NOs.: 66 and 67) and orfX-specific primer (SEQ ID NO.: 64), 0.4 µM of each of the SCCmec-specific primers (SEQ ID NOs.: 79 and 80), 0.2 µM of the FAM-labeled molecular beacon probe (SEQ ID NO.: 84), 330 µM of each of the four dNTPs (Pharmacia Biotech), 3.45 µg/µl of BSA (Sigma), and 0.875 U of Taq polymerase (Promega) coupled with TaqStart™ Antibody (BD Biosciences). The PCR amplification on the Smart Cycler® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. The detection of fluorescence was done at the end of each annealing step. Sensitivity tests performed by using purified genomic DNA from several MRSA strains of each MREP type showed a detection limit of 2 genome copies (Table 20). None of the 26 MRCNS or 8 MSCNS were positive with this multiplex assay. Again, as observed with the Hiramatsu primers, 13 MSSA strains were also detected non-specifically (Table 21). Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable.

Example 8

Developement of real-time PCR assays on the Smart Cycler® for detection and identification of MRSA based on MREP types vi, viii, ix. Upon analysis of the new MREP types vi, viii and ix sequence data described in the present invention, one new primers specific to MREP type vi (SEQ ID NO.: 201), one primer specific to MREP type viii (SEQ ID NO.: 115), a primer specific to MREP type ix (SEQ ID NO.: 109) and a primer specific to both MREP types viii and ix (SEQ ID NO.: 116) were designed. Each PCR primer was used in combination with the orfX-specific primer (SEQ ID NO.: 64) and tested against its specific target strain. Each PCR reaction contained 50 mM KCl, 10 mM Tris-HCl (pH 9.0), 0.1% Triton X-100, 3.45 mM $MgCl_2$, 0.4 µM of each of the SCCmec- and orfX-specific primers, 200 µM of each of the four dNTPs, 3.4 µg/µl of BSA, and 0.875 U Taq polymerase coupled with TaqStart™ Antibody. The PCR amplification was performed as described en Example 7. Sensitivity tests performed by using genomic DNA purified from their respective MRSA target strains showed that the best primer pair combination was SEQ ID NOs.: 64 and 115 for the detection of MREP types viii and ix simultaneously. These new SCCmec-specific primers may be used in multiplex with primers specific to MREP types i, ii, ii, iv, v and vii (SEQ ID NOs.: 64, 66, 67, 79 and 80) described in previous examples to provide a more ubiquitous MRSA assay.

In conclusion, we have improved the ubiquity of detection of MRSA strains. New MREJ types iv to x have been identified. Amongst strains representative of these new types, Hiramitsu's primers and/or probes succeeded in detecting less than 50% thereof. We have therefore amply passed the bar of at least 50% ubiquity, since our primers and probes were designed to detect 100% of the strains tested as representatives of MREJ types iv to ix. Therefore, although ubiquity depends on the pool of strains and representatives that are under analyse, we know now that close to 100% ubiquity is an attainable goal, when using the sequences of the right junctions (EJ) to derive probes and primers dealing with polymorphism in this region. Depending on how many unknown types of MREJ exist, we have a margin of manoeuver going from 50% (higher than Hiramitsu's primers for the tested strains) to 100% if we sequence all the existing MEJs to derive properly the present diagnostic tools and methods, following the above teachings.

This invention has been described herein above, and it is readily apparent that modifications can be made thereto without departing from the spirit of this invention. These modifications are under the scope of this invention, as defined in the appended claims.

TABLE 1

PCR amplification primers reported by Hiramatsu et al. in U.S. Pat. No. 6,156,507 found in the sequence listing

| SEQ ID NO.: (present invention) | Target | Position[a,b] | SEQ ID NO.: (U.S. Pat. No. 6,156,507) |
|---|---|---|---|
| 52 | MREP types i and ii | 480 | 18 |
| 53 | MREP types i and ii | 758 | 19 |
| 54 | MREP types i and ii | 927 | 20 |
| 55 | MREP types i and ii | 1154 | 21 |
| 56 | MREP types i and ii | 1755 | 22 |
| 57 | MREP types i and ii | 2302 | 23 |
| 58 | MREP type iii | 295[c] | 24 |
| 59 | orfX | 1664 | 25 |
| 60 | orfSA0022[d] | 3267 | 28 |
| 61 | orfSA0022[d] | 3585 | 27 |
| 62 | orfX | 1389 | 26 |
| 63 | orfSA0022[d] | 2957 | 29 |

[a]Position refers to nucleotide position of the 5' end of primer.
[b]Numbering for SEQ ID NOs.: 52-57 refers to SEQ ID NO.: 2; numbering for SEQ ID NO.: 58 refers to SEQ ID NO.: 4; numbering for SEQ ID NOs.: 59-63 refers to SEQ ID NO.: 3.
[c]Primer is reverse-complement of target sequence.
[d]orfSA0022 refers to the open reading frame designation from GenBank accession number AP003129 (SEQ ID NO.: 231).

TABLE 2

Specificity and ubiquity tests performed on a standard thermocycler using the optimal set of primers described by Hiramatsu et al. (SEQ ID NOs.: 22, 24 and 28 in U.S. Pat. No. 6,156,507 corresponding to SEQ ID NOs.: 56, 58 and 60, respectively, in the present invention) for the detection of MRSA

| Strains | PCR results for SCCmec - orfX right extremity junction | |
|---|---|---|
| | Positive (%) | Negative (%) |
| MRSA - 39 strains | 19 (48.7) | 20 (51.2) |
| MSSA - 41 strains | 13 (31.7) | 28 (68.3) |
| MRCNS - 9 strains* | 0 (0%) | 9 (100%) |
| MSCNS - 11 strains* | 0 (0%) | 11 (100%) |

*Details regarding CNS strains:
MRCNS: S. caprae (1)
S. cohni cohnii (1)
S. epidermidis (1)
S. haemolyticus (2)
S. hominis (1)
S. sciuri (1)
S. simulans (1)
S. warneri (1)
MSCNS: S. cohni cohnii (1)
S. epidermidis (1)
S. equorum (1)
S. gallinarum (1)
S. haemolyticus (1)
S. lentus (1)
S. lugdunensis (1)
S. saccharolyticus (1)
S. saprophyticus (2)
S. xylosus (1)

TABLE 3

Origin of MRSA strains not amplifiable using primers developed by Hiramatsu et al. (SEQ ID NOs.: 22, 24 and 28 in U.S. Pat. No. 6,156,507 corresponding to SEQ ID NOs.: 56, 58 and 60, respectively, in the present invention) as well as primers developed in the present invention targeting MREP types i, ii and iii (SEQ ID NOs.: 64, 66 and 67)

| Staphylococcus aureus strain designation: | | |
|---|---|---|
| Original | CCRI[a] | Origin |
| ATCC BAA-40[b] | CCRI-9504 | Portugal |
| ATCC 33592 | CCRI-178 | USA |
| R991282 | CCRI-2025 | Québec, Canada |
| 4508 | CCRI-9208 | Québec, Canada |

TABLE 3-continued

Origin of MRSA strains not amplifiable using primers developed by Hiramatsu et al. (SEQ ID NOs.: 22, 24 and 28 in U.S. Pat. No. 6,156,507 corresponding to SEQ ID NOs.: 56, 58 and 60, respectively, in the present invention) as well as primers developed in the present invention targeting MREP types i, ii and iii (SEQ ID NOs.: 64, 66 and 67)

| Staphylococcus aureus strain designation: | | |
|---|---|---|
| Original | CCRI[a] | Origin |
| 19121 | CCRI-8895 | Denmark |
| Z109 | CCRI-8903 | Denmark |
| 45302 | CCRI-1263 | Ontario, Canada |
| R655 | CCRI-1324 | Québec, Canada |
| MA 50428 | CCRI-1311 | Québec, Canada |
| MA 50609 | CCRI-1312 | Québec, Canada |
| MA 51363 | CCRI-1331 | Québec, Canada |
| MA 51561 | CCRI-1325 | Québec, Canada |
| 14A0116 | CCRI-9681 | Poland |
| 23 (CCUG 41787) | CCRI-9860 | Sweden |
| SE26-1 | CCRI-9770 | Ontario, Canada |
| SE1-1 | CCRI-9583 | Ontario, Canada |
| ID-61880[c] | CCRI-9589 | Ontario, Canada |
| SE47-1 | CCRI-9773 | Ontario, Canada |
| SE49-1 | CCRI-9774 | Ontario, Canada |
| 39795-2 | CCRI-1377 | Québec, Canada |

[a]CCRI stands for "Collection of the Centre de Recherche en Infectiologie".
[b]Portuguese clone.
[c]Canadian clone EMRSA1.

TABLE 4

Staphylococcus aureus MREJ nucleotide sequences revealed in the present invention

| SEQ ID NO. | Staphylococcus aureus strain designation: Original | CCRI[a] | Genetic Target |
|---|---|---|---|
| 27 | R991282 | CCRI-2025 | mecA |
| 28 | 45302 | CCRI-1263 | mecA |
| 29 | MA 50428 | CCRI-1311 | mecA |
| 30 | MA 51363 | CCRI-1331 | mecA |
| 31 | 39795-2 | CCRI-1377 | mecA and 1.5 kb of downstream region |
| 42 | ATCC 33592 | CCRI-178 | MREP type iv |
| 43 | 19121 | CCRI-8895 | MREP type iv |
| 44 | Z109 | CCRI-8903 | MREP type iv |
| 45 | R655 | CCRI-1324 | MREP type iv |
| 46 | MA 51363 | CCRI-1331 | MREP type iv |
| 47 | 45302 | CCRI-1263 | MREP type v |
| 48 | 39795-2 | CCRI-1377 | MREP type v |
| 49 | MA 50428 | CCRI-1311 | MREP type v |
| 50 | R991282 | CCRI-2025 | MREP type v |
| 51 | ATCC BAA-40 | CCRI-9504 | MREP type iv |
| 165 | SE1-1 | CCRI-9583 | MREP type vii |
| 166 | ID-61880 | CCRI-9589 | MREP type vii |
| 167 | 23 (CCUG 41787) | CCRI-9860 | MREP type viii |
| 168 | 14A016 | CCRI-9681 | MREP type ix |
| 171 | 4508 | CCRI-9208 | MREP type vi |
| 172 | SE26-1 | CCRI-9770 | orfSA0021[b] and 75 bp of orfSA0022[b] |
| 173 | 26 (98/10618) | CCRI-9864 | MREP type ii |
| 174 | 27 (98/26821) | CCRI-9865 | MREP type ii |
| 175 | 28 (24344) | CCRI-9866 | MREP type ii |
| 176 | 12 (62305) | CCRI-9867 | MREP type ii |
| 177 | 22 (90/14719) | CCRI-9868 | MREP type ii |
| 178 | 23 (98/14719) | CCRI-9869 | MREP type ii |
| 179 | 32 (97S99) | CCRI-9871 | MREP type ii |
| 180 | 33 (97S100) | CCRI-9872 | MREP type ii |
| 181 | 38 (825/96) | CCRI-9873 | MREP type ii |
| 182 | 39 (842/96) | CCRI-9874 | MREP type ii |
| 183 | 43 (N8-892/99) | CCRI-9875 | MREP type ii |
| 184 | 46 (9805-0137) | CCRI-9876 | MREP type iii |
| 185 | 1 | CCRI-9882 | MREP type ii |
| 186 | 29 | CCRI-9885 | MREP type ii |
| 189 | SE1-1 | CCRI-9583 | mecA and 2.2 kb of downstream region, including IS431mec |
| 190 | ATCC BAA-40 | CCRI-9504 | mecA and 1.5 kb of downstream region |
| 191 | 4508 | CCRI-9208 | mecA and 0.9 kb of downstream region |
| 192 | ID-61880 | CCRI-9589 | mecA and 0.9 kb of downstream region |
| 193 | 14A016 | CCRI-9681 | mecA and 0.9 kb of downstream region |
| 195 | SE26-1 | CCRI-9770 | mecA and 1.5 kb of downstream region, including IS431mec |
| 197 | ATCC 43300 | CCRI-175 | MREP type ii |
| 198 | R522 | CCRI-1262 | MREP type iii |
| 199 | 13370 | CCRI-8894 | MREP type i |
| 219 | ATCC BAA-40 | CCRI-9504 | tetK |

| SEQ ID NO. | Staphylococcus aureus strain designation: Original | CCRI[b] | Genetic Target[a] |
|---|---|---|---|
| 220 | MA 51363 | CCRI-1331 | mecA and 1.5 kb of downstream region |
| 221 | 39795-2 | CCRI-1377 | IS431mec and 0.6 kb of upstream region |
| 222 | R991282 | CCRI-2025 | mecA and 1.5 kb of downstream region |
| 223 | R991282 | CCRI-2025 | IS431mec and 0.6 kb of upstream region |
| 224 | 23 (CCUG 41787) | CCRI-9860 | mecA and 1.5 kb of downstream region |
| 225 | 23 (CCUG 41787) | CCRI-9860 | IS431mec and 0.6 kb of upstream region |
| 233 | 14A016 | CCRI-9681 | MREP type ix |

[a]CCRI stands for "Collection of the Centre de Recherche en Infectiologie".
[b]orfSA0021 and orfSA0022 refer to the open reading frame designation from GenBank accession number AP003129 (SEQ ID NO.: 231).

TABLE 5

PCR primers developed in the present invention

| SEQ ID NO. | Target | Originating DNA Position[a] | SEQ ID NO. |
|---|---|---|---|
| 64 | orfX | 1720 | 3 |
| 70 | orfX | 1796 | 3 |
| 71 | orfX | 1712 | 3 |
| 72 | orfX | 1749 | 3 |
| 73 | orfX | 1758 | 3 |
| 74 | orfX | 1794 | 3 |
| 75 | orfX | 1797 | 3 |
| 76 | orfX | 1798 | 3 |
| 66 | MREP types i and ii | 2327 | 2 |
| 100 | MREP types i and ii | 2323 | 2 |
| 101 | MREP types i and ii | 2314 | 2 |
| 97 | MREP type ii | 2434 | 2 |
| 99 | MREP type ii | 2434 | 2 |
| 67 | MREP type iii | 207[b] | 4 |
| 98 | MREP type iii | 147[b] | 4 |
| 102 | MREP type iii | 251[b] | 4 |
| 79 | MREP type iv | 74[b] | 43 |
| 80 | MREP type v | 50[b] | 47 |
| 109 | MREP type ix | 652[b] | 168 |
| 204 | MREP type vi | 642[b] | 171 |
| 112 | MREP type vii | 503[b] | 165 |

TABLE 5-continued

PCR primers developed in the present invention

| | | Originating DNA | |
|---|---|---|---|
| SEQ ID NO. | Target | Position[a] | SEQ ID NO. |
| 113 | MREP type vii | 551[b] | 165 |
| 115 | MREP type viii | 514[b] | 167 |
| 116 | MREP type viii | 601[b] | 167 |

[a]Position refers to nucleotide position of 5' end of primer.
[b]Primer is reverse-complement of target sequence.

TABLE 6

Molecular beacon probes developed in the present invention

| SEQ ID NO. | Target | Position |
|---|---|---|
| 32 | orfX | 86[a] |
| 83 | orfX | 86[a] |
| 84 | orfX | 34[a,b] |
| 160 | orfX | 55[a,b] |
| 161 | orfX | 34[a,b] |
| 162 | orfX | 114[a] |
| 163 | orfX | 34[a,b] |
| 164 | orfX | 34[a,b] |

[a]Position refers to nucleotide position of the 5' end of the molecular beacon's loop on SEQ ID NO.: 3.
[b]Sequence of molecular beacon's loop is reverse-complement of SEQ ID NO.: 3.

TABLE 7

Length of amplicons obtained with the different primer pairs which are objects of the present invention

| SEQ ID NO. | Target[d] | Amplicon length[a] |
|---|---|---|
| 59/52[b] | orfX/MREP type i and ii | 2079 (type i); 2181 (type ii) |
| 59/53[b] | orfX/MREP type i and ii | 1801 (type i); 1903 (type ii) |
| 59/54[b] | orfX/MREP type i and ii | 1632 (type i); 1734 (type ii) |
| 59/55[b] | orfX/MREP type i and ii | 1405 (type i); 1507 (type ii) |
| 59/56[b] | orfX/MREP type i and ii | 804 (type i); 906 (type ii) |
| 59/57[b] | orfX/MREP type i and ii | 257 (type i); 359 (type ii) |
| 60/52[b] | orfSA0022/MREP type i and ii | 2794 (type i); 2896 (type ii) |
| 60/53[b] | orfSA0022/MREP type i and ii | 2516 (type i); 2618 (type ii) |
| 60/54[b] | orfSA0022/MREP type i and ii | 2347 (type i); 2449 (type ii) |
| 60/55[b] | orfSA0022/MREP type i and ii | 2120 (type i); 2222 (type ii) |
| 60/56[b] | orfSA0022/MREP type i and ii | 1519 (type i); 1621 (type ii) |
| 60/57[b] | orfSA0022/MREP type i and ii | 972 (type i); 1074 (type ii) |
| 61/52[b] | orfSA0022/MREP type i and ii | 2476 (type i); 2578 (type ii) |
| 61/53[b] | orfSA0022/MREP type i and ii | 2198 (type i); 2300 (type ii) |
| 61/54[b] | orfSA0022/MREP type i and ii | 2029 (type i); 2131 (type ii) |
| 61/55[b] | orfSA0022/MREP type i and ii | 1802 (type i); 1904 (type ii) |
| 61/56[b] | orfSA0022/MREP type i and ii | 1201 (type i); 1303 (type ii) |
| 61/57[b] | orfSA0022/MREP type i and ii | 654 (type i); 756 (type ii) |
| 62/52[b] | orfX/MREP type i and ii | 2354 (type i); 2456 (type ii) |
| 62/53[b] | orfX/MREP type i and ii | 2076 (type i); 2178 (type ii) |
| 62/54[b] | orfX/MREP type i and ii | 1907 (type i); 2009 (type ii) |
| 62/55[b] | orfX/MREP type i and ii | 1680 (type i); 1782 (type ii) |
| 62/56[b] | orfX/MREP type i and ii | 1079 (type i); 1181 (type ii) |
| 62/57[b] | orfX/MREP type i and ii | 532 (type i); 634 (type ii) |
| 63/52[b] | orfSA0022/MREP type i and ii | 3104 (type i); 3206 (type ii) |
| 63/53[b] | orfSA0022/MREP type i and ii | 2826 (type i); 2928 (type ii) |
| 63/54[b] | orfSA0022/MREP type i and ii | 2657 (type i); 2759 (type ii) |
| 63/55[b] | orfSA0022/MREP type i and ii | 2430 (type i); 2532 (type ii) |
| 63/56[b] | orfSA0022/MREP type i and ii | 1829 (type i); 1931 (type ii) |
| 63/57[b] | orfSA0022/MREP type i and ii | 1282 (type i); 1384 (type ii) |
| 59/58[b] | orfX/MREP type iii | 361 |
| 60/58[b] | orfSA0022/MREP type iii | 1076 |
| 61/58[b] | orfSA0022/MREP type iii | 758 |
| 62/58[b] | orfX/MREP type iii | 656 |
| 63/58[b] | orfSA0022/MREP type iii | 1386 |
| 70/66 | orfX/MREP type i and ii | 100 (type i); 202 (type ii) |
| 70/67 | orfX/MREP type iii | 147 (type iii) |
| 64/66[c] | orfX/MREP type i and ii | 176 (type i); 278 (type ii) |
| 64/67[c] | orfX/MREP type iii | 223 |
| 64/79[c] | orfX/MREP type iv | 215 |
| 64/80[c] | orfX/MREP type v | 196 |
| 64/97[c] | orfX/MREP type ii | 171 |
| 64/98[c] | orfX/MREP type iii | 163 |
| 64/99[c] | orfX/MREP type ii | 171 |
| 64/100[c] | orfX/MREP types i and ii | 180 (type i); 282 (type ii) |
| 64/101[c] | orfX/MREP types i and ii | 189 (type i); 291 (type ii) |
| 64/102[c] | orfX/MREP type iii | 263 |
| 64/109[c] | orfX/MREP type ix | 369 |
| 64/204[c] | orfX/MREP type vi | 348 |
| 64/112[c] | orfX/MREP type vii | 214 |
| 64/113[c] | orfX/MREP type vii | 263 |
| 64/115[c] | orfX/MREP type viii | 227 |
| 64/116[c] | orfX/MREP type viii | 318 |

[a]Amplicon length is given in base pairs for MREP types amplified by the set of primers.
[b]Set of primers described by Hiramatsu et al. in U.S. Pat. No. 6,156,507.
[c]Set of primers developed in the present invention.
[d]orfSA0022 refers to the open reading frame designation from GenBank accession number AP003129 (SEQ ID NO.: 231).

TABLE 8

Other primers developed in the present invention

| | | Originating DNA | |
|---|---|---|---|
| SEQ ID NO. | Target | Position[a] | SEQ ID NO. |
| 77 | MREP type iv | 993 | 43 |
| 65 | MREP type v | 636 | 47 |
| 70 | orfX | 1796 | 3 |
| 68 | IS431 | 626 | 92 |
| 69 | mecA | 1059 | 78 |
| 96 | mecA | 1949 | 78 |
| 81 | mecA | 1206 | 78 |
| 114 | MREP type vii | 629[b] | 165 |
| 117 | MREP type ii | 856 | 194 |
| 118 | MREP type ii | 974[b] | 194 |
| 119 | MREP type vii | 404 | 189 |
| 120 | MREP type vii | 477[b] | 189 |
| 123 | MREP type vii | 551 | 165 |
| 124 | MREP type ii | 584 | 170 |
| 125 | MREP type ii | 689[b] | 170 |
| 126 | orfSA0021 | 336 | 231 |
| 127 | orfSA0021 | 563 | 231 |
| 128 | orfSA0022[d] | 2993 | 231 |
| 129 | orfSA0022[d] | 3467[b] | 231 |
| 132 | orfX | 3700 | 231 |
| 145 | MREP type iv | 988 | 51 |
| 146 | MREP type v | 1386 | 51 |
| 147 | MREP type iv | 891[b] | 51 |
| 148 | MREP type ix | 664 | 168 |
| 149 | MREP type ix | 849[b] | 168 |
| 150 | MREP type vii | 1117[b] | 165 |
| 151 | MREP type vii | 1473 | 189 |
| 152 | IS431mec | 1592[b] | 189 |
| 154 | MREP type v | 996[b] | 50 |
| 155 | MREP type v | 935 | 50 |
| 156 | tetK from plasmid pT181 | 1169[b] | 228 |
| 157 | tetK from plasmid pT181 | 136 | 228 |
| 158 | orfX | 2714[b] | 2 |
| 159 | orfX | 2539 | 2 |
| 187 | MREP type viii | 967[b] | 167 |
| 188 | MREP type viii | 851 | 167 |

[a]Position refers to nucleotide position of the 5' end of primer.
[b]Primer is reverse-complement of target sequence.

TABLE 9

Amplification and/or sequencing primers developed in the present invention

| SEQ ID NO. | Target | Position[a] | Originating DNA SEQ ID NO. |
|---|---|---|---|
| 85 | S. aureus chromosome | 197[b] | 35 |
| 86 | S. aureus chromosome | 198[b] | 37 |
| 87 | S. aureus chromosome | 197[b] | 38 |
| 88 | S. aureus chromosome | 1265[b] | 39 |
| 89 | S. aureus chromosome | 1892 | 3 |
| 103 | orfX | 1386 | 3 |
| 105 | MREP type i | 2335 | 2 |
| 106 | MREP type ii | 2437 | 2 |
| 107 | MREP type iii | 153[b] | 4 |
| 108 | MREP type iii | 153[b] | 4 |
| 121 | MREP type vii | 1150 | 165 |
| 122 | MREP type vii | 1241[b] | 165 |
| 130 | orfX | 4029[b] | 231 |
| 131 | region between orfSA0022 and orfSA0023[d] | 3588 | 231 |
| 133 | merB from plasmid pI258 | 262 | 226 |
| 134 | merB from plasmid pI258 | 539[b] | 226 |
| 135 | merR from plasmid pI258 | 564 | 226 |
| 136 | merR from plasmid pI258 | 444 | 227 |
| 137 | merR from plasmid pI258 | 529 | 227 |
| 138 | merR from plasmid pI258 | 530[b] | 227 |
| 139 | rep from plasmid pUB110 | 796 | 230 |
| 140 | rep from plasmid pUB110 | 761[b] | 230 |
| 141 | rep from plasmid pUB110 | 600 | 230 |
| 142 | aadD from plasmid pUB110 | 1320[b] | 229 |
| 143 | aadD from plasmid pUB110 | 759 | 229 |
| 144 | aadD from plasmid pUB110 | 646 | 229 |
| 153 | MREP type vii | 1030 | 165 |
| 200 | orfSA0022[d] | 871[c] | 231 |
| 201 | orfSA0022[d] | 1006 | 231 |
| 202 | MREP type vi | 648 | 171 |
| 203 | MREP type vi | 883[b] | 171 |
| 205 | MREP type ix | 1180 | 168 |
| 206 | MREP type ix | 1311[b] | 233 |
| 207 | MREP type viii | 1337 | 167 |
| 208 | MREP type viii | 1441[b] | 167 |
| 209 | ccrA | 184 | 232 |
| 210 | ccrA | 385 | 232 |
| 211 | ccrA | 643[b] | 232 |
| 212 | ccrA | 1282[b] | 232 |
| 213 | ccrB | 1388 | 232 |
| 214 | ccrB | 1601 | 232 |
| 215 | ccrB | 2139[b] | 232 |
| 216 | ccrB | 2199[b] | 232 |
| 217 | ccrB | 2847[b] | 232 |
| 218 | ccrB | 2946[b] | 232 |

[a]Position refers to nucleotide position of the 5' end of primer.
[b]Primer is reverse-complement of target sequence.
[c]Primer contains two mismatches.
[d]orfSA0022 and orfSA0023 refer to the open reading frame designation from GenBank accession number AP003129 (SEQ ID NO.: 231).

TABLE 10

Origin of the nucleic acids and/or sequences available from public databases found in the sequence listing

| SEQ ID NO. | Staphylococcal strain | Source | Accession number | Genetic Target[a,b] |
|---|---|---|---|---|
| 1 | NCTC 10442 | Database | AB033763 | SCCmec type I MREJ |
| 2 | N315 | Database | D86934 | SCCmec type II MREJ |
| 3 | NCTC 8325 | Database | AB014440 | MSSA chromosome |
| 4 | 86/560 | Database | AB013471 | SCCmec type III MREJ |
| 5 | 86/961 | Database | AB013472 | SCCmec type III MREJ |
| 6 | 85/3907 | Database | AB013473 | SCCmec type III MREJ |
| 7 | 86/2652 | Database | AB013474 | SCCmec type III MREJ |
| 8 | 86/1340 | Database | AB013475 | SCCmec type III MREJ |
| 9 | 86/1762 | Database | AB013476 | SCCmec type III MREJ |
| 10 | 86/2082 | Database | AB013477 | SCCmec type III MREJ |
| 11 | 85/2111 | Database | AB013478 | SCCmec type III MREJ |
| 12 | 85/5495 | Database | AB013479 | SCCmec type III MREJ |
| 13 | 85/1836 | Database | AB013480 | SCCmec type III MREJ |
| 14 | 85/2147 | Database | AB013481 | SCCmec type III MREJ |
| 15 | 85/3619 | Database | AB013482 | SCCmec type III MREJ |
| 16 | 85/3566 | Database | AB013483 | SCCmec type III MREJ |
| 17 | 85/2232 | Database | AB014402 | SCCmec type II MREJ |
| 18 | 85/2235 | Database | AB014403 | SCCmec type II MREJ |
| 19 | MR108 | Database | AB014404 | SCCmec type II MREJ |
| 20 | 85/9302 | Database | AB014430 | SCCmec type I MREJ |
| 21 | 85/9580 | Database | AB014431 | SCCmec type I MREJ |
| 22 | 85/1940 | Database | AB014432 | SCCmec type I MREJ |
| 23 | 85/6219 | Database | AB014433 | SCCmec type I MREJ |
| 24 | 64/4176 | Database | AB014434 | SCCmec type I MREJ |
| 25 | 64/3846 | Database | AB014435 | SCCmec type I MREJ |
| 26 | HUC19 | Database | AF181950 | SCCmec type II MREJ |
| 33 | G3 | U.S. Pat. No. 6,156,507 | SEQ ID NO.: 15 | S. epidermidis SCCmec type II MREJ |
| 34 | SH 518 | U.S. Pat. No. 6,156,507 | SEQ ID NO.: 16 | S. haemolyticus SCCmec type II MREJ |
| 35 | ATCC 25923 | U.S. Pat. No. 6,156,507 | SEQ ID NO.: 9 | S. aureus chromosome |
| 36 | STP23 | U.S. Pat. No. 6,156,507 | SEQ ID NO.: 10 | S. aureus chromosome |
| 37 | STP43 | U.S. Pat. No. 6,156,507 | SEQ ID NO.: 12 | S. aureus chromosome |
| 38 | STP53 | U.S. Pat. No. 6,156,507 | SEQ ID NO.: 13 | S. aureus chromosome |

TABLE 10-continued

Origin of the nucleic acids and/or sequences available from public databases found in the sequence listing

| SEQ ID NO. | Staphylococcal strain | Source | Accession number | Genetic Target[a,b] |
|---|---|---|---|---|
| 39 | 476 | Genome project[c] | | *S. aureus* chromosome |
| 40 | 252 | Genome project[c] | | SCCmec type II MREJ |
| 41 | COL | Genome project[d] | | SCCmec type I MREJ |
| 78 | NCTC 8325 | Database | X52593 | mecA |
| 82 | NCTC 10442 | Database | AB033763 | mecA |
| 90 | N315 | Database | D86934 | mecA |
| 91 | 85/2082 | Database | AB037671 | mecA |
| 92 | NCTC 10442 | Database | AB033763 | IS431 |
| 93 | N315 | Database | D86934 | IS431 |
| 94 | HUC19 | Database | AF181950 | IS431 |
| 95 | NCTC 8325 | Database | X53818 | IS431 |
| 104 | 85/2082 | Database | AB037671 | SCCmec type III MREJ |
| 226 | unknown | Database | L29436 | merB on plasmid pI258 |
| 227 | unknown | Database | L29436 | merR on plasmid pI258 |
| 228 | unknown | Database | S67449 | tetK on plasmid pT181 |
| 229 | HUC19 | Database | AF181950 | aadD on plasmid pUB110 |
| 230 | HUC19 | Database | AF181950 | rep on plasmid pUB110 |
| 231 | N315 | Database | AP003129 | orfSA0021, orfSA0022, orfSA0023 |
| 232 | 85/2082 | Database | AB037671 | ccrA/ccrB |

[a]MREJ refers to mec right extremity junction and includes sequences from SCCmec-right extremity and chromosomal DNA to the right of SCCmec integration site.
[b]Unless otherwise specified, all sequences were obtained from *S. aureus* strains.
[c]Sanger Institute genome project (http://www.sanger.ac.uk).
[d]TIGR genome project (http://www.tigr.org).

TABLE 11

Analytical sensitivity of the MRSA-specific PCR assay targeting MREP types i, ii and iii on a standard thermocycler using the set of primers developed in the present invention (SEQ ID NOs.: 64, 66 and 67)

| Strain designation: | | Detection limit |
|---|---|---|
| Original | CCRI[a] (MREP type) | (number of genome copies) |
| 13370 | CCRI-8894 (I) | 5 |
| ATCC 43300 | CCRI-175 (II) | 2 |
| 35290 | CCRI-1262 (III) | 2 |

[a]CCRI stands for "Collection of the Centre de Recherche en Infectiologie".

TABLE 12

Specificity and ubiquity tests performed on a standard thermocycler using the set of primers targeting MREP types i, ii and iii developed in the present invention (SEQ ID NOs.: 64, 66 and 67) for the detection of MRSA

| | PCR results for MREJ | |
|---|---|---|
| Strains | Positive (%) | Negative (%) |
| MRSA - 208 strains | 188 (90.4) | 20 (9.6) |
| MSSA - 252 strains | 13 (5.2) | 239 (94.8) |
| MRCNS - 41 strains* | 0 | 42 (100) |
| MSCNS - 21 strains* | 0 | 21 (100) |

*Details regarding CNS strains:
MRCNS:  *S. caprae* (2)
*S. cohni cohnii* (3)
*S. cohni urealyticum* (4)
*S. epidermidis* (8)
*S. haemolyticus* (9)
*S. hominis* (4)
*S. sciuri* (4)
*S. sciuri sciuri* (1)
*S. simulans* (3)
*S. warneri* (3)

MSCNS:  *S. cohni cohnii* (1)
*S. epidermidis* (3)
*S. equorum* (2)
*S. felis* (1)
*S. gallinarum* (1)
*S. haemolyticus* (1)
*S. hominis* (1)
*S. lentus* (1)
*S. lugdunensis* (1)
*S. saccharolyticus* (1)
*S. saprophyticus* (5)
*S. simulans* (1)
*S. warneri* (1)
*S. xylosus* (1)

TABLE 13

Percentage of sequence identity for the first 500 nucleotides of SCCmec right extremities between all 9 types of MREP[a,b]

| MREP type | i | ii | iii | iv | v | vi | vii | viii | ix |
|---|---|---|---|---|---|---|---|---|---|
| i | — | 79.2 | 42.8 | 42.8 | 41.2 | 44.4 | 44.6 | 42.3 | 42.1 |
| ii | | | 43.9 | 47.5 | 44.7 | 41.7 | 45.0 | 52.0 | 57.1 |
| iii | | | | 46.8 | 44.5 | 42.9 | 45.0 | 42.8 | 45.2 |
| iv | | | | | 45.8 | 41.4 | 44.3 | 48.0 | 41.3 |
| v | | | | | | 45.4 | 43.7 | 47.5 | 44.3 |
| vi | | | | | | | 45.1 | 41.1 | 47.2 |
| vii | | | | | | | | 42.8 | 40.9 |

TABLE 13-continued

Percentage of sequence identity for the first 500 nucleotides of SCCmec right extremities between all 9 types of MREP[a,b]

| MREP type | i | ii | iii | iv | v | vi | vii | viii | ix |
|---|---|---|---|---|---|---|---|---|---|
| viii | | | | | | | | | 55.2 |
| ix | | | | | | | | | — |

[a]"First 500 nucleotides" refers to the 500 nucleotides within the SCCmec right extremity, starting from the integration site of SCCmec in the *Staphylococcus aureus* chromosome as shown on FIG. 4.
[b]Sequences were extracted from SEQ ID NOs.: 1, 2, 104, 51, 50, 171, 165, 167, and 168 for types i to ix, respectively.

TABLE 14

Reference strains used to test sensitivity and/or specificity and/or ubiquity of the MRSA-specific PCR assays targeting MREJ sequences

| Staphylococcal species | Strains | Source[a] |
|---|---|---|
| MRSA (n = 45) | 33591 | ATCC |
| | 33592 | ATCC |
| | 33593 | ATCC |
| | BAA-38 | ATCC |
| | BAA-39 | ATCC |
| | BAA-40 | ATCC |
| | BAA-41 | ATCC |
| | BAA-42 | ATCC |
| | BAA-43 | ATCC |
| | BAA-44 | ATCC |
| | F182 | CDC |
| | 23 (CCUG 41787) | HARMONY Collection |
| | ID-61880 (EMRSA1) | LSPQ |
| | MA 8628 | LSPQ |
| | MA 50558 | LSPQ |
| | MA 50428 | LSPQ |
| | MA 50609 | LSPQ |
| | MA 50884 | LSPQ |
| | MA 50892 | LSPQ |
| | MA 50934 | LSPQ |
| | MA 51015 | LSPQ |
| | MA 51056 | LSPQ |
| | MA 51085 | LSPQ |
| | MA 51172 | LSPQ |
| | MA 51222 | LSPQ |
| | MA 51363 | LSPQ |
| | MA 51561 | LSPQ |
| | MA 52034 | LSPQ |
| | MA 52306 | LSPQ |
| | MA 51520 | LSPQ |
| | MA 51363 | LSPQ |
| | 98/10618 | HARMONY Collection |
| | 98/26821 | HARMONY Collection |
| | 24344 | HARMONY Collection |
| | 62305 | HARMONY Collection |
| | 90/10685 | HARMONY Collection |
| | 98/14719 | HARMONY Collection |
| | 97S99 | HARMONY Collection |
| | 97S100 | HARMONY Collection |
| | 825/96 | HARMONY Collection |
| | 842/96 | HARMONY Collection |
| | N8-890/99 | HARMONY Collection |
| | 9805-01937 | HARMONY Collection |
| | 1 | Kreiswirth-1 |
| | 29 | Kreiswirth-1 |
| MRCNS (n = 4) | 29060 | ATCC |
| | 35983 | ATCC |
| | 35984 | ATCC |
| | 2514 | LSPQ |
| MSSA (n = 28) | MA 52263 | LSPQ |
| | 6538 | ATCC |
| | 13301 | ATCC |
| | 25923 | ATCC |
| | 27660 | ATCC |
| | 29213 | ATCC |
| | 29247 | ATCC |
| | 29737 | ATCC |
| | RN 11 | CDC |
| | RN 3944 | CDC |
| | RN 2442 | CDC |
| | 7605060113 | CDC |
| | BM 4611 | Institut Pasteur |
| | BM 3093 | Institut Pasteur |
| | 3511 | LSPQ |
| | MA 5091 | LSPQ |
| | MA 8849 | LSPQ |
| | MA 8871 | LSPQ |
| | MA 50607 | LSPQ |
| | MA 50612 | LSPQ |
| | MA 50848 | LSPQ |
| | MA 51237 | LSPQ |
| | MA 51351 | LSPQ |
| | MA 52303 | LSPQ |
| | MA 51828 | LSPQ |
| | MA 51891 | LSPQ |
| | MA 51504 | LSPQ |
| | MA 52535 | LSPQ |
| | MA 52783 | LSPQ |
| MSCNS (n = 17) | 12228 | ATCC |
| | 14953 | ATCC |
| | 14990 | ATCC |
| | 15305 | ATCC |
| | 27836 | ATCC |
| | 27848 | ATCC |
| | 29070 | ATCC |
| | 29970 | ATCC |
| | 29974 | ATCC |
| | 35539 | ATCC |
| | 35552 | ATCC |
| | 35844 | ATCC |
| | 35982 | ATCC |
| | 43809 | ATCC |
| | 43867 | ATCC |
| | 43958 | ATCC |
| | 49168 | ATCC |

[a]ATCC stands for "American Type Culture Collection". LSPQ stands for "Laboratoire de Santé Publique du Québec". CDC stands for "Center for Disease Control and Prevention".

TABLE 15

Clinical isolates used to test the sensitivity and/or specificity and/or ubiquity of the MRSA-specific PCR assays targeting MREJ sequences

| Staphylococcal species | Number of strains | Source |
|---|---|---|
| MRSA (n = 177) | 150 | Canada |
| | 10 | China |
| | 10 | Denmark |
| | 9 | Argentina |
| | 1 | Egypt |
| | 1 | Sweden |
| | 1 | Poland |
| | 3 | Japan |
| | 1 | France |
| MSSA (n = 224) | 208 | Canada |
| | 10 | China |
| | 4 | Japan |
| | 1 | USA |
| | 1 | Argentina |
| MRCNS (n = 38) | 32 | Canada |
| | 3 | China |
| | 1 | France |

TABLE 15-continued

Clinical isolates used to test the sensitivity and/or specificity and/or ubiquity of the MRSA-specific PCR assays targeting MREJ sequences

| Staphylococcal species | Number of strains | Source |
|---|---|---|
| | 1 | Argentina |
| | 1 | USA |
| MSCNS (n = 17) | 14 | UK |
| | 3 | Canada |

TABLE 16

Analytical sensitivity of tests performed on a standard thermocycler using the set of primers targeting MREP types i, ii, iii, iv and v (SEQ ID NOs.: 64, 66, 67, 79 and 80) developed in the present invention for the detection and identification of MRSA

| Staphylococcus aureus strain designation: | | Detection limit |
|---|---|---|
| Original | CCRI[a] (MREP type) | (number of genome copies) |
| 13370 | CCRI-8894 (i) | 10 |
| ATCC 43300 | CCRI-175 (ii) | 5 |
| 9191 | CCRI-2086 (ii) | 10 |
| 35290 | CCRI-1262 (iii) | 5 |
| 352 | CCRI-1266 (iii) | 10 |
| 19121 | CCRI-8895 (iv) | 5 |
| ATCC 33592 | CCRI-178 (iv) | 5 |
| MA 50428 | CCRI-1311 (v) | 5 |
| R991282 | CCRI-2025 (v) | 5 |

[a]CCRI stands for "Collection of the Centre de Recherche en Infectiologie".

TABLE 17

Specificity and ubiquity tests performed on a standard thermocycler using the set of primers targeting MREP types i, ii, iii, iv and v (SEQ ID NO.: 64, 66, 67, 79 and 80) developed in the present invention for the detection and identification of MRSA

| | PCR results for SCCmec - orfX right extremity junction | |
|---|---|---|
| Strains | Positive (%) | Negative (%) |
| MRSA - 35 strains[a] | 27 (77.1) | 8 (22.9) |
| MSSA - 44 strains | 13 (29.5) | 31 (70.5) |
| MRCNS - 9 strains* | 0 | 9 (100) |
| MSCNS - 10 strains* | 0 | 10 (100) |

[a]MRSA strains include the 20 strains listed in Table 3.
*Details regarding CNS strains:
MRCNS: S. caprae (1)
S. cohni cohnii (1)
S. epidermidis (1)
S. haemolyticus (2)
S. hominis (1)
S. sciuri (1)
S. simulans (1)
S. warneri (1)
MSCNS: S. cohni (1)
S. epidermidis (1)
S. equorum (1)
S. haemolyticus (1)
S. lentus (1)
S. lugdunensis (1)
S. saccharolyticus (1)
S. saprophyticus (2)
S. xylosus (1)

TABLE 18

Analytical sensitivity of tests performed on the Smart Cycler ® thermocycler using the set of primers targeting MREP types i, ii, iii, iv and v (SEQ ID NOs.: 64, 66, 67, 79 and 80) and molecular beacon probe (SEQ ID NO.: 84) developed in the present invention for the detection and identification of MRSA

| Staphylococcus aureus strain designation: | | Detection limit |
|---|---|---|
| Original | CCRI[a] (MREP type) | (number of genome copies) |
| 13370 | CCRI-8894 (i) | 2 |
| ATCC 43300 | CCRI-175 (ii) | 2 |
| 9191 | CCRI-2086 (ii) | 10 |
| 35290 | CCRI-1262 (iii) | 2 |
| 352 | CCRI-1266 (iii) | 10 |
| ATCC 33592 | CCRI-178 (iv) | 2 |
| MA 51363 | CCRI-1331 (iv) | 5 |
| 19121 | CCRI-8895 (iv) | 10 |
| Z109 | CCRI-8903 (iv) | 5 |
| 45302 | CCRI-1263 (v) | 10 |
| MA 50428 | CCRI-1311 (v) | 5 |
| MA 50609 | CCRI-1312 (v) | 5 |
| MA 51651 | CCRI-1325 (v) | 10 |
| 39795-2 | CCRI-1377 (v) | 10 |
| R991282 | CCRI-2025 (v) | 2 |

[a]CCRI stands for "Collection of the Centre de Recherche en Infectiologie".

TABLE 19

Specificity and ubiquity tests performed on the Smart Cycler ® thermocycler using the set of primers targeting MREP types i, ii, iii, iv and v (SEQ ID NO.: 64, 66, 67, 79 and 80) and molecular beacon probe (SEQ ID NO.: 84) developed in the present invention for the detection of MRSA

| | PCR results for MREJ | |
|---|---|---|
| Strains | Positive (%) | Negative (%) |
| MRSA - 29 strains[a] | 21 (72.4) | 8 (27.6) |
| MSSA - 35 strains | 13 (37.1) | 22 (62.9) |
| MRCNS - 14 strains | 0 | 14 (100) |
| MSCNS - 10 strains | 0 | 10 (100) |

[a]MRSA strains include the 20 strains listed in Table 3.
Details regarding CNS strains:
MRCNS: S. epidermidis (1)
S. haemolyticus (5)
S. simulans (5)
S. warneri (3)
MSCNS: S. cohni cohnii (1)
S. epidermidis (1)
S. gallinarum (1)
S. haemolyticus (1)
S. lentus (1)
S. lugdunensis (1)
S. saccharolyticus (1)

TABLE 19-continued

Specificity and ubiquity tests performed on the Smart
Cycler ® thermocycler using the set of primers
targeting MREP types i, ii, iii, iv and v (SEQ ID
NO.: 64, 66, 67, 79 and 80) and molecular beacon
probe (SEQ ID NO.: 84) developed in the present invention
for the detection of MRSA

*S. saprophyticus* (2)
*S. xylosus* (1)

TABLE 20

Analytical sensitivity of tests performed on the Smart
Cycler ® thermocycler using the set of primers
targeting MREP types i, ii, iii, iv, v and vii (SEQ ID
NOs.: 64, 66, 67, 79 and 80) and molecular beacon probe
(SEQ ID NO.: 84) developed in the present invention for
the detection and identification of MRSA

| *Staphylococcus aureus* strain designation: | | Detection limit |
|---|---|---|
| Original | CCRI[a] (MREP type) | (number of genome copies) |
| 13370 | CCRI-8894 (i) | 2 |
| ATCC 43300 | CCRI-175 (ii) | 2 |
| 35290 | CCRI-1262 (iii) | 2 |
| ATCC 33592 | CCRI-178 (iv) | 2 |
| R991282 | CCRI-2025 (v) | 2 |
| SE-41-1 | CCRI-9771 (vii) | 2 |

[a]CCRI stands for "Collection of the Centre de Recherche en Infectiologie".

TABLE 21

Specificity and ubiquity tests performed on the Smart
Cycler ® thermocycler using the set of primers
targeting MREP types i, ii, iii, iv, vi and vii (SEQ
ID NOs.: 64, 66, 67, 79 and 80) and molecular beacon
probe (SEQ ID NO.: 84) developed in the present invention
for the detection and identification of MRSA

| | PCR results for MREJ | |
|---|---|---|
| Strains | Positive (%) | Negative (%) |
| MRSA - 23 strains[a] | 19 (82.6) | 4 (17.4) |
| MSSA - 25 strains | 13 (52) | 12 (48) |
| MRCNS - 26 strains | 0 | 26 (100) |
| MSCNS - 8 strains | 0 | 8 (100) |

[a]MRSA strains include the 20 strains listed in Table 3.
Details regarding CNS strains:

| MRCNS: | *S. capitis* (2) |
|---|---|
| | *S. caprae* (1) |
| | *S. cohnii* (1) |
| | *S. epidermidis* (9) |
| | *S. haemolyticus* (5) |
| | *S. hominis* (2) |
| | *S. saprophyticus* (1) |
| | *S. sciuri* (2) |
| | *S. simulans* (1) |
| | *S. warneri* (2) |
| MSCNS: | *S. cohni cohnii* (1) |
| | *S. epidermidis* (1) |
| | *S. haemolyticus* (1) |
| | *S. lugdunensis* (1) |
| | *S. saccharolyticus* (1) |
| | *S. saprophyticus* (2) |
| | *S. xylosus* (1) |

```
              Annex I: Strategy for the selection of specific
                     amplification primers for types i and ii MREP Derived
from SEQ   SEQ           Types i and ii MREP                      orfX
ID NO:     ID NO:    2324                       2358                   2607

2          234       TAT GTCAAAAATC ATGAACCTCA TTACTTATGA TA CCT TGTGCAGGCC GTTTGATCCG CC 1          235       TAT GTCAAAAATC ATGAACCTCA TTACTTATGA TA CCT TGTGCAGGCC GTTTGATCCG CC

17[a]      236       TAT GTCAAAAATC ATGAACCTCA TTACTTATGA TA CCT TGTGCAGGCC GTTTGATCCG CC

18[a]      237       TAT GTCAAAAATC ATGAACCTCA TTACTTATGA TA CCT TGTGCAGGCC GTTTCATCCG CC

19[a]      238       TAT GTCAAAAATC ATGAACCTCA TTACTTATGA TA CCT TGTGCAGGCC GTTTCATCCG CC

20[a]      239       TAT GTCAAAAATC ATGAACCTCA TTACTTATGA TA CCT TGTGCAGGCC GTTTGATCCG CC

21[a]      240       TAT GTCAAAAATC ATGAACCTCA TTACTTATGA TA CCT TGTGCAGGCC GTTTGATCCG CC

22[a]      241       TAT GTCAAAAATC ATGAACCTCA TTACTTATGA TA CCT TGTGCAGGCC GTTTGATCCG CC

23[a]      242       TAT GTCAAAAATC ATGAACCTCA TTACTTATGA TA CCT TGTGCAGGCC GTTTGATCCG CC

24[a]      243       TAT GTCAAAAATC ATGAACCTCA TTACTTATGA TA CCT TGTGCAGGCC GTTTGATCCG CC

25[a]      244       TAT GTCAAAAATC ATGAACCTCA TTACTTATGA TA CCT TGTGCAGGCC GTTTGATCCG CC

26[a]      245       TAT GTCAAAAATC ATGAACCTCA TTACTTATCA TA CCT TGTGCACGCC GTTTGATCCG CC

33[c]      246                                                  CtT gGTGtAaaCC aTTgGagCCa CC

34[c]      247                                                  CCT caTGCAatCC aTTTGATC
```

-continued

Annex I: Strategy for the selection of specific amplification primers for types i and ii MREP

| Derived from SEQ ID NO: | SEQ ID NO: | Types i and ii MREP | | orfX | |
|---|---|---|---|---|---|
| | | 2324 | 2358 | | 2607 |

Selected sequence for type i MREP and ii primer

| (SEQ ID NO: 66) | 248 | GTCAAAAATC ATGAACCTCA TTACTTATG | | | |

Selected sequence for orfX primer[b]

| (SEQ ID NO: 64) | 249 | | | TGTGCAGGCC GTTTGATCC | |

The sequence positions refer to SEQ ID NO: 2.
Nucleotides in capitals are identical to the selected sequences or match those sequences. Mismatches are indicated by lower-case letters. Dots indicate gaps in the displayed sequences.
[a]These sequences are the reverse-complements of SEQ ID NOs.: 17-25.
[b]This sequence is the reverse-complement of the selected primer.
[c]SEQ ID NOs.: 33 and 34 were obtained from CNS species.

Annex II: Strategy for the selection of a specific molecular beacon probe for the real-time detection of MREJ

| SEQ ID NO: | SEQ ID NO: | orfX | |
|---|---|---|---|
| | | 327 | 371 |
| 165 | 250 | ACAAG GACGT CTTACAACGC AGTAACTAtG CACTA | |
| 180 | 251 | ACAAG GACGT CTTACAACGC AGTAACTAtG CACTA | |
| 181 | 252 | ACAAG GACGT CTTACAACGC AGTAACTAtG CACTA | |
| 182 | 253 | ACAAG GACGT CTTACAACGC AGThACTAtG CACTA | |
| 183 | 254 | ACAAG GACGT CTTACAACGC AGTAACTAtG CACTA | |
| 184 | 255 | ACAAG GACGT CTTACAACGC AGTAACTAtG CACTA | |
| 186 | 256 | ACAAG GACGT CTTACAACGC AGTAACTAtG CACTA | |
| 174 | 257 | ACAAG GACGT CTTACAACGt AGTAACTACG CACTA | |
| 175 | 258 | ACAAG GACGT CTTACAACGt AGTAACTACG CACTA | |
| 178 | 259 | ACAAG GACGT CTTACAACGt AGTAACTACG CACTA | |
| 176 | 260 | ACAAG GACGT CTTACAACGt AGTAACTACG CACTA | |
| 173 | 261 | ACAAG GACGT CTTACAACGt AGTAACTACG CACTA | |
| 177 | 262 | ACAAG GACGT CTTACAACGt AGTAACTACG CACTA | |
| 169 | 263 | ACAAG GACGT CTTACAACGC AGTAACTACG CACTA | |
| 199 | 264 | ACAAG GACGT CTTACAACGC AGTAACTACG CACTA | |
| 33[a,b] | 265 | ACcAa GACGT CTTACAACGC AGcAACTAtG CACTA | |
| 34[a,b] | 266 | AtgAG GACGT CTTACAACGC AGcAACTACG CACTt | |

-continued

Annex II: Strategy for the selection of a specific molecular beacon probe for the real-time detection of MREJ

| SEQ ID NO: | SEQ ID NO: | orfX | |
|---|---|---|---|
| | | 327 | 371 |

Selected sequence for orfX molecular beacon probes (SEQ ID NO: 163)[c]  267     GACGT CTTACAACGC AGTAACTAtG (SEQ ID NO: 164)[c]  268     GACGT CTTACAACGt AGTAACTACG (SEQ ID NO: 84)[c]   269     GACGT CTTACAACGC AGcAACTACG Nucleotide discrepancies between the orfX sequences and SEQ ID NO.: 84 are shown in lower-case. Other entries in the sequence listing also present similar variations. The stem of the molecular beacon probes are not shown for sake of clarity. The sequence positions refer to SEQ ID NO.: 165.
[a]These sequences are the reverse-complements of SEQ ID NOs.: 33 and 34.
[b]SEQ ID NOs.: 33 and 34 were obtained from CNS species.
[c]The sequences presented are the reverse-complement of the selected molecular beacon probes.

What is claimed is:

1. A method to detect the presence of a methicillin-resistant *Staphylococcus aureus* (MRSA) strain in a specimen, comprising:

obtaining a sample from said specimen to be analyzed for the presence of a MRSA strain that includes an SCCmec insert containing a mecA gene, said SCCmec being inserted into chromosomal DNA, thereby generating a polymorphic right extremity junction (MREJ) region sequence that includes sequence from both the SCCmec insert right extremity and chromosomal DNA adjoining that right extremity;

contacting the sample with at least two primers, wherein the at least two primers amplify the MREJ region sequence of at least one of SEQ ID NOs: 42, 43, 44, 45, 46, 51, 47, 48, 49, 50, 171, 165, 166, 167 and/or 168 under conditions of 50 mM KCl, 10 mM Tris-HCl (pH 9.0), 0.1% Triton X-100, 2.5 mM $MgCl_2$ at 55° C., and wherein said contacting takes place under annealing conditions wherein an amplicon is produced if any of said SEQ ID NOs are present in said sample, thereby generating an amplicon if a MRSA strain of at least one of MREJ types iv-ix is present in the sample; and detecting said amplicon as indicative of the presence of a MRSA strain in said specimen.

2. The method of claim 1, wherein said at least two primers further include at least two primers that amplify the MREJ region sequence of any one of SEQ ID NOs: 1, 20, 21, 22, 23, 24, 25, 41, 199, 2, 17, 18, 19, 26, 40, 173, 174, 175, 176, 177, 178, 179, 180, 181, 182, 183, 185, 186, 197, 4, 5, 6, 7, 8, 9, 10, 11, 12, 13, 14, 15, 16, 104, 184, and 198 under conditions of 50 mM KCl, 10 mM Tris-HCl (pH 9.0), 0.1% Triton X-100, 2.5 mM $MgCl_2$, at 55° C.

3. The method of claim 1, wherein said at least two primers include SEQ ID NO: 64 and at least one of the following primers: SEQ ID NO: 79 for the detection of MREJ type iv; SEQ ID NO: 80 for the detection of MREJ type v; SEQ ID NO: 204 for the detection of MREJ type vi; SEQ ID NO: 112 for the detection of MREJ type vii; SEQ ID NO: 113 for the detection of MREJ type vii; SEQ ID NO: 115 for the detection of MREJ type viii; SEQ ID NO: 116 for the detection of MREJ type viii; and SEQ ID NO: 109 for the detection of MREJ type ix.

4. The method of claim 1, further comprising detecting the presence of SEQ ID NO: 172 as indicative of the presence of MREJ type x.

5. A method for classifying a MRSA strain comprising performing the method of claim 1 and determining which of SEQ ID NOs: 42, 43, 44, 45, 46, 51, 47, 48, 49, 50, 171, 165, 166, 167 and/or 168 is present in said sample, wherein the presence of any of SEQ ID NOs: 42-46 and 51 is indicative of MREJ type iv, the presence of any of SEQ ID NOs: 47-50 is indicative of MREJ type v, the presence of SEQ ID NO: 171 is indicative of the presence of MREJ type vi, the presence of either of SEQ ID NOs: 165 and 166 is indicative of the presence of MREJ type vii, the presence of SEQ ID NO: 167 is indicative of the presence of MREJ type viii, and the presence of SEQ ID NO: 168 is indicative of the presence of MREJ type ix.

* * * * *

(12) INTER PARTES REEXAMINATION CERTIFICATE (1209th)
United States Patent
Huletsky et al.

(10) Number: US 7,449,289 C1
(45) Certificate Issued: *Dec. 7, 2015

(54) **METHODS FOR DETECTION AND IDENTIFICATION OF METHICILLIN-RESISTANT *STAPHYLOCOCCUS AUREUS***

(75) Inventors: Ann Huletsky, Sillery (CA); Valery Rossbach, Gatineau (CA)

(73) Assignee: GENEOHM SCIENCES CANADA INC., Sainte-Foy, Quebec (CA)

Reexamination Request:
No. 95/001,599, Apr. 8, 2011

Reexamination Certificate for:
Patent No.: 7,449,289
Issued: Nov. 11, 2008
Appl. No.: 10/479,674
PCT Filed: Jun. 4, 2002
PCT No.: PCT/CA02/00082
§ 371 (c)(1),
(2), (4) Date: Sep. 7, 2004
PCT Pub. No.: WO02/099034
PCT Pub. Date: Dec. 12, 2002

( * ) Notice: This patent is subject to a terminal disclaimer.

(30) Foreign Application Priority Data

Jun. 4, 2001 (CA) .................................... 2348042

(51) Int. Cl.
*C12Q 1/68* (2006.01)
*C12P 19/34* (2006.01)
*C07H 21/04* (2006.01)

(52) U.S. Cl.
CPC .................................... *C12Q 1/689* (2013.01)

(58) Field of Classification Search
USPC .............................................................. 435/6
See application file for complete search history.

(56) References Cited

To view the complete listing of prior art documents cited during the proceeding for Reexamination Control Number 95/001,599, please refer to the USPTO's public Patent Application Information Retrieval (PAIR) system under the Display References tab.

*Primary Examiner* — Sharon Turner

(57) ABSTRACT

The present invention describes novel SCCmec right extremity junction sequences for the detection of methicillin-resistant Staphyloccocus aureus (MRSA). It relates to the use of these DNA sequences for diagnostic purposes.

INTER PARTES REEXAMINATION CERTIFICATE

THE PATENT IS HEREBY AMENDED AS INDICATED BELOW.

AS A RESULT OF REEXAMINATION, IT HAS BEEN DETERMINED THAT:

The patentability of claims 3-4 is confirmed.

Claims 1, 2 and 5 are cancelled.

\* \* \* \* \*

SEQUENCE LISTING

<160> NUMBER OF SEQ ID NOS: 233

<210> SEQ ID NO 1
<211> LENGTH: 3050
<212> TYPE: DNA
<213> ORGANISM: Staphylococcus aureus

<400> SEQUENCE: 1

```
tcgtgccatt gatgcagagg gacatacatt agatatttgg ttgcgtaagc aacgagataa      60
tcattcagca tatgcgttta tcaaacgtct cattaaacaa tttggtaaac ctcaaaaggt     120
aattacagat caggcacctt caacgaaggt agcaatggct aaagtaatta agcttttaa     180 acttaaacct gactgtcatt gtacatcgaa atatctgaat aacctcattg agcaagatca     240
ccgtcatatt aaagtaagaa agacaaggta tcaaagtatc aatacagcaa agaatacttt     300
aaaaggtatt gaatgtattt acgctctata taaaaagaac cgcaggtctc ttcagatcta     360
cggattttcg ccatgccacg aaattagcat catgctagca agttaagcga acactgacat     420
gataaattag tggttagcta tattttttta ctttgcaaca gaaccgaaaa taatctcttc     480
aatttatttt tatatgaatc ctgtgactca atgattgtaa tatctaaaga tttcagttca     540
tcatagacaa tgttcttttc aacatttttt atagcaaatt gattaaataa attctctaat     600
ttctcccgtt tgatttcact accatagatt atattatcat tgatatagtc aatgaataat     660
gacaaattat cactcataac agtcccaacc cctttatttt gatagactaa ttatcttcat     720
cattgtaaaa caaattacac cctttaaatt taactcaact taaatatcga caaattaaaa     780
aacaataaaa ttacttgaat attattcata atatattaac aactttatta tactgctctt     840
tatatataaa atcattaata attaaacaag ccttaaaata tttaactttt ttgtgattat     900
tacacattat cttatctgct ctttatcacc ataaaaatag aaaaaacaag attcctaaag     960
aatataggaa tcttgtttca gactgtggac aaactgattt tttatcagtt agcttattta    1020 gaaagttta tttaaattac agtttctatt tttattagat cacaatttta ttttagctct    1080
```

```
tgttcaagta atcattttc gccaaaaact ttatactgaa tagcttctac attaaatact    1140
ttgtcaatga gatcatctac atctttaaat tcagaataat ttgcatatgg atctataaaa    1200
taaaattgtg gttctttacc ggaaacatta aatattctta atattaaata tttctgctta    1260
tattctttca tagcaaacat ttcatttagc gacataaaaa atggttcctc aatactagaa    1320
gatgtagatg ttttaatttc aataaatttt tctacagctt tatctgtatt tgttggatca    1380
aaagctacta atcatagcc atgaccgtgt tgagagcctg gattatcatt taaaatattc    1440
ctaaactgtt cttcttatc ttcgtctatt ttattatcaa ttagctcatt aaagtaattt    1500
agcgctaatt tttctccaac tttaccggtt aatttattct ctttatttga tttttcaatt    1560
tctgaatcat ttttagtagt ctttgataca ccttttttat attttggaat tattcctta    1620 ggtgcttcca cttccttgag tgtcttatct ttttgtgctg ttctaatttc ttcaatttcg    1680
ctgtcttcct gtatttcgtc tatgctattg accaagctat cataggatgt ttttgtaact    1740
tttgaagcta attcattaaa tagttctaaa aatttcttta aatcctctag catatcttct    1800
tctgtgaatc cttcattcaa atcataatat ttgaatctta ttgatccatg agaatatcct    1860
gatggataat cattttttaa atcataagat gaatctttat tttctgcgta ataaaatctt    1920
ccagtattaa attcatttga tgtaatatat ttattgagtt cggaagataa agttaatgct    1980
ctttgttttg cagcattttt atcccgcgga aacatatcac ttatctttga ccatccttga    2040
ttcaaagata agtatatgcc ttctccttcc ggatgaaaaa gatataccaa ataatatcca    2100
tcctttgttt cttttgttat attctcatca tatattgaaa tccaaggaac tttactatag    2160
ttcccagtag caaccttccc tacaactgaa tatttatctt cttttatatg cacttttaac    2220
tgcttgggta acttatcatg gactaaagtt ttatatagat cacctttatc ccaatcagat    2280 ttttaacta cattattggt acgtttctct ttaattaatt taaggacctg cataaagttg    2340
tctatcattt gaaattccct cctattataa aatatattat gtctcatttt cttcaatatg    2400
tacttattta tattttaccg taatttacta tatttagttg cagaaagaat tttctcaaag    2460
ctagaacttt gcttcactat aagtattcag tataaagaat atttcgctat tatttacttg    2520
aaatgaaaga ctgcggaggc taactatgtc aaaaatcatg aacctcatta cttatgataa    2580
gcttctcctc gcataatctt aaatgctctg tacacttgtt caattaacac aacccgcatc    2640
atttgatgtg ggaatgtcat tttgctgaat gatagtgcgt agttactgcg ttgtaagacg    2700
tccttgtgca ggccgtttga tccgccaatg acgaaaacaa agtcgctttg cccttgggtc    2760
atgcgttggt tcaattcttg ggccaatcct tcggaagata gcatctttcc ttgtatttct    2820
aatgtaatga ctgtggattg tggtttgatt ttggctagta ttcgttggcc ttcttttct    2880 tttacttgct caatttcttt gtcactcata ttttctggtg cttttcgtc tggaacttct    2940 atgatgtcta tcttggtgta tgggcctaaa cgttttcat attctgctat ggcttgcttc    3000
caatatttct cttttagttt ccctacagct aaaatggtga ttttcatgtc                3050

<210> SEQ ID NO 2
<211> LENGTH: 3050
<212> TYPE: DNA
<213> ORGANISM: Staphylococcus aureus

<400> SEQUENCE: 2
acctcattga gcaagatcac cgtcatatta aagtaagaaa gacaaggtat caaagtatca      60
atacagcaaa gaatacttta aaaggtattg aatgtattta cgctctatat aaaaagaacc     120
```

-continued

```
gcaggtctct tcagatctac ggattttcgc catgccacga aattagcatc atgctagcaa        180
gttaagcgaa cactgacatg ataaattagt ggttagctat attttttttac tttgcaacag       240 aaccgaaaat aatctcttca atttatttttt atatgaatcc tgtgactcaa tgattgtaat      300
atctaaagat ttcagttcat catagacaat gttcttttca acatttttta tagcaaattg        360
attaaataaa ttctctaatt tctcccgttt gatttcacta ccatagatta tattatcatt        420
gatatagtca atgaataatg acaaattatc actcataaca gtcccaaccc ctttcttttg        480
atagactaat tatcttcatc attgtaaaac aaattcacac ctttaaattt aactcaactt       540
aaatatcgac aaattaaaaa acaataaaat tacttgaata ttattcataa tatattaaca       600
actttattat actgctcttt atatataaaa tcattaataa ttaaacaagc cttaaaatat       660 ttaactttttt tgtgattatt acacattatc ttatctgctc tttatcacca taaaaataga     720
aaaaacaaga ttcctaaaga ataggaat cttgtttcag actgtggaca aactgatttt         780
ttatcagtta gcttatttag aaagttttat ttaaattaca gtttctattt ttattagatc       840
acaattttat tttagctctt gttcaagtaa tcattttcg ccaaaaactt tatactgaat         900
agcttctaca ttaaatactt tgtcaatgag atcatctaca tctttaaatt cagaataatt       960
tgcatatgga tctataaaat aaaattgtgg ttctttaccg gaaacattaa atattcttaa      1020
tattaaatat ttctgcttat attctttcat agcaaacatt tcatttagcg ataaaaaaa       1080 tggttcctca atactagaag atgtagatgt tttaatttca ataaatttttt ctacagcttt    1140 atctgtatttt gttggatcaa aagctactaa atcatagcca tgaccgtgtt gagagcctgg    1200
attatcattt aaaatattcc taaactgttc tttcttatct tcgtctattt tattatcaat    1260
tagctcatta aagtaattta gcgctaattt ttctccaact ttaccggtta atttattctc    1320
tttatttgat ttttcaattt ctgaatcatt tttagtagtc tttgatacac cttttttata   1380
ttttggaatt attcctttag gtgcttccac ttccttgagt gtcttatctt tttgtgctgt    1440
tctaatttct tcaatttcgc tgtcttcctg tatttcgtct atgctattga ccaagctatc   1500
ataggatgtt tttgtaactt tgaagctaa ttcattaaat agttctaaaa atttctttaa    1560
atcctctagc atatcttctt ctgtgaatcc ttcattcaaa tcataatatt tgaatcttat   1620
tgatccatga gaatatcctg atggataatc attttttaaa tcataagatg aatctttatt    1680
ttctgcgtaa taaaatcttc cagtattaaa ttcatttgat gtaatatatt tattgagttc   1740
ggaagataaa gttaatgctc tttgttttgc agcattttta tcccgcggaa acatatcact    1800
tatctttgac catccttgat tcaaagataa gtatatgcct tctccttccg gatgaaaaag    1860
atataccaaa taatatccat cctttgtttc ttttgttata ttctcatcat atattgaaat    1920
ccaaggaact ttactatagt tcccagtagc aaccttccct acaactgaat atttatcttc    1980
ttttatatgc acttttaact gcttgggtaa cttatcatgg actaaagttt tatatagatc    2040
acctttatcc caatcagatt ttttaactac attattggta cgtttctctt taattaattt    2100
aaggacctgc ataaagttgt ctatcatttg aaattccctc ctattataaa atatattatg    2160
tctcattttc ttcaatatgt acttatttat attttaccgt aatttactat atttagttgc    2220
agaaagaatt ttctcaaagc tagaactttg cttcactata agtattcagt ataaagaata    2280
tttcgctatt atttacttga aatgaaagac tgcggaggct aactatgtca aaaatcatga    2340
acctcattac ttatgataag cttcttaaaa acataacagc aattcacata aacctcatat    2400
gttctgatac attcaaaatc cctttatgaa gcggctgaaa aaaccgcatc atttatgata    2460
tgcttctcca cgcataatct taaatgctct atacacttgc tcaattaaca caacccgcat    2520
```

| | |
|---|---:|
| catttgatgt gggaatgtca tttttgctgaa tgatagtgcg tagttactgc gttgtaagac | 2580 |
| gtccttgtgc aggccgtttg atccgccaat gacgaataca aagtcgcttt gcccttgggt | 2640 |
| catgcgttgg ttcaattctt gggccaatcc ttcggaagat agcatctttc cttgtatttc | 2700 |
| taatgtaatg actgtggatt gtggtttaat tttggctagt attcgttggc cttctttttc | 2760 |
| ttttacttgc tcaatttctt tgtcgctcat attttctggt gcttttcgt ctggaacttc | 2820 |
| tatgatgtct atcttggtgt atgggcctaa acgttttca tattctgcta tggcttgctt | 2880 |
| ccaatatttc tcttttagtt tccctacagc taaaatggtg attttcatgt cgtttggtcc | 2940 |
| tccaaattgt tatcaacttt ccagttatcc acaagttatt aacttgttca cactgttccc | 3000 |
| tcttattata ccaatatttt ttgcagtttt tgatattttc ctgacattta | 3050 |

```
<210> SEQ ID NO 3
<211> LENGTH: 3183
<212> TYPE: DNA
<213> ORGANISM: Staphylococcus aureus

<400> SEQUENCE: 3
```

| | |
|---|---:|
| ctgcagaggt aattattcca acaatacca ttgatttcaa aggagaaaga gatgacgtta | 60 |
| gaacgcgtga aacaaattta ggaaacgcga ttgcagatgc tatggaagcg tatggcgtta | 120 |
| agaatttctc taaaaagact gactttgccg tgacaaatgg tggaggtatt cgtgcctcta | 180 |
| tcgcaaaagg taaggtgaca cgctatgatt taatctcagt attaccattt ggaaatacga | 240 |
| ttgcgcaaat tgatgtaaaa ggttcagacg tctggacggc tttcgaacat agtttaggcg | 300 |
| caccaacaac acaaaaggac ggtaagacag tgttaacagc gaatggcggt ttactacata | 360 |
| tctctgattc aatccgtgtt tactatgata taaataaacc gtctggcaaa cgaattaatg | 420 |
| ctattcaaat tttaaataaa gagacaggta agtttgaaaa tattgattta aaacgtgtat | 480 |
| atcacgtaac gatgaatgac ttcacagcat caggtgcga cggatatagt atgttcggtg | 540 |
| gtcctagaga agaaggtatt tcattagatc aagtactagc aagttattta aaaacagcta | 600 |
| acttagctaa gtatgatacg acagaaccac aacgtatgtt attaggtaaa ccagcagtaa | 660 |
| gtgaacaacc agctaaagga caacaaggta gcaaaggtag taagtctggt aaagatacac | 720 |
| aaccaattgg tgacgacaaa gtgatggatc cagcgaaaaa accagctcca ggtaaagttg | 780 |
| ttttgttgct agcgcataga ggaactgtta gtagcggtac agaaggttct ggtcgcacaa | 840 |
| tagaaggagc tactgtatca agcaagagtg ggaaacaatt ggctagaatg tcagtgccta | 900 |
| aaggtagcgc gcatgagaaa cagttaccaa aaactggaac taatcaaagt tcaagcccag | 960 |
| aagcgatgtt tgtattatta gcaggtatag gtttaatcgc gactgtacga cgtagaaaag | 1020 |
| ctagctaaaa tatattgaaa ataatactac tgtatttctt aaataagagg tacggtagtg | 1080 |
| ttttttatg aaaaaagcg ataaccgttg ataaatatgg gatataaaaa cgaggataag | 1140 |
| taataagaca tcaaggtgtt tatccacaga atggggata gttatccaga attgtgtaca | 1200 |
| atttaaagag aaatacccac aatgcccaca gagttatcca caaatacaca ggttatacac | 1260 |
| taaaaatcgg gcataaatgt caggaaaata tcaaaaactg caaaaaatat tggtataata | 1320 |
| agagggaaca gtgtgaacaa gttaataact tgtggataac tggaaagttg ataacaattt | 1380 |
| ggaggaccaa acgacatgaa aatcaccatt ttagctgtag ggaaactaaa agagaaatat | 1440 |
| tggaagcaag cctagcagaa atatgaaaaa cgtttaggcc catacaccaa gatagacatc | 1500 |
| atagaagttc cagacgaaaa agcaccagaa aatatgagtg acaaagaaat tgagcaagta | 1560 |

-continued

```
aaagaaaaag aaggccaacg aatactagcc aaaatcaaac cacaatccac agtcattaca    1620
ttagaaatac aaggaaagat gctatcttcc gaaggattgg cccaagaatt gaaccaacgc    1680
atgacccaag ggcaaagcga ctttgttttc gtcattggcg gatcaaacgg cctgcacaag    1740
gacgtcttac aacgcagtaa ctacgcacta tcattcagca aaatgacatt cccacatcaa    1800
atgatgcggg ttgtgttaat tgaacaagtg tacagagcat ttaagattat gcgaggagag    1860
gcgtatcata gtaaaacta aaaaattctg tatgaggaga taataatttg gagggtgtta    1920
aatggtggac attaaatcca cgttcattca atatataaga tatatcacga taattgcgca    1980
tataacttaa gtagtagcta acagttgaaa ttaggcccta tcaaattggt ttatatctaa    2040
aatgattaat atagaatgct tcttttttgtc cttattaaat tataaaagta actttgcaat    2100
agaaacagtt atttcataat caacagtcat tgacgtagct aagtaatgat aaataatcat    2160
aaataaaatt acagatattg acaaaaaata gtaaatattc caatgaagtt tcaaaagaac    2220
aattccaaga aattgagaat gtaaataata aggtcaaaga attttattaa gatttgaaag    2280
agtatcaatc aagaaagatg tagttttttta ataaactatt tggaaaataa ttatcataat    2340
ttaaaaactg acaatttgcg agactcataa aatgtaataa tggaaataga gtaaaatat    2400 aattaagggg tgtaatatga agattaatat ttataaatct atttataatt ttcaggaaac    2460
aaatacaaat ttttttagaga atctagaatc tttaaatgat gacaattatg aactgcttaa    2520
tgataaagaa cttgttagtg attcaaatga attaaaatta attagtaaag tttatatacg    2580
taaaaaagac aaaaaactat tagattggca attattaata aagaatgtat acctagatac    2640
tgaagaagat gacaatttat tttcagaatc cggtcatcat tttgatgcaa tattatttct    2700
caaagaagat actacattac aaaataatgt atatatttata ccttttggac aagcatatca    2760
tgatataaat aatttgattg attatgactt cggaattgat tttgcagaaa gagcaatcaa    2820
aaatgaagac atagttaata aaaatgttaa ttttttttcaa caaaacaggc ttaaagagat    2880
tgttaattat agaaggaata gtgtagatta cgttagacct tcagaatctt atatatcagt    2940
ccaaggacat ccacagaatc ctcaaatttt tggaaaaaca atgacttgtg gtacaagtat    3000
ttcattgcgt gtaccgaata gaaagcagca attcatgat aaaattagtg tgataatcaa    3060
agaaataaac gctattatta atcttcctca aaaaattagt gaatttccta gaatagtaac    3120
tttaaaagac ttgaataaaa tagaagtatt agatacttta ttgctaaaaa aactatcgaa    3180
ttc                                                                  3183
```

<210> SEQ ID NO 4
<211> LENGTH: 479
<212> TYPE: DNA
<213> ORGANISM: Staphylococcus aureus

<400> SEQUENCE: 4

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaccat ttttcaacta    300 ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaaca    479
```

<210> SEQ ID NO 5
<211> LENGTH: 480
<212> TYPE: DNA
<213> ORGANISM: Staphylococcus aureus

<400> SEQUENCE: 5

```
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataac atgcctacga ttaataaaag gaagtttatt agattttgtg ttagaaacag     480
```

<210> SEQ ID NO 6
<211> LENGTH: 480
<212> TYPE: DNA
<213> ORGANISM: Staphylococcus aureus

<400> SEQUENCE: 6

```
ttcgtcattg gcggatcaaa cggcctgcac aaggacgtct tacaacgcag taactacgca      60
ctatcattca gcaaaatgac atccccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataca atgcctacga ttaataaaag gaagtttatt agatttgtgt tagaaacagt     480
```

<210> SEQ ID NO 7
<211> LENGTH: 480
<212> TYPE: DNA
<213> ORGANISM: Staphylococcus aureus

<400> SEQUENCE: 7

```
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataca atgcctacga ttaataaaag gaagtttatt agattttgtg ttagaaacag     480
```

<210> SEQ ID NO 8
<211> LENGTH: 309
<212> TYPE: DNA
<213> ORGANISM: Staphylococcus aureus
<220> FEATURE:

<221> NAME/KEY: misc_feature
<222> LOCATION: (237)..(237)
<223> OTHER INFORMATION: N = INOSINE

<400> SEQUENCE: 8

| | | | | | |
|---|---|---|---|---|---|
| ggcggatcaa | acggcctgca | caaggacgtc | ttacaacgca | gtaactacgc | actatcattc | 60 |
| agcaaaatga | cattcccaca | tcaaatgatg | cgggttgtgt | taattgaaca | agtgtacaga | 120 |
| gcatttaaga | ttatgcgtgg | agaagcgtat | cataaataaa | actaaaaatt | aggttgtgta | 180 |
| taatttaaaa | atctaatgag | atgtggagga | attacatata | tgaaatattg | gattatncct | 240 |
| tgcaatatca | tacgatgttt | atagagtgtt | aataaaacca | ttttttcaact | attgatgatc | 300 |
| tacaatata | | | | | | 309 |

<210> SEQ ID NO 9
<211> LENGTH: 471
<212> TYPE: DNA
<213> ORGANISM: Staphylococcus aureus

<400> SEQUENCE: 9

| | | | | | |
|---|---|---|---|---|---|
| ttggcggatc | aaacggcctg | cacaaggacg | tcttacaacg | cagtaactac | gcactatcat | 60 |
| tcagcaaaat | gacattccca | catcaaatga | tgcgggttgt | gttaattgaa | caagtgtaca | 120 |
| gagcatttaa | gattatgcgt | ggagaagcgt | atcataaata | aaactaaaaa | ttaggttgtg | 180 |
| tataatttaa | aaatttaatg | agatgtggag | gaattacata | tatgaaatat | tggattatac | 240 |
| cttgcaatat | catacgatgt | tttatagagtg | tttaataaac | catttttcaa | ctattgatga | 300 |
| tctagaatat | ataataactg | tacaaattat | attgattatg | aactacaat | taaattaaga | 360 |
| aattgatgat | gaaattttaa | atttaaacta | atggaatcaa | gaaagaatga | aaggaaatat | 420 |
| acaatgccta | cgattaataa | aaggaagttt | attagatttt | gtgttagaaa | c | 471 |

<210> SEQ ID NO 10
<211> LENGTH: 480
<212> TYPE: DNA
<213> ORGANISM: Staphylococcus aureus

<400> SEQUENCE: 10

| | | | | | |
|---|---|---|---|---|---|
| ttcgtcattg | gcggatcaaa | cggcctgcac | aaggacgtct | tacaacgcag | taactacgca | 60 |
| ctatcattca | gcaaaatgac | attcccacat | caaatgatgc | gggttgtgtt | aattgaacaa | 120 |
| gtgtacagag | catttaagat | tatgcgtgga | gaagcgtatc | ataaataaaa | ctaaaaatta | 180 |
| ggttgtgtat | aatttaaaaa | tttaatgaga | tgtggaggaa | ttacatatat | gaaatattgg | 240 |
| attatacctt | gcaatatcat | acgatgttta | tagagtgttt | aataaaccat | ttttcaacta | 300 |
| ttgatgatct | agaatatata | ataactgtac | aaattatatt | gattatggaa | ctacaattaa | 360 |
| attaagaaat | tgatgatgaa | attttaaatt | taaactaatg | gaatcaagaa | agaatgaaag | 420 |
| gaaatataca | atgcctacga | ttaataaaag | gaagtttatt | agattttgtg | ttagaaacag | 480 |

<210> SEQ ID NO 11
<211> LENGTH: 480
<212> TYPE: DNA
<213> ORGANISM: Staphylococcus aureus

<400> SEQUENCE: 11

| | | | | | |
|---|---|---|---|---|---|
| ttcgtcattg | gcggatcaaa | cggcctgcac | aaggacgtct | tacaacgcag | taactacgca | 60 |
| ctatcattca | gcaaaatgac | attcccacat | caaatgatgc | gggttgtgtt | aattgaacaa | 120 |
| gtgtacagag | catttaagat | tatgcgtgga | gaagcgtatc | ataaataaaa | ctaaaaatta | 180 |

```
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa atttttaaatt taaactaatg gaatcaagaa agaatgaaag    420
gaaatataca atgcctacga ttaataaaag gaagtttatt agattttgtg ttagaaacag    480

<210> SEQ ID NO 12
<211> LENGTH: 480
<212> TYPE: DNA
<213> ORGANISM: Staphylococcus aureus

<400> SEQUENCE: 12
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaacag    480

<210> SEQ ID NO 13
<211> LENGTH: 478
<212> TYPE: DNA
<213> ORGANISM: Staphylococcus aureus

<400> SEQUENCE: 13
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaac    478

<210> SEQ ID NO 14
<211> LENGTH: 479
<212> TYPE: DNA
<213> ORGANISM: Staphylococcus aureus

<400> SEQUENCE: 14
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
```

```
attaagaaat tgatgatgaa attttaaatt taaactaatg gaatcaagaa agaatgaaag      420
gaaatataca atgcctacga ttaataaaag gaagtttatt agattttgtg ttagaaaca       479
```

<210> SEQ ID NO 15
<211> LENGTH: 480
<212> TYPE: DNA
<213> ORGANISM: Staphylococcus aureus
<220> FEATURE:
<221> NAME/KEY: misc_feature
<222> LOCATION: (406)..(406)
<223> OTHER INFORMATION: N = INOSINE

<400> SEQUENCE: 15

```
ttcgtcattg gcggatcaaa cggcctgcac aaggacgtct tacaacgcag taactacgca      60
ctatcattca gcaaaatgac attcccacat caaatgatgc gggttgtgtt aattgaacaa      120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240 attataccttt gcaatatcat acgatgttta tagagtgttt aataaaccat ttttcaacta    300
ttgatgatct agaatatata ataactgtac aaattatatt gattatggaa ctacaattaa     360
attaagaaat tgatgatgaa attttaaatt taaactaatg gaatcncgaa agaatgaaag     420
gaaatataca atgcctacga ttaataaaag gaagtttatt agattttgtg ttagaaacag    480
```

<210> SEQ ID NO 16
<211> LENGTH: 480
<212> TYPE: DNA
<213> ORGANISM: Staphylococcus aureus

<400> SEQUENCE: 16

```
ttcgtcattg gcggatcaaa cggcctgcac aaggacgtct tacaacgcag taactacgca      60
ctatcattca gcaaaatgac attcccacat caaatgatgc gggttgtgtt aattgaacaa      120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240 attataccttt gcaatatcat acgatgttta tagagtgttt aataaaccat ttttcaacta    300
ttgatgatct agaatatata ataactgtac aaattatatt gattatggaa ctacaattaa     360
attaagaaat tgatgatgaa attttaaatt taaactaatg gaatcaagaa agaatgaaag     420
gaaatataca atgcctacga ttaataaaag gaagtttatt agattttgtg ttagaaacag    480
```

<210> SEQ ID NO 17
<211> LENGTH: 480
<212> TYPE: DNA
<213> ORGANISM: Staphylococcus aureus

<400> SEQUENCE: 17

```
ttcgtcattg gcggatcaaa cggcctgcac aaggacgtct tacaacgcag taactacgca      60
ctatcattca gcaaaatgac attcccacat caaatgatgc gggttgtgtt aattgaacaa      120
gtgtacagag catttaagat tatgcgtgga gaagcatatc ataaatgatg cggttttttc    180
agccgcttca taagggatt tgaatgtat cagaacatat gaggtttatg tgaattgctg      240
ttatgttttt aagaagctta tcataagtaa tgaggttcat gattttttgac atagttagcc    300 tccgcagtct ttcatttcaa gtaaataata gcgaaatatt ctttatactg aatacttata     360
gtgaagcaaa gttctagctt tgagaaaatt ctttctgcaa ctaaatatag taaattacgg      420
taaaatataa ataagtacat attgaagaaa atgagacata atatattta taataggagg      480
```

<210> SEQ ID NO 18
<211> LENGTH: 480
<212> TYPE: DNA
<213> ORGANISM: Staphylococcus aureus

<400> SEQUENCE: 18

```
ttcgtcattg gcggatcaaa cggcctgcac aaggacgtct tacaacgcag taactacgca      60
ctatcattca gcaaaatgac attcccacat caaatgatgc gggttgtgtt aattgagcaa     120
gtgtatagag catttaagat tatgcgtgga gaagcatatc ataaatgatg cggttttttc     180
agccgcttca taagggatt ttgaatgtat cagaacatat gaggtttatg tgaattgctg     240
ttatgttttt aagaagctta tcataagtaa tgaggttcat gatttttgac atagttagcc     300
tccgcagtct ttcatttcaa gtaaataata gcgaaatatt ctttatactg aatacttata     360
gtgaagcaaa gttctagctt tgagaaaatt ctttctgcaa ctaaatatag taaattacgg     420
taaaatataa ataagtacat attgaagaaa atgagacata atatattta taataggagg     480
```

<210> SEQ ID NO 19
<211> LENGTH: 458
<212> TYPE: DNA
<213> ORGANISM: Staphylococcus aureus

<400> SEQUENCE: 19

```
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcatatc ataaatgatg cggttttttc     180
agccgcttca taagggatt ttgaatgtat cagaacatat gaggtttatg tgaattgctg     240
ttatgttttt aagaagctta tcataagtaa tgaggttcat gatttttgac atagttagcc     300
tccgcagtct ttcatttcaa gtaaataata gcgaaatatt ctttatactg aatacttata     360
gtgaagcaaa gttctagctt tgagaaaatt ctttctgcaa ctaaatatag taaattacgg     420
taaaatataa ataagtacat attgaagaaa atgagaca                             458
```

<210> SEQ ID NO 20
<211> LENGTH: 385
<212> TYPE: DNA
<213> ORGANISM: Staphylococcus aureus

<400> SEQUENCE: 20

```
ttcgtcattg gcggatcaaa cggcctgcac aaggacgtct tacaacgcag taactacgca      60
ctatcattca gcaaaatgac attcccacat caaatgatgc gggttgtgtt aattgagcaa     120
gtgtatagag catttaagat tatgcgtgga gaagcttatc ataagtaatg aggttcatga     180
tttttgacat agttagcctc cgcagtcttt catttcaagt aaataatagc gaaatattct     240
ttatactgaa tacttatagt gaagcaaagt tctagctttg agaaaattct ttctgcaact     300
aaatatagta aattacggta aaatataaat aagtacatat tgaagaaaat gagacataat     360
atattttata ataggaggga atttc                                           385
```

<210> SEQ ID NO 21
<211> LENGTH: 385
<212> TYPE: DNA
<213> ORGANISM: Staphylococcus aureus

<400> SEQUENCE: 21

```
ttcgtcattg gcggatcaaa cggcctgcac aaggacgtct tacaacgcag taactacgca    60
ctatcattca gcaaaatgac attcccacat caaatgatgc gggttgtgtt aattgagcaa   120
gtgtatagag catttaagat tatgcgtgga gaagcttatc ataagtaatg aggttcatga   180
tttttgacat agttagcctc cgcagtcttt catttcaagt aaataatagc gaaatattct   240
ttatactgaa tacttatagt gaagcaaagt tctagctttg agaaaattct ttctgcaact   300
aaatatagta aattacggta aaatataaat aagtacatat tgaagaaaat gagacataat   360
atattttata ataggaggga atttc                                         385
```

<210> SEQ ID NO 22
<211> LENGTH: 385
<212> TYPE: DNA
<213> ORGANISM: Staphylococcus aureus

<400> SEQUENCE: 22

```
ttcgtcattg gcggatcaaa cggcctgcac aaggacgtct tacaacgcag taactacgca    60
ctatcattca gcaaaatgac attcccacat caaatgatgc gggttgtgtt aattgagcaa   120
gtgtatagag catttaagat tatgcgtgga gaagcttatc ataagtaatg aggttcatga   180
tttttgacat agttagcctc cgcagtcttt catttcaagt aaataatagc gaaatattct   240
ttatactgaa tacttatagt gaagcaaagt tctagctttg agaaaattct ttctgcaact   300
aaatatagta aattacggta aaatataaat aagtacatat tgaagaaaat gagacataat   360
atattttata ataggaggga atttc                                         385
```

<210> SEQ ID NO 23
<211> LENGTH: 385
<212> TYPE: DNA
<213> ORGANISM: Staphylococcus aureus

<400> SEQUENCE: 23

```
ttcgtcattg gcggatcaaa cggcctgcac aaggacgtct tacaacgcag taactacgcg    60
ctatcattca gcaaaatgac attcccacat caaatgatgc gggttgtgtt aattgaacaa   120
gtgtacaaag catttaagat tatgcgagga gaagcttatc ataagtaatg aggttcatga   180
tttttgacat agttagcctc cgcagtctttt catttcaagt aaataatagc gaaatattct   240
ttatactgaa tacttatagt gaagcaaagt tctagctttg agaaaattct ttctgcaact   300
aaatatagta aattacggta aaatataaat aagtacatat tgaagaaaat gagacataat   360
atattttata ataggaggga atttc                                         385
```

<210> SEQ ID NO 24
<211> LENGTH: 340
<212> TYPE: DNA
<213> ORGANISM: Staphylococcus aureus

<400> SEQUENCE: 24

```
cgcagtaact acgcgctatc attcagcaaa atgacattcc cacatcaaat gatgcgggtt    60
gtgttagttg agcaagtgta catagcattt aagattatgc gaggagaagc ttatcataag   120
taatgaggtt catgattttt gacatagtta gcctccgcag tctttcattt caagtaaata   180
atagcgaaat attctttata ctgaatactt atagtgaagc aaagttctag ctttgagaaa   240
attctttctg caactaaata tagtaaatta cggtaaaata taaataagta catattgaag   300
aaaatgagac ataatatatt ttataatagg agggaatttc                         340
```

<210> SEQ ID NO 25
<211> LENGTH: 369
<212> TYPE: DNA
<213> ORGANISM: Staphylococcus aureus

<400> SEQUENCE: 25

| | | | | | |
|---|---|---|---|---|---|
| caaacggcct | gcacaaggac | gtcttacaac | gcagtaacta | cgcactatca | ttcagcaaaa | 60 |
| tgacattccc | acatcaaatg | atgcggttg | tgttaattga | acaagtgtac | agagcattta | 120 |
| agattatgcg | aggagaagct | tatcataagt | aatgaggttc | atgattttg | acatagttag | 180 |
| cctccgcagt | ctttcatttc | aagtaaataa | tagcgaaata | ttctttatac | tgaatactta | 240 |
| tagtgaagca | aagttctagc | tttgagaaaa | ttctttctgc | aactaaatat | agtaaattac | 300 |
| ggtaaaatat | aaataagtac | atattgaaga | aatgagaca | taatatattt | tataatagga | 360 |
| gggaatttc | | | | | 369 |

<210> SEQ ID NO 26
<211> LENGTH: 3050
<212> TYPE: DNA
<213> ORGANISM: Staphylococcus aureus

<400> SEQUENCE: 26

| | | | | | |
|---|---|---|---|---|---|
| aatttggtaa | acctcaaaag | gtaattacag | atcaggcacc | ttcaacgaag | gtagcaatgg | 60 |
| ctaaagtaat | taaagcttt | aaacttaaac | ctgactgtca | ttgtacatcg | aaatatctga | 120 |
| ataacctcat | tgagcaagat | caccgtcata | ttaaagtaag | aaagacaagg | tatcaaagta | 180 |
| tcaatacagc | aaagaatact | ttaaaaggta | ttgaatgtat | tcacgctcta | tataaaaaga | 240 |
| accgcaggtc | tcttcagatc | tacggatttt | cgccatgcca | cgaaattagc | atcatgctag | 300 |
| caagttaagc | gaacactgac | atgataaatt | agtggttagc | tatatttttt | tactttgcaa | 360 |
| cagaaccgaa | aataatctct | tcaatttatt | tttatatgaa | tcctgtgact | caatgattgt | 420 |
| aatatctaaa | gatttcagtt | catcatagac | aatgttcttt | tcaacatttt | ttatagcaaa | 480 |
| ttgattaaat | aaattctcta | atttctcccg | tttgatttca | ctaccataga | ttatattatc | 540 |
| attgatatag | tcaatgaata | atgacaaatt | atcactcata | acagtcccaa | ccccttttatt | 600 |
| ttgatagact | aattatcttc | atcattgtaa | aacaaattac | acccttaaa | tttaactcaa | 660 |
| cttaaatatc | gacaaattaa | aaaacaataa | aattacttga | atattattca | taatatatta | 720 |
| acaactttat | tatactgctc | tttatatata | aaatcattaa | taattaaaca | agccttaaaa | 780 |
| tatttaactt | ttttgtgatt | attacacatt | atcttatctg | ctcttatca | ccataaaaat | 840 |
| agaaaaaaca | agattcctaa | agaatatagg | aatcttgttt | cagactgtgg | acaaactgat | 900 |
| tttttatcag | ttagcttatt | tagaaagttt | tatttaaatt | acagtttcta | ttttttattag | 960 |
| atcacaattt | tattttagct | cttgttcaag | taatcattt | tcgccaaaaa | ctttatactg | 1020 |
| aatagcttct | acattaaata | cttgtcaatg | agatcatcta | catctttaaa | ttcagaataa | 1080 |
| ttcgcatatg | gatctataaa | ataaaattgt | ggttctttac | cggaaacatt | aaatattctt | 1140 |
| aatattaaat | atttctgctt | atattctttc | atagcaaaca | tttcatttag | cgacataaaa | 1200 |
| aatggttcct | caatactaga | agatgtagat | gttttaattt | caataaattt | ttctacagct | 1260 |
| ttatctgtat | ttgttggatc | aaaagctact | aaatcatagc | catgaccgtg | ttgagagcct | 1320 |
| ggattatcat | ttaaaatatt | cctaaactgt | tctttcttat | cttcgtctat | tttattatca | 1380 |
| attagctcat | taaagtaatt | tagcgctaat | ttttctccaa | ctttaccggt | taatttattc | 1440 |
| tctttatttg | attttcaat | ttctgaatca | ttttagtag | tctttgatac | acctttttta | 1500 |

```
tattttggaa ttattccttt aggtgcttcc acttccttga gtgtcttatc tttttgtgct      1560
gttctaattt cttcaatttc gctgtcttcc tgtatttcgt ctatgctatt gaccaagcta      1620
tcataggatg tttttgtaac ttttgaagct aattcattaa atagttctaa aaatttcttt      1680
aaatcctcta gcatatcttc ttctgtgaat ccttcattca atcataata tttgaatctt       1740 attgatccat gagaatatcc tgatggataa tcattttta aatcataaga tgaatcttta      1800
ttttctgcgt aataaaatct tccagtatta aattcatttg atgtaatata tttattgagt      1860
tcggaagata aagttaatgc tcttgttttt gcagcatttt tatcccgcgg aaacatatca     1920
cttatctttg accatccttg attcaaagat aagtatatgc cttctccttc cggatgaaaa     1980
agatatacca ataatgtcc atcctttgtt tcttttgtta tattctcatc atatattgaa       2040
atccaaggaa ctttactata gttcccagta gcaaccttcc ctacaactga atatttatct     2100
tcttttatat gcacttttaa ctgcttgggt aacttatcat ggactaaagt tttatataga    2160
tcacctttat cccaatcaga ttttttaact acattattgg tacgtttctc tttaattaat    2220
ttaaggacct gcataaagtt gtctatcatt tgaaattccc tcctattata aaatatatta    2280
tgtctcattt tcttcaatat gtacttattt atattttacc gtaatttact atatttagtt    2340
gcagaaagaa ttttctcaaa gctagaactt tgcttcacta aagtattca gtataaagaa      2400 tatttcgcta ttatttactt gaaatgaaag actgcggagg ctaactatgt caaaaatcat     2460
gaacctcatt acttatgata agcttcttaa aaacataaca gcaattcaca taaacctcat    2520
atgttctgat acattcaaaa tccctttatg aagcggctga aaaaaccgca tcatttatga    2580
tatgcttctc ctcgcataat cttaaatgct ctgtacactt gttcaattaa cacaacccgc    2640
atcatttgat gtgggaatgt catttgctg aatgatagtg cgtagttact gcgttgtaag     2700
acgtccttgt gcaggccgtt tgatccgcca atgacgaaaa caaagtcgct ttgcccttgg    2760
gtcatgcgtt ggttcaattc ttgggccaat ccttcggaag atagcatctt tccttgtatt    2820
tctaatgtaa tgactgtgga ttgtggtttg attttggcta gtattcgttg gccttcttt    2880 tcttttactt gctcaatttc tttgtcactc atatttctg gtgcttttc gtctggaact      2940 tctatgatgt ctatcttggt gtatgggcct aaacgttttt catattctgc tatggcttgc    3000
ttccaatatt tctcttttag ttccctaca gctaaaatgg tgattttcat                3050
```

<210> SEQ ID NO 27
<211> LENGTH: 657
<212> TYPE: DNA
<213> ORGANISM: Staphylococcus aureus

<400> SEQUENCE: 27

```
ccaccttcat atgacgtcta tccatttatg tatggcatga gtaacgaaga atataataaa       60
ttaaccgaag ataaaaaaga acctctgctc aacaagttcc agattacaac ttcaccaggt      120
tcaactcaaa aaatattaac agcaatgatt gggttaaata caaaacatt agacgataaa       180 acaagttata aaatcgatgg taaaggttgg caaaaagata atcttgggg tggttacaac      240 gttacaagat atgaagtggt aaatggtaat atcgacttaa acaagcaat agaatcatca       300 gataacattt tctttgctag agtagcactc gaattaggca gtaagaaatt tgaaaaaggc    360 atgaaaaac taggtgttgg tgaagatata ccaagtgatt atccatttta taatgctcaa     420
atttcaaaca aaaatttaga taatgaaata ttattagctg attcaggtta cggacaaggt     480
gaaatactga ttaacccagt acagatcctt tcaatctata gcgcattaga aaataatggc    540
aatattaacg cacctcactt attaaaagac acgaaaaaca aagtttggaa gaaaaatatt    600
```

-continued

| atttccaaag aaaatatcaa tctattaact gatggtatgc aacaagtcgt aaataaa | 657 |

<210> SEQ ID NO 28
<211> LENGTH: 782
<212> TYPE: DNA
<213> ORGANISM: Staphylococcus aureus

<400> SEQUENCE: 28

| caccttcata tgacgtctat ccatttatgt atggcatgag taacgaagaa tataataaat | 60 |
| taaccgaaga taaaaagaa cctctgctca acaagttcca gattacaact tcaccaggtt | 120 |
| caactcaaaa atattaaca gcaatgattg gttaaataa caaaacatta gacgataaaa | 180 |
| caagttataa atcgatggt aaaggttggc aaaaagataa atcttggggt ggttacaacg | 240 |
| ttacaagata tgaagtggta atggtaata tcgacttaaa acaagcaata gaatcatcag | 300 |
| ataacatttt ctttgctaga gtagcactcg aattaggcag taagaaattt gaaaaaggca | 360 |
| tgaaaaaact aggtgttggt gaagatatac caagtgatta tccatttat aatgctcaaa | 420 |
| tttcaaacaa aaatttagat aatgaaatat tattagctga ttcaggttac ggacaaggtg | 480 |
| aaatactgat taacccagta cagatccttt caatctatag cgcattagaa aataatggca | 540 |
| atattaacgc acctcactta ttaaaagaca cgaaaaacaa agtttggaag aaaaatatta | 600 |
| tttccaaaga aaatatcaat ctattaactg atggtatgca acaagtcgta aataaaacac | 660 |
| ataaagaaga tatttataga tcttatgcaa acttaattgg caaatccggt actgcagaac | 720 |
| tcaaaatgaa acaaggagaa actggcagac aaattgggtg gtttatatca tatgataaag | 780 |
| at | 782 |

<210> SEQ ID NO 29
<211> LENGTH: 744
<212> TYPE: DNA
<213> ORGANISM: Staphylococcus aureus

<400> SEQUENCE: 29

| tatgacgtct atccatttat gtatggcatg agtaacgaag aatataataa attaaccgaa | 60 |
| gataaaaaag aacctctgct caacaagttc cagattacaa cttcaccagg ttcaactcaa | 120 |
| aaatattaa cagcaatgat tgggttaaat aacaaaacat tagacgataa aacaagttat | 180 |
| aaaatcgatg gtaaaggttg gcaaaaagat aaatctttggg gtggttacaa cgttacaaga | 240 |
| tatgaagtgg taaatggtaa tatcgactta aaacaagcaa tagaatcatc agataacatt | 300 |
| ttctttgcta gagtagcact cgaattaggc agtaagaaat ttgaaaaagg catgaaaaaa | 360 |
| ctaggtgttg gtgaagatat accaagtgat tatccatttt ataatgctca aatttcaaac | 420 |
| aaaaatttag ataatgaaat attattagct gattcaggtt acggacaagg tgaaatactg | 480 |
| attaacccag tacagatcct ttcaatctat agcgcattag aaaataatgg caatattaac | 540 |
| gcacctcact tattaaaaga cacgaaaaac aaagtttgga gaaaaatat tatttccaaa | 600 |
| gaaaatatca atctattaac tgatggtatg caacaagtcg taaataaaac acataaagaa | 660 |
| gatatttata gatcttatgc aaacttaatt ggcaaatccg gtactgcaga actcaaaatg | 720 |
| aaacaaggag aaactggcag acaa | 744 |

<210> SEQ ID NO 30
<211> LENGTH: 652
<212> TYPE: DNA
<213> ORGANISM: Staphylococcus aureus

<400> SEQUENCE: 30

```
ccaccttcat atgacgtcta tccatttatg tatggcatga gtaacgaaga atataataaa      60
ttaaccgaag ataaaaaaga acctctgctc aacaagttcc agattacaac ttcaccaggt     120
tcaactcaaa aatattaac agcaatgatt gggttaaata caaaacatt agacgataaa      180
acaagttata aatcgatgg taaaggttgg caaaaagata atcttggggg tggttacaac     240
gttacaagat atgaagtggt aaatggtaat atcgacttaa acaagcaat agaatcatca     300
gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaatttaga taatgaaata ttattagctg attcaggtta cggacaaggt     480
gaaatactga ttaacccagt acagatcctt tcaatctata gcgcattaga aaataatggc    540
aatattaacg cacctcactt attaaaagac acgaaaaaca agtttggaa gaaaaatatt     600
atttccaaag aaaatatcaa tctattaact gatggtatgc aacaagtcgt aa           652
```

<210> SEQ ID NO 31
<211> LENGTH: 2436
<212> TYPE: DNA
<213> ORGANISM: Staphylococcus aureus

<400> SEQUENCE: 31

```
ccaccttcat atgacgtcta tccatttatg tatggcatga gtaacgaaga atataataaa      60
ttaaccgaag ataaaaaaga acctctgctc aacaagttcc agattacaac ttcaccaggt     120
tcaactcaaa aatattaac agcaatgatt gggttaaata caaaacatt agacgataaa      180
acaagttata aatcgatgg taaaggttgg caaaaagata atcttggggg tggttacaac     240
gttacaagat atgaagtggt aaatggtaat atcgacttaa acaagcaat agaatcatca     300
gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaatttaga taatgaaata ttattagctg attcaggtta cggacaaggt     480
gaaatactga ttaacccagt acagatcctt tcaatctata gcgcattaga aaataatggc    540
aatattaacg cacctcactt attaaaagac acgaaaaaca agtttggaa gaaaaatatt     600
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga acaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960
gttttattat gaattattaa taagtgctgt tacttctccc ttaaatacaa tttcttcatt   1020
ttcattgtat gttgaaagtg acactgtaac gagtccattt tcttttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgatacctt taaatctact   1260
ttgttctgct ttttctttat ctatatgcat atattgagga tcaaaagttg ttgcaaattg   1320
gataatttct tcttctgtaa tatgaaggct ttttgttttg aatgtttctc ctactataaa   1380
atcatcgtat ttcatatatg tctctctttc ttattcaaat taattttta gtatgtaaca   1440
```

-continued

```
tgttaaaggt aagtctaccg tcactgaaac gtaagactca cctctaactt tctattgaga    1500
caaatgcacc attttatctg cattgtctgt aaagatacca tcaactcccc aattagcaag    1560
ttggtttgca cgtgctggtt tgtttacagt ccatacgttc aattcataac ccgcttcttt    1620
taccattttt acttttgctt tagtaagttt ggcatcttca gtgtttacta ttttagcatt    1680
acagtaatct aaaagtgttc tccagtcttc acgaaacgaa gttgtatgga atataactgc    1740
tctgttatat tgtggcatga tttcttctgc aagtttaaca agcacaacat taaagcttga    1800
aatgagcact tcttgattct gatttaagtt tgttaattgt tcttccactt gcttaaccat    1860
acttttagaa agtgctagtc cattcggtcc agtaatacct tttaattcta catttaaatt    1920
catattatat tcatttgcta tttttactac atcatcgaaa gttggcaaat gttcatcttt    1980 gaattttca ccaaccaag atcctgcaga agcatcttta atttcatcat aattcaattc       2040
agttatttcc ccggacatat ttgtagtccg ttctaaataa tcatcatgaa tgataatcag    2100
ttgttcatct tttgtaattg caacatctaa ctccaaccag tttatacctt ctacttctga    2160
agcagcttta aatgatgcaa ttgtattttc cggagcttta ctaggtaatc ctctatgtcc    2220
atatacagtt agcatattac ctctccttgc atttttattt ttttaattaa cgtaactgta    2280
ttatcacatt aatcgcactt ttatttccat taaaaagaga tgaatatcat aaataaagaa    2340
gtcgatagat tcgtattgat tatggagtta atctacgtct catctcattt ttaaaaaatc    2400
atttatgtcc caagctccat tttgtaatca agtcta                              2436
```

<210> SEQ ID NO 32
<211> LENGTH: 36
<212> TYPE: DNA
<213> ORGANISM: Artificial
<220> FEATURE:
<223> OTHER INFORMATION: OLIGONUCLEOTIDE

<400> SEQUENCE: 32

```
cgcttgccac atcaaatgat gcgggttgtg caagcg                              36
```

<210> SEQ ID NO 33
<211> LENGTH: 336
<212> TYPE: DNA
<213> ORGANISM: Staphylococcus epidermidis

<400> SEQUENCE: 33

```
ctcattactt atgataagct tcttaaaaac ataacagcaa ttcacataaa cctcatatgt    60
tctgatacat tcaaaatccc tttatgaagc ggctgaaaaa accgcatcat ttatgatatg   120
cttcgcctct catgatctta aatgcgcgat aaatttgttc gatcaatatg acgcgcatat   180
ttggtgtggg aaggtcatat tgctaaaaga taaagcatag ttgctgcgtt gtaagacgtc   240
ttggtgtaaa ccattggagc cacctatgac aaatgtaaag tcgctttgac cttgtgtcat   300
gcgtgtttgt agttctttag cgagtccttc tgaaga                             336
```

<210> SEQ ID NO 34
<211> LENGTH: 260
<212> TYPE: DNA
<213> ORGANISM: Staphylococcus haemolyticus

<400> SEQUENCE: 34

```
ctcattactt atgataagct tcttaaaaac ataacagcaa tccacataaa cctcatatgt    60
tctgatacat tcaaaatccc tttatgaagc ggctgaaaaa accgcatcat ttatgatatg   120
```

```
cttccctcgc atgattttaa atgctctgta tacttgctcg attaagacaa cgcgcatcat    180
ttgatgtggg aatgtcattt tactgaatga aagtgcgtag ttgctgcgtt gtaagacgtc    240
ctcatgcaat ccatttgatc                                                260

<210> SEQ ID NO 35
<211> LENGTH: 225
<212> TYPE: DNA
<213> ORGANISM: Staphylococcus aureus

<400> SEQUENCE: 35
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaggcgtatc acaaataaaa ctaaaaatgg    180
agtaactatt aatatagtat aaattcaata tggtgataaa aacag                    225

<210> SEQ ID NO 36
<211> LENGTH: 225
<212> TYPE: DNA
<213> ORGANISM: Staphylococcus aureus

<400> SEQUENCE: 36
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaggcgtatc acaaataaaa ctaaaaatgg    180
agtaactatt aatatagtat aaattcaata tggtgataaa aacag                    225

<210> SEQ ID NO 37
<211> LENGTH: 225
<212> TYPE: DNA
<213> ORGANISM: Staphylococcus aureus

<400> SEQUENCE: 37
ttcgtcattg gcggatcaaa cggcctgcac aaggacgtct tacaacgtag taactacgca     60
ctatcattca gcaaaatgac atttccacat caaatgatgc gggttgtgtt aattgaacaa    120
gtgtacagag catttaagat tatgcgtgga gaggcgtatc ataagtaatg aggttcatga    180
tttttgacat agttagcctc cgcagtcttt caagtaaata atatc                    225

<210> SEQ ID NO 38
<211> LENGTH: 225
<212> TYPE: DNA
<213> ORGANISM: Staphylococcus aureus

<400> SEQUENCE: 38
ttcgtcattg gcggatcaaa cggcctgcac aaggacgtct tacaacgcag taactacgca     60
ctatcattta gcaaaatgac attcccacat caaatgatgc gggttgtgtt aattgaacaa    120
gtgtatagag catttaagat tatgcgtgga gaggcgtatc ataagtgatg cttgttagaa    180 tgattttttaa caatatgaaa tagctgtgga agctcaaaca tttgt                   225

<210> SEQ ID NO 39
<211> LENGTH: 1500
<212> TYPE: DNA
<213> ORGANISM: Staphylococcus aureus

<400> SEQUENCE: 39
tgagtctggt aaagatacac aaccaattgg taaagagaaa gtgatgaatc cagcgaaaca     60
```

```
accagcgaca ggtaaagttg tgttgttacc agcgcataga ggaactgtta gtagcggtac    120
agaaggttct gatcgcgcat tagaaggaac tgctgtatca agtaagagtg ggaaacaatt    180
ggctaacatg tcagcgccta aaggtagcgc acatgagaaa cagttaccaa aaactggaac    240
tgatcaaagt tcaagcccag cagcgatgtt tgtattagta acaggtatag gtttaatcgc    300
gactgtacga cgtagaaaag ctagctaaaa tatattgaaa acaatactac tgtatttctt    360
aaataagagg tacggtagtg ttttttttatg gaaaaaagct ataaccgttg ataaatatgg    420
gatataaaaa cggggataag taataagaca tcaaggtatt tatccacaga atgggggata    480
gttatccaga attgtgtaca atttaaagag aaatacccac aatgcccaca gagttatcca    540
caaatacaca agttatacac tgaaaattgg gcatgaatgt cagaaaaata tcaaaaactg    600
caaaaaaact tggtataata agagggaaaa gtgtgaacaa gttaataact tgtggataac    660
tggaaagttg ataacaattt ggaggaccaa acgacatgaa atcaccatt ttagctgtag     720 ggaaactaaa agagaaatat tggaagcaag ccatagcaga atatgaaaaa cgtttaggcc    780
catacaccaa gatagacatc atagaagtta cagacgaaaa agcaccagaa atatgagcg     840 acaaagaaat cgagcaagta aagaaaaag aaggccaacg aatactagcc aaaatcaaac     900
cacaatccac agtcattaca ttagaaatac aaggaaagat gctatcttcc gaaggattgg    960
cccaagaatt gaaccaacgc atgacccaag gcaaagcga ctttgtattc gtcattggcg     1020
gatcaaacgg cctgcacaag gacgtcttac aacgtagtaa ctacgcacta tcattcagca    1080
aaatgacatt tccacatcaa atgatgcggg ttgtgttaat tgaacaagtg tacagagcat    1140
ttaagattat gcgtggagaa gcttatcata aatgatgcgg tttttttcttg aaaaatttaa    1200 ttagatatta gaatcccttta atttatttga aaatcagaag tgagtaacaa tggtaagtga    1260
aatagttagt gcaataattg gaattatagg gatttattga gatgtatgga gatgcggggc    1320
atttatcgag tagattacaa ttagagcatg taggtgattt gctttttcat gcaagtaaag    1380
ataaactttt aaaaatccta taagaattta gaaactttag aataactaaa tattaaaaaa    1440
atatcgtatg aaagtgaaat taggatgaga gaccatagct aaattaaaaa ttttagcaaa    1500
```

<210> SEQ ID NO 40
<211> LENGTH: 1501
<212> TYPE: DNA
<213> ORGANISM: Staphylococcus aureus

<400> SEQUENCE: 40

```
ttgcacaacc aattggtaaa gacaaagtga tggatccagc gaaacaacca gcgccaagta     60
aagttgtatt gttgccagcg catagaggaa ctgttagtag tggtagagaa ggttctgatc    120
gcgcattgga aggaactgct gtatcaagta agagcgggaa acaattggct agcatgtcag    180
cgcctaaagg tagcacacat gagaagcagt taccaaaaac tggaactgat caaagttcaa    240
gcccagcagc gatgtttgta ttagtagcag gtataggttt aattgcgact gtacgacgta    300
gaaaagctag ctaaaatata ttgaaaacaa tactactgta tttcttaaac aagaggtacg    360
gtagtgtttt tttatgaaaa aaagctataa ccgttgataa atatgggata taaaaacggg    420
gataagtaat aagacatcaa ggtatttatc cacagaaatg gggatagtta tccagaattg    480
tgtacaattt aaagagaaat acccacaatg cccacagagt tatccacaaa tacacaggtt    540
atacactaaa aattgggcat gaatgtcaga aaaatatcaa aactgcaaa gaatattggt     600 ataataagag ggaacagtgt gaacaagtta ataacttgtg gataactgga aagttgataa    660
```

-continued

| | |
|---|---|
| caatttggag gaccaaacga catgaaaatc accattttag ctgtagggaa actaaaagag | 720 |
| aaatattgga agcaagccat agcagaatat gaaaaacgtt taggcccata caccaagata | 780 |
| gacatcatag aagttccaga cgaaaaagca ccagaaaata tgagcgacaa agaaattgag | 840 |
| caagtaaaag aaaagaagg ccaacgaata ctagccaaaa tcaaaccaca atcaacagtc | 900 |
| attacattag aaatacaagg aaagatgcta tcttccgaag gattggccca agaattgaac | 960 |
| caacgcatga cccaagggca aagcgacttt gtattcgtca ttggcggatc aaacggcctg | 1020 |
| cacaaggacg tcttacaacg cagtaactac gcactatcat tcagcaaaat gacattccca | 1080 |
| catcaaatga tgcgggttgt gttaattgaa caagtgtaca gagcatttaa gattatgcgt | 1140 |
| ggagaagcat atcataaatg atgcggtttt ttcagccgct tcataaaggg attttgaatg | 1200 |
| tatcagaaca tatgaggttt atgtgaattg ctgttatgtt tttaagaagc ttatcataag | 1260 |
| taatgaggtt catgattttt gacatagtta gcctccgcag tctttcattt caagtaaata | 1320 |
| atagcgaaat attctttata ctgaatactt atagtgaagc aaagttctag ctttgagaaa | 1380 |
| attctttctg caactaaata tagtaaatta cggtaaaata taaataagta catattgaag | 1440 |
| aaaatgagac ataatatatt ttataatagg agggaatttc aaatgataga caactttatg | 1500 |
| c | 1501 |

<210> SEQ ID NO 41
<211> LENGTH: 2480
<212> TYPE: DNA
<213> ORGANISM: Staphylococcus aureus

<400> SEQUENCE: 41

| | |
|---|---|
| aaaccgtctg gcaaacgaat taatgctatt caaattttaa ataaagagac aggtaagttt | 60 |
| gaaaatattg atttaaaacg tgtatatcac gtaacgatga atgacttcac agcatcaggt | 120 |
| ggcgacggat atagtatgtt cggtggtcct agagaagaag gtatttcatt agatcaagta | 180 |
| ctagcaagtt atttaaaaac agctaactta gctaagtatg atacgacaga accacaacgt | 240 |
| atgttattag gtaaaccagc agtaagtgaa caaccagcta aggacaacaa aggtagcaaa | 300 |
| ggtagtaagt ctggtaaaga tacacaacca attggtgacg acaaagtgat ggatccagcg | 360 |
| aaaaaaccag ctccaggtaa agttgtattg ttgctagcgc atagaggaac tgttagtagc | 420 |
| ggtacagaag gttctggtcg cacaatagaa ggagctactg tatcaagcaa gagtgggaaa | 480 |
| caattggcta aatgtcagt gcctaaaggt agcgcgcatg agaaacagtt accaaaaact | 540 |
| ggaactaatc aaagttcaag cccagaagcg atgtttgtat tattagcagg tataggttta | 600 |
| atcgcgactg tacgacgtag aaaagctagc taaaatatat tgaaataat actactgtat | 660 |
| ttcttaaata agaggtacgg tagtgttttt ttatgaaaaa aagcgataac cgttgataaa | 720 |
| tatgggatat aaaaacgagg ataagtaata agacatcaag gtgtttatcc acagaaatgg | 780 |
| ggatagttat ccagaattgt gtacaattta agagaaaata cccacaatgc ccacagagtt | 840 |
| acccacaaat acacaggtta tacactaaaa atcgggcata atgtcagga aaatatcaaa | 900 |
| aactgcaaaa atattggta taataagagg aacagtgtg aacaagttaa taacttgtgg | 960 |
| ataactggaa agttgataac aatttggagg accaaacgac atgaaaatca ccattttagc | 1020 |
| tgtagggaaa ctaaagaga aatattgaa gcaagccata gcagaatatg aaaaacgttt | 1080 |
| aggcccatac accaagatag acatcataga agttccagac gaaaaagcac cagaaaatat | 1140 |
| gagtgacaaa gaaattgagc aagtaaaaga aaaagaaggc caacgaatac tagccaaaat | 1200 |
| caaaccacaa tccacagtca ttacattaga aatacaagga aagatgctat cttccgaagg | 1260 |

```
attggcccaa gaattgaacc aacgcatgac ccaagggcaa agcgactttg ttttcgtcat   1320
tggcggatca aacggcctgc acaaggacgt cttacaacgc agtaactacg cactatcatt   1380
cagcaaaatg acattcccac atcaaatgat gcgggttgtg ttaattgaac aagtgtacag   1440
agcatttaag attatgcgag gagaagctta tcataagtaa tgaggttcat gattttttgac  1500 atagttagcc tccgcagtct ttcatttcaa gtaaataata gcgaaatatt ctttatactg   1560
aatacttata gtgaagcaaa gttctagctt tgagaaaatt ctttctgcaa ctaaatatag   1620
taaattacgg taaatataaa ataagtacat attgaagaaa atgagacata atatatttta   1680
taataggagg gaatttcaaa tgatagacaa ctttatgcag gtccttaaat taattaaaga   1740
gaaacgtacc aataatgtag ttaaaaaatc tgattgggat aaaggtgatc tatataaaac   1800
tttagtccat gataagttac ccaagcagtt aaaagtgcat ataaagaag ataaatattc    1860 agttgtaggg aaggttgcta ctgggaacta tagtaaagtt ccttggattt caatatatga   1920
tgagaatata acaaaagaaa caaggatgg atattatttg gtatatcttt ttcatccgga    1980
aggagaaggc atatacttat ctttgaatca aggatggtca aagataagtg atatgtttcc   2040
gcgggataaa aatgctgcaa acaaagagc attaactta tcttccgaac tcaataaata     2100
tattacatca aatgaattta atactggaag attttattac gcagaaaata aagattcatc   2160
ttatgattta aaaaatgatt atccatcagg atattctcat ggatcaataa gattcaaata   2220
ttatgatttg aatgaaggat tcacagaaga agatatgcta gaggatttaa agaaatttt    2280 agaactattt aatgaattag cttcaaaagt tacaaaaaca tcctatgata gcttggtcaa   2340
tagcatagac gaaatacagg aagacagcga aattgaagaa attagaacag cacaaaaaga   2400
taagacactc aaggaagtgg aagcacctaa aggaataatt ccaaaatata aaaaggtgt    2460 atcaaagact actaaaaatg                                                2480

<210> SEQ ID NO 42
<211> LENGTH: 1045
<212> TYPE: DNA
<213> ORGANISM: Staphylococcus aureus

<400> SEQUENCE: 42
ccagtttttt gtttaatgaa caaggtaaat tacgagataa tatttgaaga aaacaataaa     60
gtagagatgg atttccatat cctctttagt agcggttttt atctgtaagg tttattaata   120
attaaataaa taggcgggat agttatatat agcttattaa tgaaagaata tgattattaa   180
tttagtatta tattttaata ttaaaaagaa gatatgaaat aattattcat accttccacc   240
ttacaataat tagttttcaa tcgaatatta agattattag tagtcttaaa agttaagact   300
tccttatatt aatgacctaa tttattattt gcctcatgaa ttatcttttt atttctttga   360
tatgtcccaa accacatcgt gatatacact acaataaata ttatgatgaa actaataata   420
ttctcaaagt tcagatggaa ccaacctgct agaatagcga gtgggaagaa taggattatc   480
atcaatataa agtgaactac agtctgtttt gttatactcc aatcggtatc tgtaaatatc   540
aaattaccat aagtaaacaa aattccaatc aatgcccata gtgctacaca tattagcata   600
ataaccgctt cattaaagtt ttcataataa attttaccca taaagaatc tggatatagt    660 ggtacatatt tatcccttga aaaaaataag tgaagtaatg acagaaatca taagaccagt   720
gaacgcacct ttttgaacag cgtggaataa ttttttcata gtgagatgga ccattccatt   780
tgtttctaac ttcaagtgat caatgtaatt tagattgata atttctgatt ttgaaatacg   840
```

-continued

| | |
|---|---|
| cacgaatatt gaaccgacaa gctcttcaat ttggtaaagt cgctgataaa gttttaaagc | 900 |
| tttattattc attgttatcg catacctgtt tatcttctac tatgaactgt gcaatttgtt | 960 |
| ctagatcaat tgggtaaaca tgatggttct gttgcaaagt aaaaaaatat agctaaccac | 1020 |
| taatttatca tgtcagtgtt cgctt | 1045 |

<210> SEQ ID NO 43
<211> LENGTH: 1118
<212> TYPE: DNA
<213> ORGANISM: Staphylococcus aureus

<400> SEQUENCE: 43

| | |
|---|---|
| cagagcattt aagattatgc gtggagaagc gtaccacaaa tgatgcggtt ttttatccag | 60 |
| tttttgttt aatgaacaag gtaaattacg agataatatt tgaagaaaac aataaagtag | 120 |
| agatggattt ccatatcctc tttagtagcg gttttatct gtaaggttta ttaataatta | 180 |
| aataaatagg cgggatagtt atatatagct tattaatgaa agaatatgat tattaattta | 240 |
| gtattatatt ttaatattaa aaagaagata tgaaataatt attcatacct tccaccttac | 300 |
| aataattagt tttcaatcga atattaagat tattagtagt cttaaaagtt aagacttcct | 360 |
| tatattaatg acctaattta ttatttgcct catgaattat cttttatttt ctttgatatg | 420 |
| tcccaaacca catcgtgata tacactacaa taaatattat gatgaaacta ataatattct | 480 |
| caaagttcag atggaaccaa cctgctagaa tagcgagtgg gaagaatagg attatcatca | 540 |
| atataaagtg aactcagtc tgttttgtta tactccaatc ggtatctgta aatatcaaat | 600 |
| taccataagt aaacaaaatt ccaatcaatg cccatagtgc tacacatatt agcataataa | 660 |
| ccgcttcatt aaagttttca taataaattt tacccataaa agaatctgga tatagtagta | 720 |
| catatttatc ccttgaaaaa aataagtgaa gtaatgacag aaatcataag accagtgaac | 780 |
| gcacctttt gaacagcgtg gaataatttt ttcatagtga gatggaccat tccatttgtt | 840 |
| tctaacttca agtgatcaat gtaatttaga ttgataattt ctgattttga aatacgcacg | 900 |
| aatattgaac cgacaagctc ttcaatttgg taaagtcgct gataaagttt taagctttta | 960 |
| ttattcattg ttatcgcata cctgtttatc ttctactatg aactgtgcaa tttgttctag | 1020 |
| atcaattggg taaacatgat ggttctgttg caaagtaaaa aatatagct aaccactaat | 1080 |
| ttatcatgtc agtgttcgct taacttgcta gcatgatg | 1118 |

<210> SEQ ID NO 44
<211> LENGTH: 1118
<212> TYPE: DNA
<213> ORGANISM: Staphylococcus aureus

<400> SEQUENCE: 44

| | |
|---|---|
| cagagcattt aagattatgc gtggagaagc gtaccacaaa tgatgcggtt ttttatccag | 60 |
| tttttgttt aatgaacaag gtaaattacg agataatatt tgaagaaaac aataaagtag | 120 |
| agatggattt ccatatcctc tttagtagcg gttttatct gtaaggttta ttaataatta | 180 |
| aataaatagg cgggatagtt atatatagct tattaatgaa agaatatgat tattaattta | 240 |
| gtattatatt ttaatattaa aaagaagata tgaaataatt attcatacct tccaccttac | 300 |
| aataattagt tttcaatcga atattaagat tattagtagt cttaaaagtt aagacttcct | 360 |
| tatattaatg acctaattta ttatttgcct catgaattat cttttatttt ctttgatatg | 420 |
| tcccaaacca catcgtgata tacactacaa taaatattat gatgaaacta ataatattct | 480 |
| caaagttcag atggaaccaa cctgctagaa tagcgagtgg gaagaatagg attatcatca | 540 |

```
ataaaagtg aactacagtc tgttttgtta tactccaatc ggtatctgta aatatcaaat      600
taccataagt aaacaaaatt ccaatcaatg cccatagtgc tacacatatt agcataataa      660
ccgcttcatt aaagttttca taataaattt tacccataaa agaatctgga tatagtagta      720
catatttatc ccttgaaaaa aataagtgaa gtaatgacag aaatcataag accagtgaac      780 gcacctttt gaacagcgtg gaataatttt ttcatagtga gatggaccat tccatttgtt      840
tctaacttca agtgatcaat gtaatttaga ttgataattt ctgattttga aatacgcacg      900
aatattgaac cgacaagctc ttcaatttgg taaagtcgct gataaagttt taaagcttta      960
ttattcattg ttatcgcata cctgtttatc ttctactatg aactgtgcaa tttgttctag     1020
atcaattggg taaacatgat ggttctgttg caaagtaaaa aaatatagct aaccactaat     1080
ttatcatgtc agtgttcgct taacttgcta gcatgatg                             1118

<210> SEQ ID NO 45
<211> LENGTH: 1113
<212> TYPE: DNA
<213> ORGANISM: Staphylococcus aureus

<400> SEQUENCE: 45
agcatttaag attatgcgtg gagaagcgta ccacaaatga tgcggttttt tatccagttt       60
tttgtttaat gaacaaggta aattacgaga taatatttga agaaaacaat aaagtagaga      120
tggatttcca tatcctcttt agtagcggtt tttatctgta aggtttatta ataattaaat      180
aaataggcgg gatagttata tatagcttat taatgaaaga atatgattat taatttagta      240
ttatatttta atattaaaaa gaagatatga ataattatt catacctccc accttacaat       300 aattagttttt caatcgaata ttaagattat tagtagtctt aaaagttaag acttccttat      360
attaatgacc taatttatta tttgcctcat gaattatctt tttatttctt tgatatgtcc      420
caaaccacat cgtgatatac actacaataa atattatgat gaaactaata atattctcaa      480
agttcagatg gaaccaacct gctagaatag cgagtgggaa gaataggatt atcatcaata      540
taaagtgaac tacagtctgt tttgttatac tccaatcggt atctgtaaat atcaaattac      600
cataagtaaa caaattcca atcaatgccc atagtgctac acatattagc ataataaccg      660
cttcattaaa gttttcataa taaattttac ccataaaaga atctggatat agtggtacat      720
atttatccct tgaaaaaaat aagtgaagta atgacagaaa tcataagacc agtgaacgca      780 ccttttttgaa cagcgtggaa taattttttc atagtgagat ggaccattcc atttgtttct     840
aacttcaagt gatcaatgta atttagattg ataatttctg attttgaaat acgcacgaat      900
attgaaccga caagctcttc aatttggtaa agtcgctgat aaagttttaa agctttatta      960
ttcattgtta tcgcatacct gtttatcttc tactatgaac tgtgcaattt gttctagatc     1020
aattgggtaa acatgatggt tctgttgcaa agtaaaaaaa tatagctaac cactaattta     1080
tcatgtcagt gttcgcttaa cttgctagca tga                                  1113

<210> SEQ ID NO 46
<211> LENGTH: 2153
<212> TYPE: DNA
<213> ORGANISM: Staphylococcus aureus

<400> SEQUENCE: 46
ctgtagggaa actaaaagag aaatactgga agcaagccat agcagaatat gaaaaacgtt       60
taggcccata caccaagata gacatcatag aagttccaga cgaaaaagca ccagaaaata      120
```

```
tgagcgacaa agaaatcgag caagtaaaag aaaagaagg ccaacgaata ctagccaaaa      180
tcaaaccaca atccacagtc attacattag aaatacaagg aaagatgcta tcttccgaag      240
gattggccca agaattgaac caacgcatga cccaagggca aagcgacttt gtattcgtca      300
ttggcggatc aaacggcctg cacaaggacg tcttacaacg cagtaactac gcactatcat      360
tcagcaaaat gacattccca catcaaatga tgcgggttgt gttaattgaa caagtgtaca      420
gagcatttaa gattatgcgt ggagaagcgt accacaaatg atgcggtttt ttatccagtt      480
ttttgtttaa tgaacaaggt aaattacgag ataatatttg aagaaaacaa taaagtagag      540
atggatttcc atatcctctt tagtagcggt ttttatctgt aaggtttatt aataattaaa      600
taaataggcg ggatagttat atatagctta ttaatgaaag aatatgatta ttaatttagt      660
attatatttt aatattaaaa agaagatatg aaataattat tcataccttc caccttacaa      720
taattagttt tcaatcgaat attaagatta ttagtagtct aaaagttaa gacttcctta      780 tattaatgac ctaattttatt atttgcctca tgaattatct ttttatttct ttgatatgtc      840
ccaaaccaca tcgtgatata cactacaata aatattatga tgaaactaat aatattctca      900
aagttcagat ggaaccaacc tgctagaata gcgagtggga agaataggat tatcatcaat      960
ataaagtgaa ctacagtctg ttttgttata ctccaatcgg tatctgtaaa tatcaaatta     1020
ccataagtaa acaaaattcc aatcaatgcc catagtgcta cacatattag cataataacc     1080
gcttcattaa agttttcata ataaattta cccataaaag aatctggata tagtggtaca     1140
tatttatccc ttgaaaaaaa taagtgaagt aatgacagaa atcataagac cagtgaacgc     1200 accttttga acagcgtgga ataatttttt catagtgaga tggaccattc catttgtttc     1260
taacttcaag tgatcaatgt aatttagatt gataatttct gattttgaaa tacgcacgaa     1320
tattgaaccg acaagctctt caatttggta aagtcgctga taaagtttta aagctttatt     1380
attcattgtt atcgcatacc tgtttatctt ctactatgaa ctgtgcaatt tgttctagat     1440
caattgggta aacatgatgg ttctgttgca aagtaaaaaa atatagctaa ccactaattt     1500
atcatgtcag tgttcgctta acttgctagc atgatgctaa tttcgtggca tggcgaaaat     1560
ccgtagatct gatgagacct gcggttcttt ttatatagag cgtaaataca ttcaatacct     1620
tttaaagtat tctttgctgt attgatactt tgataccttg tctttcttac tttaatatga     1680
cggtgatctt gctcaatgag gttattcaaa tatttcgatg tacaatgaca gtcaggttta     1740
agtttaaaag ctttaattac tttagccatt gctaccttcg ttgaaggtgc ctgatctgta     1800 attaccttt gaggtttacc aaattgttta atgagacgtt taataaacgc atatgctgaa     1860
tgattatctc gttgcttacg caaccaaata tctaatgtat gtccctctgc atcaatggca     1920
cgatataaat agctccattt tcctttattt ttgatgtacg tctcatcaat acgccatttg     1980
taataagctt ttttatgctt tttcttccaa atttgatata aaattggggc atattcttga     2040
acccaacggt agaccgttga atgatgaacg tttacaccac gtcccttaa tatttcgat      2100 atatcacgat aactcaatgc atatcttaga tagtagccaa cggctacagt gat           2153
```

<210> SEQ ID NO 47
<211> LENGTH: 737
<212> TYPE: DNA
<213> ORGANISM: Staphylococcus aureus

<400> SEQUENCE: 47

```
tttaagatta tgcgtggaga agcatatcat aaatgatgcg gttatttcag ccgtaatttt       60
ataatataaa gcagagttta ttaaatttta atgattactt tttattaaga attaattcta      120
```

```
gttgatatat tataatgtga aacacaaaat aataatttgt aattgttagt ttataggcat      180
ctgtatttgg aatttttgt agactattta aaaaatagtg tatataagta ttgagttcat       240
gtattaactg tcttttttca tcgttcatca agtataagga tgtagagatt tgttggataa      300
tttcttcgga tgttttaaa attatcatta aattagatgg tatctgatct tgagttttgt      360
ttttagtgta tgtatatttt aaaaaatttt tgattgttgt tatttgactc tcttttaatt     420
tgacaccctc atcaataaat gtgttaaata tatcttcatt tgtacttaaa tcatcaaaat     480
ttgccaacaa atatttgaac gtctctaaat cattatgttt gagttccgtt ttgctattcc     540
ataattccaa accatttggt agaaagccca agctgtgatt ttgatctccc catatagctg     600
aatttaaatc agtgagttga ttaatttttt caacacagaa atgtaatttt ggaatgagga     660
atcgaagttg ttcttctact tgctgtactt ttcttttgtt ttcaataaaa tttctacacc    720
atactgttat caaaccg                                                    737

<210> SEQ ID NO 48
<211> LENGTH: 1592
<212> TYPE: DNA
<213> ORGANISM: Staphylococcus aureus

<400> SEQUENCE: 48
aactaaaaga gaaatattgg aagcaagcca tagcagaata tgaaaaacgt ttaggcccat      60
acaccaagat agacatcata gaagttccag acgaaaaagc accagaaaat atgagtgaca     120
aagaaattga gcaagtaaaa gaaaagaag gccaacgaat actagccaaa atcaaaccac      180
aatccacagt cattacatta gaaatacaag gaaagatgct atcttccgaa ggattggccc     240
aagaattgaa ccaacgcatg acccaagggc aaagcgactt tgttttcgtc attggcggat     300
caaacggcct gcacaaggac gtcttacaac gcagtaacta cgcactatca ttcagcaaaa     360
tgacattccc acatcaaatg atgcgggttg tgttaattga acaagtgtac agagcattta     420
agattatgcg aggagaagca tatcataaat gatgcggtta tttcagccgt aattttataa     480
tataaagcag agtttattaa attttaatga ttactttta ttaagaatta attctagttg      540
atatattata atgtgaaaca caaataataa atttgtaatt gttagtttat aggcatctgt     600
atttggaatt ttttgtagac tatttaaaaa atagtgtata taagtattga gttcatgtat     660
taactgtctt ttttcatcgt tcatcaagta taaggatgta gagatttgtt ggataatttc     720
ttcggatgtt tttaaaatta tcattaaatt agatggtatc tgatcttgag ttttgttttt     780
agtgtatgta tattaaaaa aattttgat tgttgttatt tgactctctt ttaatttgac      840
accctcatca ataaatgtgt taaatatatc ttcatttgta cttaaatcat caaaatttgc     900
caacaaatat ttgaacgtct ctaaatcatt atgtttgagt tccgtttgc tattccataa     960 ttccaaacca tttggtagaa agcccaagct gtgattttga tctccccata tagctgaatt    1020
taaatcagtg agttgattaa tttttcaac acagaaatgt aattttggaa tgaggaatcg     1080
aagttgttct tctacttgct gtactttct tttgttttca ataaaattc tacaccatac     1140 tgttatcaaa ccgccaatta ttgtgcacaa tcctccaatg attgtagata aaattgacaa    1200
tatattacac acctttctta gaggtttatt aacatctatt tttgaattta aaattattac    1260
tttggtagcg ttataaccta tttaacagat tagagaaaaa ttgaatgatc gattgaagaa    1320
tttccaaaat accgtcccat atgcgttgaa ggagatttct attttcttct gtattcaaat    1380
ctttggcttt atcctttgct ttattcaata aatcatctga gttttttca atatttttta    1440
```

-continued

| atacatcttt ggcattttgt ttaaatactt taggatcgga agttagggca ttagagtttg | 1500 |
| ccacattaat catattatta ttaatcattt gaatttgatt atctgataat atctctgata | 1560 |
| acctacgctc atcgaggact ttattaacag tg | 1592 |

<210> SEQ ID NO 49
<211> LENGTH: 730
<212> TYPE: DNA
<213> ORGANISM: Staphylococcus aureus

<400> SEQUENCE: 49

| agcatttaag attatgcgtg gagaagcata tcataaatga tgcggttatt tcagccgtaa | 60 |
| ttttataata taaagcagag tttattaaat tttaatgatt acttttttatt aagaattaat | 120 |
| tctagttgat atattataat gtgaaacaca aaataataat ttgtaattgt tagtttatag | 180 |
| gcatctgtat ttggaatttt ttgtagacta tttaaaaaat agtgtatata agtattgagt | 240 |
| tcatgtatta actgtctttt ttcatcgttc atcaagtata aggatgtaga gatttgttgg | 300 |
| ataatttctt cggatgtttt taaaattatc attaaattag atggtatctg atcttgagtt | 360 |
| ttgttttttag tgtatgtata ttttaaaaaa ttttgattg ttgttatttg actctctttt | 420 |
| aatttgacac cctcatcaat aaatgtgtta aatatatctt catttgtact taaatcatca | 480 |
| aaatttgcca acaaatattt gaacgtctct aaatcattat gtttgagttc cgttttgcta | 540 |
| ttccataatt ccaaaccatt tggtagaaag cccaagctgt gattttgatc tccccatata | 600 |
| gctgaattta aatcagtgag ttgattaatt ttttcaacac agaaatgtaa ttttggaatg | 660 |
| aggaatcgaa gttgttcttc tacttgctgt acttttcttt tgttttcaat aaaatttcta | 720 |
| caccatactg | 730 |

<210> SEQ ID NO 50
<211> LENGTH: 1696
<212> TYPE: DNA
<213> ORGANISM: Staphylococcus aureus

<400> SEQUENCE: 50

| aaagagaaat attggaagca agccatagca gaatatgaaa aacgtttagg cccatacacc | 60 |
| aagatagaca tcatagaagt tccagacgaa aaagcaccag aaaatatgag tgacaaagaa | 120 |
| attgagcaag taaagaaaa agaaggccaa cgaatactag ccaaaatcaa accacaatcc | 180 |
| acagtcatta cattagaaat acaaggaaag atgctatctt ccgaaggatt ggcccaagaa | 240 |
| ttgaaccaac gcatgaccca agggcaaagc gactttgttt cgtcattgg cggatcaaac | 300 |
| ggcctgcaca aggacgtctt acaacgcagt aactacgcac tatcattcag caaaatgaca | 360 |
| tcccacatc aaatgatgcg ggttgtgtta attgaacaag tgtacagagc atttaagatt | 420 |
| atgcgaggag aagcatatca taaatgatgc ggttatttca gccgtaattt tataatataa | 480 |
| agcagagttt attaaatttt aatgattact ttttattaag aattaattct agttgatata | 540 |
| ttataatgtg aaacacaaaa taataatttg taattgttag tttataggca tctgtatttg | 600 |
| gaattttttg tagactattt aaaaaatagt gtatataagt attgagttca tgtattaact | 660 |
| gtctttttc atcgttcatc aagtataagg atgtagagat tgttggata atttcttcgg | 720 |
| atgttttaa aattatcatt aaattagatg gtatctgatc ttgagttttg ttttagtgt | 780 |
| atgtatattt taaaaaattt ttgattgttg ttatttgact ctcttttaat ttgacccct | 840 |
| catcaataaa tgtgttaaat atatcttcat ttgtacttaa atcatcaaaa tttgccaaca | 900 |
| aatatttgaa cgtctctaaa tcattatgtt tgagttccgt tttgctattc cataattcca | 960 |

```
aaccatttgg tagaaagccc aagctgtgat tttgatctcc ccatatagct gaatttaaat    1020
cagtgagttg attaatttt tcaacacaga aatgtaattt tggaatgagg aatcgaagtt    1080
gttcttctac ttgctgtact tttcttttgt tttcaataaa atttctacac catactgtta    1140
tcaaaccgcc aattattgtg cacaatcctc caatgattgt agataaaatt gacaatatat    1200
tacacacctt tcttagaggt ttattaacat ctattttga atttaaaatt attactttgg    1260
tagcgttata acctatttaa cagattagag aaaaattgaa tgatcgattg aagaatttcc    1320
aaaataccgt cccatatgcg ttgaaggaga tttctatttt cttctgtatt caaatctttg    1380
gctttatcct ttgctttatt caataaatca tctgagtttt tttcaatatt ttttaataca    1440
tctttggcat tttgtttaaa tactttagga tcggaagtta gggcattaga gtttgccaca    1500
ttaatcatat tattattaat catttgaatt tgattatctg ataatatctc tgataaccta    1560
cgctcatcga ggactttatt aacagtgtct tcaacttgtt gttgtgtgat ttgtttatct    1620
tgattttgtt taatatctgc aagttgttct ttaatatctg ctatagaagc atttaaagct    1680
tcatctgaat acccat                                                    1696

<210> SEQ ID NO 51
<211> LENGTH: 2122
<212> TYPE: DNA
<213> ORGANISM: Staphylococcus aureus

<400> SEQUENCE: 51
ggaaactaaa agagaaatat tggaagcaag ccatagcaga atatgaaaaa cgtttaggcc      60
catacaccaa gatagacatc atagaagttc cagacgaaaa agcaccagaa aatatgagcg     120
acaaagaaat tgagcaagta aagaaaaag aaggccaacg aatactagcc aaaatcaaac     180
cacaatcaac agtcattaca ttagaaatac aaggaaagat gctatcttcc gaaggattgg     240
cccaagaatt gaaccaacgc atgacccaag ggcaaagcga ctttgtattc gtcattggcg     300
gatcaaacgg cctgcacaag gacgtcttac aacgcagtaa ctacgcacta tcattcagca     360
aaatgacatt cccacatcaa atgatgcggg ttgtgttaat tgaacaagtg tacagagcat     420
ttaagattat gcgtggagaa gcgtaccaca aatgatgcgg tttttatcc agttttttgt     480 ttaatgaaca aggtaaatta cgagataata tttgaagaaa acaataaagt agagatggat     540
ttccatatcc tctttagtag cggttttat ctgtaaggtt tattaataat taaataaata     600
ggcgggatag ttatatatag cttattaatg aaagaatatg attattaatt tagtattata     660
ttttaatatt aaaagaaga tatgaaataa ttattcatac cttccacctt acaataatta     720
gttttcaatc gaatattaag attattagta gtcttaaaag ttaagacttc cttatattaa     780
tgacctaatt tattatttgc ctcatgaatt atcttttat ttctttgata tgtcccaaac     840
cacatcgtga tatacactac aataaatatt atgatgaaac taataatatt ctcaaagttc     900
agatggaacc aacctgctag aatagcgagt gggaagaata ggattatcat caatataaag     960
tgaactacag tctgttttgt tatactccaa tcggtatctg taaatatcaa attaccataa    1020
gtaaacaaaa ttccaatcaa tgcccatagt gctacacata ttagcataat aaccgcttca    1080
ttaaagtttt cataataaat tttacccata aagaatctg gatatagtgg tacatattta    1140
tcccttgaaa aaataagtg aagtaatgac agaaatcata agaccagtga acgcacctt    1200 ttgaacagcg tggaataatt tttcatagt gagatggacc attccatttg tttctaactt    1260
caagtgatca atgtaattta gattgataat ttctgatttt gaaatacgca cgaatattga    1320
```

```
accgacaagc tcttcaattt ggtaaagtcg ctgataaagt tttaaagctt tattattcat   1380
tgttatcgca tacctgttta tcttctacta tgaactgtgc aatttgttct agatcaattg   1440
ggtaaacatg atggttctgt tgcaaagtaa aaaaatatag ctaaccacta atttatcatg   1500
tcagtgttcg cttaacttgc tagcatgatg ctaatttcgt ggcatggcga aaatccgtag   1560
atctgatgag acctgcggtt ctttttatat agagcgtaaa tacattcaat acctttaaa    1620 gtattctttg ctgtattgat actttgatac cttgtctttc ttactttaat atgacggtga   1680
tcttgctcaa tgaggttatt cagatatttc gatgtacaat gacagtcagg tttaagttta   1740
aaagctttaa ttactttagc cattgctacc ttcgttgaag gtgcctgatc tgtaattacc   1800
ttttgaggtt taccaaattg tttaatgaga cgtttgataa acgcatatgc tgaatgatta   1860
tctcgttgct tacgcaacca aatatctaat gtatgtccct ctgcatcaat ggcacgatat   1920
aaatagctcc attttccttt tattttgatg tacgtctcat caatacgcca tttgtaataa   1980
gcttttttat gcttttctt ccaaatttga tacaaaattg gggcatattc ttgaacccaa    2040
cggtagaccg ttgaatgatg aacgtttaca ccacgttccc ttaatatttc agatatatca   2100
cgataactca atgtatatct ta                                            2122
```

<210> SEQ ID NO 52
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 52

```
gatagactaa ttatcttcat c                                               21
```

<210> SEQ ID NO 53
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 53

```
cagactgtgg acaaactgat t                                               21
```

<210> SEQ ID NO 54
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 54

```
tgagatcatc tacatcttta                                                 20
```

<210> SEQ ID NO 55
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 55

```
ggatcaaaag ctactaaatc                                                 20
```

<210> SEQ ID NO 56
<211> LENGTH: 20

```
<212> TYPE: DNA
<213> ORGANISM: Artificial
<220> FEATURE:
<223> OTHER INFORMATION: OLIGONUCLEOTIDE

<400> SEQUENCE: 56
atgctctttg ttttgcagca                                              20

<210> SEQ ID NO 57
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 57
atgaaagact gcggaggcta act                                          23

<210> SEQ ID NO 58
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 58
atattctaga tcatcaatag ttg                                          23

<210> SEQ ID NO 59
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 59
aagaattgaa ccaacgcatg a                                            21

<210> SEQ ID NO 60
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 60
gttcaagccc agaagcgatg t                                            21

<210> SEQ ID NO 61
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 61
tcgggcataa atgtcaggaa aat                                          23

<210> SEQ ID NO 62
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 62
```

| aaacgacatg aaaatcacca t | 21 |

<210> SEQ ID NO 63
<211> LENGTH: 33
<212> TYPE: DNA
<213> ORGANISM: Artificial
<220> FEATURE:
<223> OTHER INFORMATION: OLIGONUCLEOTIDE

<400> SEQUENCE: 63

| ttattaggta aaccagcagt aagtgaacaa cca | 33 |

<210> SEQ ID NO 64
<211> LENGTH: 19
<212> TYPE: DNA
<213> ORGANISM: Artificial
<220> FEATURE:
<223> OTHER INFORMATION: OLIGONUCLEOTIDE

<400> SEQUENCE: 64

| ggatcaaacg gcctgcaca | 19 |

<210> SEQ ID NO 65
<211> LENGTH: 26
<212> TYPE: DNA
<213> ORGANISM: Artificial
<220> FEATURE:
<223> OTHER INFORMATION: OLIGONUCLEOTIDE

<400> SEQUENCE: 65

| cacagaaatg taattttgga atgagg | 26 |

<210> SEQ ID NO 66
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 66

| gtcaaaaatc atgaacctca ttacttatg | 29 |

<210> SEQ ID NO 67
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 67

| atttcatata tgtaattcct ccacatctc | 29 |

<210> SEQ ID NO 68
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 68

| tctacggatt ttcgccatgc | 20 |

<210> SEQ ID NO 69
<211> LENGTH: 27
<212> TYPE: DNA
<213> ORGANISM: Artificial

```
<220> FEATURE:
<223> OTHER INFORMATION: OLIGONUCLEOTIDE

<400> SEQUENCE: 69
aacaggtgaa ttattagcac ttgtaag                                         27

<210> SEQ ID NO 70
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 70
atcaaatgat gcgggttgtg t                                               21

<210> SEQ ID NO 71
<211> LENGTH: 19
<212> TYPE: DNA
<213> ORGANISM: Artificial
<220> FEATURE:
<223> OTHER INFORMATION: OLIGONUCLEOTIDE

<400> SEQUENCE: 71
tcattggcgg atcaaacgg                                                  19

<210> SEQ ID NO 72
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 72
acaacgcagt aactacgcac ta                                              22

<210> SEQ ID NO 73
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 73
taactacgca ctatcattca gc                                              22

<210> SEQ ID NO 74
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 74
acatcaaatg atgcgggttg tg                                              22

<210> SEQ ID NO 75
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 75
tcaaatgatg cgggttgtgt ta                                              22
```

```
<210> SEQ ID NO 76
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 76
caaatgatgc gggttgtgtt aatt                                          24

<210> SEQ ID NO 77
<211> LENGTH: 26
<212> TYPE: DNA
<213> ORGANISM: Artificial
<220> FEATURE:
<223> OTHER INFORMATION: OLIGONUCLEOTIDE

<400> SEQUENCE: 77
ctactatgaa ctgtgcaatt tgttct                                        26

<210> SEQ ID NO 78
<211> LENGTH: 2007
<212> TYPE: DNA
<213> ORGANISM: Staphylococcus aureus

<400> SEQUENCE: 78
atgaaaaaga taaaaattgt tccacttatt ttaatagttg tagttgtcgg gtttggtata     60
tatttttatg cttcaaaaga taagaaattt aataatacta ttgatgcaat tgaagataaa    120
aatttcaaac aagtttataa agatagcagt tatatttcta aaagcgataa tggtgaagta    180
gaaatgactg aacgtccgat aaaaatatat aatagtttag gcgttaaaga tataaacatt    240
caggatcgta aaataaaaaa agtatctaaa aataaaaaac gagtagatgc tcaatataaa    300
attaaaacaa actacggtaa cattgatcgc aacgttcaat ttaattttgt taagaagat    360 ggtatgtgga agttagattg ggatcatagc gtcattattc caggaatgca gaaagaccaa    420
agcatacata ttgaaaattt aaatcagaa cgtggtaaaa ttttagaccg aaacaatgtg    480
gaattggcca atacaggaac acatatgaga ttaggcatcg ttccaaagaa tgtatctaaa    540
aaagattata agcaatcgc taagaactaa gtatttctg aagactatat caacaacaaa    600
tggatcaaaa ttgggtacaa gatgatacct tcgttccact ttaaaaccgt taaaaaaatg    660
gatgaatatt taagtgattt cgcaaaaaaa tttcatctta caactaatga aacagaaagt    720
cgtaactatc ctctagaaaa agcgacttca catctattag gttatgttgg tcccattaac    780
tctgaagaat taaaacaaaa agaatataaa ggctataaag atgatgcagt tattggtaaa    840
aagggactcg aaaaactta cgataaaaag ctccaacatg aagatggcta tcgtgtcaca    900
atcgttgacg ataatagcaa tacaatcgca catacattaa tagagaaaaa gaaaaaagat    960
ggcaaagata ttcaactaac tattgatgct aaagttcaaa agagtattta taacaacatg   1020
aaaaatgatt atggctcagg tactgctatc caccctcaaa caggtgaatt attagcactt   1080
gtaagcacac cttcatatga cgtctatcca tttatgtatg gcatgagtaa cgaagaatat   1140
aataaattaa ccgaagataa aaaagaacct ctgctcaaca gttccagat tacaacttca   1200 ccaggttcaa ctcaaaaaat attaacagca atgattgggt taataacaa aacattagac   1260 gataaaacaa gttataaaat cgatggtaaa ggttggcaaa agataaaatc ttggggtggt   1320
tacaacgtta caagatatga agtggtaaat ggtaatatcg acttaaaaca agcaataaa   1380 tcatcagata acattttctt tgctagagta gcactcgaat taggcagtaa gaaatttgaa   1440
```

```
aaaggcatga aaaaactagg tgttggtgaa gatataccaa gtgattatcc attttataat      1500
gctcaaattt caaacaaaaa tttagataat gaaatattat tagctgattc aggttacgga      1560
caaggtgaaa tactgattaa cccagtacag atcctttcaa tctatagcgc attagaaaat      1620
aatggcaata ttaacgcacc tcacttatta aaagacacga aaaacaaagt tggaagaaa       1680 aatattattt ccaaagaaaa tatcaatcta ttaaatgatg gtatgcaaca agtcgtaaat      1740
aaaacacata agaagatat ttatagatct tatgcaaact taattggcaa atccggtact       1800
gcagaactca aaatgaaaca aggagaaagt ggcagacaaa ttgggtggtt tatatcatat      1860
gataaagata atccaaacat gatgatggct attaatgtta aagatgtaca agataaagga     1920
atggctagct acaatgccaa aatctcaggt aaagtgtatg atgagctata tgagaacggt      1980
aataaaaaat acgatataga tgaataa                                         2007
```

<210> SEQ ID NO 79
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 79

```
caaatattat ctcgtaattt accttgttc                                         29
```

<210> SEQ ID NO 80
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 80

```
ctctgcttta tattataaaa ttacggctg                                         29
```

<210> SEQ ID NO 81
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 81

```
attgctgtta atatttttg agttgaa                                            27
```

<210> SEQ ID NO 82
<211> LENGTH: 1957
<212> TYPE: DNA
<213> ORGANISM: Staphylococcus aureus

<400> SEQUENCE: 82

```
atgaaaaaga taaaaattgt tccacttatt ttaatagttg tagttgtcgg ttgatgcaat       60
tgaagataaa aatttcaaac aagtttataa agatagcagt tatatttcta aaagcgataa     120
tggtgaagta gaaatgactg aacgtccgat aaaaatatat aatagtttag gcgttaaaga     180
tataaacatt caggatcgta aaataaaaaa agtatctaaa aataaaaaac gagtagatgc     240
tcaatataaa attaaaacaa actacggtaa cattgatcgc aacgttcaat ttaattttgt     300
taaagaagat ggtatgtgga agttagattg ggatcatagc gtcattattc caggaatgca     360
gaaagaccaa agcatacata ttgaaaattt aaaatcagaa cgtggtaaaa ttttagaccg     420
```

```
aaacaatgtg gaattggcca atacaggaac agcatatgag ataggcatcg ttccaaagaa    480
tgtatctaaa aagattata aagcaatcgc taaagaacta agtatttctg aagactatat    540
caaacaacaa atggatcaaa attgggtaca agatgatacc ttcgttccac ttaaaaccgt    600 taaaaaatg gatgaatatt taagtgattt cgcaaaaaaa tttcatctta caactaatga    660
aacagaaagt cgtaactatc ctctagaaaa agcgacttca catctattag gttatgttgg    720
tcccattaac tctgaagaat taaaacaaaa agaatataaa ggctataaag atgatgcagt    780
tattggtaaa aagggactcg aaaaacttta cgataaaaag ctccaacatg aagatggcta    840
tcgtgtcaca atcgttgacg ataatagcaa tacaatcgca catacattaa tagagaaaaa    900
gaaaaaagat ggcaaagata ttcaactaac tattgatgct aaagttcaaa gagtatttta    960
taacaacatg aaaaatgatt atggctcagg tactgctatc caccctcaaa caggtgaatt   1020
attagcactt gtaagcacac cttcatatga cgtctatcca tttatgtatg catgagtaa    1080 cgaagaatat aataaattaa ccgaagataa aaaagaacct ctgctcaaca agttccagat   1140
tacaacttca ccaggttcaa ctcaaaaaat attaacagca atgattgggt taaataacaa   1200
aacattagac gataaaacaa gttataaaat cgatggtaaa ggttggcaaa agataaaatc   1260
ttggggtggt tacaacgtta caagatatga agtggtaaat ggtaatatcg acttaaaaca   1320
agcaatagaa tcatcagata acatttttctt tgctagagta gcactcgaat taggcagtaa   1380
gaaatttgaa aaaggcatga aaaaactagg tgttggtgaa gatataccaa gtgattatcc   1440
attttataat gctcaaattt caaacaaaaa tttagataat gaaatattat tagctgattc   1500
aggttacgga caaggtgaaa tactgattaa cccagtacag atcctttcaa tctatagcgc   1560
attagaaaat aatggcaata ttaacgcacc tcacttatta aaagacacga aaaacaaagt   1620
ttggaagaaa aatattattt ccaaagaaaa tatcaatcta ttaactgatg gtatgcaaca   1680
agtcgtaaat aaaacacata agaagatat ttatagatct tatgcaaact taattggcaa   1740
atccggtact gcagaactca aaatgaaaca aggagaaact ggcagacaaa ttgggtggtt   1800
tatatcatat gataaagata atccaaacat gatgatggct attaatgtta aagatgtaca   1860
agataaagga atggctagct acaatgccaa aatctcaggt aaagtgtatg atgagctata   1920
tgagaacggt aataaaaaat acgatataga tgaataa                             1957
```

<210> SEQ ID NO 83
<211> LENGTH: 36
<212> TYPE: DNA
<213> ORGANISM: Artificial
<220> FEATURE:
<223> OTHER INFORMATION: OLIGONUCLEOTIDE

<400> SEQUENCE: 83
cccaccccac atcaaatgat gcgggttgtg ggtggg                                36

<210> SEQ ID NO 84
<211> LENGTH: 37
<212> TYPE: DNA
<213> ORGANISM: Artificial
<220> FEATURE:
<223> OTHER INFORMATION: OLIGONUCLEOTIDE

<400> SEQUENCE: 84
cccgcgcgta gttactgcgt tgtaagacgt ccgcggg                               37

<210> SEQ ID NO 85
<211> LENGTH: 27

```
<212> TYPE: DNA
<213> ORGANISM: Artificial
<220> FEATURE:
<223> OTHER INFORMATION: OLIGONUCLEOTIDE

<400> SEQUENCE: 85
gtttttatca ccatattgaa tttatac                                          27

<210> SEQ ID NO 86
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 86
atttacttga aagactgcgg aggag                                            25

<210> SEQ ID NO 87
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 87
tgtttgagct tccacagcta tttc                                             24

<210> SEQ ID NO 88
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 88
ccctataatt ccaattattg cactaac                                          27

<210> SEQ ID NO 89
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 89
atgaggagat aataatttgg agggt                                            25

<210> SEQ ID NO 90
<211> LENGTH: 2007
<212> TYPE: DNA
<213> ORGANISM: Staphylococcus aureus

<400> SEQUENCE: 90
atgaaaaaga taaaaattgt tccacttatt ttaatagttg tagttgtcgg gtttggtata      60
tatttttatg cttccaaaga taagaaaatt aataatacta ttgatgcaat tgaagataaa     120
aatttcaaac aagtttataa agatagcagt tatatttcta aaagcgataa tggtgaagta     180
gaaatgactg aacgtccgat aaaaatatat aatagtttag gcgttaaaga tataaacatt     240
caggatcgta aaataaaaaa agtatctaaa aataaaaaac gagtagatgc tcaatataaa     300
attaaaacaa actacggtaa cattgatcgc aacgttcaat ttaatttgt taaagaagat     360 ggtatgtgga gttagattg ggatcatagc gtcattattc aggaatgca gaaagaccaa     420
```

| | |
|---|---:|
| agcatacata ttgaaaattt aaaatcagaa cgtggtaaaa ttttagaccg aaacaatgtg | 480 |
| gaattggcca atacaggaac agcatatgag ataggcatcg ttccaaagaa tgtatctaaa | 540 |
| aaagattata aagcaatcgc taagaactaa agtatttctg aagactatat caaacaacaa | 600 |
| atggatcaaa attgggtaca agatgatacc ttcgttccac ttaaaaccgt taaaaaaatg | 660 |
| gatgaatatt taagtgattt cgcaaaaaaa tttcatctta caactaatga aacagaaagt | 720 |
| cgtaactatc ctctaggaaa agcgacttca catctattag gttatgttgg tcccattaac | 780 |
| tctgaagaat aaaacaaaa agaatataaa ggctataaag atgatgcagt tattggtaaa | 840 |
| aagggactcg aaaaacttta cgataaaaag ctccaacatg aagatggcta tcgtgtcaca | 900 |
| atcgttgacg ataatagcaa tacaatcgca catacattaa tagagaaaaa gaaaaaagat | 960 |
| ggcaaagata ttcaactaac tattgatgct aaagttcaaa agagtattta taacaacatg | 1020 |
| aaaaatgatt atggctcagg tactgctatc caccctcaaa caggtgaatt attagcactt | 1080 |
| gtaagcacac cttcatatga cgtctatcca tttatgtatg gcatgagtaa cgaagaatat | 1140 |
| aataaattaa ccgaagataa aaagaaccct ctgctcaaca agttccagat acaacttca | 1200 |
| ccaggttcaa ctcaaaaaat attaacagca atgattgggt taaataacaa aacattagac | 1260 |
| gataaaacaa gttataaaat cgatggtaaa ggttggcaaa agataaaatc ttggggtggt | 1320 |
| tacaacgtta caagatatga agtggtaaat ggtaatatcg acttaaaaca agcaatagaa | 1380 |
| tcatcagata acatttttctt tgctagagta gcactcgaat taggcagtaa gaaatttgaa | 1440 |
| aaaggcatga aaaaactagg tgttggtgaa gatataccaa gtgattatcc attttataat | 1500 |
| gctcaaattt caaacaaaaa tttagataat gaaatattat agctgattc aggttacgga | 1560 |
| caaggtgaaa tactgattaa cccagtacag atcctttcaa tctatagcgc attagaaaat | 1620 |
| aatggcaata ttaacgcacc tcacttatta aaagacacga aaaacaaagt ttggaagaaa | 1680 |
| aatattattt ccaaagaaaa tatcaatcta ttaactgatg gtatgcaaca agtcgtaaat | 1740 |
| aaaacacata agaagatat ttatagatct tatgcaaact taattggcaa atccggtact | 1800 |
| gcagaactca aaatgaaaca aggagaaact ggcagacaaa ttgggtggtt tatatcatat | 1860 |
| gataaagata atccaaacat gatgatggct attaatgtta aagatgtaca agataaagga | 1920 |
| atggctagct acaatgccaa aatctcaggt aaagtgtatg atgagctata tgagaacggt | 1980 |
| aataaaaaat acgatataga tgaataa | 2007 |

<210> SEQ ID NO 91
<211> LENGTH: 2007
<212> TYPE: DNA
<213> ORGANISM: Staphylococcus aureus

<400> SEQUENCE: 91

| | |
|---|---:|
| atgaaaaaga taaaaattgt tccacttatt ttaatagttg tagttgtcgg gtttggtata | 60 |
| tatttttatg cttcaaaaga taagaaaatt aataatacta ttgatgcaat tgaagataaa | 120 |
| aatttcaaac aagtttataa agatagcagt tatatttcta aaagcgataa tggtgaagta | 180 |
| gaaatgactg aacgtccgat aaaaatatat aatagtttag gcgttaaaga tataaacatt | 240 |
| caggatcgta aaataaaaaa agtatctaaa aataaaaaac gagtagatgc tcaatataaa | 300 |
| attaaaacaa actacggtaa cattgatcgc aacgttcaat ttaattttgt taagaagat | 360 |
| ggtatgtgga agttagattg ggatcatagc gtcattattc caggaatgca gaaagaccaa | 420 |
| agcatacata ttgaaaattt aaaatcagaa cgtggtaaaa ttttagaccg aaacaatgtg | 480 |
| gaattggcca atacaggaac agcatatgag ataggcatcg ttccaaagaa tgtatctaaa | 540 |

```
aaagattata aagcaatcgc taaagaacta agtatttctg aagactatat caaacaacaa      600
atggatcaaa gtgggtaca agatgatacc ttcgttccac ttaaaaccgt taaaaaaatg      660
gatgaatatt taagtgattt cgcaaaaaaa tttcatctta caactaatga aacagaaagt      720
cgtaactatc ctctagaaaa agcgacttca catctattag gttatgttgg tcccattaac      780
tctgaagaat taaacaaaa agaatataaa ggctataaag atgatgcagt tattggtaaa      840
aagggactcg aaaaacttta cgataaaaag ctccaacatg aagatggcta tcgtgtcaca      900
atcgttgacg ataatagcaa tacaatcgca catacattaa tagagaaaaa gaaaaaagat      960
ggcaaagata ttcaactaac tattgatgct aaagttcaaa agagtattta taacaacatg     1020
aaaaatgatt atggctcagg tactgctatc caccctcaaa caggtgaatt attagcactt     1080
gtaagcacac cttcatatga cgtctatcca tttatgtatg gcatgagtaa cgaagaatat     1140
aataaattaa ccgaagataa aaaagaacct ctgctcaaca gttccagat acaacttca     1200 ccaggttcaa ctcaaaaaat attaacagca atgattgggt taataacaa acattagac     1260 gataaaacaa gttataaaat cgatggtaaa ggttggcaaa aagataaatc ttggggtggt     1320
tacaacgtta caagatatga agtggtaaat ggtaatatcg acttaaaaca agcaatagaa     1380
tcatcagata acattttctt tgctagagta gcactcgaat taggcagtaa gaaatttgaa     1440
aaaggcatga aaaaactagg tgttggtgaa gatataccaa gtgattatcc atttttataat     1500 gctcaaattt caaacaaaaa tttagataat gaaatattat tagctgattc aggttacgga     1560
caaggtgaaa tactgattaa cccagtacag atcctttcaa tctatagcgc attagaaaat     1620
aatggcaata ttaacgcacc tcacttatta aaagacacga aaaacaaagt ttggaagaaa     1680
aatattattt ccaaagaaaa tatcaatcta ttaactgatg gtatgcaaca agtcgtaaat     1740
aaaacacata agaagatat ttatagatct tatgcaaact taattggcaa atccggtact     1800
gcagaactca aaatgaaaca aggagaaact ggcagacaaa ttgggtggtt tatatcatat     1860
gataaagata atccaaacat gatgatggct attaatgtta agatgtaca agataaagga     1920 atggctagct acaatgccaa aatctccagg aaagtgtatg atgagctata tgagaacggt     1980
aataaaaaat acgatataga tgaataa                                        2007
```

<210> SEQ ID NO 92
<211> LENGTH: 675
<212> TYPE: DNA
<213> ORGANISM: Staphylococcus aureus

<400> SEQUENCE: 92

```
atgaactatt tcagatataa acaatttaac aaggatgtta tcactgtagc cgttggctac       60
tatctaagat atacattgag ttatcgtgat atatctgaaa tattaaggga acgtggtgta      120
aacgttcatc attcaacggt ctaccgttgg gttcaagaat atgccccaat tttgtatcaa      180
atttggaaga aaaagcataa aaaagcttat tacaaatggc gtattgatga gacgtacatc      240
aaaataaaag gaaatggag ctatttatat cgtgccattg atgcagaggg acatacatta      300
gatatttggt tgcgtaagca acgagataat cattcagcat atgcgtttat caaacgtctc      360
attaaacaat ttggtaaacc tcaaaaggta attacagatc aggcaccttc aacgaaggta      420
gcaatggcta agtaattaa agcttttaaa cttaaacctg actgtcattg tacatcgaaa      480
tatctgaata acctcattga gcaagatcac cgtcatatta agtaagaaa gacaaggtat      540 caaagtatca atacagcaaa gaatacttta aaaggtattg aatgtattta cgctctatat      600
```

```
aaaaagaacc gcaggtctct tcagatctac ggattttcgc catgccacga aattagcatc    660
atgctagcaa gttaa                                                     675
```

<210> SEQ ID NO 93
<211> LENGTH: 675
<212> TYPE: DNA
<213> ORGANISM: Staphylococcus aureus

<400> SEQUENCE: 93

```
atgaactatt tcagatataa acaatttaac aaggatgtta tcactgtagc cgttggctac     60
tatctaagat atacattgag ttatcgtgat atatctgaaa tattaaggga acgtggtgta    120
aacgttcatc attcaacggt ctaccgttgg gttcaagaat atgccccaat tttgtatcaa    180
atttggaaga aaaagcataa aaaagcttat tacaaatggc gtattgatga gacgtacatc    240
aaaataaaag gaaaatggag ctatttatat cgtgccattg atgcagaggg acatacatta    300
gatatttggt tgcgtaagca acgagataat cattcagcat atgcgtttat caaacgtctc    360
attaaacaat ttggtaaacc tcaaaaggta attacagatc aggcaccttc aacgaaggta    420
gcaatggcta aagtaattaa agcttttaaa cttaaacctg actgtcattg tacatcgaaa    480
tatctgaata acctcattga gcaagatcac cgtcatatta agtaagaaa  gacaaggtat    540 caaagtatca atacagcaaa gaatacttta aaaggtattg aatgtattta cgctctatat    600
aaaaagaacc gcaggtctct tcagatctac ggattttcgc catgccacga aattagcatc    660
atgctagcaa gttaa                                                     675
```

<210> SEQ ID NO 94
<211> LENGTH: 675
<212> TYPE: DNA
<213> ORGANISM: Staphylococcus aureus

<400> SEQUENCE: 94

```
atgaactatt tcagatataa acaatttaac aaggatgtta tcactgtagc cgttggctac     60
tatctaagat atacattgag ttatcgtgat atatctgaaa tattaaggga acgtggtgta    120
aacgttcatc attcaacggt ctaccgttgg gttcaagaat atgccccaat tttgtatcaa    180
atttggaaga aaaagcataa aaaagcttat tacaaatggc gtattgatga gacgtacatc    240
aaaataaaag gaaaatggag ctatttatat cgtgccattg atgcagaggg acatacatta    300
gatatttggt tgcgtaagca acgagttaat cattcagcat atgcgtttat caaacgtctc    360
attaaacaat ttggtaaacc tcaaaaggta attacagatc aggcaccttc aacgaaggta    420
gcaatggcta aagtaattaa agcttttaaa cttaaacctg actgtcattg tacatcgaaa    480
tatctgaata acctcattga gcaagatcac cgtcatatta agtaagaaa  gacaaggtat    540 caaagtatca atacagcaaa gaatacttta aaaggtattg aatgtattca cgctctatat    600
aaaaagaacc gcaggtctct tcagatctac ggattttcgc catgccacga aattagcatc    660
atgctagcaa gttaa                                                     675
```

<210> SEQ ID NO 95
<211> LENGTH: 675
<212> TYPE: DNA
<213> ORGANISM: Staphylococcus aureus

<400> SEQUENCE: 95

```
atgaactatt tcagatataa acaatttaac aaggatgtta tcactgtagc cgttggctac     60
tatctaagat atacattgag ttatcgtgat atatctgaaa tattaaggga acgtggtgta    120
```

```
aacgttcatc attcaacggt ctaccgttgg gttcaagaat atgccccaat tttgtatcaa    180
atttggaaga aaaagcataa aaaagcttat tacaaatggc gtattgatga gacgtacatc    240
aaaataaaag gaaatggag ctatttatat cgtgccattg atgcagaggg acatacatta    300
```
(Note: line "aaaataaaag gaaatggag..." reads as printed.)

```
aacgttcatc attcaacggt ctaccgttgg gttcaagaat atgccccaat tttgtatcaa    180
atttggaaga aaaagcataa aaaagcttat tacaaatggc gtattgatga gacgtacatc    240
aaaataaaag gaaatggag ctatttatat cgtgccattg atgcagaggg acatacatta    300
gatatttggt tgcgtaagca acgagataat cattcagcat atgcgtttat caaacgtctc    360
attaaacaat ttggtaaacc tcaaaaggta attacagatc aggcaccttc aacgaaggta    420
gcaatggcta aagtaattaa agcttttaaa cttaaacctg actgtcattg tacatcgaaa    480
tatctgaata acctcattga gcaagatcac cgtcatatta agtaagaaa gacaaggtat    540 caaagtatca atacagcaaa gaatacttta aaaggtattg aatgtattta cgctctatat    600
aaaaagaacc gcaggtctct tcagatctac ggattttcgc catgccacga aattagcatc    660
atgctagcaa gttaa                                                    675
```

<210> SEQ ID NO 96
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 96
gtaaagtgta tgatgagcta tatgagaa                                       28

<210> SEQ ID NO 97
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 97
gctgaaaaaa ccgcatcatt trtgrta                                        27

<210> SEQ ID NO 98
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 98
tttagtttta tttatgatac gcttctcca                                      29

<210> SEQ ID NO 99
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 99
gctgaaaaaa ccgcatcatt tatgata                                        27

<210> SEQ ID NO 100
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 100
ctatgtcaaa aatcatgaac ctcattac                                            28

<210> SEQ ID NO 101
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 101
ggaggctaac tatgtcaaaa atc                                                 23

<210> SEQ ID NO 102
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 102
ctctataaac atcgtatgat attgc                                               25

<210> SEQ ID NO 103
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 103
accaaacgac atgaaaatca                                                     20

<210> SEQ ID NO 104
<211> LENGTH: 1256
<212> TYPE: DNA
<213> ORGANISM: Staphylococcus aureus

<400> SEQUENCE: 104
ttcagaaaaa tgattaatgt gtttcaataa aatctctcct tctttgtgaa catattcatt         60
tttatactaa ttaatataat ttccaaaaaa gtttctgttt aaaagtgaaa aatattattt        120
accgtttgac ttaaatcttc aatatatagg tgtttatatg tatcattttg cgccaatttg        180
aataaacggg aatcaagtct gtttctgagt ttatttcaac tttcttatag taaacattgt        240
cttaatatga tgaacttcaa taaaactttc cctatgcccc ataaaatttt ctcaaaatca        300
aaaataacat accttacaac ttttaccgtc gatatcaatt gctcttttct taatttagga        360
ttgctttcaa attttgtact ataacgtgaa actactttc cttctttata attaaaattt         420
actaattcac aatcattttt acttccattt acaaaaacat ccactgtttc taacacaaaa        480
tctaataaac ttccttttat taatcgtagg cattgtatat ttcctttcat tctttcttga        540
ttccattagt ttaaatttaa aatttcatcc atcaatttct taatttaatt gtagttccat        600
aatcaatata atttgtacag ttattatata ttctagatca tcaatagttg aaaaatggtt        660
tattaaacac tctataaaca tcgtatgata ttgcaaggta taatccaata tttcatatat        720
gtaattcctc cacatctcat taaattttta aattatacac aacctaattt ttagttttat        780
ttatgatacg cttctccacg cataatctta aatgctctgt acacttgttc aattaacaca        840
acccgcatca tttgatgtgg gaatgtcatt ttgctgaatg atagtgcgta gttactgcgt        900
tgtaagacgt cctgtgcag gccgtttgat ccgccaatga cgaatacaaa gtcgctttgc         960
ccttgggtca tgcgttggtt caattcttgg gccaatcctt cggaagatag catctttcct       1020

-continued

```
tgtatttcta atgtaatgac tgttgattgt ggtttgattt tggctagtat tcgttggcct    1080
tctttttctt ttacttgctc aatttctttg tcgctcatat tttctggtgc tttttcgtct    1140
ggaacttcta tgatgtctat cttggtgtat gggcctaaac gttttcata ttctgctatg     1200 gcttgcttcc aatatttctc ttttagtttc cctacagcta aaatggtgat tttcat        1256
```

```
<210> SEQ ID NO 105
<211> LENGTH: 28
<212> TYPE: DNA
<213> ORGANISM: Artificial
<220> FEATURE:
<223> OTHER INFORMATION: OLIGONUCLEOTIDE
<220> FEATURE:
<221> NAME/KEY: misc_feature
<222> LOCATION: (27)..(27)
<223> OTHER INFORMATION: n =inosine

<400> SEQUENCE: 105
tcatgaacct cattacttat gataagnt                                         28

<210> SEQ ID NO 106
<211> LENGTH: 28
<212> TYPE: DNA
<213> ORGANISM: Artificial
<220> FEATURE:
<223> OTHER INFORMATION: OLIGONUCLEOTIDE
<220> FEATURE:
<221> NAME/KEY: misc_feature
<222> LOCATION: (27)..(27)
<223> OTHER INFORMATION: N = INOSINE

<400> SEQUENCE: 106
gaaaaaaccg catcatttat gatatgnt                                         28

<210> SEQ ID NO 107
<211> LENGTH: 30
<212> TYPE: DNA
<213> ORGANISM: Artificial
<220> FEATURE:
<223> OTHER INFORMATION: OLIGONUCLEOTIDE
<220> FEATURE:
<221> NAME/KEY: misc_feature
<222> LOCATION: (29)..(29)
<223> OTHER INFORMATION: N = INOSINE

<400> SEQUENCE: 107
cctaattttt agttttattt atgatacgnt                                       30

<210> SEQ ID NO 108
<211> LENGTH: 35
<212> TYPE: DNA
<213> ORGANISM: Artificial
<220> FEATURE:
<223> OTHER INFORMATION: OLIGONUCLEOTIDE
<220> FEATURE:
<221> NAME/KEY: misc_feature
<222> LOCATION: (34)..(34)
<223> OTHER INFORMATION: N = INOSINE

<400> SEQUENCE: 108
cacaacctaa tttttagttt tatttatgat acgnt                                 35

<210> SEQ ID NO 109
<211> LENGTH: 24
<212> TYPE: DNA
<213> ORGANISM: Artificial
<220> FEATURE:
```

```
<223> OTHER INFORMATION: OLIGONUCLEOTIDE

<400> SEQUENCE: 109
tgataagcca ttcattcacc ctaa                                              24

<210> SEQ ID NO 110
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 110
aaggactcct aatttatgtc taattcc                                           27

<210> SEQ ID NO 111
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 111
atgggagtcc ttcgctattc tgtg                                              24

<210> SEQ ID NO 112
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 112 cacttttat tcttcaaaga tttgagc                                            27

<210> SEQ ID NO 113
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 113
atggaaattc ttaatctttta cttgtacc                                         28

<210> SEQ ID NO 114
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 114
agcatcttct ttacatcgct tact                                              24

<210> SEQ ID NO 115
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 115
cagcaattcw cataaacctc ata                                               23
```

<210> SEQ ID NO 116
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 116
acaaactttg agggatttt tagtaaa                                          27

<210> SEQ ID NO 117
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 117
tatattgtgg catgatttct tc                                              22

<210> SEQ ID NO 118
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 118
cgaatggact agcactttct aaa                                             23

<210> SEQ ID NO 119
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 119
ttgaggatca aaagttgttg c                                               21

<210> SEQ ID NO 120
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 120
cgatgatttt atagtaggag a                                               21

<210> SEQ ID NO 121
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 121
ttcaatctct aaatctaaat cagttttg                                        28

<210> SEQ ID NO 122
<211> LENGTH: 24
<212> TYPE: DNA
<213> ORGANISM: Artificial
<220> FEATURE:
<223> OTHER INFORMATION: OLIGONUCLEOTIDE

```
<400> SEQUENCE: 122
aggcgagaaa atggaacata tcaa                                          24

<210> SEQ ID NO 123
<211> LENGTH: 26
<212> TYPE: DNA
<213> ORGANISM: Artificial
<220> FEATURE:
<223> OTHER INFORMATION: OLIGONUCLEOTIDE

<400> SEQUENCE: 123
ggtacaagta aagattaaga atttcc                                        26

<210> SEQ ID NO 124
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 124
agacaacttt atgcaggtcc tt                                            22

<210> SEQ ID NO 125
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 125
taactgcttg ggtaacctta tc                                            22

<210> SEQ ID NO 126
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 126
tattgcaggt ttcgatgttg a                                             21

<210> SEQ ID NO 127
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 127
tgacccatat cgcctaaaat ac                                            22

<210> SEQ ID NO 128
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 128
aaaggacaac aaggtagcaa ag                                            22

<210> SEQ ID NO 129
<211> LENGTH: 22
```

```
<212> TYPE: DNA
<213> ORGANISM: Artificial
<220> FEATURE:
<223> OTHER INFORMATION: OLIGONUCLEOTIDE

<400> SEQUENCE: 129
tctgtggata aacaccttga tg                                          22

<210> SEQ ID NO 130
<211> LENGTH: 18
<212> TYPE: DNA
<213> ORGANISM: Artificial
<220> FEATURE:
<223> OTHER INFORMATION: OLIGONUCLEOTIDE

<400> SEQUENCE: 130
gtttgatccg ccaatgac                                               18

<210> SEQ ID NO 131
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 131
ggcataaatg tcaggaaaat atc                                         23

<210> SEQ ID NO 132
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 132
gaggaccaaa cgacatgaaa atc                                         23

<210> SEQ ID NO 133
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 133
ttcgaggttg atgggaagca                                             20

<210> SEQ ID NO 134
<211> LENGTH: 18
<212> TYPE: DNA
<213> ORGANISM: Artificial
<220> FEATURE:
<223> OTHER INFORMATION: OLIGONUCLEOTIDE

<400> SEQUENCE: 134
cgctcgactc agggtgtt                                               18

<210> SEQ ID NO 135
<211> LENGTH: 18
<212> TYPE: DNA
<213> ORGANISM: Artificial
<220> FEATURE:
<223> OTHER INFORMATION: OLIGONUCLEOTIDE

<400> SEQUENCE: 135
```
cgttgaagat gcctttga                                          18

<210> SEQ ID NO 136
<211> LENGTH: 18
<212> TYPE: DNA
<213> ORGANISM: Artificial
<220> FEATURE:
<223> OTHER INFORMATION: OLIGONUCLEOTIDE

<400> SEQUENCE: 136
ttttgcaaca gccattcg                                          18

<210> SEQ ID NO 137
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 137
gcacacatgt tgtaagtttg c                                      21

<210> SEQ ID NO 138
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 138
acgcaaactt acaacatgtg tg                                     22

<210> SEQ ID NO 139
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 139
cgtttgtctg atttggagga ag                                     22

<210> SEQ ID NO 140
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 140
tttcttcatc atcggtcata aaat                                   24

<210> SEQ ID NO 141
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 141
ctacgtgaat caaaaacaat gga                                    23

<210> SEQ ID NO 142
<211> LENGTH: 22
<212> TYPE: DNA
<213> ORGANISM: Artificial

```
<220> FEATURE:
<223> OTHER INFORMATION: OLIGONUCLEOTIDE

<400> SEQUENCE: 142
tactgcaaag tctcgttcat cc                                              22

<210> SEQ ID NO 143
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 143
cataccattt tgaacgatga cctc                                            24

<210> SEQ ID NO 144
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 144
atgtctggtc aactttccga ctc                                             23

<210> SEQ ID NO 145
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 145
caatcggtat ctgtaaatat caaat                                           25

<210> SEQ ID NO 146
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 146 tcgcataccct gtttatcttc tact                                           24

<210> SEQ ID NO 147
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 147
ttggttccat ctgaactttg ag                                              22

<210> SEQ ID NO 148
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 148
aatggcttat caaagtgaat atgc                                            24
```

<210> SEQ ID NO 149
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 149
taatttcctt ttttttccatt cctc                                              24

<210> SEQ ID NO 150
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 150
actagaatct ccaaatgaat ccagt                                             25

<210> SEQ ID NO 151
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 151
tggagttaat ctacgtctca tctc                                              24

<210> SEQ ID NO 152
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 152
gttcatacag aagactcctt tttg                                              24

<210> SEQ ID NO 153
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 153
agttttgatt atccgaataa atgct                                             25

<210> SEQ ID NO 154
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 154
tttaaattca gctatatggg gaga                                              24

<210> SEQ ID NO 155
<211> LENGTH: 22
<212> TYPE: DNA
<213> ORGANISM: Artificial
<220> FEATURE:
<223> OTHER INFORMATION: OLIGONUCLEOTIDE

```
<400> SEQUENCE: 155
ttccgttttg ctattccata at                                              22

<210> SEQ ID NO 156
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 156
cctctgataa aaaacttgtg aaat                                            24

<210> SEQ ID NO 157
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 157
actactcctg gaattacaaa ctgg                                            24

<210> SEQ ID NO 158
<211> LENGTH: 23
<212> TYPE: DNA
<213> ORGANISM: Artificial
<220> FEATURE:
<223> OTHER INFORMATION: OLIGONUCLEOTIDE

<400> SEQUENCE: 158
gccaaaatta aaccacaatc cac                                             23

<210> SEQ ID NO 159
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 159
cattttgctg aatgatagtg cgta                                            24

<210> SEQ ID NO 160
<211> LENGTH: 48
<212> TYPE: DNA
<213> ORGANISM: Artificial
<220> FEATURE:
<223> OTHER INFORMATION: OLIGONUCLEOTIDE

<400> SEQUENCE: 160
cgaccggatt cccacatcaa atgatgcggg ttgtgttaat tccggtcg                  48

<210> SEQ ID NO 161
<211> LENGTH: 37
<212> TYPE: DNA
<213> ORGANISM: Artificial
<220> FEATURE:
<223> OTHER INFORMATION: OLIGONUCLEOTIDE

<400> SEQUENCE: 161
cccgcgcrta gttactrcgt tgtaagacgt ccgcggg                              37

<210> SEQ ID NO 162
```

```
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 162
ccccgtagtt actgcgttgt aagacgggg                                        29

<210> SEQ ID NO 163
<211> LENGTH: 37
<212> TYPE: DNA
<213> ORGANISM: Artificial
<220> FEATURE:
<223> OTHER INFORMATION: OLIGONUCLEOTIDE

<400> SEQUENCE: 163
cccgcgcata gttactgcgt tgtaagacgt ccgcggg                               37

<210> SEQ ID NO 164
<211> LENGTH: 37
<212> TYPE: DNA
<213> ORGANISM: Artificial
<220> FEATURE:
<223> OTHER INFORMATION: OLIGONUCLEOTIDE

<400> SEQUENCE: 164
cccgcgcgta gttactacgt tgtaagacgt ccgcggg                               37

<210> SEQ ID NO 165
<211> LENGTH: 1282
<212> TYPE: DNA
<213> ORGANISM: Staphylococcus aureus

<400> SEQUENCE: 165 accatttta g ctgtagggaa actaaaagag aaatattgga agcaagccat agcagaatat      60 gaaaacgtt taggcccata caccaagata gacatcatag aagttccaga cgaaaaagca      120
ccagaaaata tgagcgacaa agaaattgag caagtaaaag aaaagaagg ccaacgaata      180 ctagccaaaa tcaaaccaca atccacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactat    360
gcactatcat ttagcaaaat gacattccca catcaaatga tgcgggttgt gttaattgaa    420
caagtgtata gagcatttaa gattatgcgt ggagaagcgt accacaaata aaactaaaaa    480
atatgagaaa attattaaat tagctcaaat ctttgaagaa taaaagtga atattaagtt    540 tgataattta ggtacaagta aagattaaga atttccatta tttaatacat ggtgtgtaaa    600
tcgacttctt tttgtattag atgtttgcag taagcgatgt aaagaagatg ctaataaata    660
tgtgaggaat gattacgata ctagataagc ggctaatgaa attttttaaa gtacatatat    720
agacatattt ttcatttagt aaaatttga atttcacttt gctaagacta gtgtctagaa    780
atttataatg attattaac acctatttga aacttaagta taataaatga ttcggatttt    840
atttttaata aagacaaact tgaacgtagc aaagtagttt ttatgataaa taataagttt    900
taataatgtg acgcttttat ataagcacat tattatgaac aatgtgaatt gagcatctac    960
aattacatta ataaatatat aaatgatgat ttaaattcac atatatttat aatacacata   1020
ctatatgaaa gttttgatta tccgaataaa tgctaaaatt aataaaataa ttaaaggaat   1080
catacttatt atacgtatac gtttagctac tgaactactg gattcatttg gagattctag   1140
```

| | |
|---|---:|
| tagttcttttt tcaatctcta aatctaaatc agttttgtaa taaccattaa ttcctaatct | 1200 |
| ttcatctagc tctgtacttt tttcatcatt tttatctttg ttgatatgtt ccattttctc | 1260 |
| gcctcttttt aatcaagtag aa | 1282 |

<210> SEQ ID NO 166
<211> LENGTH: 1108
<212> TYPE: DNA
<213> ORGANISM: Staphylococcus aureus

<400> SEQUENCE: 166

| | |
|---|---:|
| accattttag ctgtagggaa actaaaagag aaatattgga agcaagccat agcagaatat | 60 |
| gaaaaacgtt taggcccata caccaagata gacatcatag aagttccaga cgaaaaagca | 120 |
| ccagaaaata tgagcgacaa agaaattgag caagtaaaag aaaagaagg ccaacgaata | 180 |
| ctagccaaaa tcaaaccaca atccacagtc attacattag aaatacaagg aaagatgcta | 240 |
| tcttccgaag gattggccca agaattgaac caacgcatga cccagggca agcgacttt | 300 |
| gtattcgtca ttggcggatc aaacggcctg cacaaggacg tcttacaacg cagtaactat | 360 |
| gcactatcat ttagcaaaat gacattccca catcaaatga tgcgggttgt gttaattgaa | 420 |
| caagtgtata gagcatttaa gattatgcgt ggagaagcgt accacaaata aaactaaaaa | 480 |
| atatgagaaa attattaaat tagctcaaat ctttgaagaa taaaaagtga atattaagtt | 540 |
| tgataattta ggtacaagta aagattaaga atttccatta tttaatacat ggtgtgtaaa | 600 |
| tcgacttctt tttgtattag atgtttgcag taagcgatgt aaagaagatg ctaataaata | 660 |
| tgtgaggaat gattacgata ctagataagc ggctaatgaa attttttaaa gtacatatat | 720 |
| agacatattt ttcatttagt aaaattttga atttcacttt gctaagacta gtgtctagaa | 780 |
| atttataatg atttattaac acctatttga aacttaagta taataaatga ttcggatttt | 840 |
| attttttaata aagacaaact tgaacgtagc aaagtagttt ttatgataaa taataagttt | 900 |
| taataatgtg acgcttttat ataagcacat tattatgaac aatgtgaatt gagcatctac | 960 |
| aattacatta ataaatatat aaatgatgat ttaaattcac atatatttat aatacacata | 1020 |
| ctatatgaaa gttttgatta tccgaataaa tgctaaaatt aataaaataa ttaaaggaat | 1080 |
| catacttatt atacgtatac gtttagct | 1108 |

<210> SEQ ID NO 167
<211> LENGTH: 1530
<212> TYPE: DNA
<213> ORGANISM: Staphylococcus aureus

<400> SEQUENCE: 167

| | |
|---|---:|
| ttagctgtag ggaaactaaa agagaaatat tggaagcaag ccatagcaga atatgaaaaa | 60 |
| cgtttaggcc catacaccaa gatagacatc atagaagttc cagacgaaaa agcaccagaa | 120 |
| aatatgagcg acaaagaaat tgagcaagta aaagaaaaag aaggccaacg aatactagcc | 180 |
| aaaatcaaac cacaatccac agtcattaca ttagaaatac aaggaaagat gctatcttcc | 240 |
| gaaggattgg cccaagaatt gaaccaacgc atgacccaag ggcaaagcga ctttgtattc | 300 |
| gtcattggcg gatcaaacgg cctgcacaag gacgtcttac aacgcagtaa ctatgcacta | 360 |
| tcatttagca aaatgacatt cccacatcaa atgatgcggg ttgtgttaat tgaacaagtg | 420 |
| tatagagcat ttaagattat gcgtggagaa gcatatcata aatgatgcgg ttttttcagc | 480 |
| cgcttcataa agggggtga tcatatcgga acgtatgagg tttatgagaa ttgctgctat | 540 |

```
gttttttatga agcgtatcat aaatgatgca gttttttgata attttttctt tatcagagat      600
tttactaaaa atcccctcaa agtttgtttt tttcaacttc aactttgaag ggaataaata      660
aggaacttat ttatatttat cctttatctc attaatatct attttttat taataatatt       720 ataaatatta aattctttag aaaagtcact atcactctta ttcttcatac taaacgttat      780
taatctaata atatcagcta ctatttcttt aaattctatt gcatcttctt ttttataagt      840
agcgcctgta tgaacaattt tatttctcat accatagtaa tctttcatat attttttttac     900 acaattttta atttcattag aattatccaa atctagatta tcaattgtct ttaataaatg      960
atcattaaca acattagcat acccacatcc aagcttcttt tttatctctt catcacttaa     1020
attttcatct aatttataat atctttctaa aaaatttgtg ataaaaactt ctaatgcagt     1080
ctgaatttgt acaattgcta aattatagtc agatttataa aaagaacgtt caccttttct     1140
catagccaaa acataaatat tgctaggatg attattgaaa atattataat tttttttaat     1200
atttaataaa tcacttttttt tgatagatga atactgatct tcttctatct ttccaggcat     1260
gtcaatcatg aaaatactca tctcttttat atttccatct atagtatata ttatataata     1320
tggaatactt aatatatccc ctaatgatag ctggtatata ttatgatact gatatttaac     1380
gctaataatt ttaataagat tatttagaca attaaattgc ttattaaaaa ttttcgttag     1440
actattactt ttctttgatt ccctagaagt agaatttgat ttcaattttt taaactgatt     1500
gtgcttgatt attgaagtta tttcaacata                                         1530

<210> SEQ ID NO 168
<211> LENGTH: 1256
<212> TYPE: DNA
<213> ORGANISM: Staphylococcus aureus

<400> SEQUENCE: 168
gctgtaggga aactaaaaga gaaatattgg aagcaagcca tagcagaata tgaaaaacgt        60
ttaggcccat acaccaagat agacatcata gaagttccag acgaaaaagc accagaaaat      120
atgagcgaca agaaattga gcaagtaaaa gaaaaagaag gccaacgaat actagccaaa       180
attaaaccac aatccacagt cattacatta gaaatacaag gaaagatgct atcttccgaa      240
ggattggccc aagaattgaa ccaacgcatg acccaagggc aaagcgactt tgtattcgtc      300
attggcggat caaacggcct gcacaaggac gtcttacaac gcagtaacta cgcactatca      360
ttcagcaaaa tgacattccc acatcaaatg atgcgggttg tgttaattga gcaagtgtat      420
agagcattta agattatgcg tggagaagca tatcataaat gatgcggttt tttcagccgc      480
ttcataaagg gattttgaat gtatcagaac atatgaggtt tatgtgaatt gctgttatgt      540
ttttaagaag catatcataa gtgatgcggt ttttattaat tagttgctaa aaaatgaagt     600
atgcaatatt aattattatt aaattttgat atatttaaag aaagattaag tttagggtga      660
atgaatggct tatcaaagtg aatatgcatt agaaaatgaa gtacttcaac aacttggagga    720 attgaactat gaaagagtaa atatacataa tattaaatta gaattaatg aatatctcaa      780 agaactagga gtgttgaaaa atgaataagc agacaaatac tccagaacta agatttccag    840
agtttgatga ggaatggaaa aaaggaaat taggtgaagt agtaaattat aaaaatggtg      900
gttcatttga agtttagtg aaaaaccatg gtgtatataa actcataact cttaaatctg     960
ttaatacaga aggaaagttg tgtaattctg gaaaatatat cgatgataaa tgtgttgaaa   1020
cattgtgtaa tgatacttta gtaatgatac tgagcgagca agcaccagga ctagttggaa    1080
tgactgcaat tatacctaat aataatgagt atgtactaaa tcaacgagta gcagcactag    1140
```

```
tgcctaaaca atttatagat agtcaatttc tatctaagtt aattaataga aaccagaaat   1200
atttcagtgt gagatctgct ggaacaaaag tgaaaaatat ttctaaagga catgta       1256
```

<210> SEQ ID NO 169
<211> LENGTH: 846
<212> TYPE: DNA
<213> ORGANISM: Staphylococcus aureus

<400> SEQUENCE: 169

```
ttacattaga aatacaagga aagatgctat cttccgaagg attggcccaa gaattgaacc     60
aacgcatgac ccaagggcaa agcgactttg ttttcgtcat tggcggatca aacggcctgc    120
acaaggacgt cttacaacgc agtaactacg cactatcatt cagcaaaatg acattcccac    180
atcaaatgat gcgggttgtg ttaattgaac aagtgtacag agcatttaag attatgcgag    240
gagaagctta tcataagtaa tgaggttcat gatttttgac atagttagcc tccgcagtct    300
ttcatttcaa gtaaataata gcgaaatatt ctttatactg aatacttata gtgaagcaaa    360
gttctagctt tgagaaaatt ctttctgcaa ctaaatatag taaattacgg taaaatataa    420
ataagtacat attgaagaaa atgagacata atatatttta taataggagg gaatttcaaa    480
tgatagacaa ctttatgcag gtccttaaat taattaaaga gaaacgtacc aataatgtag    540
ttaaaaaatc tgattgggat aaaggtgatc tatataaaac tttagtccat gataagttac    600
ccaagcagtt aaaagtgcat ataaaagaag ataaatattc agttgtaggg aaggttgcta    660
ctgggaacta tagtaaagtt ccttggattt caatatatga tgagaatata acaaaagaaa    720
caaaggatgg atattatttg gtatatcttt ttcatccgga aggagaaggc atatacttat    780
ctttgaatca aggatggtca aagataagtg atatgtttcc gcgggataaa aatgctgcaa    840
aacaaa                                                                846
```

<210> SEQ ID NO 170
<211> LENGTH: 1270
<212> TYPE: DNA
<213> ORGANISM: Staphylococcus aureus

<400> SEQUENCE: 170

```
cattagaaat acaaggaaag atgctatctt ccgaaggatt ggcccaagaa ttgaaccaac     60
gcatgaccca agggcaaagc gactttgtat tcgtcattgg cggatcaaac ggcctgcaca    120
aggacgtctt acaacgcagt aactatgcac tatcatttag caaaatgaca ttcccacatc    180
aaatgatgcg ggttgtgtta attgaacaag tgtatagagc atttaagatt atgcgtggag    240
aagcatatca taaatgatgc ggttttttca gccgcttcat aaagggattt tgaatgtatc    300
agaacatatg aggtttatgt gaattgctgt tatgttttta agaagcttat cataagtaat    360
gaggttcatg atttttgaca tagttagcct ccgcagtctt tcatttcaag taaataatag    420
cgaaatattc tttatactga atacttatag tgaagcaaag ttctagcttt gagaaaattc    480
tttctgcaac taaatatagt aaattacggt aaaatataaa taagtacata ttgaagaaaa    540
tgagacataa tatattttat aataggaggg aatttcaaat gatagacaac tttatgcagg    600
tccttaaatt aattaaagag aaacgtacca ataatgtagt taaaaaatct gattgggata    660
aaggtgatct atataaaact ttagtccatg ataagttacc caagcagtta aaagtgcata    720
taaaagaaga taaatattca gttgtaggga aggttgctac tgggaactat agtaaagttc    780
cttggatttc aatatatgat gagaatataa caaaagaaac aaaggatgga tattatttgg    840
```

| | |
|---|---:|
| tatatcttttt tcatccggaa ggagaaggca tatacttatc tttgaatcaa ggatggtcaa | 900 |
| agataagtga tatgtttccg cgggataaaa atgctgcaaa acaaagagca ttaactttat | 960 |
| cttccgaact caataaatat attacatcaa atgaatttaa tactggaaga ttttattacg | 1020 |
| cagaaaataa agattcatct tatgatttaa aaaatgatta ccatcagga tattctcatg | 1080 |
| gatcaataag attcaaatat tatgatttga atgaaggatt cacagaagaa gatatgctag | 1140 |
| aggatttaaa gaaattttta gaactattta atgaattagc ttcaaaagtt acaaaaacat | 1200 |
| cctatgatag cttggtcaat agcatagacg aaatacagga agacagcgaa attgaagaaa | 1260 |
| ttagaacagc | 1270 |

<210> SEQ ID NO 171
<211> LENGTH: 991
<212> TYPE: DNA
<213> ORGANISM: Staphylococcus aureus

<400> SEQUENCE: 171

| | |
|---|---:|
| accattttag ctgtagggaa actaaaagag aaatactgga agcaagccat agcagaatat | 60 |
| gaaaaacgtt taggcccata caccaagata gacatcatag aagttccaga cgaaaaagca | 120 |
| ccagaaaata tgaactacaa agaaattgag caagtaaaag aaaaagaagg ccaacgaata | 180 |
| ctagccaaaa tcaaaccaca atcaacagtc attacattag aaatacaagg aaagatgcta | 240 |
| tcttccgaag gattggccca agaattgaac caacgcatga cccaagggca aagcgacttt | 300 |
| gtattcgtca ttggcggatc aaacggcctg cacaaggacg tcttacaacg cagtaactac | 360 |
| gcactatcat tcagcaaaat gacattccca catcaaatga tgcgggttgt gttaattgaa | 420 |
| caagtgtaca gagcatttaa gattatgcga ggagaagcgt atcataagtg atggtaaaaa | 480 |
| atatgagtaa gtagatgaag agtgaaaatc agattaatta ataataatgt atcaaattta | 540 |
| aataaagggg ttttttaagta tgaatttaag aggtcatgaa aatagactta aatttcatgc | 600 |
| gaaatatgat gtgacaccta tcacatttt aaaattatta gaaggtcaaa agaaagacgg | 660 |
| tgaaggcggc atactgacag atagctatta ctgttttca tacagcttaa aaggtaattc | 720 |
| taaaaaagtt ttaggtacgt ttaattgtgg ttatcatatt gctgaagatt tactaaaatt | 780 |
| atcaaatcaa gataaattac ctttatttaa cccgtttaaa gtaattaatg aaggtaatca | 840 |
| attgcagggc gtaacgaata aaggtaattt aaatattaat aggcaaagaa aacagtataa | 900 |
| tgaagtggct ttacagcttt caaatgctat taatttaatc ataatttgtt atgaggataa | 960 |
| tattaaagaa ccactttcaa cgataaaata c | 991 |

<210> SEQ ID NO 172
<211> LENGTH: 748
<212> TYPE: DNA
<213> ORGANISM: Staphylococcus aureus

<400> SEQUENCE: 172

| | |
|---|---:|
| atcgtttaac gtgtcacatg atgcgataga tccgcaattt tatattttcc ataataacta | 60 |
| taagaagttt acgattttaa cagatacggg ttacgtgtct gatcgtatga aaggtatgat | 120 |
| acgtggcagc gatgcattta tttttgagag taatcatgac gtcgatatgt tgagaatgtg | 180 |
| tcgttatcca tggaagacga aacaacgcat tttaggcgat atgggtcatg tatctaatga | 240 |
| ggatgcgggt catgcgatga cagacgtgat tacaggtaac acgaaacgta tttacttatc | 300 |
| gcatttatca agataaata atatgaaaga tttggcgcgt atgagtgttg gccaagtatt | 360 |
| gaacgaacac gatattgata cggaaaaaga agtattgcta tgtgatacgg ataaagctat | 420 |

```
tccaacacca atatatacaa tataaatgag agtcatccga taaagttccg cactgctgtg    480
aaacgacttt atcgggtgct tttttatgtt gttggtggga atggctgtt gttgagttga    540 atcggattga ttgaaatgtg taaaataatt cgatattaaa tgtaatttat aaataattta    600
cataaaatca acatttaa tataaggatt atgataatat attggtgtat gacagttaat     660
ggagggaacg aaatgaaagc tttattactt aaaacaagtg tatggctcgt tttgcttttt    720
agtgtgatgg gattatggca tgtctcga                                      748

<210> SEQ ID NO 173
<211> LENGTH: 917
<212> TYPE: DNA
<213> ORGANISM: Staphylococcus aureus

<400> SEQUENCE: 173
aaatacaagg aaagatgcta tcttccgaag gattggccca agaattgaac caacgcatga     60
cccaagggca aagcgacttt gtattcgtca ttggcggatc aaacggcctg cacaaggacg    120
tcttacaacg tagtaactac gcactatcat tcagcaaaat gacattccca catcaaatga    180
tgcgggttgt gttaattgag caagtgtata gagcatttaa gattatgcgt ggagaagcat    240
atcataaatg atgcggtttt ttcagccgct tcataaaggg attttgaatg tatcagaaca    300
tatgaggttt atgtgaattg ctgttatgtt tttaagaagc ttatcataag taatgaggtt    360
catgattttt gacatagtta gcctccgcag tctttcattt caagtaaata atagcgaaat    420
attctttata ctgaatactt atagtgaagc aaagttctag ctttgagaaa attctttctg    480
caactaaata tagtaaatta cggtaaaata taaataagta catattgaag aaaatgagac    540
ataatatatt ttataatagg agggaatttc aaatgataga caactttatg caggtcctta    600
aattaattaa agagaaacgt accaataatg tagttaaaaa atctgattgg gataaaggtg    660
atctatataa aactttagtc catgataagt tacccaagca gttaaaagtg catataaaag    720
aagataaata ttcagttgta gggaaggttg ctactgggaa ctatagtaaa gttccttgga    780
tttcaatata tgatgagaat ataacaaaag aaacaaagga tggatattat ttggtatatc    840
tttttcatcc ggaaggagaa ggcatatact tatctttgaa tcaaggatgg tcaaagataa    900
gtgatatgtt tccgcgg                                                  917

<210> SEQ ID NO 174
<211> LENGTH: 1132
<212> TYPE: DNA
<213> ORGANISM: Staphylococcus aureus

<400> SEQUENCE: 174
gctgtaggga aactaaaaga gaaatattgg aagcaagcca tagcagaata tgaaaaacgt     60
ttaggcccat acaccaagat agacatcata gaagttccag acgaaaaagc accagaaaat    120
atgagcgaca agaaattga gcaagtaaaa gaaaaagaag gccaacgaat actagccaaa    180
atcaaaccac aatcaacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gtagtaacta cgcactatca    360
ttcagcaaaa tgacattccc acatcaaatg atgcgggttg tgttaattga gcaagtgtat    420
agagcattta agattatgcg tggagaagca tatcataaat gatgcggttt tttcagccgc    480
ttcataaagg gattttgaat gtatcagaac atatgaggtt tatgtgaatt gctgttatgt    540
```

```
tttaagaag cttatcataa gtaatgaggt tcatgatttt tgacatagtt agcctccgca    600
gtctttcatt tcaagtaaat aatagcgaaa tattctttat actgaatact tatagtgaag    660
caaagttcta gctttgagaa aattctttct gcaactaaat atagtaaatt acggtaaaat    720
ataaataagt acatattgaa gaaatgaga cataatatat tttataatag gagggaattt    780
caaatgatag acaactttat gcaggtcctt aaattaatta agagaaacg taccaataat    840
gtagttaaaa aatctgattg ggataaaggt gatctatata aaactttagt ccatgataag    900
ttacccaagc agttaaaagt gcatataaaa gaagataaat attcagttgt agggaaggtt    960
gctactggga actatagtaa agttccttgg atttcaatat atgatgagaa tataacaaaa   1020
gaaacaaagg atggatatta tttggtatat cttttcatc cggaaggaga aggcatatac   1080
ttatctttga atcaaggatg gtcaaagata agtgatatgt ttccgcggga ta          1132
```

<210> SEQ ID NO 175
<211> LENGTH: 1133
<212> TYPE: DNA
<213> ORGANISM: Staphylococcus aureus

<400> SEQUENCE: 175

```
agctgtaggg aaactaaaag agaaatattg gaagcaagcc atagcagaat atgaaaaacg     60
tttaggccca taccaagata gacatcat agaagttcca gacgaaaaag caccagaaaa    120
tatgagcgac aaagaaattg agcaagtaaa agaaaagaa ggccaacgaa tactagccaa    180
aatcaaacca caatcaacag tcattacatt agaaatacaa ggaaagatgc tatcttccga    240
aggattggcc caagaattga ccaacgcat gacccaaggg caaagcgact tgtattcgt     300
cattggcgga tcaaacggcc tgcacaagga cgtcttacaa cgtagtaact acgcactatc    360
attcagcaaa atgacattcc cacatcaaat gatgcgggtt gtgttaattg agcaagtgta    420
tagagcattt aagattatgc gtggagaagc atatcataaa tgatgcggtt ttttcagccg    480
cttcataaag ggatttgaa tgtatcagaa catatgaggt tatgtgaat tgctgttatg    540
tttttaagaa gcttatcata gtaatgagg ttcatgattt tgacatagt agcctccgc     600
agtctttcat ttcaagtaaa taatagcgaa atattcttta tactgaatac ttatagtgaa    660
gcaaagttct agctttgaga aaattctttc tgcaactaaa tatagtaaat tacggtaaaa    720
tataaataag tacatattga gaaaatgag acataatata tttataata ggagggaatt     780
tcaaatgata gacaacttta tgcaggtcct taaattaatt aaagagaaac gtaccaataa    840
tgtagttaaa aaatctgatt gggataaagg tgatctatat aaaactttag tccatgataa    900
gttacccaag cagttaaag tgcatataaa gaagataaa tattcagttg tagggaaggt     960
tgctactggg aactatagta agttccttg gatttcaata tatgatgaga atataacaaa    1020
agaaacaaag gatggatatt atttggtata tcttttcat ccggaaggag aaggcatata    1080
cttatctttg aatcaaggat ggtcaaagat aagtgatatg tttccgcggg ata          1133
```

<210> SEQ ID NO 176
<211> LENGTH: 1087
<212> TYPE: DNA
<213> ORGANISM: Staphylococcus aureus

<400> SEQUENCE: 176

```
actaaaagag aaatattgga agcaagccat agcagaatat gaaaaacgtt taggcccata     60
caccaagata gacatcatag aagttccaga cgaaaaagca ccagaaaata tgagcgacaa    120
agaaattgag caagtaaaag aaaagaagg ccaacgaata ctagccaaaa tcaaaccaca    180
```

```
atcaacagtc attacattag aaatacaagg aaagatgcta tcttccgaag gattggcaca      240
agaattgaac caacgcatga cccaagggca aagcgacttt gtattcgtca ttggcggatc      300
aaacggcctg cacaaggacg tcttacaacg tagtaactac gcactatcat tcagcaaaat      360
gacattccca catcaaatga tgcgggttgt gttaattgag caagtgtata gagcgtttaa      420
gattatgcgt ggagaagcat atcataaatg atgcggtttt ttcagccgct tcataaaggg      480
attttgaatg tatcagaaca tatgaggttt atgtgaattg ctgttatgtt tttaagaagc      540
ttatcataag taatgaggtt catgattttt gacatagtta gcctccgcag tctttcattt      600
caagtaaata atagcgaaat attctttata ctgaatactt atagtgaagc aaagttctag      660
ctttgagaaa attctttctg caactaaata tagtaaatta cggtaaaata taaataagta      720
catattgaag aaaatgagac ataatatatt ttataatagg agggaatttc aaatgataga      780
caactttatg caggtcctta aattaattaa agagaaacgt accaatgtg tagttaaaaa      840 atctgattgg gataaaggtg atctatataa aactttagtc catgataagt acccaagca      900 gttaaaagtg catataaaag aagataaata ttcagttgta gggaaggttg ctactgggaa      960
ctatagtaaa gttccttgga tttcaatata tgatgagaat ataacaaaag aaacaaagga     1020
tggatattat ttggtatatc tttttcatcc ggaaggagaa ggcatatact tatctttgaa     1080
tcaagga                                                              1087
```

<210> SEQ ID NO 177
<211> LENGTH: 903
<212> TYPE: DNA
<213> ORGANISM: Staphylococcus aureus

<400> SEQUENCE: 177

```
caaggaaaga tgctatcttc cgaaggattg gcccaagaat tgaaccaacg catgacccaa       60
gggcaaagcg actttgtatt cgtcattggc ggatcaaacg gcctgcacaa ggacgtctta      120
caacgtagta actacgcact atcattcagc aaaatgacat tcccacatca aatgatgcgg      180
gttgtgttaa ttgagcaagt gtatagagca tttaagatta tgcgtggaga agcatatcat      240
aaatgatgcg gttttttcag ccgcttcata agggattttt gaatgtatca gaacatatga      300
ggtttatgtg aattgctgtt atgttttaa gaagcttatc ataagtaatg aggttcatga      360 ttttttgacat agttagcctc cgcagtcttt catttcaagt aaataatagc gaaatattct      420
ttatactgaa tacttatagt gaagcaaagt tctagctttg agaaaattct ttctgcaact      480
aaatatagta aattacggta aaatataaat aagtacatat tgaagaaaat gagacataat      540
atattttata ataggaggga atttcaaatg atagacaact ttatgcaggt ccttaaatta      600
attaaagaga aacgtaccaa taatgtagtt aaaaaatctg attgggataa aggtgatcta      660
tataaaactt tagtccatga taagttaccc aagcagttaa aagtgcatat aaagaagat      720 aaatattcag ttgtagggaa ggttgctact gggaactata gtaaagttcc ttggatttca      780
atatatgatg agaatataac aaaagaaaca aaggatggat tatttggt atatcttttt      840 catccggaag gagaaggcat atacttatct tgaatcaag gatggtcaaa gataagtgat      900
atg                                                                   903
```

<210> SEQ ID NO 178
<211> LENGTH: 1114
<212> TYPE: DNA
<213> ORGANISM: Staphylococcus aureus

<400> SEQUENCE: 178

```
ggaaactaaa agagaaatat tggaagcaag ccatagcaga atatgaaaaa cgtttaggcc      60
catacaccaa gatagacatc atagaagttc cagacgaaaa agcaccagaa atatgagcg      120
acaaagaaat tgagcaagta aagaaaaag aaggccaacg aatactagcc aaaatcaaac      180
cacaatcaac agtcattaca ttagaaatac aaggaaagat gctatcttcc gaaggattgg      240
cccaagaatt gaaccaacgc atgacccaag gcaaagcga ctttgtattc gtcattggcg      300
gatcaaacgg cctgcacaag gacgtcttac aacgtagtaa ctacgcacta tcattcagca      360
aaatgacatt cccacatcaa atgatgcggg ttgtgttaat tgagcaagtg tatagagcat      420
ttaagattat gcgtggagaa gcatatcata aatgatgcgg ttttttcagc cgcttcataa      480
agggattttg aatgtatcag aacatatgag gtttatgtga attgctgtta tgtttttaag      540
aagcttatca taagtaatga ggttcatgat ttttgacata gttagcctcc gcagtctttc      600
atttcaagta aataatagcg aaatattctt tatactgaat acttatagtg aagcaaagtt      660
ctagctttga gaaaattctt tctgcaacta aatatagtaa attacggtaa aatataaata      720
agtacatatt gaagaaaatg agacataata tattttataa taggagggaa tttcaaatga      780
tagacaactt tatgcaggtc cttaaattaa ttaaagagaa acgtaccaat aatgtagtta      840
aaaaatctga ttgggataaa ggtgatctat ataaaacttt agtccatgat aagttaccca      900
agcagttaaa agtgcatata aaagaagata atattcagt tgtagggaag gttgctactg      960
ggaactatag taaagttcct tggatttcaa tatatgatga gaatataaca aaagaaacaa     1020
aggatggata ttatttggta tatctttttc atccggaagg agaaggcata tacttatctt     1080
tgaatcaagg atggtcaaag ataagtgata tgtt                                 1114
```

<210> SEQ ID NO 179
<211> LENGTH: 1121
<212> TYPE: DNA
<213> ORGANISM: Staphylococcus aureus

<400> SEQUENCE: 179

```
ggaaactaaa agagaaatat tggaagcaag ccatagcaga atatgaaaaa cgtttaggcc      60
catacaccaa gatagacatc atagaagttc cagacgaaaa agcaccagaa atatgagcg      120
acaaagaaat tgagcaagta aagaaaaag aaggccaacg aatactagcc aaaatcaaac      180
cacaatccac agtcattaca ttagaaatac aaggaaagat gctatcttcc gaaggattgg      240
cccaagaatt gaaccaacgc atgacccaag gcaaagcga ctttgtattc gtcattggcg      300
gatcaaacgg cctgcacaag gacgtcttac aacgcagtaa ctatgcacta tcatttagca      360
aaatgacatt cccacatcaa atgatgcggg ttgtgttaat tgaacaagtg tatagagcat      420
ttaagattat gcgtggagaa gcatatcata aatgatgcgg ttttttcagc cgcttcataa      480
agggattttg aatgtatcag aacatatgag gtttatgtga attgctgtta tgtttttaag      540
aagcttatca taagtaatga ggttcatgat ttttgacata gttagcctcc gcagtctttc      600
atttcaagta aataatagcg aaatattctt tatactgaat acttatagtg aagcaaagtt      660
ctagctttga gaaaattctt tctgcaacta aatatagtaa attacggtaa aatataaata      720
agtacatatt gaagaaaatg agacataata tattttataa taggagggaa tttcaaatga      780
tagacaactt tatgcaggtc cttaaattaa ttaaagagaa acgtaccaat aatgtagtta      840
aaaaatctga ttgggataaa ggtgatctat ataaaacttt agtccatgat aagttaccca      900
agcagttaaa agtgcatata aaagaagata atattcagt tgtagggaag gttgctactg      960
```

```
ggaactatag taaagttcct tggatttcaa tatatgatga aatataaca aaagaaacaa    1020 aggatggata ttatttggta tatcttttc atccggaagg agaaggcata tacttatctt    1080
tgaatcaagg atggtcaaag ataagtgata tgtttccgcg g                       1121
```

<210> SEQ ID NO 180
<211> LENGTH: 1121
<212> TYPE: DNA
<213> ORGANISM: Staphylococcus aureus

<400> SEQUENCE: 180

```
tagctgtagg gaaactaaaa gagaaatatt ggaagcaagc catagcagaa tatgaaaaac     60
gtttaggccc atacaccaag atagacatca tagaagttcc agacgaaaaa gcaccagaaa    120
atatgagcga caaagaaatt gagcaagtaa aagaaaaaga aggccaacga atactagcca    180
aaatcaaacc acaatccaca gtcattacat tagaaataca aggaaagatg ctatcttccg    240
aaggattggc ccaagaattg aaccaacgca tgacccaagg gcaaagcgac tttgtattcg    300
tcattggcgg atcaaacggc ctgcacaagg acgtcttaca acgcagtaac tatgcactat    360
catttagcaa aatgacattc ccacatcaaa tgatgcgggt tgtgttaatt gaacaagtgt    420
atagagcatt taagattatg cgtggagaag catatcataa atgatgcggt tttttcagcc    480
gcttcataaa gggattttga atgtatcaga acatatgagg tttatgtgaa ttgctgttat    540
gtttttaaga agcttatcat aagtaatgag gttcatgatt tttgacatag ttagcctccg    600
cagtctttca tttcaagtaa ataatagcga atattctt tactgaata cttatagtga    660 agcaaagttc tagctttgag aaaattcttt ctgcaactaa atatagtaaa ttacggtaaa    720
atataaataa gtacatattg aagaaaatga acataatat attttataat aggagggaat    780
ttcaaatgat agacaacttt atgcaggtcc ttaaattaat taaagagaaa cgtaccaata    840
atgtagttaa aaaatctgat tgggataaag gtgatctata taaaacttta gtccatgata    900
agttacccaa gcagttaaaa gtgcatataa aagaagataa atattcagtt gtagggaagg    960
ttgctactgg gaactatagt aaagttcctt ggatttcaat atatgatgag aatataacaa    1020
aagaaacaaa ggatggatat tatttggtat atcttttca tccggaagga gaaggcatat    1080
acttatcttt gaatcaagga tggtcaaaga taagtgatat g                       1121
```

<210> SEQ ID NO 181
<211> LENGTH: 1131
<212> TYPE: DNA
<213> ORGANISM: Staphylococcus aureus

<400> SEQUENCE: 181

```
ctgtagggaa actaaaagag aaatattgga agcaagccat agcagaatat gaaaaacgtt     60
taggcccata caccaagata gacatcatag aagttccaga cgaaaaagca ccagaaaata    120
tgagcgacaa agaaattgag caagtaaaag aaaagaagg ccaacgaata ctagccaaaa    180
tcaaaccaca atccacagtc attacattag aaatacaagg aaagatgcta tcttccgaag    240
gattggccca agaattgaac caacgcatga cccaagggca aagcgacttt gtattcgtca    300
ttggcggatc aaacggcctg cacaaggacg tcttacaacg cagtaactat gcactatcat    360
ttagcaaaat gacattccca catcaaatga tgcggttgt gttaattgaa caagtgtata    420
gagcatttaa gattatgcgt ggagaagcat atcataaatg atgcggtttt ttcagccgct    480
tcataaaggg attttgaatg tatcagaaca tatgaggttt atgtgaattg ctgttatgtt    540
```

```
tttaagaagc ttatcataag taatgaggtt catgattttt gacatagtta gcctccgcag      600
tctttcattt caagtaaata atagcgaaat attcttata ctgaatactt atagtgaagc       660
aaagttctag ctttgagaaa attctttctg caactaaata tagtaaatta cggtaaaata      720
taaataagta catattgaag aaaatgagac ataatatatt ttataatagg agggaatttc      780
aaatgataga caactttatg caggtcctta aattaattaa agagaaacgt accaataatg      840
tagttaaaaa atctgattgg gataaaggtg atctatataa aactttagtc catgataagt      900
tacccaagca gttaaaagtg catataaaag aagataaata ttcagttgta gggaaggttg      960
ctactgggaa ctatagtaaa gttccttgga tttcaatata tgatgagaat ataacaaaag     1020
aaacaaagga tggatattat ttggtatatc ttttcatcc ggaaggagaa ggcatatact      1080
tatctttgaa tcaaggatgg tcaaagataa gtgatatgtt ccgcgggat a              1131

<210> SEQ ID NO 182
<211> LENGTH: 896
<212> TYPE: DNA
<213> ORGANISM: Staphylococcus aureus

<400> SEQUENCE: 182
cattagaaat acaaggaaag atgctatctt ccgaaggatt ggcccaagaa ttgaaccaac       60
gcatgaccca gggcaaagc gactttgtat tcgtcattgg cggatcaaac ggcctgcaca       120
aggacgtctt acaacgcagt aactatgcac tatcatttag caaaatgaca ttcccacatc      180
aaatgatgcg ggttgtgtta attgaacaag tgtatagagc atttaagatt atgcgtggag      240
aagcatatca taaatgatgc ggttttttca gccgcttcat aaagggattt tgaatgtatc      300
agaacatatg aggtttatgt gaattgctgt tatgttttta agaagcttat cataagtaat      360
gaggttcatg atttttgaca tagttagcct ccgcagtctt tcatttcaag taaataatag      420
cgaaatattc tttatactga atacttatag tgaagcaaag ttctagcttt gagaaaattc      480
tttctgcaac taaatatagt aaattacggt aaaatataaa taagtacata ttgaagaaaa      540
tgagacataa tatatttat aataggaggg aatttcaaat gatagacaac tttatgcagg      600
tccttaaatt aattaaagag aaacgtacca ataatgtagt taaaaatct gattgggata      660 aggtgatct atataaaact ttagtccatg ataagttacc caagcagtta aaagtgcata      720
taaaagaaga taaatattca gttgtaggga aggttgctac tgggaactat agtaaagttc      780
cttggatttc aatatatgat gagaatataa caaagaaac aaaggatgga tattatttgg      840
tatatctttt tcatccggaa ggagaaggca tatacttatc tttgaatcaa ggatgg         896

<210> SEQ ID NO 183
<211> LENGTH: 1125
<212> TYPE: DNA
<213> ORGANISM: Staphylococcus aureus

<400> SEQUENCE: 183
ggaaactaaa agagaaatat tggaagcaag ccatatcaga atatgaaaaa cgtttaggcc        60
catacaccaa gatagacatc atagaagttc cagacgaaaa agcaccagaa atatgagcg       120 acaaagaaat cgagcaagta aaagaaaag aaggccaacg aatactagcc aaaatcaaac       180
cacaatcaac agtcattaca ttagaaatac aaggaaagat gctatcttcc gaaggattgg       240
ctcaagaatt gaaccaacgc atgacccaag gcaaagcga ctttgtattc gttattggcg       300
gatcaaacgg cctgcacaag gacgtcttac aacgcagtaa ctatgcacta tcattcgcag       360
aaatgacatt tccacatcag atgatgcggg ttgtgttaat tgagcaagtg tatagagcat       420
```

```
ttaagattat gcgtggggaa gcatatcata aatgatgcgg ttttttcagc cgcttcataa      480
agggattttg aatgtatcag aacatatgag gtttatgtga attgctgtta tgttttttaag    540 aagcttatca taagtaatga ggttcatgat ttttgacata gttagcctcc gcagtctttc    600
atttcaagta aataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaaatctga ttgggataaa ggtgatctat ataaaacttt agtccatgat aagttaccca    900
agcagttaaa agtgcatata aagaagata aatattcagt tgtagggaag gttgctactg      960
ggaactatag taaagttcct tggatttcaa tatatgatga gaatataaca aaagaaacaa    1020
aggatggata ttatttggta tatctttttc atccggaagg agaaggcata tacttatctt    1080
tgaatcaagg atggtcaaag ataagtgata tgtttccgcg ggata                    1125

<210> SEQ ID NO 184
<211> LENGTH: 679
<212> TYPE: DNA
<213> ORGANISM: Staphylococcus aureus

<400> SEQUENCE: 184
ataagaggga acagtgtgaa caagttaata acttgtggat aactggaaag ttgataacaa      60
tttggaggac caaacgacat gaaaatcacc attttagctg tagggaaact aaaagagaaa    120
tattggaagc aagccatagc agaatatgaa aaacgtttag gcccatacac caagatagac    180
atcatagaag ttccagacga aaaagcacca gaaaatatga gcgacaaaga aattgagcaa    240
gtaaaagaaa aagaaggcca acgaatacta gccaaaatca aaccacaatc cacagtcatt    300
acattagaaa tacaaggaaa gatgctatct tccgaaggat tggcccaaga attgaaccaa    360
cgcatgaccc aagggcaaag cgactttgta ttcgtcattg gcggatcaaa cggcctgcac    420
aaggacgtct tacaacgcag taactatgca ctatcattta gcaaaatgac attcccacat    480
caaatgatgc gggttgtgtt aattgaacaa gtgtatagag catttaagat tatgcgtgga    540
gaggcttatc ataaataaaa ctaaaaatta gattgtgtat aatttaaaaa tttaatgaga    600
tgtggaggaa ttacatatat gaaatattgg agtataccttg caatatcat acgatgttta    660 tagagtgttt aataaaacca                                                  679

<210> SEQ ID NO 185
<211> LENGTH: 1125
<212> TYPE: DNA
<213> ORGANISM: Staphylococcus aureus

<400> SEQUENCE: 185
ggaaactaaa agagaaatat tggaagcaag ccatagcaga atatgaaaaa cgtttaggcc      60
catacaccaa gatagacatc atagaagttc cagacgaaaa agcaccagaa atatgagcg    120 acaaagaaat tgagcaagta aagaaaaag aaggccaacg aatactagcc aaaatcaaac    180
cacaatcaac agtcattaca ttagaaatac aaggaaagat gctatcttcc gaaggattgg    240
cacaagaatt gaaccaacgc atgacccaag ggcaaagcga ctttgtattc gtcattggcg    300
gatcaaacgg cctgcacaag gacgtcttac aacgtagtaa ctacgcacta tcattcagca    360
aaatgacatt cccacatcaa atgatgcggg ttgtgttaat tgagcaagtg tatagagcgt    420
```

```
ttaagattat gcgtggagaa gcatatcata aatgatgcgg ttttttcagc cgcttcataa        480
agggattttg aatgtatcag aacatatgag gtttatgtga attgctgtta tgtttttaag        540
aagcttatca taagtaatga ggttcatgat ttttgacata gttagcctcc gcagtctttc        600
atttcaagta aataatagcg aaatattctt tatactgaat acttatagtg aagcaaagtt        660
ctagctttga gaaaattctt tctgcaacta aatatagtaa attacggtaa aatataaata        720
agtacatatt gaagaaaatg agacataata tattttataa taggagggaa tttcaaatga        780
tagacaactt tatgcaggtc cttaaattaa ttaaagagaa acgtaccaat aatgtagtta        840
aaaaatctga ttgggataaa ggtgatctat ataaaacttt agtccatgat aagttaccca        900
agcagttaaa agtgcatata aagaagata atattcagt tgtagggaag gttgctactg          960
ggaactatag taaagttcct tggatttcaa tatatgatga gaatataaca aaagaaacaa       1020
aggatggata ttatttggta tatcttttc atccggaagg agaaggcata tacttatctt       1080
tgaatcaagg atggtcaaag ataagtgata tgtttccgcg ggata                       1125
```

<210> SEQ ID NO 186
<211> LENGTH: 926
<212> TYPE: DNA
<213> ORGANISM: Staphylococcus aureus

<400> SEQUENCE: 186

```
tacattagaa atacaaggaa agatgctatc ttccgaagga ttggcccaag aattgaacca         60
acgcatgacc caagggcaaa gcgactttgt attcgtcatt ggcggatcaa acggcctgca       120
caaggacgtc ttacaacgca gtaactatgc actatcattt agcaaaatga cattcccaca       180
tcaaatgatg cgggttgtgt taattgaaca agtgtataga gcatttaaga ttatgcgtgg       240
agaagcatat cataaatgat gcggtttttt cagccgcttc ataagggat tttgaatgta       300 tcagaacata tgaggtttat gtgaattgct gttatgtttt taagaagctt atcataagta       360
atgaggttca tgattttga catagttagc ctccgcagtc tttcatttca gtaaataat        420 agcgaaatat tctttatact gaatacttat agtgaagcaa agttctagct ttgagaaaat      480
tctttctgca actaaatata gtaaattacg gtaaaatata ataagtaca tattgaagaa       540 aatgagacat aatatatttt ataataggag ggaatttcaa atgatagaca acttatgca       600 ggtccttaaa ttaattaaag agaaacgtac caataatgta gttaaaaaat ctgattggga       660
taaaggtgat ctatataaaa ctttagtcca tgataagtta cccaagcagt taaaagtgca       720
tataaaagaa gataaatatt cagttgtagg gaaggttgct actgggaact atagtaaagt       780
tccttggatt tcaatatatg atgagaatat aacaaaagaa acaaaggatg gatattattt       840
ggtatatctt tttcatccgg aaggagaagg catatactta tctttgaatc aaggatggtc       900
aaagataagt gatatgtttc cgcggg                                             926
```

<210> SEQ ID NO 187
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 187

```
ggatgtgggt atgctaatgt tgtt                                               24
```

<210> SEQ ID NO 188
<211> LENGTH: 27

```
<212> TYPE: DNA
<213> ORGANISM: Artificial
<220> FEATURE:
<223> OTHER INFORMATION: OLIGONUCLEOTIDE

<400> SEQUENCE: 188
tgaacaattt tatttctcat accatag                                              27

<210> SEQ ID NO 189
<211> LENGTH: 2154
<212> TYPE: DNA
<213> ORGANISM: Staphylococcus aureus

<400> SEQUENCE: 189
cggtaataaa aaatacgata tagatgaata acaaaacagt gaagcaatcc gtaacgatgg     60
ttgcttcact gttttattat gaattattaa taagtgctgt tacttctccc ttaaatacaa    120
tttcttcatt tcattgtat gttgaaagtg acactgtaac gagtccattt tcttttttta    180
tggatttctt atttgtaatt tcagcgataa cgtacaatgt attacctggg tatacaggtt    240
taataaattt aacgttattc atttgtgttc ctgctacaac ttcttctccg tatttacctt    300
cttctaccca taatttaaat gatattgaaa gtgtatgcat gccagatgca atgataccct    360
taaatctact tgttctgct ttttcttat ctatatgcat atattgagga tcaaagttg    420
ttgcaaattg gataatttct tctctgtaa tatgaaggct ttttgttttg aatgtttctc    480
ctactataaa atcatcgtat tcatatatg tctctctttc ttattcaaat taatttttta    540
gtatgtaaca tgttaaaggt aagtctaccg tcactgaaac gtaagactca cctctaactt    600
tctattgaga caaatgcacc attttatctg cattgtctgt aaagatacca tcaactcccc    660
aattagcaag ttggtttgca cgtgctggtt tgtttacagt ccatacgttc aattcataac    720
ccgcttcttt taccatttt acttttgctt tagtaagttt ggcatcttca gtgtttacta    780
ttttagcatt acagtaatct aaaagtgttc tccagtcttc acgaaacgaa gttgtatgga    840
atataactgc tctgttatat tgtggcatga tttcttctgc aagtttaaca agcacaacat    900
taaagcttga aatgagcact tcttgattct gatttaagtt tgttaattgt tcttccactt    960
gcttaaccat acttttagaa agtgctagtc cattcggtcc agtaatacct tttaattcta   1020
catttaaatt catattatat tcatttgcta ttttactac atcatcgaaa gttggcaaat   1080
gttcatcttt gaattttca ccaaaccaag atcctgcaga agcatcttta atttcatcat   1140
aattcaattc agttatttcc ccggacatat ttgtagtccg ttctaaataa tcatcatgaa   1200
tgataatcag ttgttcatct tttgtaattg caacatctaa ctccaaccag tttataccctt   1260
ctacttctga agcagcttta aatgatgcaa ttgtattttc cggagcttta ctaggtaatc   1320
ctctatgtcc atatacagtt agcatattac ctctccttgc attttatttt ttttaattaa   1380
cgtaactgta ttatcacatt aatcgcactt ttatttccat taaaaagaga tgaatatcat   1440
aaataaagaa gtcgatagat tcgtattgat tatggagtta atctacgtct catctcattt   1500
ttaaaaatc atttatgtcc caagctccat tttgtaatca agtctagttt ttcggttctg   1560
ttgcaaagtt gaatttatag tataatttta acaaaaagga gtcttctgta tgaactattt   1620
cagatataaa caatttaaca aggatgttat cactgtagcc gttggctact atctaagata   1680
tacattgagt tatcgtgata tatctgaaat attaagggaa cgtggtgtaa acgttcatca   1740
ttcaacggtc taccgttggg ttcaagaata tgccccaatt ttgtatcaaa tttggaagaa   1800
aaagcataaa aaagcttatt acaaatggcg tattgatgag acgtacatca aaataaaagg   1860
```

-continued

| | |
|---|---|
| aaaatggagc tatttatatc gtgccattga tgcagaggga catacattag atatttggtt | 1920 |
| gcgtaagcaa cgagataatc attcagcata tgcgtttatc aaacgtctca ttaaacaatt | 1980 |
| tggtaaacct caaaaggtaa ttacagatca ggcaccttca acgaaggtag caatggctaa | 2040 |
| agtaattaaa gcttttaaac ttaaacctga ctgtcattgt acatcgaaat atctgaataa | 2100 |
| cctcattgag caagatcacc gtcatattaa agtaagaaag acaaggtatc aaag | 2154 |

<210> SEQ ID NO 190
<211> LENGTH: 2410
<212> TYPE: DNA
<213> ORGANISM: Staphylococcus aureus

<400> SEQUENCE: 190

| | |
|---|---|
| ccaccttcat atgacgtcta tccatttatg tatggcatga gtaacgaaga atataataaa | 60 |
| ttaaccgaag ataaaaaaga acctctgctc aacaagttcc agattacaac ttcaccaggt | 120 |
| tcaactcaaa aatattaac agcaatgatt gggttaaata acaaacatt agacgataaa | 180 |
| acaagttata aaatcgatgg taaaggttgg caaaaagata aatcttgggg tggttacaac | 240 |
| gttacaagat atgaagtggt aaatggtaat atcgacttaa acaagcaat agaatcatca | 300 |
| gataacattt tctttgctag agtagcactc gaattaggca gtaagaaatt tgaaaaggc | 360 |
| atgaaaaaac taggtgttgg tgaagatata ccaagtgatt atccatttta taatgctcaa | 420 |
| atttcaaaca aaaatttaga taatgaaata ttattagctg attcaggtta cggacaaggt | 480 |
| gaaatactga ttaacccagt acagatcctt tcaatctata gcgcattaga aaataatggc | 540 |
| aatattaacg cacctcactt attaaaagac acgaaaaaca aagtttggaa gaaaaatatt | 600 |
| atttccaaag aaaatatcaa tctattaact gatggtatgc aacaagtcgt aaataaaaca | 660 |
| cataaagaag atatttatag atcttatgca aacttaattg gcaaatccgg tactgcagaa | 720 |
| ctcaaaatga acaaggaga aactggcaga caaattgggt ggtttatatc atatgataaa | 780 |
| gataatccaa acatgatgat ggctattaat gttaaagatg tacaagataa aggaatggct | 840 |
| agctacaatg ccaaaatctc aggtaaagtg tatgatgagc tatatgagaa cggtaataaa | 900 |
| aaatacgata tagatgaata acaaaacagt gaagcaatcc gtaacgatgg ttgcttcact | 960 |
| gttttattat gaattattaa taagtgctgt tacttctccc ttaaatacaa tttcttcatt | 1020 |
| ttcattgtat gttgaaagtg acactgtaac gagtccattt tctttttta tggatttctt | 1080 |
| atttgtaatt tcagcgataa cgtacaatgt attacctggg tatacaggtt taataaattt | 1140 |
| aacgttattc atttgtgttc ctgctacaac ttcttctccg tatttacctt cttctaccca | 1200 |
| taatttaaat gatattgaaa gtgtatgcat gccagatgca atgataccttt aaatctact | 1260 |
| ttgttctgct ttttcttat ctatatgcat atattgagga tcaaagttg ttgcaaattg | 1320 |
| gataatttct tcttctgtaa tatgaaggct ttttgttttg aatgtttctc ctactataaa | 1380 |
| atcatcgtat ttcatatatg tctctctttc ttattcaaat taatttttta gtatgtaaca | 1440 |
| tgttaaaggt aagtctaccg tcactgaaac gtaagactca cctctaactt tctattgaga | 1500 |
| caaatgcacc attttatctg cattgtctgt aaagatacca tcaactcccc aattagcaag | 1560 |
| ttggtttgca cgtgctggtt tgtttacagt ccatacgttc aattcataac ccgcttcttt | 1620 |
| taccatttt acttttgctt tagtaagttt ggcatcttca gtgtttacta ttttagcatt | 1680 |
| acagtaatct aaaagtgttc tccagtcttc acgaaacgaa gttgtatgga atataactgc | 1740 |
| tctgttatat tgtggcatga tttcttctgc aagtttaaca agcacaacat taaagcttga | 1800 |
| aatgagcact tcttgattct gatttaagtt tgttaattgt tcttccactt gcttaaccat | 1860 |

```
acttttagaa agtgctagtc cattcggtcc agtaatacct tttaattcta catttaaatt    1920
catattatat tcatttgcta ttttactac atcatcgaaa gttggcaaat gttcatcttt    1980
gaatttttca ccaaaccaag atcctgcaga agcatcttta atttcatcat aattcaattc    2040
agttatttcc ccggacatat ttgtagtccg ttctaaataa tcatcatgaa tgataatcag    2100
ttgttcatct tttgtaattg caacatctaa ctccaaccag tttatacctt ctacttctga    2160
agcagcttta aatgatgcaa ttgtattttc cggagcttta ctaggtaatc ctctatgtcc    2220
atatacagtt agcatattac ctctccttgc atttttattt ttttaattaa cgtaactgta    2280
ttatcacatt aatcgcactt ttatttccat taaaaagaga tgaatatcat aaataaagaa    2340
gtcgatagat tcgtattgat tatggagtta atctacgtct catctcattt ttaaaaaatc    2400
atttatgtcc                                                          2410

<210> SEQ ID NO 191
<211> LENGTH: 1858
<212> TYPE: DNA
<213> ORGANISM: Staphylococcus aureus

<400> SEQUENCE: 191
caccttcata tgacgtctat ccatttatgt atggcatgag taacgaagaa tataataaat      60
taaccgaaga taaaaagaa cctctgctca acaagttcca gattacaact tcaccaggtt     120
caactcaaaa aatattaaca gcaatgattg ggttaaataa caaaacatta gacgataaaa     180
caagttataa aatcgatggt aaaggttggc aaaaagataa atcttggggt ggttacaacg     240
ttacaagata tgaagtggta aatggtaata tcgacttaaa acaagcaata gaatcatcag     300
ataacatttt ctttgctaga gtagcactcg aattaggcag taagaaattt gaaaaaggca     360
tgaaaaaact aggtgttggt gaagatatac caagtgatta tccattttat aatgctcaaa     420
tttcaaacaa aaatttagat aatgaaatat tattagctga ttcaggttac ggacaaggtg     480
aaatactgat taacccagta cagatccttt caatctatag cgcattagaa ataatggca     540 atattaacgc acctcactta ttaaaagaca cgaaaaacaa agtttggaag aaaaatatta     600
tttccaaaga aaatatcaat ctattaactg atggtatgca acaagtcgta aataaaacac     660
ataaagaaga tatttataga tcttatgcaa acttaattgg caaatccggt actgcagaac     720
tcaaaatgaa acaaggagaa actggcagac aaattgggtg gtttatatca tatgataaag     780
ataatccaaa catgatgatg gctattaatg ttaaagatgt acaagataaa ggaatggcta     840
gctacaatgc caaaatctca ggtaaagtgt atgatgagct atatgagaac ggtaataaaa     900
aatacgatat agatgaataa caaaacagtg aagcaatccg taacgatggt tgcttcactg     960
ttttattatg aattattaat aagtgctgtt acttctcct taaatacaat ttcttcattt    1020
tcattgtatg ttgaaagtga cactgtaacg agtccatttt cttttttat ggatttctta    1080 tttgtaattt cagcgataac gtacaatgta ttacctgggt atacaggttt aataaattta    1140
acgttattca tttgtgttcc tgctacaact tcttctccgt atttaccttc ttctacccat    1200
aatttaaatg atattgaaag tgtatgcatg ccagatgcaa tgatacctt aaatctactt    1260 tgttctgctt tttcttatc tatatgcata tattgaggat caaagttgt tgcaaattgg    1320 ataatttctt cttctgtaat atgaaggctt tttgttttga atgtttctcc tactataaaa    1380
tcatcgtatt tcatatatgt ctctctttct tattcaaatt aatttttag tatgtaacat    1440 gttaaaggta agtctaccgt cactgaaacg taagactcac ctctaacttt ctattgagac    1500
```

```
aaatgcacca ttttatctgc attgtctgta aagataccat caactcccca attagcaagt    1560
tggtttgcac gtgctggttt gtttacagtc catacgttca attcataacc cgcttctttt    1620 accatttta cttttgcttt agtaagtttg gcatcttcag tgtttactat tttagcatta    1680
cagtaatcta aaagtgttct ccagtcttca cgaaacgaag ttgtatggaa ataactgct    1740 ctgttatatt gtggcatgat ttcttctgca agtttaacaa gcacaacatt aaagcttgaa    1800
atgagcactt cttgattctg atttaagttt gttaattgtt cttccacttg cttaacca    1858
```

<210> SEQ ID NO 192
<211> LENGTH: 1861
<212> TYPE: DNA
<213> ORGANISM: Staphylococcus aureus

<400> SEQUENCE: 192

```
ccaccttcat atgacgtcta tccatttatg tatggcatga gtaacgaaga atataataaa      60
ttaaccgaag ataaaaaaga acctctgctc aacaagttcc agattacaac ttccaccaggt    120 tcaactcaaa aaatattaac agcaatgatt gggttaaata caaaacatt agacgataaa     180 acaagttata aaatcgatgg taaaggttgg caaaaagata atcttgggg tggttacaac     240 gttacaagat atgaagtggt aaatggtaat atcgacttaa acaagcaat agaatcatca     300 gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aataatggc    540 aatattaacg caactcactt attaaaagac acgaaaaaca aagtttggaa gaaaaatatt    600
atttccaaag aaaatatcaa tctattaact gatggtatgc aacaagtcgt aaataaaaca    660
cataaagaag atatttataga atcttatgca aacttaattg gcaaatccgg tactgcagaa    720
ctcaaaatga acaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960 gtttattat gaattattaa taagtgctgt tacttctccc ttaaatacaa tttcttcatt    1020
ttcattgtat gttgaaagtg acactgtaac gagtccatt tcttttttta tggattcstt    1080
atttgtaatt tcagcgataa cgtacaatgt attacctggg tatacaggtt taataaattt    1140
aacgttattc atttgtgttc ctgctacaac ttcttctccg tatttacctt cttctacccca    1200 taatttaaat gatattgaaa gtgtatgcat gccagatgca atgataccctt taaatctact    1260 ttgttctgct ttttcttta tctatatgcat atattgagga tcaaaagttg ttgcaaattg    1320
gataattcct tcttctgtaa tatgaaggct ttttgttttg aatgtttctc ctactataaa    1380
atcatcgtat ttcatatatg tctctctttc ttattcaaat taattttta gtatgtaaca    1440 tgttaaaggt aagtctaccg tcactgaaac gtaagactca cctctaactt tctattgaga    1500
caaatgcacc attttatctg cattgtctgt aaagatacca tcaactcccc aattagcaag    1560
ttggtttgca cgtgctggtt tgtttacagt ccatacgttc aattcataac cgcttctttt    1620 taccatttt acttttgctt tagtaagttt ggcatcttca gtgttactta ttttagcatt    1680
acagtaatct aaaagtgttc tccagtcttc acgaaacgaa gttgtatgga atataactgc    1740
tctgttatat tgtggcatga tttcttctgc aagtttaaca agcacaacat aaagcttga    1800
```

```
aatgagcact tcttgattct gatttaagtt tgttaattgt tcttccactt gcttaaccat    1860
a                                                                   1861

<210> SEQ ID NO 193
<211> LENGTH: 1861
<212> TYPE: DNA
<213> ORGANISM: Staphylococcus aureus

<400> SEQUENCE: 193
ccaccttcat atgacgtcta tccatttatg tatggcatga gtaacgaaga atataataaa      60
ttaaccgaag ataaaaaaga acctctgctc aacaagttcc agattacaac ttcaccaggt     120
tcaactcaaa aaatattaac agcaatgatt gggttaaata acaaaacatt agacgataaa     180
acaagttata aaatcgatgg taaaggttgg caaaaagata atcttgggg tggttacaac      240
gttacaagat atgaagtggt aaatggtaat atcgacttaa acaagcaat agaatcatca      300
gataacattt tctttgctag agtagcactc gaattaggca gtaagaaatt tgaaaaaggc    360
atgaaaaaac taggtgttgg tgaagatata ccaagtgatt atccattttta taatgctcaa   420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga acaaggaga actggcaga caaattgggt ggtttatatc atatgataaa      780
gataatccaa acatgatgat ggctattaat gttaaagatg tacaagataa aggaatggct   840
agctacaatg ccaaaatctc aggtaaagtg tatgatgagc tatatgagaa cggtaataaa   900
aaatacgata tagatgaata acaaaacagt gaagcaatcc gtaacgatgg ttgcttcact    960
gttttattat gaattattaa taagtgctgt tacttctccc ttaaatacaa tttcttcatt    1020
ttcattgtat gttgaaagtg acactgtaac gagtccattt tctttttta tggatttctt    1080
atttgtaatt tcagcgataa cgtacaatgt attacctggg tatacaggtt aataaattt    1140
aacgttattc atttgtgttc ctgctacaac ttcttctccg tatttacctt cttctaccca   1200
taatttaaat gatattgaaa gtgtatgcat gccagatgca atgataccttt aaatctact   1260
ttgttctgct ttttctttat ctatatgcat atattgagga tcaaaagttg ttgcaaattg   1320
gataatttct tcttctgtaa tatgaaggct ttttgtttg aatgtttctc ctactataaa    1380
atcatcgtat ttcatatatg tctctctttc ttattcaaat taattttta gtatgtaaca    1440
tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt acttttgctt tagtaagttt ggcatcttca gtgtttacta ttttagcatt    1680
acagtaatct aaaagtgttc tccagtcttc acgaaacgaa gttgtatgga atataactgc    1740
tctgttatat tgtggcatga tttcttctgc aagtttaaca agcacaacat taaagcttga   1800
aatgagcact tcttgattct gatttaagtt tgttaattgt tcttccactt gcttaaccat    1860
a                                                                   1861

<210> SEQ ID NO 194
```

```
<211> LENGTH: 1052
<212> TYPE: DNA
<213> ORGANISM: Staphylococcus aureus

<400> SEQUENCE: 194
cggtaataaa aaatacgata tagatgaata acaaaacagt gaagcaatcc gtaacgatgg      60
ttgcttcact gttttattat gaattattaa taagtgctgt tacttctccc ttaaatacaa     120
tttcttcatt ttcattgtat gttgaaagtg acactgtaac gagtccattt tctttttta     180 tggatttctt atttgtaatt tcagcgataa cgtacaatgt attacctggg tatacaggtt     240
taataaattt aacgttattc atttgtgttc ctgctacaac ttcttctccg tatttacctt     300
cttctaccca taatttaaat gatattgaaa gtgtatgcat gccagatgca atgatacctt     360
taaatctact ttgttctgct ttttctttat ctatatgcat atattgagga tcaaaagttg     420
ttgcaaattg gataatttct tcttctgtaa tatgaaggct ttttgttttg aatgtttctc     480
ctactataaa atcatcgtat ttcatatatg tctctctttc ttattcaaat taattttta     540 gtatgtaaca tgttaaaggt aagtctaccg tcactgaaac gtaagactca cctctaactt     600
tctattgaga caaatgcacc atttttatctg cattgtctgt aaagatacca tcaactcccc     660
aattagcaag ttggtttgca cgtgctggtt tgtttacagt ccatacgttc aattcataac     720
ccgcttcttt taccatttt acttttgctt tagtaagttt ggcatcttca gtgtttacta     780
ttttagcatt acagtaatct aaaagtgttc tccagtcttc acgaaacgaa gttgtatgga     840
atataactgc tctgttatat tgtggcatga tttcttctgc aagtttaaca agcacaaacat     900 taaagcttga atgagcact tcttgattct gatttaagtt tgttaattgt tcttccactt     960
gcttaaccat acttttagaa agtgctagtc cattcggtcc agtaatacct tttaattcta    1020
catttaaatt catattatat tcatttgcta tt                                    1052

<210> SEQ ID NO 195
<211> LENGTH: 3101
<212> TYPE: DNA
<213> ORGANISM: Staphylococcus aureus

<400> SEQUENCE: 195
cttcatatga cgtctatcca tttatgtatg gcatgagtaa cgaagaatat aataaattaa      60
ccgaagataa aaaagaacct ctgctcaaca agttccagat tacaacttca ccaggttcaa     120
ctcaaaaaat attaacagca atgattgggt taaataacaa acattagac gataaaacaa     180 gttataaaat cgatggtaaa ggttggcaaa agataaatc ttggggtggt tacaacgtta     240
caagatatga agtggtaaat ggtaatatcg acttaaaaca agcaatagaa tcatcagata     300
acattttctt tgctagagta gcactcgaat taggcagtaa gaaatttgaa aaaggcatga     360
aaaaactagg tgttggtgaa gatataccaa gtgattatcc attttataat gctcaaattt     420
caaacaaaaa tttagataat gaaatattat agctgattc aggttacgga caaggtgaaa     480
tactgattaa cccagtacag atcctttcaa tctatagcgc attagaaaat aatggcaata     540
ttaacgcacc tcacttatta aaagacacga aaaacaaagt ttggaagaaa atattattt     600 ccaaagaaaa tatcaatcta ttaactgatg gtatgcaaca agtcgtaaat aaaacacata     660
aagaagatat ttatagatct tatgcaaact taattggcaa atccggtact gcagaactca     720
aaatgaaaca aggagaaact ggcagacaaa ttgggtggtt tatatcatat gataaagata     780
atccaaacat gatgatggct attaatgtta aagatgtaca agataaagga atggctagct     840
acaatgccaa aatctcaggt aaagtgtatg atgagctata tgagaacggt aataaaaaat     900
```

-continued

```
acgatataga tgaataacaa aacagtgaag caatccgtaa cgatggttgc ttcactgttt    960
tattatgaat tattaataag tgctgttact tctcccttaa atacaatttc ttcattttca   1020
ttgtatgttg aaagtgacac tgtaacgagt ccatttctt tttttatgga tttcttattt    1080
gtaatttcag cgataacgta caatgtatta cctgggtata caggtttaat aaatttaacg   1140
ttattcattt gtgttcctgc tacaacttct tctccgtatt taccttcttc tacccataat   1200
ttaaatgata ttgaaagtgt atgcatgcca gatgcaatga taccttttaaa tctactttgt  1260
tctgcttttt ctttatctat atgcatatat tgaggatcaa aagttgttgc aaattggata   1320
atttcttctt ctgtaatatg aaggcttttt gttttgaatg tttctcctac tataaaatca   1380
tcgtatttca tatatgtctc tctttcttat tcaaattaat ttttagtat gtaacatgtt    1440
aaaggtaagt ctaccgtcac tgaaacgtaa gactcacctc taactttcta ttgagacaaa   1500
tgcaccattt tatctgcatt gtctgtaaag ataccatcaa ctccccaatt agcaagttgg   1560
tttgcacgtg ctggtttgtt tacagtccat acgttcaatt cataacccgc ttctttacc    1620
attttactt ttgcttagt aagtttggca tcttcagtgt ttactatttt agcattacag     1680
taatctaaaa gtgttctcca gtcttcacga aacgaagttg tatggaatat aactgctctg   1740
ttatattgtg gcatgatttc ttctgcaagt ttaacaagca caacattaaa gcttgaaatg   1800
agcacttctt gattctgatt taagtttgtt aattgttctt ccacttgctt aaccatactt   1860
ttagaaagtg ctagtccatt cggtccagta ataccttta attctacatt taaattcata   1920
ttatattcat ttgctatttt tactacatca tcgaaagttg gcaaatgttc atctttgaat   1980
ttttcaccaa accaagatcc tgcagaagca tctttaattt catcataatt caattcagtt   2040
atttccccgg acatatttgt agtccgtcct aaataatcat catgaatgat aatcagttgt   2100
tcatcttttg taattgcaac atctaactcc aaccagttta taccttctac ttctgaagca   2160
gctttaaatg atgcaattgt attttccgga gctttactag gtaatcctct atgtccatat   2220
acagttagca tattacctct ccttgcattt ttatttttt aattaacgta actgtattat    2280
cacattaatc gcacttttat ttccattaaa aagagatgaa tatcataaat aaagaagtcg   2340
atagattcgt attgattatg gagttaatct acgtctcatc tcattttaaa aaaatcattt   2400
atgtcccaag ctccattttg taatcaagtc tagtttttcg gttctgttgc aaagttgaat   2460
ttatagtata atttaacaa aaaggagtct tctgtatgaa ctatttcaga tataaacaat   2520
ttaacaagga tgttatcact gtagccgttg gctactatct aagatataca ttgagttatc   2580
gtgatatatc tgaaatatta agggaacgtg gtgtaaacgt tcatcattca acggtctacc   2640
gttgggttca agaatatgcc ccaattttgt atcaaatttg gaagaaaaag cataaaaaag   2700
cttattacaa atggcgtatt gatgagacgt acatcaaaat aaaaggaaaa tggagctatt   2760
tatatcgtgc cattgatgca gagggacata cattagatat ttggttgcgt aagcaacgag   2820
ataatcattc agcatatgcg tttatcaaac gtctcattaa acaatttggt aaacctcaaa   2880
aggtaattac agatcaggca ccttcaacga aggtagcaat ggctaaagta attaaagctt   2940
ttaaacttaa acctgactgt cattgtacat cgaaatatct gaataacctc attgagcaag   3000
atcaccgtca tattaaagta agaaagacaa ggtatcaaag tatcaataca gcaaagaata   3060
ctttaaaagg tattgaatgt atttacgctc tatataaaaa g                       3101
```

<210> SEQ ID NO 196
<211> LENGTH: 3506
<212> TYPE: DNA

<213> ORGANISM: Staphylococcus aureus

<400> SEQUENCE: 196

```
ccaccttcat atgacgtcta tccatttatg tatggcatga gtaacgaaga atataataaa      60
ttaaccgaag ataaaaaga acctctgctc aacaagttcc agattacaac ttcaccaggt     120
tcaactcaaa aatattaac agcaatgatt gggttaaata caaaacatt agacgataaa      180
acaagttata aaatcgatgg taaaggttgg caaaaagata atcttgggg tggttacaac     240
gttacaagat atgaagtggt aaatggtaat atcgacttaa acaagcaat agaatcatca     300
gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aaataaaaca    660
cataagaag atatttatag atcttatgca aacttaattg gcaaatccgg tactgcagaa     720
ctcaaaatga acaaggaga actggcagac aaattgggt ggtttatatc atatgataaa      780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960
gttttattat gaattattaa taagtgctgt tacttctccc ttaaatacaa tttcttcatt   1020
ttcattgtat gttgaaagtg acactgtaac gagtccattt tcttttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgataccct taaatctact   1260
ttgttctgct ttttcttat ctatatgcat atattgagga tcaaaagttg ttgcaaattg    1320
gataatttct tcttctgtaa tatgaaggct ttttgttttg aatgtttctc ctactataaa    1380
atcatcgtat ttcatatatg tctctctttc ttattcaaat taattttta gtatgtaaca    1440
tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt acttttgctt tagtaagttt ggcatcttca gtgtttacta ttttagcatt   1680
acagtaatct aaaagtgttc tccagtcttc acgaaacgaa gttgtatgga atataactgc   1740
tctgttatat tgtggcatga tttcttctgc aagtttaaca agcacaacat taaagcttga   1800
aatgagcact tcttgattct gatttaagtt tgttaattgt tcttccactt gcttaaccat   1860
acttttagaa agtgctagtc cattcggtcc agtaatacct tttaattcta catttaaatt   1920
catattatat tcatttgcta ttttttactac atcatcgaaa gttggcaaat gttcatcttt   1980
gaattttca ccaaaccaag atcctgcaga agcatcttta atttcatcat aattcaattc    2040
agttatttcc ccggacatat ttgtagtccg ttctaaataa tcatcatgaa tgataatcag   2100
ttgttcatct tttgtaattg caacatctaa ctccaaccag tttataccott ctacttctga   2160
agcagcttta aatgatgcaa ttgtattttc cggagcttta ctaggtaatc ctctatgtcc   2220
atatacagtt agcatattac ctctccttgc attttatttt ttttaattaa cgtaactgta   2280
```

```
ttatcacatt aatcgcactt ttatttccat taaaaagaga tgaatatcat aaataaagaa    2340
gtcgatagat tcgtattgat tatggagtta atctacgtct catctcattt ttaaaaaatc    2400
atttatgtcc caagctccat tttgtaatca agtctagttt ttctgtaccc cttatctgca    2460
attttactta ggattgcttt taacttaccc cttatcagca attttactga gaactgcttt    2520
taacgcacct cttatctgca attttgccta gaactgcttt taacgtacct cttatctgca    2580
attttactga gaactgcttt taacttaccc cttatcagca attttgcatg gaattgcttt    2640
taacgtacct cttatctgca attttactta gaactgcttt taacaaacct cttatctgca    2700
attttactta gaactgcttt taacgtacct cttatctgta attttactga gaactgcttt    2760
taacaaacct cttatctgca attttactta gaactgcttt taacaaacct cttatctgca    2820
attttactta gaattgcttt tactattcct cttattagta taatctcagt aagaatgcgt    2880
ataaaaatga aaattacaac cgattttgta agtgctgacg cctgagggaa tagtatgtgc    2940
gagagactaa tggctcgagc catacccta  ggcaagcatg cacgtacaaa atcgtaagat    3000
aaaaaaataa gcatatcact gtaaacttta aaaaatcagt ttagtgatat gcttatttat    3060
ttcgagttag gatttatgtc ccaagctcat caagcacaat cggccactag tttatttctc    3120
tatcttatat gttctgatat ggtcttctat actgtataag tatacttttg aatatggatc    3180
ttgtgtcaat tcacgttcga aatcaaattc ttgattatca aatctgttaa agaatgtttc    3240
gtattcttcg actgataatt gctctctaga ttctagcata tttaagtgtt tctctttatc    3300
taatgctttg tcatatcctt taacgattga accactaaag atttctccta ctgctcctga    3360
accataacta aatagacata ctttctcttc tggttggaat gtgtggttct gtaataacga    3420
aattaaactt aagtataatg atcctgtata aatgttacca acatctctat tccataatac    3480
ggttctgttg caaagttgaa tttata                                          3506

<210> SEQ ID NO 197
<211> LENGTH: 928
<212> TYPE: DNA
<213> ORGANISM: Staphylococcus aureus

<400> SEQUENCE: 197
tacattagaa atacaaggaa agatgctatc ttccgaagga ttggcccaag aattgaacca      60
acgcatgacc caagggcaaa gcgactttgt attcgtcatt ggcggatcaa acggcctgca     120
caaggacgtc ttacaacgca gtaactacgc actatcattc agcaaaatga cattcccaca     180
tcaaatgatg cgggttgtgt taattgaaca agtgtacaga gcatttaaga ttatgcgtgg     240
agaagcatat cataaatgat gcggtttttt cagccgcttc ataagggat tttgaatgta      300 tcagaacata tgaggtttat gtgaattgct gttatgtttt taagaagctt atcataagta     360
atgaggttca tgattttga catagttagc ctccgcagtc tttcatttca agtaaataat      420
agcgaaatat tctttatact gaatacttat agtgaagcaa agttctagct ttgagaaaat     480
tctttctgca actaaatata gtaaattacg gtaaaatata aataagtaca tattgaagaa     540
aatgagacat aatatatttt ataataggag ggaatttcaa atgatagaca actttatgca     600
ggtccttaaa ttaattaaag agaaacgtac caataatgta gttaaaaaat ctgattggga     660
taaaggtgat ctatataaaa ctttagtcca tgataagtta cccaagcagt taaaagtgca     720
tataaaagaa gataaatatt cagttgtagg gaaggttgct actgggaact atagtaaagt     780
tccttggatt tcaatatatg atgagaatat aacaaaagaa acaaaggatg gatattattt     840
```

```
ggtatatctt tttcatccgg aaggagaagg catatactta tctttgaatc aaggatggtc    900
aaagataagt gatatgtttc cgcgggat                                       928

<210> SEQ ID NO 198
<211> LENGTH: 782
<212> TYPE: DNA
<213> ORGANISM: Staphylococcus aureus

<400> SEQUENCE: 198
caatgcccac agagttatcc acaaatacac aggttataca ctaaaaattg ggcatgaatg     60
tcagaaaaat atcaaaaact gcaaagaata ttggtataat aagagggaac agtgtgaaca   120
agttaataac ttgtggataa ctggaaagtt gataacaatt tggaggacca acgacatga    180 aaatcaccat tttagctgta gggaaactaa aagagaaata ttggaagcaa gccatagcag   240
aatatgaaaa acgtttaggc ccatacacca agatagacat catagaagtt ccagacgaaa   300
aagcaccaga aaatatgagc gacaaagaaa ttgagcaagt aaaagaaaaa gaaggccaac   360
gaatactagc caaaatcaaa ccacaatcaa cagtcattac attagaaata caaggaaaga   420
tgctatcttc cgaaggattg gcccaagaat tgaaccaacg catgacccaa gggcaaagcg   480
actttgtatt cgtcattggc ggatcaaacg gcctgcacaa ggacgtctta caacgcagta   540
actacgcact atcattcagc aaaatgacat cccacatca aatgatgcgg ttgtgttaa    600 ttgaacaagt gtacagagca tttaagatta tgcgtggaga agcgtatcat aaataaaact   660
aaaaattagg ttgtgtataa tttaaaaatt taatgagatg tggaggaatt acatatatga   720
aatattggat tataccttgc aatatcatac gatgtttata gagtgtttaa taaaccattt   780
tt                                                                 782

<210> SEQ ID NO 199
<211> LENGTH: 709
<212> TYPE: DNA
<213> ORGANISM: Staphylococcus aureus

<400> SEQUENCE: 199
tacattagaa atacaaggaa agatgctatc ttccgaagga ttggcccaag aattgaacca    60
acgcatgacc caagggcaaa gcgactttgt tttcgtcatt ggcggatcaa acggcctgca   120
caaggacgtc ttacaacgca gtaactacgc actatcattc agcaaaatga cattcccaca   180
tcaaatgatg cgggttgtgt taattgaaca agtgtacaga gcatttaaga ttatgcgagg   240
agaagcttat cataagtaat gaggttcatg attttttgaca tagttagcct ccgcagtctt   300
tcatttcaag taaataatag cgaaatattc tttatactga atacttatag tgaagcaaag   360
ttctagcttt gagaaaattc tttctgcaac taaatatagt aaattacggt aaaatataaa   420
taagtacata ttgaagaaaa tgagacataa tatattttat aataggaggg aatttcaaat   480
gatagacaac tttatgcagg tccttaaatt aattaaagag aaacgtacca ataatgtagt   540
taaaaaatct gattgggata aaggtgatct atataaaact ttagtccatg ataagttacc   600
caagcagtta aaagtgcata taaaagaaga taaatattca gttgtaggga aggttgctac   660
tgggaactat agtaaagttc cttggatttc aatatatgat gagaatata                709

<210> SEQ ID NO 200
<211> LENGTH: 22
<212> TYPE: DNA
<213> ORGANISM: Artificial
<220> FEATURE:
<223> OTHER INFORMATION: OLIGONUCLEOTIDE
```

<400> SEQUENCE: 200
gtgggaaatg gctgttgttg ag                22

<210> SEQ ID NO 201
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 201
ttcgttccct ccattaactg tc                22

<210> SEQ ID NO 202
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 202
aaaagaaaga cggtgaaggc                20

<210> SEQ ID NO 203
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 203
cacttcatta tactgttttc tttgc                25

<210> SEQ ID NO 204
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 204
tcaccgtctt tcttttgacc tt                22

<210> SEQ ID NO 205
<211> LENGTH: 25
<212> TYPE: DNA
<213> ORGANISM: Artificial
<220> FEATURE:
<223> OTHER INFORMATION: OLIGONUCLEOTIDE

<400> SEQUENCE: 205
tgagatctgc tggaacaaaa gtgaa                25

<210> SEQ ID NO 206
<211> LENGTH: 20
<212> TYPE: DNA
<213> ORGANISM: Artificial
<220> FEATURE:
<223> OTHER INFORMATION: OLIGONUCLEOTIDE

<400> SEQUENCE: 206
cggtcgagtt tgctgaagaa                20

<210> SEQ ID NO 207

```
<211> LENGTH: 26
<212> TYPE: DNA
<213> ORGANISM: Artificial
<220> FEATURE:
<223> OTHER INFORMATION: OLIGONUCLEOTIDE

<400> SEQUENCE: 207
tcccctaatg atagctggta tatatt                                          26

<210> SEQ ID NO 208
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 208
tctagggaat caaagaaaag taatagt                                         27

<210> SEQ ID NO 209
<211> LENGTH: 32
<212> TYPE: DNA
<213> ORGANISM: Artificial
<220> FEATURE:
<223> OTHER INFORMATION: OLIGONUCLEOTIDE

<400> SEQUENCE: 209
caacaargrc aatgtgayrt attatgytgt ta                                   32

<210> SEQ ID NO 210
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 210
gataayatwg gmgaacaagt caraaatgg                                       29

<210> SEQ ID NO 211
<211> LENGTH: 35
<212> TYPE: DNA
<213> ORGANISM: Artificial
<220> FEATURE:
<223> OTHER INFORMATION: OLIGONUCLEOTIDE

<400> SEQUENCE: 211
ccrtattgat tgwtracacg rccacartaa ttwgg                                35

<210> SEQ ID NO 212
<211> LENGTH: 32
<212> TYPE: DNA
<213> ORGANISM: Artificial
<220> FEATURE:
<223> OTHER INFORMATION: OLIGONUCLEOTIDE
<220> FEATURE:
<221> NAME/KEY: misc_feature
<222> LOCATION: (30)..(30)
<223> OTHER INFORMATION: N = INOSINE

<400> SEQUENCE: 212
atrttsartg gttcattttt gaaatagatn cc                                   32

<210> SEQ ID NO 213
<211> LENGTH: 32
<212> TYPE: DNA
<213> ORGANISM: Artificial
```

```
<220> FEATURE:
<223> OTHER INFORMATION: OLIGONUCLEOTIDE

<400> SEQUENCE: 213
acgtgtcggt atctatgtwc gtgtatcaac rg                                32

<210> SEQ ID NO 214
<211> LENGTH: 30
<212> TYPE: DNA
<213> ORGANISM: Artificial
<220> FEATURE:
<223> OTHER INFORMATION: OLIGONUCLEOTIDE

<400> SEQUENCE: 214
tgttatgrtc tacaaaacaa accgaytagc                                   30

<210> SEQ ID NO 215
<211> LENGTH: 34
<212> TYPE: DNA
<213> ORGANISM: Artificial
<220> FEATURE:
<223> OTHER INFORMATION: OLIGONUCLEOTIDE

<400> SEQUENCE: 215
gawtaataat rggggaatgc ttaccttcag ctat                              34

<210> SEQ ID NO 216
<211> LENGTH: 26
<212> TYPE: DNA
<213> ORGANISM: Artificial
<220> FEATURE:
<223> OTHER INFORMATION: OLIGONUCLEOTIDE

<400> SEQUENCE: 216
ggtttttgac tgacttgttt tttacg                                       26

<210> SEQ ID NO 217
<211> LENGTH: 29
<212> TYPE: DNA
<213> ORGANISM: Artificial
<220> FEATURE:
<223> OTHER INFORMATION: OLIGONUCLEOTIDE

<400> SEQUENCE: 217
tagaaytgtt ttttatgatt accrtctttt                                   29

<210> SEQ ID NO 218
<211> LENGTH: 26
<212> TYPE: DNA
<213> ORGANISM: Artificial
<220> FEATURE:
<223> OTHER INFORMATION: OLIGONUCLEOTIDE

<400> SEQUENCE: 218
ggcaaaaaya aagacgaagt gctgag                                       26

<210> SEQ ID NO 219
<211> LENGTH: 721
<212> TYPE: DNA
<213> ORGANISM: Staphylococcus aureus

<400> SEQUENCE: 219
tgtagcttta ggtgaagggt taggtccttc aataggggga ataatagcac attatattca    60
ttggtcttac ctacttatac ttcctatgat tacaatagta actataccttt ttcttattaa  120
```

```
agtaatggta cctggtaaat caacaaaaaa tacattagat atcgtaggta ttgttttaat      180
gtctataagt attatatgtt ttatgttatt tacgacaaat tataattgga cttttttaat      240
actcttcaca atcttttttg tgattttat taaacatatt tcaagagttt ctaacccttt       300
tattaatcct aaactaggga aaaacattcc gtttatgctt ggtttgtttt ctggtgggct      360
aatattttct atagtagctg ttttatatc aatggtgcct tatatgatga aaactattta      420
tcatgtaaat gtagcgacaa taggtaatag tgttattttt cctggaacca tgagtgttat      480 tgttttggt tattttggtg gttttttagt ggatagaaaa ggatcattat ttgttttat       540 tttaggatca ttgtctatct ctataagttt tttaactatt gcattttttg ttgagtttag      600
tatgtggttg actactttta tgtttatatt tgttatgggc ggattatctt ttactaaaac      660
agttatatca aaatagtat caagtagtct ttctgaagaa gaagttgctt ctggaagagt       720
t                                                                      721

<210> SEQ ID NO 220
<211> LENGTH: 1791
<212> TYPE: DNA
<213> ORGANISM: Staphylococcus aureus

<400> SEQUENCE: 220
atccggtact gcagaactca aaatgaaaca aggagaaact ggcagacaaa ttgggtggtt       60
tatatcatat gataaagata atccaaacat gatgatggct attaatgtta aagatgtaca      120
agataaagga atggctagct acaatgccaa aatctcaggt aaagtgtatg atgagctata      180
tgagaacggt aataaaaaat acgatataga tgaataacaa acagtgaag caatccgtaa       240 cgatggttgc ttcactgttt tattatgaat tattaataag tgctgttact tctcccttaa      300
atacaatttc ttcattttca ttgtatgttg aaagtgacac tgtaacgagt ccattttctt      360
tttttatgga tttcttattt gtaatttcag cgataacgta caatgtatta cctgggtata      420
caggttaaat aaatttaacg ttattcattt gtgttcctgc tacaacttct tctccgtatt      480
taccttcttc tacccataat ttaaatgata ttgaaagtgt atgcatgcca gatgcaatga      540
tacctttaaa tctactttgt tctgctttt ctttatctat atgcatatat tgaggatcaa       600
aagttgttgc aaattggata atttcttctt ctgtaatatg aaggcttttt gtttgaatg       660 tttctcctac tataaaatca tcgtatttca tatatgtctc tctttcttat tcaaattaat      720 ttttagtat gtaacatgtt aaaggtaagt ctaccgtcac tgaaacgtaa gactcacctc       780
taactttcta ttgagacaaa tgcaccattt tatctgcatt gtctgtaaag ataccatcaa      840
ctccccaatt agcaagttgg tttgcacgtg ctggtttgtt tacagtccat acgttcaatt      900
cataacccgc ttctttttacc attttttactt ttgcttagt aagtttggca tcttcagtgt     960
ttactatttt agcattacag taatctaaaa gtgttctcca gtcttcacga aacgaagttg     1020 tatgaatat aactgctctg ttatattgtg gcatgatttc ttctgcaagt ttaacaagca     1080
caacattaaa gcttgaaatg agcacttctt gattctgatt taagtttgtt aattgttctt     1140
ccacttgctt aaccatactt ttagaaagtg ctagtccatt cggtccagta ataccttta       1200 attctacatt taaattcata ttatattcat ttgctatttt tactacatca tcgaaagttg     1260
gcaaatgttc atctttgaat ttttcaccaa accaagatcc tgcagaagca tctttaattt     1320
catcataatt caattcagtt atttccccgg acatatttgt agtccgttct aaataatcat     1380
catgaatgat aatcagttgt tcatcttttg taattgcaac atctaactcc aaccagttta    1440
taccttctac ttctgaagca gctttaaatg atgcaattgt attttccgga gctttactag     1500
```

```
gtaatcctct atgtccatat acagttagca tattacctct ccttgcattt ttatttttt   1560 aattaacgta actgtattat cacattaatc gcactttat ttccattaaa aagagatgaa   1620
tatcataaat aaagaagtcg atagattcgt attgattatg gagttaatct acgtctcatc   1680
tcatttttaa aaaatcattt atgtcccaag ctccattttg taatcaagtc tagtttttct   1740 gtaccccta tctgcaattt tacttaggat tgcttttaac ttacccctta t            1791

<210> SEQ ID NO 221
<211> LENGTH: 600
<212> TYPE: DNA
<213> ORGANISM: Staphylococcus aureus

<400> SEQUENCE: 221
aagtgctgac gcctgaggga atagtatgtg cgagagacta atggctcgag ccatacccct    60
aggcaagcat gcacgtacaa aatcgtaaga taaaaaaata agcatatcac tgtaaacttt   120
aaaaaatcag tttagtgata tgcttattta tttcgagtta ggatttatgt cccaagctca   180
tcaagcacaa tcggccacta gtttatttct ctatcttata tgttctgata tggtcttcta   240
tactgtataa gtatacttt gaatatggat cttgtgtcaa ttcacgttcg aaatcaaatt   300
cttgattatc aaatctgtta aagaatgttt cgtattcttc gactgataat tgctctctag   360
attctagcat atttaagtgt ttctctttat ctaatgcttt gtcatatcct ttaacgattg   420
aaccactaaa gatttctcct actgctcctg aaccataact aaatagacat actttctctt   480
ctggttggaa tgtgtggttc tgtaataacg aaattaaact taagtataat gatcctgtat   540
aaatgttacc aacatctcta ttccataata cggttctgtt gcaaagttga atttatagta   600

<210> SEQ ID NO 222
<211> LENGTH: 1640
<212> TYPE: DNA
<213> ORGANISM: Staphylococcus aureus

<400> SEQUENCE: 222
gggtggttta tatcatatga taaagataat ccaaacatga tgatggctat taatgttaaa    60
gatgtacaag ataaaggaat ggctagctac aatgccaaaa tctcaggtaa agtgtatgat   120
gagctatatg agaacggtaa taaaaaatac gatatagatg aataacaaaa cagtgaagca   180
atccgtaacg atggttgctt cactgttta ttatgaatta ttaataagtg ctgttacttc   240
tcccttaaat acaatttctt cattttcatt gtatgttgaa agtgacactg taacgagtcc   300
attttctttt tttatggatt tcttatttgt aatttcagcg ataacgtaca atgtattacc   360
tgggtataca ggtttaataa atttaacgtt attcatttgt gttcctgcta caacttcttc   420
tccgtattta ccttcttcta cccataattt aaatgatatt gaaagtgtat gcatgccaga   480
tgcaatgata cctttaaatc tactttgttc tgcttttct ttatctatat gcatatattg   540
aggatcaaaa gttgttgcaa attggataat ttcttcttct gtaatatgaa ggcttttgt   600 tttgaatgtt tctcctacta taaaatcatc gtatttcata tatgtctctc tttcttattc   660
aaattaattt tttagtatgt aacatgttaa aggtaagtct accgtcactg aaacgtaaga   720
ctcacctcta actttctatt gagacaaatg caccatttta tctgcattgt ctgtaaagat   780
accatcaact ccccaattag caagttggtt tgcacgtgct ggtttgttta cagtccatac   840
gttcaattca taaccccgctt cttttaccat ttttactttt gctttagtaa gtttggcatc   900
ttcagtgttt actattttag cattacagta atctaaaagt gttctccagt cttcacgaaa   960
```

```
cgaagttgta tggaatataa ctgctctgtt atattgtggc atgatttctt ctgcaagttt    1020
aacaagcaca acattaaagc ttgaaatgag cacttcttga ttctgattta agtttgttaa    1080
ttgttcttcc acttgcttaa ccatactttt agaaagtgct agtccattcg gtccagtaat    1140 acctttaat tctacattta aattcatatt atattcattt gctatttta ctacatcatc     1200 gaaagttggc aaatgttcat ctttgaattt ttcaccaaac caagatcctg cagaagcatc    1260
tttaatttca tcataattca attcagttat ttccccggac atatttgtag tccgttctaa    1320
ataatcatca tgaatgataa tcagttgttc atcttttgta attgcaacat ctaactccaa    1380
ccagtttata ccttctactt ctgaagcagc tttaaatgat gcaattgtat tttccggagc    1440
tttactaggt aatcctctat gtccatatac agttagcata ttacctctcc ttgcattttt    1500 attttttaa ttaacgtaac tgtattatca cattaatcgc acttttattt ccattaaaaa    1560
gagatgaata tcataaataa agaagtcgat agattcgtat tgattatgga gttaatctac    1620
gtctcatctc attttaaaa                                                 1640

<210> SEQ ID NO 223
<211> LENGTH: 592
<212> TYPE: DNA
<213> ORGANISM: Staphylococcus aureus

<400> SEQUENCE: 223
aattcaactt tgcaacagaa ccgtattatg gaatagagat gttggtaaca tttatacagg     60
atcattatac ttaagtttaa tttcgttatt acagaaccac acattccaac cagaagagaa    120
agtatgtcta tttagttatg gttcaggagc agtaggagaa atctttagtg gttcaatcgt    180
taaaggatat gacaaagcat tagataaaga gaaacactta aatatgctag aatctagaga    240
gcaattatca gtcgaagaat acgaaacatt ctttaacaga tttgataatc aagaatttga    300
tttcgaacgt gaattgacac aagatccata ttcaaaagta tacttataca gtatagaaga    360
ccatatcaga acatataaga tagagaaata aactagtggc cgattgtgct tgatgagctt    420
gggacataaa tcctaactcg aaataaataa gcatatcact aaactgattt tttaaagttt    480
acagtgatat gcttatttt ttatcttacg attttgtacg tgcatgcttg cctaggggta    540
tggctcgagc cattagtctc tcgcacatac tattccctca ggcgtcagca ct           592

<210> SEQ ID NO 224
<211> LENGTH: 2386
<212> TYPE: DNA
<213> ORGANISM: Staphylococcus aureus

<400> SEQUENCE: 224
caccttcata tgacgtctat ccatttatgt atggcatgag taacgaagaa tataataaat     60
taaccgaaga taaaaagaa cctctgctca acaagttcca gattacaact tcaccaggtt    120
caactcaaaa atattaaca gcaatgattg ggttaaataa caaaacatta gacgataaaa    180
caagttataa aatcgatggt aaaggttggc aaaaagataa atcttggggt ggttacaacg    240
ttacaagata tgaagtggta atggtaata tcgacttaaa acaagcaata gaatcatcag    300
ataacatttt ctttgctaga gtagcactcg aattaggcag taagaaattt gaaaaaggca    360
tgaaaaaact aggtgttggt gaagatatac caagtgatta tccatttat aatgctcaaa    420 tttcaaacaa aaatttagat aatgaaatat tattagctga ttcaggttac ggacaaggtg    480
aaatactgat taacccagta cagatccttt caatctatag cgcattagaa ataatggca    540 atattaacgc acctcactta ttaaaagaca cgaaaaacaa agtttggaag aaaaatatta    600
```

-continued

```
tttccaagaa aaatatcaat ctattaactg atggtatgca acaagtcgta aataaaacac      660
ataaagaaga tatttataga tcttatgcaa acttaattgg caaatccggt actgcagaac      720
tcaaaatgaa acaaggagaa actggcagac aaattgggtg gtttatatca tatgataaag      780
ataatccaaa catgatgatg gctattaatg ttaaagatgt acaagataaa ggaatggcta      840
gctacaatgc caaatctca ggtaaagtgt atgatgagct atgagaac ggtaataaaa         900 aatacgatat agatgaataa caaaacagtg aagcaatccg taacgatggt tgcttcactg      960
ttttattatg aattattaat aagtgctgtt acttctccct taaatacaat ttcttcattt     1020
tcattgtatg ttgaaagtga cactgtaacg agtccatttt cttttttat ggatttctta     1080 tttgtaattt cagcgataac gtacaatgta ttacctgggt atacaggttt aataaattta     1140
acgttattca tttgtgttcc tgctacaact tcttctccgt atttaccttc ttctacccat     1200
aatttaaatg atattgaaag tgtatgcatg ccagatgcaa tgatacccttt aaatctactt    1260 tgttctgctt tttctttatc tatatgcata tattgaggat caaaagttgt tgcaaattgg     1320
ataatttctt cttctgtaat atgaaggctt tttgttttga atgtttctcc tactataaaa     1380
tcatcgtatt tcatatatgt ctctctttct tattcaaatt aattttttag tatgtaacat     1440
gttaaaggta agtctaccgt cactgaaacg taagactcac ctctaacttt ctattgagac     1500
aaatgcacca ttttatctgc attgtctgta aagataccat caactcccca attagcaagt     1560
tggtttgcac gtgctggttt gtttacagtc catacgttca attcataacc cgcttctttt     1620 accatttta cttttgcttt agtaagtttg gcatcttcag tgtttactat tttagcatta     1680
cagtaatcta aaagtgttct ccagtcttca cgaaacgaag ttgtatggaa tataactgct     1740
ctgttatatt gtggcatgat tcttctgca agtttaacaa gcacaacatt aaagcttgaa     1800
atgagcactt cttgattctg atttaagttt gttaattgtt cttccacttg cttaaccata     1860
cttttagaaa gtgctagtcc attcggtcca gtaatacctt taattctac atttaaattc     1920 atattatatt catttgctat ttttactaca tcatcgaaag ttggcaaatg ttcatctttg     1980
aattttccac caaaccaaga tcctgcagaa gcatctttaa tttcatcata attcaattca     2040
gttatttccc cggacatatt tgtagtccgt tctaaataat catcatgaat gataatcagt     2100
tgttcatctt ttgtaattgc aacatctaac tccaaccagt ttataccttc tacttctgaa     2160
gcagctttaa atgatgcaat tgtattttcc ggagctttac taggtaatcc tctatgtcca     2220
tatacagtta gcatattacc tctccttgca tttttatttt tttaattaac gtaactgtat     2280
tatcacatta atcgcacttt tatttccatt aaaaagagat gaatatcata aataaagaag     2340
tcgatagatt cgtattgatt atggagttaa tctacgtctc atctca                  2386
```

<210> SEQ ID NO 225
<211> LENGTH: 623
<212> TYPE: DNA
<213> ORGANISM: Staphylococcus aureus

<400> SEQUENCE: 225

```
tgaaaattac aaccgatttt gtaagtgctg acgcctgagg gaatagtatg tgcgagagac       60
taatggctcg agccataccc ctaggcaagc atgcacgtac aaaatcgtaa gataaaaaaa     120
taagcatatc actgtaaact ttaaaaaatc agtttagtga tatgcttatt tatttcgagt     180
taggatttat gtcccaagct catcaagcac aatcggccac tagtttattt ctctatctta     240
tatgttctga tatggtcttc tatactgtat aagtatactt ttgaatatgg atcttgtgtc     300
```

-continued

```
aattcacgtt cgaaatcaaa ttcttgatta tcaaatctgt taaagaatgt ttcgtattct      360
tcgactgata attgctctct agattctagc atatttaagt gtttctcttt atctaatgct      420
ttgtcatatc ctttaacgat tgaaccacta aagatttctc ctactgctcc tgaaccataa      480
ctaaatagac atactttctc ttctggttgg aatgtgtggt tctgtaataa cgaaattaaa      540
cttaagtata atgatcctgt ataaatgtta ccaacatctc tattccataa acggttctg      600 ttgcaaagtt gaatttatag tat                                              623

<210> SEQ ID NO 226
<211> LENGTH: 651
<212> TYPE: DNA
<213> ORGANISM: Staphylococcus aureus

<400> SEQUENCE: 226
atgaaaaata tttcagaatt ctcagcccaa cttgatcaaa cttttgatca aggggaagcc       60
gtctctatgg agtggttatt ccgtccgttg ctaaaaatgc tggcggaggg cgatccagtc      120
cccgttgagg acatcgcggc ggagaccggg aagcccgtcg aggaagttaa gcaagtccta      180
cagactctac ctagtgtgga acttgatgag cagggccgtg tcgtcggtta tggcctcaca      240
ctgttcccta ccccccatcg cttcgaggtt gatgggaagc aactatatgc atggtgcgcc      300
cttgacacac ttatgttccc agcactcatc ggcggacgg tccacatcgc ttcgccttgt       360
cacggcaccg gtaagtccgt ccggttgacg gtggaaccgg accgcgttgt aagcgtcgag      420
ccttcaacag ccgttgtctc gattgttaca ccagatgaaa tggcctcggt tcggtcggcc      480
ttctgtaacg acgttcactt tttcagttca ccgagtgcag cccaagactg gcttaaccaa      540 cacccctgagt cgagcgtttt gcccgttgaa gatgcctttg aactgggtcg ccatttggga      600
gcgcgttatg aggagtcagg acctactaat gggtcctgtt gtaacattta a              651

<210> SEQ ID NO 227
<211> LENGTH: 563
<212> TYPE: DNA
<213> ORGANISM: Staphylococcus aureus

<400> SEQUENCE: 227
atgaatcttg aaaaagggaa tatagaaagg aaaaaacatg gtgtccatgt taatgagtat       60
ttgcaaagtg taagtaaccc gaatgtctat gcagctggag atgctgcagc aacggatggc      120
ttgcccctca cacctgtagc cagtgcagat tctcatgtcg tagcatctaa tttattgaaa      180
gggaacagca aaaaaattga atatcccgtg attccatctg ctgtatttac cgtacctaaa      240
atggcatcgg taggtatgag cgaggaggaa gccaaaaact ctggccggaa tattaaagta      300
aagcagaaaa acatctccga ctggtttacg tataaacgga caaatgagga ctttgctgcg      360
tttaaagtgc tgattgacga agatcatgat caaattgttg gtgctcattt gattagtaat      420
gaagccgatg aactgattaa tcattttgca acagccattg gttttgggat ttcaaccaaa      480
gaattgaaac aaatgatatt tgcctatcca acggcagctt cggacattgc acacatgttg      540
taagtttgcg ttttgtgaga tgt                                              563

<210> SEQ ID NO 228
<211> LENGTH: 1380
<212> TYPE: DNA
<213> ORGANISM: Staphylococcus aureus

<400> SEQUENCE: 228
ttgtttagtt tatataaaaa atttaaaggt ttgttttata gcgttttatt ttggctttgt       60
```

| | |
|---|---|
| attctttcat tttttagtgt attaaatgaa atggttttaa atgtttcttt acctgatatt | 120 |
| gcaaatcatt ttaatactac tcctggaatt acaaactggg taaacactgc atatatgtta | 180 |
| acttttcga taggaacagc agtatatgga aaattatctg attatataaa tataaaaaaa | 240 |
| ttgttaatta ttggtattag tttgagctgt cttggttcat tgattgcttt tattggtcac | 300 |
| aatcactttt ttatttgat ttttggtagg ttagtacaag gagtaggatc tgctgcattc | 360 |
| ccttcactga ttatggtggt tgtagctaga aatattacaa gaaaaaaca aggcaaagcc | 420 |
| tttggttta taggatcaat tgtagcttta ggtgaagggt taggtccttc aataggggga | 480 |
| ataatagcac attatattca ttggtcttac ctacttatac ttcctatgat tacaatagta | 540 |
| actataccttt tcttattaa agtaatggta cctggtaaat caacaaaaaa tacattagat | 600 |
| atcgtaggta ttgttttaat gtctataagt attatatgtt ttatgttatt tacgacaaat | 660 |
| tataattgga cttttttaat actcttcaca atctttttg tgattttat taaacatatt | 720 |
| tcaagagttt ctaaccctt tattaatcct aaactaggga aaacattcc gtttatgctt | 780 |
| ggtttgtttt ctggtgggct aatattttct atagtagctg ttttatatc aatggtgcct | 840 |
| tatatgatga aaactatta tcatgtaaat gtagcgacaa taggtaatag tgttattttt | 900 |
| cctggaacca tgagtgttat tgttttggt tattttggtg ttttttagt ggatagaaaa | 960 |
| ggatcattat ttgttttat tttaggatca ttgtctatct ctataagttt tttaactatt | 1020 |
| gcatttttg ttgagtttag tatgtggttg actacttta tgtttatatt tgttatgggc | 1080 |
| ggattatctt ttactaaaac agttatatca aaaatagtat caagtagtct ttctgaagaa | 1140 |
| gaagttgctt ctggaatgag tttgctaaat ttcacaagtt ttttatcaga gggaacaggt | 1200 |
| atagcaattg taggaggttt attgtcacta caattgatta atcgtaaact agttctggaa | 1260 |
| tttataaatt attcttctgg agtgtatagt aatattcttg tagccatggc tatccttatt | 1320 |
| attttatgtt gtcttttgac gattattgta tttaaacgtt ctgaaaagca gtttgaatag | 1380 |

<210> SEQ ID NO 229
<211> LENGTH: 1365
<212> TYPE: DNA
<213> ORGANISM: Staphylococcus aureus

<400> SEQUENCE: 229

| | |
|---|---|
| atgagaatag tgaatggacc aataataatg actagagaag aaagaatgaa gattgttcat | 60 |
| gaaattaagg aacgaatatt ggataaatat ggggatgatg ttaaggctat tggtgtttat | 120 |
| ggctctcttg gtcgtcagac tgatgggccc tattcggata ttgagatgat gtgtgtcatg | 180 |
| tcaacagaag aagcagagtt cagccatgaa tggacaaccg gtgagtggaa ggtggaagtg | 240 |
| aattttgata gcgaagagat tctactagat tatgcatctc aggtggaatc agattggcct | 300 |
| cttacacatg gtcaattttt ctctattttg ccgatttatg attcaggtgg atacttagag | 360 |
| aaagtgtatc aaactgctaa atcggtagaa gcccaaacgt tccacgatgc gatttgtgcc | 420 |
| cttatcgtag aagagctgtt tgaatatgca ggcaaatggc gtaatattcg tgtgcaagga | 480 |
| ccgacaacat ttctaccatc cttgactgta caggtagcaa tggcaggtgc catgttgatt | 540 |
| ggtctgcatc atcgcatctg ttatacgacg agcgcttcgg tcttaactga agcagttaag | 600 |
| caatcagatc ttccttcagg ttatgaccat ctgtgccagt tcgtaatgtc tggtcaactt | 660 |
| tccgactctg agaacttct ggaatcgcta gagaatttct ggaatgggat tcaggagtgg | 720 |
| acagaacgac acggatatat agtggatgtg tcaaaacgca taccattttg aacgatgacc | 780 |

```
tctaataatt gttaatcatg ttggttacgt atttattaac ttctcctagt attagtaatt    840
atcatggctg tcatggcgca ttaacggaat aaagggtgtg cttaaatcgg gccatttgc     900 gtaataagaa aaaggattaa ttatgagcga attgaattaa taataaggta atagatttac    960
attagaaaat gaaaggggat tttatgcgtg agaatgttac agtctatccc ggcattgcca   1020
gtcgtggata ttaaaaagag tataggtttt tattgcgata aactaggttt cactttggtt   1080
caccatgaag atggattcgc agttctaatg tgtaatgagg ttcggattca tctatgggag   1140
gcaagtgatg aaggctggcg ctctcgtagt aatgattcac cggtttgtac aggtgcggag   1200
tcgtttattg ctggtactgc tagttgccgc attgaagtag agggaattga tgaattatat   1260
caacatatta agcctttggg cattttgcac cccaatacat cattaaaaga tcagtggtgg   1320
gatgaacgag actttgcagt aattgatccc gacaacaatt tgatt                   1365

<210> SEQ ID NO 230
<211> LENGTH: 831
<212> TYPE: DNA
<213> ORGANISM: Staphylococcus aureus

<400> SEQUENCE: 230
atgggggttt cttttaatat tatgtgtcct aatagtagca tttattcaga tgaaaaatca    60
agggttttag tggacaagac aaagagtgga aaagtgagac catggagaga aagaaaatc    120 gctaatgttg attactttga acttctgcat attcttgaat ttaaaaaggc tgaaagagta   180
aaagattgtg ctgaaatatt agagtataaa caaaatcgtg aaacaggcga agaaagttg    240 tatcgagtgt ggttttgtaa atccaggctt tgtccaatgt gcaactggag gagagcaatg   300
aaacatggca ttcagtcaca aaaggttgtt gctgaagtta ttaaacaaaa gccaacagtt   360
cgttggttgt ttctcacatt aacagttaaa aatgtttatg atggcgaaga attaaataag   420
agtttgtcag atatggctca aggatttcgc cgaatgacgc aatataaaaa attaataaaa   480
aatcttgttg gttttatgcg tgcaacggaa gtgacaataa ataataaaga taattcttat   540
aatcagcaca tgcatgtatt ggtatgtgtg gaaccaactt attttaagaa tacagaaaac   600
tacgtgaatc aaaaacaatg gattcaattt tggaaaaagg caatgaaatt agactatgat   660
ccaaatgtaa aagttcaaat gattcgaccg aaaaataaat ataaatcgga tatacaatcg   720
gcaattgacg aaactgcaaa atatcctgta aaggatacgg atttttatgac cgatgatgaa   780 gaaaagaatt tgtaacgttt gtctgatttg gaggaaggtt tacaccgtaa a            831

<210> SEQ ID NO 231
<211> LENGTH: 4193
<212> TYPE: DNA
<213> ORGANISM: Staphylococcus aureus

<400> SEQUENCE: 231
atgagccgct tgatacgcat gagtgtatta gcaagtggta gtacaggtaa cgccacttt     60 gtagaaaatg aaaaaggtag tctattagtt gatgttggtt tgactggcaa gaaaatggaa   120
gaattgttta gtcaaattga ccgtaatatt caagatttaa atggtatttt agtaaccccat  180 gaacatattg atcatattaa aggattaggt gttttggcgc gtaaatatca attgccaatt   240
tatgcgaatg aaaagacttg gcaggcaatt gaaaagaaag atagtcgcat ccctatggat   300
cagaaattca tttttaatcc ttatgaaaca aaatctattg caggtttcga tgttgaatcg   360
tttaacgtgt cacatgatgc aatagatccg caattttata ttttccataa aactataag    420 aagtttacga ttttaacgga tacgggttac gtgtctgatc gtatgaaagg tatgatacgt   480
```

```
ggcagcgatg cgtttatttt tgagagtaat catgacgtcg atatgttgag aatgtgtcgt    540
tatccatgga agacgaaaca acgtatttta ggcgatatgg gtcatgtatc taatgaggat    600
gcgggtcatg cgatgacaga tgtgattaca ggtaacacga aacgtattta cctatcgcat    660
ttatcacaag acaataacat gaaagatttg gcgcgtatga gtgttggcca agtattgaac    720
gaacacgata ttgatacgga aaaagaagta ttgctatgtg atacggataa agctattcca    780
acgccaatat atacaatata atgagagtc accctataaa gttcggcact gctgtgagac    840
gactttatcg ggtgcttttt tatgttattg gtgggaaatg gctgttgttg gaattaaggt    900
tctatttgaa atgtaaaaaa taattcgata ttaaatgtaa tttataaata atttacataa    960
aatcaatcat tttaatataa ggattatgat aatatattgg tgtatgacag ttaatggagg   1020
gaacgaaatg aaagctttat tacttaaaac aagtgtatgg ctcgttttgc tttttagtgt   1080
gatgggatta tggcaagtct cgaacgcggc tgagcagtat acaccaatca agcacatgt   1140 agtaacaacg atagacaaag caacaacaga taagcaacaa gtaacgccaa caaggaagc   1200 ggctcatcaa tttggtgaag aagcggcaac caacgtatca gcatcagcac agggaacagc   1260
tgatgaaata aacaataaag taacatccaa cgcattttct aacaaaccat ctacagcagt   1320
ttcaacaaaa gtaaacgaaa cgcacgatgt agatacacaa caagcctcaa cacaaaaacc   1380
aactcaatca gcaacattca cattatcaaa tgctaaaaca gcatcacttt caccacgaat   1440
gtttgctgcc aatgtaccac aaacaacaac acataaaata ttacatacaa atgatatcca   1500
tggccgacta gccgaagaaa aagggcgtgt catcggtatg gctaaattaa aaacaataaa   1560
agaacaagaa aagcctgatt taatgttaga cgcaggagac gccttccaag gtttaccact   1620
ttcaaaccag tctaaaggtg aagaaatggc taaagcaatg aatgcagtag ttatgatgc   1680 tatggcagtg ggtaaccatg aatttgactt tggatacgat cagttgaaaa agttagaggg   1740
tatgttagac ttcccgatgc taagtactaa cgtttacaaa gatgggaaac gcgcgtttaa   1800
gccttcaaca attgtaacga aaatggtat tcgttatgga attattggcg taacgacacc   1860
agaaacaaag acgaaaacaa gacctgaggg cattaaaggt gttgaattta gagatccatt   1920
acaaagtgtg acagcagaaa tgatgcgtat ttataaagac gtagatacat tgttgttat   1980 atcacattta gggattgatc cttcaacaca agaaacatgg cgtggtgatt acttagtgaa   2040
acaattaagt caaaatccac aattgaagaa acgtattaca gtcattgatg gtcattcaca   2100
taccgtactt caaaatggtc aaatttataa caatgatgca ttagcacaaa caggtacagc   2160
acttgcgaat atcggtaagg ttacatttaa ttaccgcaat ggagaggtat caaatattaa   2220
accgtcattg attaatgtta aagacgttga aaatgtaaca ccgaacaaag cattagctga   2280
acaaattaat caagctgatc aaacatttag agcacaaaca gcagaggtta ttattccaaa   2340
taataccatt gatttcaaag gagaaagaga tgacgttaga acgcgtgaaa caaatttagg   2400
aaacgcgatt gcagatgcta tggaagcgta tggcgttaag aatttctcta aaagactga   2460 ctttgccgtg acaaatggtg gaggtattcg tgcctctatc gcaaaggta aggtgacacg   2520 ctatgattta atctcagtat taccatttgg aaatacgatt gcgcaaattg atgtaaaagg   2580
ttcgagcgtc tggacagctt tcgaacatag tttaggtgca ccaacaacac aaaaagacgg   2640
taagacagta ttaacagcga atggcggttt actacatatc tctgattcaa ttcgtgttta   2700
ctatgatatg aataaaccgt ctggcaaacg aattaacgct attcaaattt taaataaga   2760 gacaggtaag tttgaaaata ttgatttaaa acgtgtatat catgtaacga tgaatgactt   2820
```

| | |
|---|---|
| cacagcatca ggtggcgacg gatatagtat gttcggtggc cctagagaag aaggtatttc | 2880 |
| attagatcaa gtactagcaa gttatttaaa aacagctaac atagctaagt atgatacgac | 2940 |
| agaaccacaa cgtatgttat taggtaaacc agcagtaagt gaacaaccag ctaaaggaca | 3000 |
| acaaggtagc aaaggtagtg agtctggtaa agatgtacaa ccaattggtg acgacaaagc | 3060 |
| gatgaatcca gcgaaacaac cagcgacagg taaagttgta ttgttaccaa cgcatagagg | 3120 |
| aactgttagt agcggtacag aaggttctgg tcgcacatta gaaggagcta ctgtatcaag | 3180 |
| caagagtggg aaccaattgg ttagaatgtc agtgcctaaa ggtagcgcgc atgagaaaca | 3240 |
| gttaccaaaa actggaacta atcaaagctc aagcccagca gcgatgtttg tattagtagc | 3300 |
| aggtataggt ttaatcgcga ctgtacgacg tagaaaagct agttaaaata tattgaaaac | 3360 |
| aatactactg tatttcttaa ataagaggta cggtagtgtt tttttatgga aaaaagctat | 3420 |
| aaacgttgat aaacatggga tataaaaacg gggataagta ataagacatc aaggtgttta | 3480 |
| tccacagaaa tggggatagt tatccagaat tgtgtacaat ttaaagagaa atacccacaa | 3540 |
| tgcccacaga gttatccaca aatacacaag ttatacacta aaaattgggc ataaatgtca | 3600 |
| ggaaaatatc aaaaactgca aaaaatattg gtataataag agggaacagt gtgaacaagt | 3660 |
| taataacttg tggataactg gaaagttgat aacaatttgg aggaccaaac gacatgaaaa | 3720 |
| tcaccatttt agctgtaggg aaactaaaag agaaatattg gaagcaagcc atagcagaat | 3780 |
| atgaaaaacg tttaggccca tacaccaaga tagacatcat agaagttcca gacgaaaaag | 3840 |
| caccagaaaa tatgagcgac aaagaaattg agcaagtaaa agaaaaagaa ggccaacgaa | 3900 |
| tactagccaa aattaaacca caatccacag tcattacatt agaaatacaa ggaaagatgc | 3960 |
| tatcttccga aggattggcc caagaattga accaacgcat gacccaaggg caaagcgact | 4020 |
| ttgtattcgt cattggcgga tcaaacggcc tgcacaagga cgtcttacaa cgcagtaact | 4080 |
| acgcactatc attcagcaaa atgacattcc cacatcaaat gatgcgggtt gtgttaattg | 4140 |
| agcaagtgta tagagcattt aagattatgc gtggagaagc atatcataaa tga | 4193 |

<210> SEQ ID NO 232
<211> LENGTH: 2996
<212> TYPE: DNA
<213> ORGANISM: Staphylococcus aureus

<400> SEQUENCE: 232

| | |
|---|---|
| atgaaacgag ccattggtta tttgcgccaa agtacaacga acaacaatc actcccagct | 60 |
| caaaagcaag caatagaatt attagctcca aagcacaata ttcaaaatat ccaatacatt | 120 |
| agtgataagc aatcaggcag aacagataat cgaacaggct atcaacaagt caccgaacgc | 180 |
| atccaacaaa gacaatgtga cgtattatgt tgttatcgct tgaatcgact tcatcgcaac | 240 |
| ttgaaaaatg cattaaaact catgaaactc tgtcaaaaat atcatgttca tattctaagt | 300 |
| gttcatgatg gctattttga tatggataaa gcgtttgatc gcctaaaact caatatattc | 360 |
| atgagtctgg ctgaacttga atccgataat attggagaac aagtcaaaaa tggacttaga | 420 |
| gaaaaggcaa acaaggtaa actcataacg acccatgcgc ctttcggtta tcactatcaa | 480 |
| aatggtactt tcatcattaa taatgatgaa tcacctaccg tcaaagctgt attcaattat | 540 |
| tatcttcaag gatatggcta caagaagatt gcacaatatt tagaagacga taataaactt | 600 |
| attacccgca agccttatca ggtacgaaat ataattatga acccaaatta ttgtggtcgt | 660 |
| gtcatcaatc aatatggtca atataacaat atggtaccac ctattgtttc ggcaacgaaa | 720 |
| tatgaacatg ctcaagcaat ccgtaataag aagcaacttc actgtatacc ttcagagaat | 780 |

| | |
|---|---|
| cagctgaaac aaaagatcaa atgtccttgt tgtgactcaa cactgacaaa tatgacaata | 840 |
| agaaaaaaac atacattgcg atattatatt tgtcctaaaa atatgaatga atctcgcttt | 900 |
| gtctgttcat tcaaaggaat aaatgcacaa aaattagaag ttcaagtctt agctacatgt | 960 |
| cagaacttct ttcaaaacca acagctctat tcaaaaatta ataatgcaat tcatcaacgc | 1020 |
| ctcaaaaaac aaagagtgat agaagctaaa agtacgctaa ctcaagaaca actgatagat | 1080 |
| aaacttgcca aaggtatgat tgatgctgaa tcattcagaa acagactca tttgatgaat | 1140 |
| caaaagcaca aaaccatatc ctccataagt gataatcagt tacaaacatc actacaaaag | 1200 |
| gttatacaga aaagtttcac gttaaacatg ctgcatccct atattgatga aattcgcatt | 1260 |
| acaaaaaata aagcccttgt tgggatctat ttcaaaaatg aaccattgaa cattgtgaac | 1320 |
| caaacctcgc aatcatcgat tgcttaatca gaaaggatga aaaaatcatg caacaactca | 1380 |
| aacaaaaacg tgtcggtatc tatgttcgtg tatcaacgga aatccaaagt actgaaggct | 1440 |
| atagtatcga tggacaaatc aatcaaattc gagaatattg tgatttcaat aactttgttg | 1500 |
| ttgtagatgt atacgcggat agaggtatct ctggaaaatc tatgaaccga ccagaactac | 1560 |
| aacgtttgtt aaaagatgcg aacgaaggtc agattgattc tgttatggtc tacaaaacaa | 1620 |
| accgactagc acgtaacact tctgacttac tcaaaattgt tgaagacctt catcgtcaaa | 1680 |
| atgtcgaatt cttcagctta tctgagcgta tggaagtcaa tacaagcagt ggtaaattga | 1740 |
| tgctacaaat tctagcgagt ttttcagaat ttgaaagaaa taatattgtc gaaaatgtat | 1800 |
| tcatgggtca aacccgacgc gctcaagaag gctattatca aggcaatttg ccgctgggct | 1860 |
| atgacaaaat accggatagc aagcatgaac tcatgataaa ccaacatgaa gcgaatattg | 1920 |
| tcaaatatat atttgagtca tatgctaaag gccacggata tcgtaaaatt gcgaatgcac | 1980 |
| tcaatcacaa aggatacgtg actaaaaaag gaaagccttt cagtattggt tcagtgacct | 2040 |
| atatcttatc taatccattc tatgttggta aaattcaatt cgcaaagtac aaagattgga | 2100 |
| atgaaaagcg tcgtaaaggg ctgaatgata accaataat agctgaaggt aagcattccc | 2160 |
| ctattattat tcaagactta tgggataaag tccaattacg taaaaaacaa gtcagtcaaa | 2220 |
| aacctcaagt ccacggtaaa ggaactaatc tattaacagg tatcgttcat tgtccacaat | 2280 |
| gtggtgcacc aatggcagct agtaacacaa cgaacacatt gaaagatggt accaagaagc | 2340 |
| gaatacgtta ttattcttgc agtaacttcc gaaacaaagg ctcaaaagta tgttctgcga | 2400 |
| atagcgttag agctgatgtg attgagaaat acgtcatgga tcaaatactc gaaattgtca | 2460 |
| aaagtgataa agtcattaac caagtcttag aacgtgtcaa tcaagaaaat aaagtcgata | 2520 |
| ttggtgcatt gaaccacgat atcgcttata acaacaaca atacgatgaa gtcagcggga | 2580 |
| aactccataa tttagttaaa accattgaag ataatccgga cctaacatct gcattgaaag | 2640 |
| caactattca tcaatatgaa acacaactca atgacattac aaatcaaatg aatcaactca | 2700 |
| aacagcaaca aaatcaagag aaactatctt atgatacgaa acaaatcgct gccctattac | 2760 |
| aacgaatatt tcaaaatata gaatcaatgg ataaagcaca actcaaagca ttatatctta | 2820 |
| cagtcattga ccgtattgat attcgtaaag acggtaatca taaaaaacag ttctacgtta | 2880 |
| cactaaaact caataatgaa attattaaac aacttttcaa taatacccct ctcgacgaag | 2940 |
| tgctcctcag cacttcgtct ttattttgc ctcaaacgct ctttcttcaa atctaa | 2996 |

<210> SEQ ID NO 233
<211> LENGTH: 1410
<212> TYPE: DNA

-continued

<213> ORGANISM: Staphylococcus aureus

<400> SEQUENCE: 233

```
gctgtaggga aactaaaaga gaaatattgg aagcaagcca tagcagaata tgaaaaacgt      60
ttaggcccat acaccaagat agacatcata gaagttccag acgaaaaagc accagaaaat     120
atgagcgaca aagaaattga gcaagtaaaa gaaaagaag gccaacgaat actagccaaa     180
attaaaccac aatccacagt cattacatta gaaatacaag gaaagatgct atcttccgaa     240
ggattggccc aagaattgaa ccaacgcatg acccaagggc aaagcgactt tgtattcgtc     300
attggcggat caaacggcct gcacaaggac gtcttacaac gcagtaacta cgcactatca     360
ttcagcaaaa tgacattccc acatcaaatg atgcgggttg tgttaattga gcaagtgtat     420
agagcattta agattatgcg tggagaagca tatcataaat gatgcggttt tttcagccgc     480
ttcataaagg gattttgaat gtatcagaac atatgaggtt tatgtgaatt gctgttatgt     540
ttttaagaag catatcataa gtgatgcggt ttttattaat tagttgctaa aaaatgaagt     600
atgcaatatt aattattatt aaattttgat atatttaaag aaagattaag tttagggtga     660
atgaatggct tatcaaagtg aatatgcatt agaaaatgaa gtacttcaac aacttgagga     720
attgaactat gaaagagtaa atatacataa tattaaatta gaaattaatg aatatctcaa     780
agaactagga gtgttgaaaa atgaataagc agacaaatac tccagaacta agatttccag     840
agtttgatga ggaatggaaa aaaaggaaat taggtgaagt agtaaattat aaaaatggtg     900
gttcatttga aagtttagtg aaaaaccatg gtgtatataa actcataact cttaaatctg     960
ttaatacaga aggaaagttg tgtaattctg gaaaatatat cgatgataaa tgtgttgaaa    1020
cattgtgtaa tgatactta gtaatgatac tgagcgagca agcaccagga ctagttggaa    1080
tgactgcaat tatacctaat aataatgagt atgtactaaa tcaacgagta gcagcactag    1140
tgcctaaaca atttatagat agtcaatttc tatctaagtt aattaataga aaccagaaat    1200
atttcagtgt gagatctgct ggaacaaaag tgaaaaatat ttctaaagga catgtagaaa    1260
actttaatt tttatctcct aattacactg aacaacaaaa aataggtaat ttcttcagca    1320
aactcgaccg ccagattgag ttagaagaag agaaacttga actcttatag caacaaaagc    1380
gtggatatat ttcagaagat ttttctcaag                                    1410
```